United States Patent
Charneau et al.

(10) Patent No.: US 9,822,153 B2
(45) Date of Patent: Nov. 21, 2017

(54) LENTIVIRAL VECTOR BASED IMMUNOLOGICAL COMPOUNDS AGAINST MALARIA

(71) Applicants: Pierre Charneau, Paris (FR); Frederic Philippe Coutant, Rodez (FR)

(72) Inventors: Pierre Charneau, Paris (FR); Frederic Philippe Coutant, Rodez (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 14/799,633

(22) Filed: Jul. 15, 2015

(65) Prior Publication Data

US 2015/0368307 A1 Dec. 24, 2015

Related U.S. Application Data

(62) Division of application No. 13/695,683, filed as application No. PCT/EP2011/056887 on Apr. 29, 2011, now Pat. No. 9,109,234.

(30) Foreign Application Priority Data

May 3, 2010 (EP) .................................... 10290238

(51) Int. Cl.
| | | |
|---|---|---|
| *C12N 15/867* | (2006.01) | |
| *C07K 14/445* | (2006.01) | |
| *A61K 39/015* | (2006.01) | |
| *C12N 7/00* | (2006.01) | |
| *C12N 15/86* | (2006.01) | |
| *A61K 39/00* | (2006.01) | |

(52) U.S. Cl.
CPC .......... *C07K 14/445* (2013.01); *A61K 39/015* (2013.01); *C12N 7/00* (2013.01); *C12N 15/86* (2013.01); *C12N 15/867* (2013.01); *A61K 2039/525* (2013.01); *A61K 2039/5256* (2013.01); *A61K 2039/5258* (2013.01); *C12N 2740/15023* (2013.01); *C12N 2740/15043* (2013.01); *C12N 2740/16023* (2013.01); *C12N 2740/16043* (2013.01); *C12N 2810/6081* (2013.01)

(58) Field of Classification Search
None
See application file for complete search history.

(56) References Cited

U.S. PATENT DOCUMENTS 7,521,229 B2 4/2009 Pau

FOREIGN PATENT DOCUMENTS

| WO | 9428930 | 12/1994 |
| WO | 2004043488 A1 | 5/2004 |
| WO | 2007027860 A2 | 3/2007 |
| WO | 2007052165 A2 | 5/2007 |
| WO | 2007095201 A2 | 8/2007 |
| WO | 2009019612 A2 | 2/2009 |

OTHER PUBLICATIONS

Coutant, Frederic, et al., "A Nonintegrative Lentiviral Vector-Based Vaccine Provides Long-Term Sterile Protection Against Maleria," PLOS ONE, vol. 7, Issue 11, e48644, pp. 1-14 (2012).
Fenton, Brian, et al., "Structural and Antigenic Polymorphism of the 35- to 48-Kilodalton Merozoite Surface Antigen (MSA-2) of the Malaria Parasite Plasmodium falciparum," Moleculuar and Cellular Biology, vol. 11, No. 2, pp. 963-971 (1991).
Langhorn, Jean, et al., "Malaria," Encyclopedia of Immunology, pp. 1658-1663 (1998).
Marussig, M., et al., "Linear and multiple antigen peptides containing defined T and B epitopes of the Plasmodium yoelii circumsporozoite protein: antibody-mediated protection and boosting by sporozoite infection," International Immunology, vol. 9, No. 12, pp. 1817-1824 (1997).
Mishra, Satish, et al., "Identification of non-CSP antigens bearing CD8 epitopes in mice immunized with irradiated sporozoites," Vaccine, vol. 29, pp. 7335-7342.
Ramasamy, Ranjan, et al., "Antibodies and Plasmodium falciparum merozoites," Trends in Parasitology, vol. 17, No. 4, pp. 194-197 (2001).
Rzepczyk, Christine M., "Comparative Study of the T Cell Response to Two Alelic Forms of a Malarial Vaccine Candidate Protein," The Journal of Immunology, vol. 148, No. 4, pp. 1197-1204 (1992).
Sheehy, Susanne H., "Phase la Clinical Evaluation of the Plasmodium falciparum Blood-stage Antigen MSP1 in ChAd63 and MVA Vaccine Vectors," Molecular Therapy, pp. 1-8 (Aug. 23, 2011).
Tamminga, Cindy, et al., "Adenovirus-5-Vectored P. falciparum Faccine Expressing CSP and AMA1. Part B: Safety, Immunogenicity and Protective Efficacy of teh CSP Component," PLoS ONE, vol. 6, No. 10, e25868, pp. 1-20 (2011).
Tarun, Alice S., "Protracted Sterile Protection with Plasmodium yoelii Pre-erythrocytic Genetically Attenuated Parasite Malaria Vaccines Is Independent of Significant Liver-Stage Persistence and Is Mediated by CD8+ T Cells," The Journal of Infectious Diseases, vol. 196, pp. 608-616 (2007).
Mishra, Satish, et al., "Identification of non-CSP antigens bearing CD8 epitopes in mice immunized with irradiated sporozoites," Vaccine, vol. 29, pp. 7335-7342 (2011).
GenBank: M28887.1, Apr. 26, 1993.
GenBank: M60972.1, Apr. 26, 1993.
Bowie, et al., Science, 1990, 247: 1306-1310).
Greenspan, et al., Nature Biotechnology, 1999, 7: 936-937.
Genbank Locus AAA48370.1, Oct. 21, 2002.
Audran, Regine, et al., PLoS ONE, vol. 4, Issue 10, e7304 (Oct. 2009).
GenBank Locus AY135360.1, Oct. 11, 2005.
GenBank Locus AY674050.1, Aug. 1, 2005.
Beignon, Anne-Sophie, et al., Journal of Virology, vol. 83, No. 21, pp. 10963-10974 (2009).

(Continued)

*Primary Examiner* — Brian J Gangle
(74) *Attorney, Agent, or Firm* — Arrigo, Lee & Guttman LLP

(57) ABSTRACT

The invention relates to lentiviral vector particles pseudotyped with a determined heterologous viral envelope protein or viral envelope proteins originating from a RNA virus and which comprise in its genome at least one recombinant polynucleotide encoding at least one polypeptide(s) carrying epitope(s) of an antigen of a *Plasmodium* parasite capable of infecting a mammalian host. The lentiviral vector particles are used in order to elicit an immunological response against malaria parasites.

17 Claims, 15 Drawing Sheets

(56) References Cited

OTHER PUBLICATIONS

Figure 1:
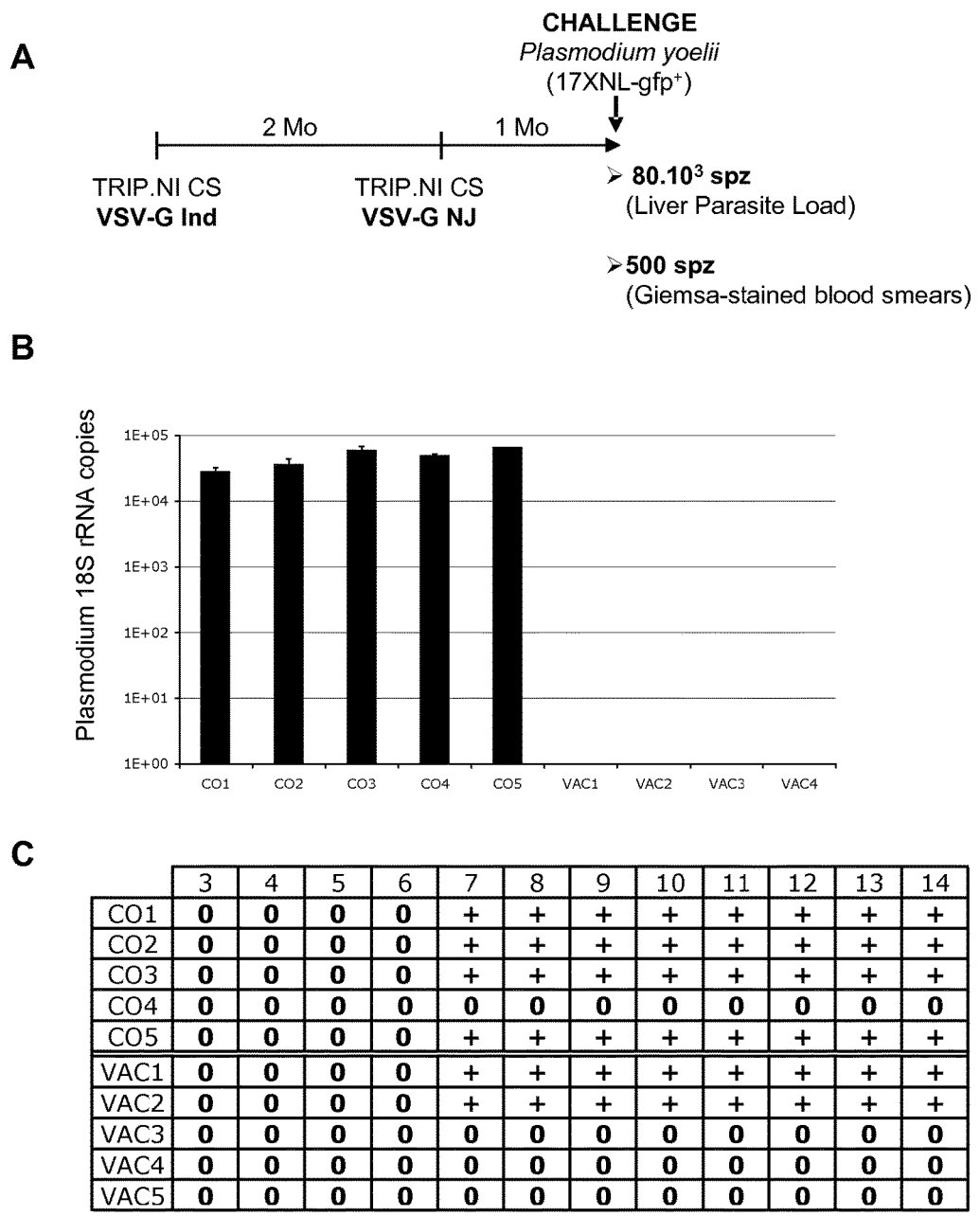

Beignon, A., et al., Retrovirology, vol. 6, Suppl. 3, p. 302 (2009).
Bruna-Romero, Oscar, et al., PNAS, vol. 98, No. 20, pp. 11491-11496 (2001).
Bruna-Romero, Oscar, et al., Vaccine, vol. 22, pp. 3575-3584 (2004).
Cockrell, Adam S., et al., Molecular Therapy, vol. 14, No. 2, pp. 276-284 (2006).
Cockrell, Adam S., et al., Mol. Biotechnol. vol. 36, pp. 184-204 (2007).
Coutant, Frederic, et al., PLoS ONE, vol. 3, Issue 12, e3973 (2008).
Cronin, James, et al., Curr. Gene Ther., vol. 5, No. 4, pp. 387-398 (2005).
Developing a Malaria Vaccine Fact Sheet, Jul. 2009.
Daneshvar, Cyrus, Clinical Infectious Disease, vol. 49, pp. 852-860 (2009).
Dobano, C., et al., Molecular Immunology, vol. 44, pp. 3037-3048 (2007).
Dobano, Carlota, et al., Experimental Parasitology, vol. 122, pp. 112-123 (2009).
GenBank Locus DQ350294.2, Sep. 25, 2009.
Firat, Huseyin, et al., The Journal of Gene Medicine, vol. 4, pp. 38-45 (2002).
Gonzalez-Aseguinolaza, Gloria, et al., Journal of Virology, vol. 77, No. 21, pp. 11859-11866 (2003).
Ikeda, Yasuhiro, et al., Nature Biotechnology, vol. 21, pp. 569-572 (2003).
GenBank Locus J02695.1, Mar. 14, 1994.
GenBank Locus J03992.1, Mar. 14, 1994.
Jones, Stephanie, et al., Human Gene Therapy, vol. 20, pp. 630-640 (2009).
Kafri, Tal, et al., Journal of Virology, vol. 73, No. 1, pp. 576-584 (1999).
Limbach, K. J., Parasite Immunology, vol. 31, pp. 501-519 (2009).
GenBank Locus M15505.1, Apr. 26, 1993.
GenBank Locus M28887.1.
GenBank Locus M60972.1.
Maeda, Ken, et al., Viral Immunology, vol. 18, No. 4, pp. 657-667 (2005).
Miyahira, Y., et al., PNAS, vol. 95, pp. 3954-3959 (1998).
Nussenzweig, Victor, Am. J. Trop. Hyg., vol. 35, No. 4, pp. 678-688 (1986).
Ophorst, O. J. A. E., Infection and Immunity, vol. 74, No. 1, pp. 313-320 (2006).
Ophorst, Olga J. A. E., Vaccine, vol. 25, pp. 6501-6510 (2007).
Overstreet, M. G., Immunol. Rev., vol. 225, No. 1, pp. 272-283 (2008).
Rocha, C. D., International Microbiology, vol. 7, pp. 83-94 (2004).
Rodrigues, E. G., Journal of Immunology, vol. 158, pp. 1268-1274 (1997).
Speake, C., Parasite Immunology, vol. 31, pp. 539-546 (2009).
Tine, J. A., Infection and Immunity, vol. 64, No. 9, pp. 3833-3844 (1996).
GenBank Locus U65959.1, Nov. 7, 1996.
Vandendriessche, T., et al., Blood, vol. 100, No. 3, pp. 813-822 (2002).
Vaughan, K., et al., Parasite Immunology, vol. 31, pp. 78-97 (2009).
Xu, K., et al., Molecular Therapy, vol. 3, No. 1, pp. 97-104 (2001).
Zennou, V., et al., Cell, vol. 101, pp. 173-185 (2000).

A

```
        2 Mo              5 Mo              1 Mo    CHALLENGE        3 weeks
                                                    Plasmodium yoelii (17XNL)
                                                    500 spz
                                                         ↓                              Sacrifice
   |---------------|----------------|----------------|========================|-----► of mice
   TRIP.NI CS      TRIP.NI CS       TRIP.NI CS         Giemsa-stained blood smears  (Immune response)
   VSV-G Ind       VSV-G NJ         VSV-G Cocal
```

B

|     | Protected/Challenged | % sterile immunity |
|-----|----------------------|--------------------|
| CO  | 0/8                  | 0                  |
| VAC | 5/8                  | 62,5               |

C Parasitemia (%) vs days — CO, VAC, VAC

D d10 — Parasitemia (%): CO, VAC, VAC

FIGURE 2

A. Hep17-specific CD4+ T cell responses
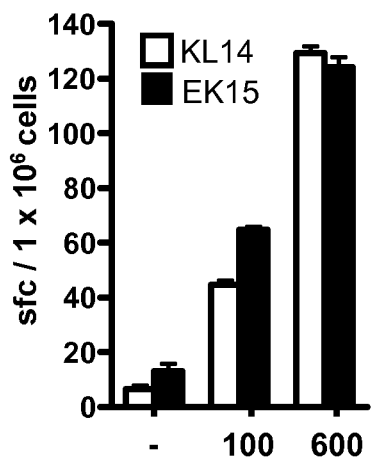
B. Hep17-specific CD8+ T cell responses
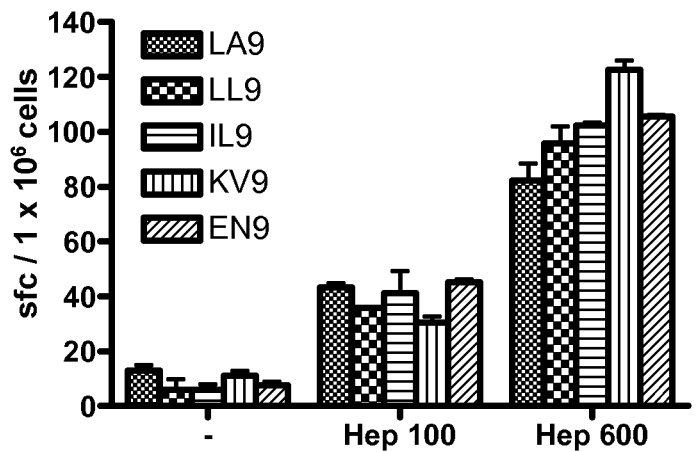
FIGURE 6

A. Hep17-specific CD4+ T cell responses
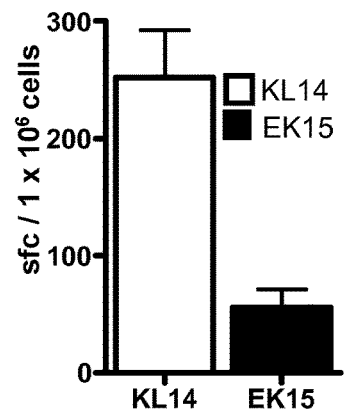
B. Hep17-specific CD8+ T cell responses
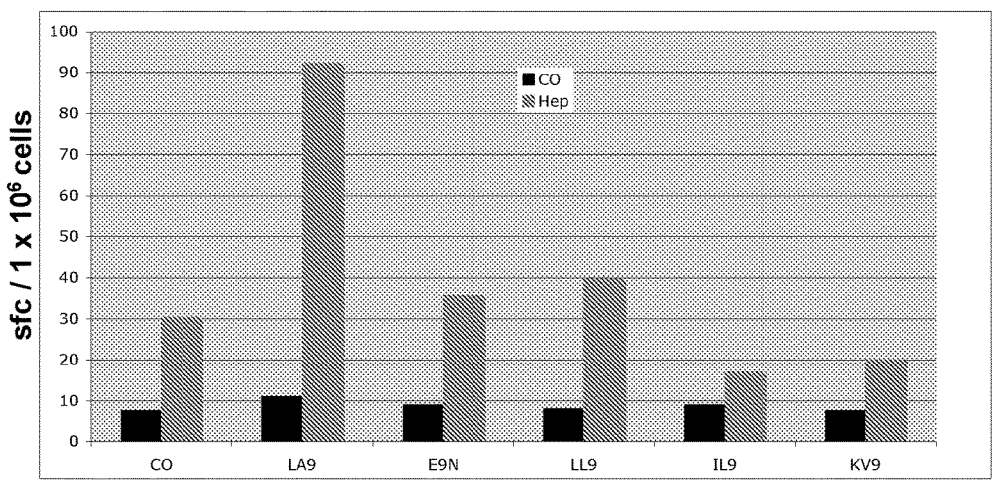
FIGURE 7

ALIGNMENTS

```
                                  1                                                50
CSP Plasmodium falciparum    (1)  ---------------------------------MMRKLAILSVSSFL
     CSP Plasmodium yoleii   (1)  ---------------------------------MKKCTILVVASLL
    CSP Plasmodium berghei   (1)  ---------------------------------MKKCTILVVASLL
   CSP Plasmodium malariae   (1)  MKKLSVLAISSFLIVDFLFPGYHHNSNSTKSRNLSELCYNNVDTKLPNEL
    CSP Plasmodium coatneyi  (1)  ---------------------------------------MKNFILLAVSSIL
    CSP Plasmodium knowlesi  (1)  ---------------------------------------MRNFILLAVSSIL
  CSP Plasmodium reichenowi  (1)  ---------------------------------MMRKLAILSVSSFL
  CSP Plasmodium gallinaceum (1)  ---------------------------------MKKLAILSASSFL
                  Consensus  (1)                                   MKK  ILSVSSIL 51                                               100
CSP Plasmodium falciparum   (15)  FVEALFQEYQCYGSSSNTRVLNELN--YDNAGTNLYNELEMNYYGKQENW
     CSP Plasmodium yoleii  (14)  LVDSLLPGYGQNKSVQAQRNLNELCY-------NEENDNKLYHVLNSKNG
    CSP Plasmodium berghei  (14)  LVNSLLPGYGQNKIIQAQRNLNELCY-------NEGNDNKLYHVLNSKNG
   CSP Plasmodium malariae  (51)  EVRYSTNQDHFYNYNKTIRLLNENNNEKDGNVTNERKKKPKTKAVENKLKQ
    CSP Plasmodium coatneyi (14)  LVDLFPTHFGHNVDLSRAINLNGVS----------FNNVDTSLLGAAQVR
    CSP Plasmodium knowlesi (14)  LVDLFPTHFEHNVDLSRAINVNGVS----------FNNVDTSSLGAAQVR
  CSP Plasmodium reichenowi (15)  FVEALFQEYQCYGSSSNTRVLNELNY--DNAGTNLYNELEMNYYGKQENW
  CSP Plasmodium gallinaceum (14) FADFLFQEYQHNGNYKNFRLLNEVCY--NNMNIQLYNELEMENYMSNTYF
                  Consensus (51)  LVDAL Q Y  N  LS  RNLNEL Y         N YNELEM HVG A N 101                                              150
CSP Plasmodium falciparum   (63)  YSLKKNSRSLGENDDGNNEDNEKLRKP----------KHKKLKQPADGN
     CSP Plasmodium yoleii  (57)  KIYNRNIVNRLLGDALNGKPEEKKD--------------DPPKDGNKDD
    CSP Plasmodium berghei  (57)  KIYNRNTVNRLLADAPEGKKNEKKN--------------EKIERNNKLK
   CSP Plasmodium malariae (101)  PPGDDDG---AGNDAGNDAGNDAGN-------------AAGNAAGNAAGN
    CSP Plasmodium coatneyi (54)  QSASRGRGLGEK--PKKKAEK---------------KEEEPKKPNENK
    CSP Plasmodium knowlesi (54)  QSASRGRGLGEK--RKEGADKEKKKE-----------KEEEPKKPNENK
  CSP Plasmodium reichenowi (63)  YSLKKNSRSLGENDDADNGDADNGDEGIDENRRHRNKEGKEKLKKPKHNK
  CSP Plasmodium gallinaceum (62) YNNKKTIRLLGENDNEANVNRANNNVAND---------NRANGNRGNVNR
                  Consensus (101) S  RN     G ND    AD EK                  E  KKPN NK 151                                              200
CSP Plasmodium falciparum  (102)  PDPNANPNVDPNANPNVDPNANPNVDPNANPNANPNANPNANPNANPNAN
     CSP Plasmodium yoleii (92)   LPKEEKKDDLPKEEKKDDPPKDPKKDDPPK-----EAQNKLNQPVVADEN
    CSP Plasmodium berghei (92)   QPP-------PPPNPNDPPPPNPNDPPPP-------------------N
   CSP Plasmodium malariae (135)  AAGNAAGNAAGNAAGNAAGNAAGNAAGNDAGNAAGNAAGNAAGNAAGNAA
    CSP Plasmodium coatneyi (85)  LKQPVDGARDGPA-PAADGARDGPAPAADGA-------RDGPAPAADGAR
    CSP Plasmodium knowlesi (90)  LKQPDQAAPGAGG-EQPAPGAGGEQPAPGAG--------GERPAPGAGGE-
  CSP Plasmodium reichenowi (113) LKQPGNDNVDPNANPNVDPNANPNVDPNANP---------NVDPNANPNVD
  CSP Plasmodium gallinaceum (103) ANDRNIPYFRENVVNLNQPVGGNGGVQPAGGNGGVQPAGGNGVQPAGGN
                  Consensus (151) L           PNA PN DP A PN    PAAG           A A A AN 201                                              250
CSP Plasmodium falciparum  (152)  PNANPNANPNANPNANPNANPNANPNANPNANPNANPNANPNANPNVDPN
     CSP Plasmodium yoleii (137)  VDQGPGAPQGPGAPQGPGAPQGPGAPQGPGAPQGPGAPQGPGAPQGPGAP
    CSP Plasmodium berghei (115)  PNDPP--PPNPNDPAPPNANDPAPPNANDPAPPNANDPAPPNANDPAPPN
   CSP Plasmodium malariae (185)  GNDAGNAAGNAAGNAAGNAAGNAAGNAAGNAAGNAAGNAAGNAAGNDAGN
    CSP Plasmodium coatneyi (127) DGPAPAADGARDGPAPAADGARDGPAPAADGARDGPAPAADGARDGPAPP
    CSP Plasmodium knowlesi (131) -QPAPGAGGE--QPAPGAGGERPAPGAGGEQPAPGAGGEQPAPGAGGEQP
  CSP Plasmodium reichenowi (155) PNANPNVNPNANPNVDPNANPNVNPNANPNVNPNANPNVNPNANPNANPN
  CSP Plasmodium gallinaceum (153) GGVQPAGGNGGVQPAGGNGGVQPAGGNGGVQPAGGNGGAQPVAAGGGAQP
                  Consensus (201) N APAA  NA   PA PNAG N APNAGG AP NANG ANPNA  GAAPP 251                                              300
CSP Plasmodium falciparum  (202)  ANPNANPNANPNANPNANPNANPN--ANPNANPNANPNANPNANPNANPN
     CSP Plasmodium yoleii (187)  QGPGAPQGPGPGAPQGPGAPQGPGA---PQGPGAPQGPGAPQGPGAPQEPPQ
    CSP Plasmodium berghei (163)  ANDPAPPNANDPAPPNANDPP--------PPNPNDPAPPQGNNNPQ--PQ
   CSP Plasmodium malariae (235)  AAGNAAGNAAGNAAGNAAGNAAGN--AAGNAAGNAAGNAAGNAAGNAAGN
    CSP Plasmodium coatneyi (177) ADGARDGPAPPAADGARDGPAP----PAADGARDGPAPPAGQGGGN----
    CSP Plasmodium knowlesi (178) APGAGGEQPAPGAGGERPAPGAGGERPAPGAGGEQPAPGAGGEQPA----
  CSP Plasmodium reichenowi (205) ANPNANPNANPNANPNANPNAN------PNANPNANPNANPNANPNANPN
  CSP Plasmodium gallinaceum (203) VVADGGVQPLRQEGDAEEDGGNGGAQPAGGNGGAQPAGGNGGAQPAGGNG
                  Consensus (251) A G A   NA  PNAGPNA     A G   PAG AAPNAPA ANGNANPNA  PN
```

FIGURE 10(A)

```
CSP Plasmodium falciparum  (250) ANPNANPNANPNANPNANPNANPNANPNKNNQGNGQGHNMPNDPNRNVDENANA
     CSP Plasmodium yoleii (234) QPPQQPPQQPPQQPPQQPPQQPPQQ----------------PRPQPDG
    CSP Plasmodium berghei (203) PRPQPQPQPQPQPQPQPQPQPRPQ------------------PQPQPGG
   CSP Plasmodium malariae (283) AAGNAAGNAAGNAAGNAAGNAAGNAAGNAAG------NEKAKNKDNKVDA
   CSP Plasmodium coatneyi (219) ---AAGQAQGGGNAGNKKAGDAAGN-------------------------
   CSP Plasmodium knowlesi (224) ---PAPRREQPAPGPGAGDGARGGN-------------------------
  CSP Plasmodium reichenowi(249) ANPNANPNANPNANPNRNNEANGQGHN--------------KPNDQNRNV
 CSP Plasmodium gallinaceum(253) GAQPAGGNGGAQPAGGNDAAKPDGG-----------------NDDDKPE
                 Consensus (301) A PNA PNANPN APN    NA GQ                  D N  A 351                                              400
CSP Plasmodium falciparum  (300) NSAVKNN---NNEE---PSDKHIKEYLNKIQNSLSTEWSPCSVTCGNGIQ
     CSP Plasmodium yoleii (266) NNNNNNNNGNNNEDSYVPSAEQILEFVKQISSQLTEEWSQCSVTCGSGVR
    CSP Plasmodium berghei (234) NNNNKNNN---NDDSYIPSAEKILEFVKQIRDSITEEWSQCNVTCGSGIR
   CSP Plasmodium malariae (327) NTNKKDNQEENNDSSNGPSEEHIKNYLESIRNSITEEWSPCSVTCGSGIR
   CSP Plasmodium coatneyi (241) -AGAAKGQGQNNEGANVPNEKVVNDYLQKIRSTVTTEWTPCSVTCGNGVR
   CSP Plasmodium knowlesi (246) -AGAGKGQGQNNQGANVPNEKVVNDYLHKIRSSVTTEWTPCSVTCGNGVR
  CSP Plasmodium reichenowi(285) NENANANNAGRNNNNEEPSDKHIEEFLKQIQNNLSTEWSPCSVTCGNGIQ
 CSP Plasmodium gallinaceum(285) GGDEKSEEEKEDEPIPDPTQEEIDKYLKSILGNVTSEWTNCNVTCGKGIQ
                 Consensus (351) N N K NNG NNE S VPSEK I EYLK IR SLTTEWSPCSVTCGNGIR 401                                              450
CSP Plasmodium falciparum  (344) VRIKPGSANKPKDELDYANDIEKKICKMEKCS-SVFNVVNSSIGLIMVLS
     CSP Plasmodium yoleii (316) VRKRKNVNKQ--PENLTLEDIDTEICKMDKCS-SIFNIVSNSLGFVILLV
    CSP Plasmodium berghei (281) VRKRKGSNKK--AEDLTLEDIDTEICKMDKCS-SIFNIVSNSLGFVILLV
   CSP Plasmodium malariae (377) ARRKVGAKNK-KPAELVLSDLETEICSLDKCS-SIFNVVSNSLGIVLVLV
   CSP Plasmodium coatneyi (290) LRRKAHAEKK-KPEDLTMDDLDVEVCAMDKCA-GIFNFVSNSLGLVILLV
   CSP Plasmodium knowlesi (295) IRRRQNAGNK-KAEDLTMDDLEVEACVMDKCA-GIFNVVSNSLGLVILLV
  CSP Plasmodium reichenowi(335) VRIKPGSAGKPKDQLDYENDLEKKICKMEKCS-SVFNVVNSSIGLIMVLS
 CSP Plasmodium gallinaceum(335) AKIKSTSANK-KREEITPNDVEVKICELERCSFSIFNVISNSLGLAIILT
                 Consensus (401) VRRK GSANK K EDLTLDDLE EICKMDKCS SIFNVVSNSLGLVILLV 451
CSP Plasmodium falciparum  (393) FLFLN
     CSP Plasmodium yoleii (363) LVFFN
    CSP Plasmodium berghei (328) LVFFN
   CSP Plasmodium malariae (425) LILFH
   CSP Plasmodium coatneyi (338) LAFN-
   CSP Plasmodium knowlesi (343) LALFN
  CSP Plasmodium reichenowi(384) FLFLN
 CSP Plasmodium gallinaceum(384) FLFFY
                 Consensus (451) LLFFN
```

FIGURE 10(B)

pTRIP-DeltaU3-CMV-eGFP
4024 bp pTRIP-DeltaU3-CMV-MSP1(42)-CO-WPRE
4927 bp pTRIP-DeltaU3-CMV-HEP17 CO-WPRE
4300 bp pTRIP-DeltaU3-CMV-Hep17 dSP CO WPRE
4261 bp

SEQUENCE LISTING

<160> NUMBER OF SEQ ID NOS: 90

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtaccggat ccgccaccat gaagaaatgc acc                                33

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agctcgagtc atcacaggct gttggacacg atgttgaaga tgc                      43

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      sequence coding for the secretion signal of the calreticuline

<400> SEQUENCE: 3

Met Leu Leu Ser Val Pro Leu Leu Leu Gly Leu Leu Gly Leu Ala Val
1               5                   10                  15

Ala

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggggattggt tttgacgttt ttgcg                                          25

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagcattaaa taaagcgaat acatccttat                                     30

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide from Plasmodium yoelii cs protein

<400> SEQUENCE: 6

Ser Tyr Val Pro Ser Ala Glu Gln Ile
1               5

<210> SEQ ID NO 7
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide from Plasmodium yoelii cs protein

<400> SEQUENCE: 7

Ile Tyr Asn Arg Asn Ile Val Asn Arg Leu
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide from Plasmodium yoelii cs protein

<400> SEQUENCE: 8

Ser Tyr Val Pro Ser Ala Glu Gln Ile Leu Glu Phe Val Lys Gln Ile
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide from Plasmodium yoelii CSP

<400> SEQUENCE: 9

Lys Ile Tyr Asn Arg Asn Ile Val Asn Arg Leu Leu Gly Asp
1               5                   10

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide from Plasmodium yoelii CSP

<400> SEQUENCE: 10

Tyr Asn Arg Asn Ile Val Asn Arg Leu Leu Gly Asp Ala Leu Asn Gly
1               5                   10                  15

Lys Pro Glu Glu Lys
            20

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide from Plasmodium yoelii Hep17 protein

<400> SEQUENCE: 11

Leu Arg Lys Ile Asn Val Ala Leu Ala
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide from Plasmodium yoelii Hep17 protein

<400> SEQUENCE: 12

Glu Glu Ile Val Lys Leu Thr Lys Asn
```

```
<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide from Plasmodium yoelii Hep17 protein

<400> SEQUENCE: 13

Lys Lys Ser Leu Arg Lys Ile Asn Val
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide from Plasmodium yoelii Hep17 protein

<400> SEQUENCE: 14

Ile Asn Val Ala Leu Ala Thr Ala Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide from Plasmodium yoelii Hep17 protein

<400> SEQUENCE: 15

Leu Ser Val Val Ser Ala Ile Leu Leu
1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide from Plasmodium yoelii Hep17 protein

<400> SEQUENCE: 16

Glu Glu Ile Val Lys Leu Thr Lys Asn Lys Lys Ser Leu Arg Lys
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide from Plasmodium yoelii Hep17 protein

<400> SEQUENCE: 17

Lys Ser Leu Arg Lys Ile Asn Val Ala Leu Ala Thr Ala Leu
1               5                   10

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 18
cgtggatcca tggacggcat ggatctgctg                                     30

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gatgaattcg gagctgctgc tgcagaacac g                                   31

<210> SEQ ID NO 20
<211> LENGTH: 367
<212> TYPE: PRT
<213> ORGANISM: Plasmodium yoelii
<220> FEATURE:
<221> NAME/KEY: MISC_FEATURE
<222> LOCATION: (1)..(367)
<223> OTHER INFORMATION: CSP protein

<400> SEQUENCE: 20

Met Lys Lys Cys Thr Ile Leu Val Val Ala Ser Leu Leu Leu Val Asp
 1               5                  10                  15

Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Pro Gln Pro Gln Gln Pro
225                 230                 235                 240

Gln Gln Pro Pro Gln Gln Pro Pro Gln Gln Pro Pro Gln Gln Pro Pro
                245                 250                 255
```

```
Gln Gln Pro Arg Pro Gln Pro Asp Gly Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350

Asn Ser Leu Gly Phe Val Ile Leu Leu Val Leu Val Phe Phe Asn
        355                 360                 365

<210> SEQ ID NO 21
<211> LENGTH: 355
<212> TYPE: PRT
<213> ORGANISM: Plasmodium yoelii
<220> FEATURE:
<221> NAME/KEY: MISC_FEATURE
<222> LOCATION: (1)..(355)
<223> OTHER INFORMATION: CSP DGPI protein (deletion from residues
      GFVILLVLVFFN from CSP)

<400> SEQUENCE: 21

Met Lys Lys Cys Thr Ile Leu Val Val Ala Ser Leu Leu Leu Val Asp
1               5                   10                  15

Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Lys Glu Ala Gln Asn Lys Leu Asn
            115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Pro Gln Gln Pro Pro Gln Gln Pro Pro
225                 230                 235                 240
```

Gln Gln Pro Pro Gln Gln Pro Gln Gln Pro Gln Gln Pro Pro
                245                 250                 255

Gln Gln Pro Arg Pro Gln Pro Asp Gly Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350

Asn Ser Leu
        355

<210> SEQ ID NO 22
<211> LENGTH: 349
<212> TYPE: PRT
<213> ORGANISM: Plasmodium yoelii
<220> FEATURE:
<221> NAME/KEY: MISC_FEATURE
<222> LOCATION: (1)..(349)
<223> OTHER INFORMATION: CSP NTer protein (Deletion of residues 1-19
      from CSP)

<400> SEQUENCE: 22

Met Pro Gly Tyr Gly Gln Asn Lys Ser Val Gln Ala Gln Arg Asn Leu
1               5                   10                  15

Asn Glu Leu Cys Tyr Asn Glu Glu Asn Asp Asn Lys Leu Tyr His Val
            20                  25                  30

Leu Asn Ser Lys Asn Gly Lys Ile Tyr Asn Arg Asn Ile Val Asn Arg
        35                  40                  45

Leu Leu Gly Asp Ala Leu Asn Gly Lys Pro Glu Glu Lys Lys Asp Asp
    50                  55                  60

Pro Pro Lys Asp Gly Asn Lys Asp Asp Leu Pro Lys Glu Glu Lys Lys
65                  70                  75                  80

Asp Asp Leu Pro Lys Glu Glu Lys Lys Asp Asp Pro Pro Lys Asp Pro
                85                  90                  95

Lys Lys Asp Asp Pro Pro Lys Glu Ala Gln Asn Lys Leu Asn Gln Pro
            100                 105                 110

Val Val Ala Asp Glu Asn Val Asp Gln Gly Pro Gly Ala Pro Gln Gly
        115                 120                 125

Pro Gly Ala Pro Gln Gly Pro Gly Ala Pro Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Glu Pro Pro Gln Gln Pro Gln Gln Pro Pro Gln Gln
    210                 215                 220

```
Pro Pro Gln Gln Pro Pro Gln Gln Pro Pro Gln Gln Pro Pro Gln Gln
225                 230                 235                 240

Pro Arg Pro Gln Pro Asp Gly Asn Asn Asn Asn Asn Asn Asn Asn Gly
                245                 250                 255

Asn Asn Asn Glu Asp Ser Tyr Val Pro Ser Ala Glu Gln Ile Leu Glu
            260                 265                 270

Phe Val Lys Gln Ile Ser Ser Gln Leu Thr Glu Glu Trp Ser Gln Cys
            275                 280                 285

Ser Val Thr Cys Gly Ser Gly Val Arg Val Arg Lys Arg Lys Asn Val
            290                 295                 300

Asn Lys Gln Pro Glu Asn Leu Thr Leu Glu Asp Ile Asp Thr Glu Ile
305                 310                 315                 320

Cys Lys Met Asp Lys Cys Ser Ser Ile Phe Asn Ile Val Ser Asn Ser
                325                 330                 335

Leu Gly Phe Val Ile Leu Leu Val Leu Val Phe Phe Asn
                340                 345
```

<210> SEQ ID NO 23
<211> LENGTH: 397
<212> TYPE: PRT
<213> ORGANISM: Plasmodium falciparum
<220> FEATURE:
<221> NAME/KEY: MISC_FEATURE
<222> LOCATION: (1)..(397)
<223> OTHER INFORMATION: CSP protein

<400> SEQUENCE: 23

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
                100                 105                 110

Asn Ala Asn Pro Asn Val Asp Pro Asn Ala Asn Pro Asn Val Asp Pro
            115                 120                 125

Asn Ala Asn Pro Asn Ala Asn Pro Asn Ala Asn Pro Asn Ala Asn Pro
        130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
                180                 185                 190

Asn Ala Asn Pro Asn Val Asp Pro Asn Ala Asn Pro Asn Ala Asn Pro
            195                 200                 205

Asn Ala Asn Pro Asn Ala Asn Pro Asn Ala Asn Pro Asn Ala Asn Pro
        210                 215                 220

Asn Ala Asn Pro Asn Ala Asn Pro Asn Ala Asn Pro Asn Ala Asn Pro
```

```
                    225                 230                 235                 240
Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
                260                 265                 270

Asn Lys Asn Asn Gln Gly Asn Gly Gln Gly His Asn Met Pro Asn Asp
                275                 280                 285

Pro Asn Arg Asn Val Asp Glu Asn Ala Asn Ala Asn Ser Ala Val Lys
            290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
                340                 345                 350

Lys Pro Lys Asp Glu Leu Asp Tyr Ala Asn Asp Ile Glu Lys Lys Ile
            355                 360                 365

Cys Lys Met Glu Lys Cys Ser Ser Val Phe Asn Val Val Asn Ser Ser
        370                 375                 380

Ile Gly Leu Ile Met Val Leu Ser Phe Leu Phe Leu Asn
385                 390                 395

<210> SEQ ID NO 24
<211> LENGTH: 368
<212> TYPE: PRT
<213> ORGANISM: Plasmodium falciparum
<220> FEATURE:
<221> NAME/KEY: MISC_FEATURE
<222> LOCATION: (1)..(368)
<223> OTHER INFORMATION: CSP DGPI protein

<400> SEQUENCE: 24

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
            35                  40                  45

Asn Glu Leu Glu Met Asn Tyr Tyr Gly Lys Gln Glu Asn Trp Tyr Ser
        50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
                100                 105                 110

Asn Ala Asn Pro Asn Val Asp Pro Asn Ala Asn Pro Asn Val Asp Pro
            115                 120                 125

Asn Ala Asn Pro Asn Ala Asn Pro Asn Ala Asn Pro Asn Ala Asn Pro
        130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190
```

```
Asn Ala Asn Pro Asn Val Asp Pro Asn Ala Asn Pro
        195                 200                 205

Asn Ala Asn Pro Asn Ala Asn Pro Asn Ala Asn Pro
        210                 215                 220

Asn Ala Asn Pro Asn Ala Asn Pro Asn Ala Asn Pro
225                 230                 235                 240

Asn Ala Asn Pro Asn Ala Asn Pro Asn Ala Asn Pro
            245                 250                 255

Asn Ala Asn Pro Asn Ala Asn Pro Asn Ala Asn Pro
        260                 265                 270

Asn Lys Asn Asn Gln Gly Asn Gly Gln Gly His Asn Met Pro Asn Asp
            275                 280                 285

Pro Asn Arg Asn Val Asp Glu Asn Ala Asn Ala Asn Ser Ala Val Lys
        290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
            325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365
```

<210> SEQ ID NO 25
<211> LENGTH: 378
<212> TYPE: PRT
<213> ORGANISM: Plasmodium falciparum
<220> FEATURE:
<221> NAME/KEY: MISC_FEATURE
<222> LOCATION: (1)..(378)
<223> OTHER INFORMATION: CSP NTer protein

<400> SEQUENCE: 25

```
Met Gln Glu Tyr Gln Cys Tyr Gly Ser Ser Ser Asn Thr Arg Val Leu
1               5                   10                  15

Asn Glu Leu Asn Tyr Asp Asn Ala Gly Thr Asn Leu Tyr Asn Glu Leu
            20                  25                  30

Glu Met Asn Tyr Tyr Gly Lys Gln Glu Asn Trp Tyr Ser Leu Lys Lys
        35                  40                  45

Asn Ser Arg Ser Leu Gly Glu Asn Asp Asp Gly Asn Asn Glu Asp Asn
    50                  55                  60

Glu Lys Leu Arg Lys Pro Lys His Lys Lys Leu Lys Gln Pro Ala Asp
65                  70                  75                  80

Gly Asn Pro Asp Pro Asn Ala Asn Pro Asn Val Asp Pro Asn Ala Asn
                85                  90                  95

Pro Asn Val Asp Pro Asn Ala Asn Pro Asn Val Asp Pro Asn Ala Asn
            100                 105                 110

Pro Asn Ala Asn Pro Asn Ala Asn Pro Asn Ala Asn Pro Asn Ala Asn
        115                 120                 125

Pro Asn Ala Asn Pro Asn Ala Asn Pro Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175
```

Pro Asn Val Asp Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
            195                 200                 205

Pro Asn Ala Asn Pro Asn Ala Asn Pro Asn Ala Asn Pro Asn Ala Asn
            210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Ala Asn Pro Asn Lys Asn
            245                 250                 255

Asn Gln Gly Asn Gly Gln Gly His Asn Met Pro Asn Asp Pro Asn Arg
            260                 265                 270

Asn Val Asp Glu Asn Ala Asn Ala Asn Ser Ala Val Lys Asn Asn Asn
            275                 280                 285

Asn Glu Glu Pro Ser Asp Lys His Ile Lys Glu Tyr Leu Asn Lys Ile
            290                 295                 300

Gln Asn Ser Leu Ser Thr Glu Trp Ser Pro Cys Ser Val Thr Cys Gly
305                 310                 315                 320

Asn Gly Ile Gln Val Arg Ile Lys Pro Gly Ser Ala Asn Lys Pro Lys
            325                 330                 335

Asp Glu Leu Asp Tyr Ala Asn Asp Ile Glu Lys Lys Ile Cys Lys Met
            340                 345                 350

Glu Lys Cys Ser Ser Val Phe Asn Val Val Asn Ser Ser Ile Gly Leu
            355                 360                 365

Ile Met Val Leu Ser Phe Leu Phe Leu Asn
            370                 375

<210> SEQ ID NO 26
<211> LENGTH: 329
<212> TYPE: PRT
<213> ORGANISM: Plasmodium berghei
<220> FEATURE:
<221> NAME/KEY: MISC_FEATURE
<222> LOCATION: (1)..(329)
<223> OTHER INFORMATION: CSP protein

<400> SEQUENCE: 26

Met Lys Lys Cys Thr Ile Leu Val Val Ala Ser Leu Leu Leu Val Asn
1               5                   10                  15

Ser Leu Leu Pro Gly Tyr Gly Gln Asn Lys Ile Ile Gln Ala Gln Arg
            20                  25                  30

Asn Leu Asn Glu Leu Cys Tyr Asn Glu Gly Asn Asp Asn Lys Leu Tyr
            35                  40                  45

His Val Leu Asn Ser Lys Asn Gly Lys Ile Tyr Asn Arg Asn Thr Val
            50                  55                  60

Asn Arg Leu Leu Ala Asp Ala Pro Glu Gly Lys Lys Asn Glu Lys Lys
65                  70                  75                  80

Asn Glu Lys Ile Glu Arg Asn Asn Lys Leu Lys Pro Pro Pro Asn Pro
            85                  90                  95

Asn Asp Pro Pro Pro Asn Pro Asn Asp Pro Pro Pro Asn Pro Asn Pro
            100                 105                 110

Asn Asp Pro Pro Pro Asn Pro Asn Asp Pro Ala Pro Pro Asn Ala Asn
            115                 120                 125

Asn Asp Pro Ala Pro Pro Asn Ala Asn Asp Pro Ala Pro Pro Asn Ala
            130                 135                 140

Asn Asp Pro Ala Pro Pro Asn Ala Asn Asp Pro Ala Pro Pro Asn Ala

```
                145                 150                 155                 160
Asn Asp Pro Ala Pro Asn Ala Asn Asp Pro Ala Pro Pro Asn Ala
                    165                 170                 175
Asn Asp Pro Pro Pro Asn Pro Asn Asp Pro Ala Pro Pro Gln Gly
                    180                 185                 190
Asn Asn Asn Pro Gln Pro Gln Pro Arg Pro Gln Pro Gln Pro Pro
                    195                 200                 205
Gln Pro Gln Pro Gln Pro Gln Pro Gln Pro Arg Pro Gln Pro
    210                 215                 220
Gln Pro Gln Pro Gly Gly Asn Asn Asn Lys Asn Asn Asn Asp
225                 230                 235                 240
Asp Ser Tyr Ile Pro Ser Ala Glu Lys Ile Leu Glu Phe Val Lys Gln
                    245                 250                 255
Ile Arg Asp Ser Ile Thr Glu Glu Trp Ser Gln Cys Asn Val Thr Cys
                    260                 265                 270
Gly Ser Gly Ile Arg Val Arg Lys Arg Lys Gly Ser Asn Lys Lys Ala
                    275                 280                 285
Glu Asp Leu Thr Leu Glu Asp Ile Asp Thr Glu Ile Cys Lys Met Asp
                    290                 295                 300
Lys Cys Ser Ser Ile Phe Asn Ile Val Ser Asn Ser Leu Gly Phe Val
305                 310                 315                 320
Ile Leu Leu Val Leu Val Phe Phe Asn
                    325

<210> SEQ ID NO 27
<211> LENGTH: 429
<212> TYPE: PRT
<213> ORGANISM: Plasmodium malariae
<220> FEATURE:
<221> NAME/KEY: MISC_FEATURE
<222> LOCATION: (1)..(429)
<223> OTHER INFORMATION: CSP protein

<400> SEQUENCE: 27

Met Lys Lys Leu Ser Val Leu Ala Ile Ser Ser Phe Leu Ile Val Asp
1               5                   10                  15
Phe Leu Phe Pro Gly Tyr His His Asn Ser Asn Ser Thr Lys Ser Arg
                    20                  25                  30
Asn Leu Ser Glu Leu Cys Tyr Asn Asn Val Asp Thr Lys Leu Phe Asn
                35                  40                  45
Glu Leu Glu Val Arg Tyr Ser Thr Asn Gln Asp His Phe Tyr Asn Tyr
        50                  55                  60
Asn Lys Thr Ile Arg Leu Leu Asn Glu Asn Asn Asn Glu Lys Asp Gly
65                  70                  75                  80
Asn Val Thr Asn Glu Arg Lys Lys Lys Pro Thr Lys Ala Val Glu Asn
                    85                  90                  95
Lys Leu Lys Gln Pro Pro Gly Asp Asp Asp Gly Ala Gly Asn Asp Ala
                    100                 105                 110
Gly Asn Asp Ala Gly Asn Asp Ala Gly Asn Ala Ala Gly Asn Ala Ala
                115                 120                 125
Gly Asn Ala Ala Gly Asn Ala Ala Gly Asn Ala Ala Gly Asn Ala Ala
            130                 135                 140
Gly Asn Ala Ala Gly Asn Ala Ala Gly Asn Ala Ala Gly Asn Ala Ala
145                 150                 155                 160
Gly Asn Asp Ala Gly Asn Ala Ala Gly Asn Ala Ala Gly Asn Ala Ala
                    165                 170                 175
```

Gly Asn Ala Ala Gly Asn Ala Ala Gly Asn Asp Ala Gly Asn Ala Ala
            180                 185                 190

Gly Asn Ala Ala Gly Asn Ala Ala Gly Asn Ala Ala Gly Asn Ala Ala
            195                 200                 205

Gly Asn Ala Ala Gly Asn Ala Ala Gly Asn Ala Ala Gly Asn Ala Ala
            210                 215                 220

Gly Asn Ala Ala Gly Asn Asp Ala Gly Asn Ala Ala Gly Asn Ala Ala
225                 230                 235                 240

Gly Asn Ala Ala Gly Asn Ala Ala Gly Asn Ala Ala Gly Asn Ala Ala
            245                 250                 255

Gly Asn Ala Ala Gly Asn Ala Ala Gly Asn Ala Ala Gly Asn Ala Ala
            260                 265                 270

Gly Asn Ala Ala Gly Asn Ala Ala Gly Asn Ala Ala Gly Asn Ala Ala
            275                 280                 285

Gly Asn Ala Ala Gly Asn Ala Ala Gly Asn Ala Ala Gly Asn Ala Ala
            290                 295                 300

Gly Asn Ala Ala Gly Asn Ala Ala Gly Asn Glu Lys Ala Lys Asn Lys
305                 310                 315                 320

Asp Asn Lys Val Asp Ala Asn Thr Asn Lys Lys Asp Asn Gln Glu Glu
            325                 330                 335

Asn Asn Asp Ser Ser Asn Gly Pro Ser Glu Glu His Ile Lys Asn Tyr
            340                 345                 350

Leu Glu Ser Ile Arg Asn Ser Ile Thr Glu Glu Trp Ser Pro Cys Ser
            355                 360                 365

Val Thr Cys Gly Ser Gly Ile Arg Ala Arg Arg Lys Val Gly Ala Lys
            370                 375                 380

Asn Lys Lys Pro Ala Glu Leu Val Leu Ser Asp Leu Glu Thr Glu Ile
385                 390                 395                 400

Cys Ser Leu Asp Lys Cys Ser Ser Ile Phe Asn Val Val Ser Asn Ser
            405                 410                 415

Leu Gly Ile Val Leu Val Leu Val Leu Ile Leu Phe His
            420                 425

<210> SEQ ID NO 28
<211> LENGTH: 344
<212> TYPE: PRT
<213> ORGANISM: Plasmodium coatneyi
<220> FEATURE:
<221> NAME/KEY: MISC_FEATURE
<222> LOCATION: (1)..(344)
<223> OTHER INFORMATION: CSP protein

<400> SEQUENCE: 28

Met Lys

Asp Gly Pro Ala Pro Ala Ala Asp Gly Ala Arg Asp Gly Pro Ala Pro
            100                 105                 110

Ala Ala Asp Gly Ala Arg Asp Gly Pro Ala Pro Ala Ala Asp Gly Ala
        115                 120                 125

Arg Asp Gly Pro Ala Pro Ala Ala Asp Gly Ala Arg Asp Gly Pro Ala
    130                 135                 140

Pro Ala Ala Asp Gly Ala Arg Asp Gly Pro Ala Pro Ala Ala Asp Gly
145                 150                 155                 160

Ala Arg Asp Gly Pro Ala Pro Ala Ala Asp Gly Ala Arg Asp Gly Pro
                165                 170                 175

Ala Pro Pro Ala Asp Gly Ala Arg Asp Gly Pro Ala Pro Pro Ala Ala
            180                 185                 190

Asp Gly Ala Arg Asp Gly Pro Ala Pro Pro Ala Ala Asp Gly Ala Arg
        195                 200                 205

Asp Gly Pro Ala Pro Pro Ala Gly Gln Gly Gly Asn Ala Ala Gly
    210                 215                 220

Gln Ala Gln Gly Gly Asn Ala Gly Asn Lys Lys Ala Gly Asp Ala
225                 230                 235                 240

Ala Gly Asn Ala Gly Ala Ala Lys Gly Gln Gly Gln Asn Asn Glu Gly
                245                 250                 255

Ala Asn Val Pro Asn Glu Lys Val Val Asn Asp Tyr Leu Gln Lys Ile
            260                 265                 270

Arg Ser Thr Val Thr Thr Glu Trp Thr Pro Cys Ser Val Thr Cys Gly
        275                 280                 285

Asn Gly Val Arg Leu Arg Arg Lys Ala His Ala Glu Lys Lys Lys Pro
    290                 295                 300

Glu Asp Leu Thr Met Asp Asp Leu Asp Val Glu Val Cys Ala Met Asp
305                 310                 315                 320

Lys Cys Ala Gly Ile Phe Asn Phe Val Ser Asn Ser Leu Gly Leu Val
                325                 330                 335

Ile Leu Leu Val Leu Ala Phe Asn
            340

<210> SEQ ID NO 29
<211> LENGTH: 347
<212> TYPE: PRT
<213> ORGANISM: Plasmodium knowlesi
<220> FEATURE:
<221> NAME/KEY: MISC_FEATURE
<222> LOCATION: (1)..(347)
<223> OTHER INFORMATION: CSP protein

<400> SEQUENCE: 29

Met Arg Asn Phe Ile Leu Leu Ala Val Ser Ser Ile Leu Leu Val Asp
1               5                   10                  15

Leu Phe Pro Thr His Phe Glu His Asn Val Asp Leu Ser Arg Ala Ile
            20                  25                  30

Asn Val Asn Gly Val Ser Phe Asn Asn Val Asp Thr Ser Ser Leu Gly
        35                  40                  45

Ala Ala Gln Val Arg Gln Ser Ala Ser Arg Gly Arg Gly Leu Gly Glu
    50                  55                  60

Lys Arg Lys Glu Gly Ala Asp Lys Glu Lys Lys Glu Lys Glu Glu
65                  70                  75                  80

Glu Pro Lys Lys Pro Asn Glu Asn Lys Leu Lys Gln Pro Asp Gln Ala
                85                  90                  95

Ala Pro Gly Ala Gly Gly Glu Gln Pro Ala Pro Gly Ala Gly Gly Glu

```
                100                 105                 110
Gln Pro Ala Pro Gly Ala Gly Gly Glu Arg Pro Ala Pro Gly Ala Gly
            115                 120                 125
Gly Glu Gln Pro Ala Pro Gly Ala Gly Gly Glu Gln Pro Ala Pro Gly
        130                 135                 140
Ala Gly Gly Glu Arg Pro Ala Pro Gly Ala Gly Gly Glu Gln Pro Ala
145                 150                 155                 160
Pro Gly Ala Gly Gly Glu Gln Pro Ala Pro Gly Ala Gly Gly Glu Gln
                165                 170                 175
Pro Ala Pro Gly Ala Gly Gly Glu Gln Pro Ala Pro Gly Ala Gly Gly
            180                 185                 190
Glu Arg Pro Ala Pro Gly Ala Gly Glu Arg Pro Ala Pro Gly Ala
        195                 200                 205
Gly Gly Glu Gln Pro Ala Pro Gly Ala Gly Gly Glu Gln Pro Ala Pro
    210                 215                 220
Ala Pro Arg Arg Glu Gln Pro Ala Pro Gly Pro Gly Ala Gly Asp Gly
225                 230                 235                 240
Ala Arg Gly Gly Asn Ala Gly Ala Gly Lys Gly Gln Gly Gln Asn Asn
                245                 250                 255
Gln Gly Ala Asn Val Pro Asn Glu Lys Val Val Asn Asp Tyr Leu His
            260                 265                 270
Lys Ile Arg Ser Ser Val Thr Thr Glu Trp Thr Pro Cys Ser Val Thr
        275                 280                 285
Cys Gly Asn Gly Val Arg Ile Arg Arg Arg Gln Asn Ala Gly Asn Lys
    290                 295                 300
Lys Ala Glu Asp Leu Thr Met Asp Asp Leu Glu Val Glu Ala Cys Val
305                 310                 315                 320
Met Asp Lys Cys Ala Gly Ile Phe Asn Val Val Ser Asn Ser Leu Gly
                325                 330                 335
Leu Val Ile Leu Leu Val Leu Ala Leu Phe Asn
            340                 345

<210> SEQ ID NO 30
<211> LENGTH: 388
<212> TYPE: PRT
<213> ORGANISM: Plasmodium reichenowi

<400> SEQUENCE: 30

Met Met Arg Lys Leu Ala Ile Leu Ser Val Ser Ser Phe Leu Phe Val
1               5                   10                  15
Glu Ala Leu Phe Gln Glu Tyr Gln Cys Tyr Gly Ser Ser Asn Thr
            20                  25                  30
Arg Val Leu Asn Glu Leu Asn Tyr Asp Asn Ala Gly Thr Asn Leu Tyr
        35                  40                  45
Asn Glu Leu Glu Met Asn Tyr Tyr Gly Lys Gln Glu Asn Trp Tyr Ser
    50                  55                  60
Leu Lys Lys Asn Ser Arg Ser Leu Gly Glu Asn Asp Ala Asp Asn
65                  70                  75                  80
Gly Asp Ala Asp Asn Gly Asp Glu Gly Ile Asp Glu Asn Arg Arg His
                85                  90                  95
Arg Asn Lys Glu Gly Lys Glu Lys Leu Lys Lys Pro Lys His Asn Lys
            100                 105                 110
Leu Lys Gln Pro Gly Asn Asp Asn Val Asp Pro Asn Ala Asn Pro Asn
        115                 120                 125
```

Val Asp Pro Asn Ala Asn Pro Asn Val Asp Pro Asn Ala Asn Pro Asn
    130                 135                 140

Val Asp Pro Asn Ala Asn Pro Asn Val Asp Pro Asn Ala Asn Pro Asn
145                 150                 155                 160

Val Asn Pro Asn Ala Asn Pro Asn Val Asp Pro Asn Ala Asn Pro Asn
                165                 170                 175

Val Asn Pro Asn Ala Asn Pro Asn Val Asn Pro Asn Ala Asn Pro Asn
            180                 185                 190

Val Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Arg Asn Asn Glu Ala Asn Gly Gln
            260                 265                 270

Gly His Asn Lys Pro Asn Asp Gln Asn Arg Asn Val Asn Glu Asn Ala
        275                 280                 285

Asn Ala Asn Asn Ala Gly Arg Asn Asn Asn Glu Glu Pro Ser Asp
    290                 295                 300

Lys His Ile Glu Glu Phe Leu Lys Gln Ile Gln Asn Asn Leu Ser Thr
305                 310                 315                 320

Glu Trp Ser Pro Cys Ser Val Thr Cys Gly Asn Gly Ile Gln Val Arg
                325                 330                 335

Ile Lys Pro Gly Ser Ala Gly Lys Pro Lys Asp Gln Leu Asp Tyr Glu
            340                 345                 350

Asn Asp Leu Glu Lys Lys Ile Cys Lys Met Glu Lys Cys Ser Ser Val
        355                 360                 365

Phe Asn Val Val Asn Ser Ser Ile Gly Leu Ile Met Val Leu Ser Phe
    370                 375                 380

Leu Phe Leu Asn
385

<210> SEQ ID NO 31
<211> LENGTH: 388
<212> TYPE: PRT
<213> ORGANISM: Plasmodium gallinaceum

<400> SEQUENCE: 31

Met Lys Lys Leu Ala Ile Leu Ser Ala Ser Ser Phe Leu Phe Ala Asp
1               5                   10                  15

Phe Leu Phe Gln Glu Tyr Gln His Asn Gly Asn Tyr Lys Asn Phe Arg
            20                  25                  30

Leu Leu Asn Glu Val Cys Tyr Asn Asn Met Asn Ile Gln Leu Tyr Asn
        35                  40                  45

Glu Leu Glu Met Glu Asn Tyr Met Ser Asn Thr Tyr Phe Tyr Asn Asn
    50                  55                  60

Lys Lys Thr Ile Arg Leu Leu Gly Glu Asn Asp Asn Glu Ala Asn Val
65                  70                  75                  80

Asn Arg Ala Asn Asn Val Ala Asn Asp Arg Ala Asn Gly Asn
                85                  90                  95

Arg Gly Asn Val Asn Arg Ala Asn Asp Arg Asn Ile Pro Tyr Phe Arg
            100                 105                 110

```
Glu Asn Val Val Asn Leu Asn Gln Pro Val Gly Gly Asn Gly Gly Val
            115                 120                 125

Gln Pro Ala Gly Gly Asn Gly Gly Val Gln Pro Ala Gly Gly Asn Gly
        130                 135                 140

Gly Val Gln Pro Ala Gly Gly Asn Gly Gly Val Gln Pro Ala Gly Gly
145                 150                 155                 160

Asn Gly Gly Val Gln Pro Ala Gly Gly Asn Gly Gly Val Gln Pro Ala
                165                 170                 175

Gly Gly Asn Gly Gly Val Gln Pro Ala Gly Gly Asn Gly Gly Ala Gln
            180                 185                 190

Pro Val Ala Ala Gly Gly Ala Gln Pro Val Ala Asp Gly Gly
        195                 200                 205

Val Gln Pro Leu Arg Gln Glu Gly Asp Ala Glu Glu Asp Gly Gly Asn
    210                 215                 220

Gly Gly Ala Gln Pro Ala Gly Gly Asn Gly Gly Ala Gln Pro Ala Gly
225                 230                 235                 240

Gly Asn Gly Gly Ala Gln Pro Ala Gly Gly Asn Gly Gly Ala Gln Pro
                245                 250                 255

Ala Gly Gly Asn Gly Gly Ala Gln Pro Ala Gly Gly Asn Asp Ala Ala
            260                 265                 270

Lys Pro Asp Gly Gly Asn Asp Asp Lys Pro Glu Gly Gly Asp Glu
        275                 280                 285

Lys Ser Glu Glu Glu Lys Glu Asp Glu Pro Ile Pro Asp Pro Thr Gln
    290                 295                 300

Glu Glu Ile Asp Lys Tyr Leu Lys Ser Ile Leu Gly Asn Val Thr Ser
305                 310                 315                 320

Glu Trp Thr Asn Cys Asn Val Thr Cys Gly Lys Gly Ile Gln Ala Lys
                325                 330                 335

Ile Lys Ser Thr Ser Ala Asn Lys Lys Arg Glu Glu Ile Thr Pro Asn
            340                 345                 350

Asp Val Glu Val Lys Ile Cys Glu Leu Glu Arg Cys Ser Phe Ser Ile
        355                 360                 365

Phe Asn Val Ile Ser Asn Ser Leu Gly Leu Ala Ile Ile Leu Thr Phe
    370                 375                 380

Leu Phe Phe Tyr
385

<210> SEQ ID NO 32
<211> LENGTH: 258
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 32

Met Lys Lys Ile Leu Ser Val Ser Ser Ile Leu Leu Val Asp Ala Leu
1               5                   10                  15

Gln Tyr Asn Leu Ser Arg Asn Leu Asn Glu Leu Tyr Asn Tyr Asn Glu
            20                  25                  30

Leu Glu Met His Val Gly Ala Asn Ser Arg Asn Gly Asn Asp Ala Asp
        35                  40                  45

Glu Lys Glu Lys Lys Pro Asn Asn Lys Leu Pro Asn Ala Pro Asn Asp
    50                  55                  60

Pro Ala Pro Asn Pro Ala Ala Gly Ala Ala Ala Ala Asn Asn Ala Pro
```

```
                65                  70                  75                  80
Ala Ala Asn Ala Pro Ala Pro Asn Ala Gly Asn Ala Pro Asn Ala Gly
                    85                  90                  95

Gly Ala Pro Asn Ala Asn Gly Ala Asn Pro Asn Ala Gly Ala Ala Pro
                100                 105                 110

Pro Ala Gly Ala Asn Ala Pro Asn Ala Gly Pro Asn Ala Ala Gly Pro
                115                 120                 125

Ala Gly Ala Ala Pro Asn Ala Pro Ala Asn Gly Asn Ala Asn Pro
            130                 135                 140

Asn Ala Pro Asn Ala Pro Asn Ala Pro Asn Ala Asn Pro Asn Ala Pro
145                 150                 155                 160

Asn Asn Ala Gly Gln Asp Ala Asn Asn Lys Asn Asn Gly Asn Asn
                165                 170                 175

Glu Ser Val Pro Ser Glu Lys Ile Glu Tyr Leu Lys Ile Arg Ser Leu
                180                 185                 190

Thr Thr Glu Trp Ser Pro Cys Ser Val Thr Cys Gly Asn Gly Ile Arg
                195                 200                 205

Val Arg Arg Lys Gly Ser Ala Asn Lys Lys Glu Asp Leu Thr Leu Asp
            210                 215                 220

Asp Leu Glu Glu Ile Cys Lys Met Asp Lys Cys Ser Ser Ile Phe Asn
225                 230                 235                 240

Val Val Ser Asn Ser Leu Gly Leu Val Ile Leu Val Leu Leu Phe
                245                 250                 255

Phe Asn

<210> SEQ ID NO 33
<211> LENGTH: 4024
<212> TYPE: DNA
<213> ORGANISM: Artificial Sequence
<220> FEATURE:
<223> OTHER INFORMATION: Description of Artificial Sequence: PLASMID
      pTRIP-DeltaU3-CMVeGFP

<400> SEQUENCE: 33
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaaggaga gaacaccagc ttgttacaac ctgtgagcct gcatgggatg gatgacccgg     240
agagagaagt gttagagtgg aggtttgaca gccgcctagc atttcatcac ggtgcccga      300 gagctgcatc cggagtactt caagaactgc tgatatcgag cttgctacaa gggactttcc     360 gctggggac tttccaggga ggcgtggcct gggcgggact ggggagtggc gagccctcag     420
atcctgcata taagcagctg cttttttgcct gtactgggtc tctctggtta ccagatct       480 gagcctggga gctctctggc taactaggga acccactgct taagcctcaa taaagcttgc     540
cttgagtgct tcaagtagtg tgtgcccgtc tgttgtgtga ctctggtaac tagagatccc     600
tcagaccctt ttagtcagtg tggaaaatct ctagcagtgg cgcccgaaca gggacttgaa     660
agcgaaaggg aaaccagagg agctctctcg acgcaggact cggcttgctg aagcgcgcac     720
ggcaagaggc gaggggcggc gactggtgag tacgccaaaa attttgacta gcggaggcta     780
gaaggagaga gatgggtgcg agagcgtcag tattaagcgg gggagaatta gatcgcgatg     840
ggaaaaaatt cggttaaggc cagggggaaa gaaaaaatat aaattaaaac atatagtatg     900
ggcaagcagg gagctagaac gattcgcagt taatcctggc ctgttagaaa catcagaagg     960
```

```
ctgtagacaa atactgggac agctacaacc atcccttcag acaggatcag aagaacttag    1020
atcattatat aatacagtag caaccctcta ttgtgtgcat caaaggatag agataaaaga    1080
caccaaggaa gctttagaca agatagagga agagcaaaac aaaagtaaga ccaccgcaca    1140
gcaagcggcc gctgatcttc agacctggag gaggagatat gagggacaat ggagaagtg    1200 aattatataa atataaagta gtaaaaattg aaccattagg agtagcaccc accaaggcaa    1260
agagaagagt ggtgcagaga gaaaaaagag cagtgggaat aggagctttg ttccttgggt    1320
tcttgggagc agcaggaagc actatgggcg cagcgtcaat gacgctgacg gtacaggcca    1380
gacaattatt gtctggtata gtgcagcagc agaacaattt gctgagggct attgaggcgc    1440
aacagcatct gttgcaactc acagtctggg gcatcaagca gctccaggca agaatcctgg    1500
ctgtggaaag atacctaaag gatcaacagc tcctggggat ttggggttgc tctggaaaac    1560
tcatttgcac cactgctgtg ccttggaatg ctagttggag taataaatct ctggaacaga    1620
tttggaatca cacgacctgg atggagtggg acagagaaat taacaattac acaagcttaa    1680
tacactcctt aattgaagaa tcgcaaaacc agcaagaaaa gaatgaacaa gaattattgg    1740
aattagataa atgggcaagt ttgtggaatt ggtttaacat aacaaattgg ctgtggtata    1800
taaaattatt cataatgata gtaggaggct tggtaggttt aagaatagtt tttgctgtac    1860
tttctatagt gaatagagtt aggcagggat attcaccatt atcgtttcag acccacctcc    1920 caacccccgag gggacccgac aggcccgaag gaatagaaga agaaggtgga gagagagaca    1980
gagacagatc cattcgatta gtgaacggat ctcgacggta tcgccgaatt cacaaatggc    2040
agtattcatc cacaatttta aaagaaaagg ggggattggg gggtacagtg caggggaaag    2100
aatagtagac ataatagcaa cagacataca aactaaagaa ttacaaaaac aaattacaaa    2160
aattcaaaat tttcgggttt attacaggga cagcagagat ccactttggg gcgataagct    2220
tgggagttcc gcgttacata acttacggta aatggcccgc ctggctgacc gcccaacgac    2280
ccccgcccat tgacgtcaat aatgacgtat gttcccatag taacgccaat agggactttc    2340
cattgacgtc aatgggtgga gtatttacgg taaactgccc acttggcagt acatcaagtg    2400
tatcatatgc caagtacgcc ccctattgac gtcaatgacg gtaaatggcc cgcctggcat    2460
tatgcccagt acatgacctt atgggacttt cctacttggc agtacatcta cgtattagtc    2520
atcgctatta ccatggtgat gcggttttgg cagtacatca atgggcgtgg atagcggttt    2580
gactcacggg gatttccaag tctccacccc attgacgtca atgggagttt gttttggcac    2640
caaaatcaac gggactttcc aaaatgtcgt aacaactccg ccccattgac gcaaatgggc    2700
ggtaggcgtg tacggtggga ggtctatata agcagagctc gtttagtgaa ccgtcagatc    2760
gcctggagac gccatccacg ctgttttgac ctccatagaa gacaccgact ctagaggatc    2820
cccaccggtc gccaccatgg tgagcaaggg cgaggagctg ttcaccgggg tggtgcccat    2880
cctggtcgag ctggacggcg acgtaaacgg ccacaagttc agcgtgtccg gcgagggcga    2940
gggcgatgcc acctacggca agctgaccct gaagttcatc tgcaccaccg gcaagctgcc    3000
cgtgccctgg cccaccctcg tgaccaccct gacctacggc gtgcagtgct tcagccgcta    3060
ccccgaccac atgaagcagc acgacttctt caagtccgcc atgcccgaag gctacgtcca    3120
ggagcgcacc atcttcttca aggacgacgg caactacaag acccgcgccg aggtgaagtt    3180
cgagggcgac accctggtga accgcatcga gctgaagggc atcgacttca aggaggacgg    3240
caacatcctg gggcacaagc tggagtacaa ctacaacagc cacaacgtct atatcatggc    3300
```

```
cgacaagcag aagaacggca tcaaggtgaa cttcaagatc cgccacaaca tcgaggacgg    3360
cagcgtgcag ctcgccgacc actaccagca gaacaccccc atcggcgacg gccccgtgct    3420
gctgcccgac aaccactacc tgagcaccca gtccgccctg agcaaagacc ccaacgagaa    3480
gcgcgatcac atggtcctgc tggagttcgt gaccgccgcc gggatcactc tcggcatgga    3540
cgagctgtac aagtaaagcg gccggactct agctcgagac ctagaaaaac atggagcaat    3600
cacaagtagc aatacagcag ctaccaatgc tgattgtgcc tggctagaag cacaagagga    3660
ggaggaggtg ggttttccag tcacacctca ggtaccttta agaccaatga cttacaaggc    3720
agctgtagat cttagccact ttttaaaaga aaagggggga ctggaagggc taattcactc    3780
ccaacgaaga caagatcgtc gagagatgct gcatataagc agctgctttt tgcttgtact    3840
gggtctctct ggttagacca gatctgagcc tgggagctct ctggctaact agggaaccca    3900
ctgcttaagc ctcaataaag cttgccttga gtgcttcaag tagtgtgtgc ccgtctgttg    3960
tgtgactctg gtaactagag atccctcaga cccttttagt cagtgtggaa aatctctagc    4020
agtg                                                                 4024

<210> SEQ ID NO 34
<211> LENGTH: 4927
<212> TYPE: DNA
<213> ORGANISM: Artificial Sequence
<220> FEATURE:
<223> OTHER INFORMATION: Description of Artificial Sequence: plasmid
      pTRIP-deltaU3-CMV-MSP142 CO-WPRE
<220> FEATURE:
<221> NAME/KEY: misc_feature
<222> LOCATION: (1)..(4927)
<223> OTHER INFORMATION: Complete nucleotide sequence of the provirus

<400> SEQUENCE: 34
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaaggaga gaacaccagc ttgttacaac ctgtgagcct gcatgggatg gatgacccgg     240
agagagaagt gttagagtgg aggtttgaca gccgcctagc atttcatcac ggtggcccga     300
gagctgcatc cggagtactt caagaactgc tgatatcgag cttgctacaa gggactttcc     360 gctggggac tttccaggga ggcgtggcct gggcgggact ggggagtggc gagccctcag     420
atcctgcata taagcagctg ctttttgcct gtactgggtc tctctggtta gaccagatct     480
gagcctggga gctctctggc taactaggga acccactgct taagcctcaa taagcttgc     540 cttgagtgct tcaagtagtg tgtgcccgtc tgttgtgtga ctctggtaac tagagatccc     600
tcagaccctt ttagtcagtg tggaaaatct ctagcagtgg cgcccgaaca gggacttgaa     660
agcgaaaggg aaaccagagg agctctctcg acgcaggact cggcttgctg aagcgcgcac     720
ggcaagaggc gaggggcggc gactggtgag tacgccaaaa attttgacta gcggaggcta     780
gaaggagaga gatgggtgcg agagcgtcag tattaagcgg gggagaatta gatcgcgatg     840
ggaaaaaatt cggttaaggc cagggggaaa gaaaaaatat aaattaaaac atatagtatg     900
ggcaagcagg gagctagaac gattcgcagt taatcctggc ctgttagaaa catcagaagg     960
ctgtagacaa atactgggac agctacaacc atcccttcag acaggatcag aagaacttag    1020
atcattatat aatacagtag caaccctcta ttgtgtgcat caaaggatag agataaaaga    1080
caccaaggaa gctttagaca agatagagga agagcaaaac aaaagtaaga ccaccgcaca    1140
```

```
gcaagcggcc gctgatcttc agacctggag gaggagatat gagggacaat tggagaagtg   1200
aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag ataccgaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaattta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgctgct gtccgtgccc ctgctgctgg gcctgctggg actggccgtg gccgctcccg   2880
agaaggacat cctgagcgag ttcaccaacg agagcctgta cgtgtacaca aagagactgg   2940
gcagcaccta caagagcctg aagaaacaca tgctgcggga gttcagcacc atcaaagaag   3000
atatgaccaa cggcctgaac aacaagagcc agaagcggaa cgacttcctg gaggtgctgt   3060
cccacgagct ggacctgttc aaggacctga gcaccaataa gtacgtgatc cggaaccccc t   3120 accagctgct ggacaacgac aagaaggaca agcagatcgt caacctgaag tacgccacca   3180
agggcatcaa cgaggatatc gagacaacca ccgacggcat caagttcttc aacaagatgg   3240
tggagctgta caacacccag ctggccgccg tgaaggagca gatcgccacc atcgaggccg   3300
agacaaacga cacaaacaag gaggagaaga agtacatccc cccatcctg gaggacctga   3360 agggcctgta cgagacagtg attggccagg ccgaggagta cagcgaggag ctgcagaaca   3420
gactggataa ctacaagaac gagaaggccg agttcgagat cctgaccaag aacctggaga   3480
agtacatcca gatcgacgag aagctggacg agttcgtgga gcacgccgag aacaacaagc   3540
```

```
atatcgcctc tatcgccctg aacaacctga ataagagcgg cctggtggga gagggcgaga      3600
gcaaaaagat cctggctaag atgctgaaca tggacggcat ggatctgctg ggcgtggacc      3660
ccaagcacgt gtgcgtggac accagagaca tccccaagaa cgccggctgc ttcagggacg      3720
acaacggcac cgaggagtgg agatgtctgc tgggctacaa aagggcgag ggcaacacct      3780 gcgtggagaa caataacccc acctgcgaca tcaacaacgg cggctgcgac cccaccgcca      3840
gctgccagaa cgccgagagc accgagaact ccaagaagat catctgcacc tgcaaggagc      3900
ccacccccaa cgcctactac gagggcgtgt ctgcagcag cagctccttc atgggctgat      3960
gactcgagct caagcttcga attcccgata atcaacctct ggattacaaa atttgtgaaa      4020
gattgactgg tattcttaac tatgttgctc cttttacgct atgtggatac gctgctttaa      4080
tgcctttgta tcatgctatt gcttcccgta tggctttcat tttctcctcc ttgtataaat      4140
cctggttgct gtctctttat gaggagttgt ggcccgttgt caggcaacgt ggcgtggtgt      4200
gcactgtgtt tgctgacgca acccccactg gttggggcat tgccaccacc tgtcagctcc      4260
tttccgggac tttcgctttc cccctcccta ttgccacggc ggaactcatc gccgcctgcc      4320
ttgcccgctg ctggacaggg gctcggctgt tgggcactga caattccgtg gtgttgtcgg      4380
ggaagctgac gtccttttcca tggctgctcg cctgtgttgc cacctggatt ctgcgcggga      4440
cgtccttctg ctacgtccct tcggccctca atccagcgga ccttcttcc cgcggcctgc      4500 tgccggctct gcggcctctt ccgcgtcttc gccttcgccc tcagacgagt cggatctccc      4560
tttgggccgc ctccccgcgt cgacgcgtga attcggtacc tttaagacca atgacttaca      4620
aggcagctgt agatcttagc cactttttaa agaaaaggg gggactggaa gggctaattc      4680
actcccaacg aagacaagat cgtcgagaga tgctgcatat aagcagctgc tttttgcttg      4740
tactgggtct ctctggttag accagatctg agcctgggag ctctctggct aactagggaa      4800
cccactgctt aagcctcaat aaagcttgcc ttgagtgctt caagtagtgt gtgcccgtct      4860
gttgtgtgac tctggtaact agagatccct cagacccttt tagtcagtgt ggaaaatctc      4920
tagcagt                                                               4927
```

<210> SEQ ID NO 35
<211> LENGTH: 1140
<212> TYPE: DNA
<213> ORGANISM: Artificial Sequence
<220> FEATURE:
<223> OTHER INFORMATION: Description of Artificial Sequence: Plasmid
      pTRIP-deltaU3-CMV-MSP142 CO-WPRE
<220> FEATURE:
<221> NAME/KEY: misc_feature
<222> LOCATION: (1)..(1140)
<223> OTHER INFORMATION: Sequence of transgene for MSP142-CO
<220> FEATURE:
<221> NAME/KEY: CDS
<222> LOCATION: (1)..(1134)

<400> SEQUENCE: 35

```
atg ctg ctg tcc gtg ccc ctg ctg ctg ggc ctg ctg gga ctg gcc gtg        48
Met Leu Leu Ser Val Pro Leu Leu Leu Gly Leu Leu Gly Leu Ala Val
1               5                   10                  15 gcc gct ccc gag aag gac atc ctg agc gag ttc acc aac gag agc ctg        96
Ala Ala Pro Glu Lys Asp Ile Leu Ser Glu Phe Thr Asn Glu Ser Leu
            20                  25                  30 tac gtg tac aca aag aga ctg ggc agc acc tac aag agc ctg aag aaa       144
Tyr Val Tyr Thr Lys Arg Leu Gly Ser Thr Tyr Lys Ser Leu Lys Lys
        35                  40                  45
```

|   |   |
|---|---|
| cac atg ctg cgg gag ttc agc acc atc aaa gaa gat atg acc aac ggc<br>His Met Leu Arg Glu Phe Ser Thr Ile Lys Glu Asp Met Thr Asn Gly<br>50               55                    60 | 192 |
| ctg aac aac aag agc cag aag cgg aac gac ttc ctg gag gtg ctg tcc<br>Leu Asn Asn Lys Ser Gln Lys Arg Asn Asp Phe Leu Glu Val Leu Ser<br>65                  70               75              80 | 240 |
| cac gag ctg gac ctg ttc aag gac ctg agc acc aat aag tac gtg atc<br>His Glu Leu Asp Leu Phe Lys Asp Leu Ser Thr Asn Lys Tyr Val Ile<br>               85                  90              95 | 288 |
| cgg aac ccc tac cag ctg ctg gac aac gac aag aag gac aag cag atc<br>Arg Asn Pro Tyr Gln Leu Leu Asp Asn Asp Lys Lys Asp Lys Gln Ile<br>            100                105              110 | 336 |
| gtc aac ctg aag tac gcc acc aag ggc atc aac gag gat atc gag aca<br>Val Asn Leu Lys Tyr Ala Thr Lys Gly Ile Asn Glu Asp Ile Glu Thr<br>        115                120              125 | 384 |
| acc acc gac ggc atc aag ttc ttc aac aag atg gtg gag ctg tac aac<br>Thr Thr Asp Gly Ile Lys Phe Phe Asn Lys Met Val Glu Leu Tyr Asn<br>130                 135                   140 | 432 |
| acc cag ctg gcc gcc gtg aag gag cag atc gcc acc atc gag gcc gag<br>Thr Gln Leu Ala Ala Val Lys Glu Gln Ile Ala Thr Ile Glu Ala Glu<br>145                150              155              160 | 480 |
| aca aac gac aca aac aag gag gag aag aag aag tac atc ccc atc ctg<br>Thr Asn Asp Thr Asn Lys Glu Glu Lys Lys Lys Tyr Ile Pro Ile Leu<br>               165                170              175 | 528 |
| gag gac ctg aag ggc ctg tac gag aca gtg att ggc cag gcc gag gag<br>Glu Asp Leu Lys Gly Leu Tyr Glu Thr Val Ile Gly Gln Ala Glu Glu<br>            180                185              190 | 576 |
| tac agc gag gag ctg cag aac aga ctg gat aac tac aag aac gag aag<br>Tyr Ser Glu Glu Leu Gln Asn Arg Leu Asp Asn Tyr Lys Asn Glu Lys<br>        195                200              205 | 624 |
| gcc gag ttc gag atc ctg acc aag aac ctg gag aag tac atc cag atc<br>Ala Glu Phe Glu Ile Leu Thr Lys Asn Leu Glu Lys Tyr Ile Gln Ile<br>210                 215                   220 | 672 |
| gac gag aag ctg gac gag ttc gtg gag cac gcc gag aac aac aag cat<br>Asp Glu Lys Leu Asp Glu Phe Val Glu His Ala Glu Asn Asn Lys His<br>225                230              235              240 | 720 |
| atc gcc tct atc gcc ctg aac aac ctg aat aag agc ggc ctg gtg gga<br>Ile Ala Ser Ile Ala Leu Asn Asn Leu Asn Lys Ser Gly Leu Val Gly<br>               245                250              255 | 768 |
| gag ggc gag agc aaa aag atc ctg gct aag atg ctg aac atg gac ggc<br>Glu Gly Glu Ser Lys Lys Ile Leu Ala Lys Met Leu Asn Met Asp Gly<br>            260                265              270 | 816 |
| atg gat ctg ctg ggc gtg gac ccc aag cac gtg tgc gtg gac acc aga<br>Met Asp Leu Leu Gly Val Asp Pro Lys His Val Cys Val Asp Thr Arg<br>        275                280              285 | 864 |
| gac atc ccc aag aac gcc ggc tgc ttc agg gac gac aac ggc acc gag<br>Asp Ile Pro Lys Asn Ala Gly Cys Phe Arg Asp Asp Asn Gly Thr Glu<br>290                 295                   300 | 912 |
| gag tgg aga tgt ctg ctg ggc tac aag aag ggc gag ggc aac acc tgc<br>Glu Trp Arg Cys Leu Leu Gly Tyr Lys Lys Gly Glu Gly Asn Thr Cys<br>305                310              315              320 | 960 |
| gtg gag aac aat aac ccc acc tgc gac atc aac aac ggc ggc tgc gac<br>Val Glu Asn Asn Asn Pro Thr Cys Asp Ile Asn Asn Gly Gly Cys Asp<br>               325                330              335 | 1008 |
| ccc acc gcc agc tgc cag aac gcc gag agc acc gag aac tcc aag aag<br>Pro Thr Ala Ser Cys Gln Asn Ala Glu Ser Thr Glu Asn Ser Lys Lys<br>            340                345              350 | 1056 |
| atc atc tgc acc tgc aag gag ccc acc ccc aac gcc tac tac gag ggc<br>Ile Ile Cys Thr Cys Lys Glu Pro Thr Pro Asn Ala Tyr Tyr Glu Gly<br>        355                360              365 | 1104 |

```
gtg ttc tgc agc agc agc tcc ttc atg ggc tgatga                1140
Val Phe Cys Ser Ser Ser Ser Phe Met Gly
    370                 375
```

<210> SEQ ID NO 36
<211> LENGTH: 378
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 36

```
Met Leu Leu Ser Val Pro Leu Leu Gly Leu Leu Gly Leu Ala Val
1               5                   10                  15

Ala Ala Pro Glu Lys Asp Ile Leu Ser Glu Phe Thr Asn Glu Ser Leu
            20                  25                  30

Tyr Val Tyr Thr Lys Arg Leu Gly Ser Thr Tyr Lys Ser Leu Lys Lys
            35                  40                  45

His Met Leu Arg Glu Phe Ser Thr Ile Lys Glu Asp Met Thr Asn Gly
    50                  55                  60

Leu Asn Asn Lys Ser Gln Lys Arg Asn Asp Phe Leu Glu Val Leu Ser
65                  70                  75                  80

His Glu Leu Asp Leu Phe Lys Asp Leu Ser Thr Asn Lys Tyr Val Ile
                85                  90                  95

Arg Asn Pro Tyr Gln Leu Leu Asp Asn Asp Lys Lys Asp Lys Gln Ile
            100                 105                 110

Val Asn Leu Lys Tyr Ala Thr Lys Gly Ile Asn Glu Asp Ile Glu Thr
            115                 120                 125

Thr Thr Asp Gly Ile Lys Phe Phe Asn Lys Met Val Glu Leu Tyr Asn
    130                 135                 140

Thr Gln Leu Ala Ala Val Lys Glu Gln Ile Ala Thr Ile Glu Ala Glu
145                 150                 155                 160

Thr Asn Asp Thr Asn Lys Glu Glu Lys Lys Lys Tyr Ile Pro Ile Leu
                165                 170                 175

Glu Asp Leu Lys Gly Leu Tyr Glu Thr Val Ile Gly Gln Ala Glu Glu
            180                 185                 190

Tyr Ser Glu Glu Leu Gln Asn Arg Leu Asp Asn Tyr Lys Asn Glu Lys
            195                 200                 205

Ala Glu Phe Glu Ile Leu Thr Lys Asn Leu Glu Lys Tyr Ile Gln Ile
    210                 215                 220

Asp Glu Lys Leu Asp Glu Phe Val Glu His Ala Glu Asn Asn Lys His
225                 230                 235                 240

Ile Ala Ser Ile Ala Leu Asn Asn Leu Asn Lys Ser Gly Leu Val Gly
                245                 250                 255

Glu Gly Glu Ser Lys Lys Ile Leu Ala Lys Met Leu Asn Met Asp Gly
            260                 265                 270

Met Asp Leu Leu Gly Val Asp Pro Lys His Val Cys Val Asp Thr Arg
    275                 280                 285

Asp Ile Pro Lys Asn Ala Gly Cys Phe Arg Asp Asp Asn Gly Thr Glu
    290                 295                 300

Glu Trp Arg Cys Leu Leu Gly Tyr Lys Lys Gly Glu Gly Asn Thr Cys
305                 310                 315                 320

Val Glu Asn Asn Asn Pro Thr Cys Asp Ile Asn Asn Gly Gly Cys Asp
                325                 330                 335
```

```
Pro Thr Ala Ser Cys Gln Asn Ala Glu Ser Thr Glu Asn Ser Lys Lys
            340                 345                 350

Ile Ile Cys Thr Cys Lys Glu Pro Thr Pro Asn Ala Tyr Tyr Glu Gly
            355                 360                 365

Val Phe Cys Ser Ser Ser Ser Phe Met Gly
        370                 375

<210> SEQ ID NO 37
<211> LENGTH: 4300
<212> TYPE: DNA
<213> ORGANISM: Artificial Sequence
<220> FEATURE:
<223> OTHER INFORMATION: Description of Artificial Sequence: Plasmid
      pTRIP-deltaU3-CMV-Hep17 CO-WPRE
<220> FEATURE:
<221> NAME/KEY: misc_feature
<222> LOCATION: (1)..(4300)
<223> OTHER INFORMATION: Complete nucleotide sequence of the provirus

<400> SEQUENCE: 37
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaggagag gaacaccagc ttgttacaac ctgtgagcct gcatgggatg gatgacccgg     240
agagagaagt gttagagtgg aggtttgaca gccgcctagc atttcatcac ggtgcccga      300 gagctgcatc cggagtactt caagaactgc tgatatcgag cttgctacaa gggactttcc     360 gctggggac tttccaggga ggcgtggcct gggcgggact ggggagtggc gagccctcag     420
atcctgcata taagcagctg cttttttgcct gtactgggtc tctctggtta gaccagatct     480
gagcctggga gctctctggc taactaggga acccactgct taagcctcaa taaagcttgc     540
cttgagtgct tcaagtagtg tgtgcccgtc tgttgtgtga ctctggtaac tagagatccc     600
tcagaccctt ttagtcagtg tggaaaatct ctagcagtgg cgcccgaaca gggacttgaa     660
agcgaaaggg aaaccagagg agctctctcg acgcaggact cggcttgctg aagcgcgcac     720
ggcaagaggc gaggggcggc gactggtgag tacgccaaaa attttgacta gcggaggcta     780
gaaggagaga gatgggtgcg agagcgtcag tattaagcgg gggagaatta gatcgcgatg     840
ggaaaaaatt cggttaaggc cagggggaaa gaaaaaatat aaattaaaac atatagtatg     900
ggcaagcagg gagctagaac gattcgcagt taatcctggc ctgttagaaa catcagaagg     960
ctgtagacaa atactgggac agctacaacc atcccttcag acaggatcag aagaacttag    1020
atcattatat aatacagtag caaccctcta ttgtgtgcat caaaggatag agataaaaga    1080
caccaaggaa gctttagaca agatagagga agagcaaaac aaaagtaaga ccaccgcaca    1140
gcaagcggcc gctgatcttc agacctggag gaggagatat gagggacaat tggagaagtg    1200
aattatataa atataaagta gtaaaaattg aaccattagg agtagcaccc accaaggcaa    1260
agagaagagt ggtgcagaga gaaaaaagag cagtgggaat aggagctttg ttccttgggt    1320
tcttgggagc agcaggaagc actatgggcg cagcgtcaat gacgctgacg gtacaggcca    1380
gacaattatt gtctggtata gtgcagcagc agaacaattt gctgagggct attgaggcgc    1440
aacagcatct gttgcaactc acagtctggg gcatcaagca gctccaggca agaatcctgg    1500
ctgtggaaag atacctaaag gatcaacagc tcctggggat ttggggttgc tctggaaaac    1560
tcatttgcac cactgctgtg ccttggaatg ctagttggag taataaatct ctggaacaga    1620
tttggaatca cacgacctgg atggagtggg acagagaaat taacaattac acaagcttaa    1680
```

```
tacactcctt aattgaagaa tcgcaaaacc agcaagaaaa gaatgaacaa gaattattgg     1740
aattagataa atgggcaagt tgtggaatt ggtttaacat aacaaattgg ctgtggtata     1800
taaaattatt cataatgata gtaggaggct tggtaggttt aagaatagtt tttgctgtac    1860
tttctatagt gaatagagtt aggcagggat attcaccatt atcgtttcag acccacctcc    1920
caaccccgag gggacccgac aggcccgaag gaatagaaga agaaggtgga gagagagaca    1980
gagacagatc cattcgatta gtgaacggat ctcgacggta tcgccgaatt cacaaatggc    2040
agtattcatc cacaatttta aagaaaagg ggggattggg gggtacagtg caggggaaag     2100
aatagtagac ataatagcaa cagacataca aactaaagaa ttacaaaaac aaattacaaa    2160
aattcaaaat tttcgggttt attacaggga cagcagagat ccactttggc tgatacgcgt    2220
ggagttccgc gttacataac ttacggtaaa tggcccgcct ggctgaccgc caacgaccc     2280 ccgcccattg acgtcaataa tgacgtatgt tcccatagta acgccaatag ggactttcca    2340
ttgacgtcaa tgggtggagt atttacggta aactgcccac ttggcagtac atcaagtgta    2400
tcatatgcca agtacgcccc ctattgacgt caatgacggt aaatggcccg cctggcatta    2460
tgcccagtac atgaccttat gggactttcc tacttggcag tacatctacg tattagtcat    2520
cgctattacc atggtgatgc ggttttggca gtacatcaat gggcgtggat agcggtttga    2580
ctcacgggga tttccaagtc tccaccccat tgacgtcaat gggagtttgt tttggcacca    2640
aaatcaacgg gactttccaa aatgtcgtaa caactccgcc ccattgacgc aaatgggcgg    2700
taggcgtgta cggtgggagg tctatataag cagagctcgt ttagtgaacc gtcagatcgc    2760
ctggagacgc catccacgct gttttgacct ccatagaaga caccgcgatc ggatccgcca    2820
ccatgaagat caatatcgcc agcatcatct ttatcatctt cagcctgtgc ctggtcaacg    2880
acgcctacgg caagaacaag tacgggaaga acggcaagta cggcagccag aacgtgatca    2940
agaaacacgg cgagcccgtg atcaacgtgc aggacctgat cagcgacatg gtccggaaag    3000
aggaagagat cgtcaagctg accaagaaca agaagagcct gaggaagatc aacgtggccc    3060
tggccaccgc cctgagcgtg gtgtccgcca tcctgctggg cggagccggc ctggtcatgt    3120
acaacaccga aagggcaga aggcccttcc agatcggcaa gagcaagaaa ggcggcagcg    3180
ccatggccag ggacagcagc ttccccatga cgaggaaag ccccctgggc ttcagccccg     3240
aggaaatgga agccgtggcc agcaagttcc gggagagcat gctgaaggac ggcgtgcctg    3300 ccccagcaa caccccaac gtgcagaact gatgactcga gctcaagctt cgaattcccg     3360
ataatcaacc tctggattac aaaatttgtg aaagattgac tggtattctt aactatgttg    3420
ctccttttac gctatgtgga tacgctgctt taatgccttt gtatcatgct attgcttccc    3480
gtatggcttt cattttctcc tccttgtata atcctggtt gctgtctctt tatgaggagt    3540
tgtggcccgt tgtcaggcaa cgtggcgtgg tgtgcactgt gtttgctgac gcaaccccca    3600
ctggttgggg cattgccacc acctgtcagc tcctttccgg gactttcgct ttccccctcc    3660
ctattgccac ggcggaactc atcgccgcct gccttgcccg ctgctggaca ggggctcggc    3720
tgttgggcac tgacaattcc gtggtgttgt cggggaagct gacgtccttt ccatggctgc    3780
tcgcctgtgt tgccacctgg attctgcgcg gacgtccttt ctgctacgtc ccttcggccc    3840
tcaatccagc ggaccttcct tcccgcggcc tgctgccggc tctgcggcct cttccgcgtc    3900
ttcgccttcg ccctcagacg agtcggatct ccctttgggc cgcctccccg cgtcgacgcg    3960
tgaattcggt acctttaaga ccaatgactt acaaggcagc tgtagatctt agccacttt     4020
```

```
<210> SEQ ID NO 38
<211> LENGTH: 513
<212> TYPE: DNA
<213> ORGANISM: Artificial Sequence
<220> FEATURE:
<223> OTHER INFORMATION: Description of Artificial Sequence: Synthetic
      sequence for transgene for Hep17-CO
<220> FEATURE:
<221> NAME/KEY: CDS
<222> LOCATION: (1)..(507)

<400> SEQUENCE: 38 atg aag atc aat atc gcc agc atc atc ttt atc atc ttc agc ctg tgc      48
Met Lys Ile Asn Ile Ala Ser Ile Ile Phe Ile Ile Phe Ser Leu Cys
1               5                   10                  15 ctg gtc aac gac gcc tac ggc aag aac aag tac ggg aag aac ggc aag      96
Leu Val Asn Asp Ala Tyr Gly Lys Asn Lys Tyr Gly Lys Asn Gly Lys
            20                  25                  30 tac ggc agc cag aac gtg atc aag aaa cac ggc gag ccc gtg atc aac     144
Tyr Gly Ser Gln Asn Val Ile Lys Lys His Gly Glu Pro Val Ile Asn
        35                  40                  45 gtg cag gac ctg atc agc gac atg gtc cgg aaa gag gaa gag atc gtc     192
Val Gln Asp Leu Ile Ser Asp Met Val Arg Lys Glu Glu Glu Ile Val
    50                  55                  60 aag ctg acc aag aac aag aag agc ctg agg aag atc aac gtg gcc ctg     240
Lys Leu Thr Lys Asn Lys Lys Ser Leu Arg Lys Ile Asn Val Ala Leu
65                  70                  75                  80 gcc acc gcc ctg agc gtg gtg tcc gcc atc ctg ctg ggc gga gcc ggc     288
Ala Thr Ala Leu Ser Val Val Ser Ala Ile Leu Leu Gly Gly Ala Gly
                85                  90                  95 ctg gtc atg tac aac acc gag aag ggc aga agg ccc ttc cag atc ggc     336
Leu Val Met Tyr Asn Thr Glu Lys Gly Arg Arg Pro Phe Gln Ile Gly
            100                 105                 110 aag agc aag aaa ggc ggc agc gcc atg gcc agg gac agc agc ttc ccc     384
Lys Ser Lys Lys Gly Gly Ser Ala Met Ala Arg Asp Ser Ser Phe Pro
        115                 120                 125 atg aac gag gaa agc ccc ctg ggc ttc agc ccc gag gaa atg gaa gcc     432
Met Asn Glu Glu Ser Pro Leu Gly Phe Ser Pro Glu Glu Met Glu Ala
    130                 135                 140 gtg gcc agc aag ttc cgg gag agc atg ctg aag gac ggc gtg cct gcc     480
Val Ala Ser Lys Phe Arg Glu Ser Met Leu Lys Asp Gly Val Pro Ala
145                 150                 155                 160 ccc agc aac acc ccc aac gtg cag aac tgatga                          513
Pro Ser Asn Thr Pro Asn Val Gln Asn
                165

<210> SEQ ID NO 39
<211> LENGTH: 169
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 39
```

```
Met Lys Ile Asn Ile Ala Ser Ile Ile Phe Ile Ile Phe Ser Leu Cys
1               5                   10                  15

Leu Val Asn Asp Ala Tyr Gly Lys Asn Lys Tyr Gly Lys Asn Gly Lys
            20                  25                  30

Tyr Gly Ser Gln Asn Val Ile Lys Lys His Gly Glu Pro Val Ile Asn
        35                  40                  45

Val Gln Asp Leu Ile Ser Asp Met Val Arg Lys Glu Glu Ile Val
    50                  55                  60

Lys Leu Thr Lys Asn Lys Ser Leu Arg Lys Ile Asn Val Ala Leu
65              70                  75                  80

Ala Thr Ala Leu Ser Val Val Ser Ala Ile Leu Leu Gly Gly Ala Gly
                85                  90                  95

Leu Val Met Tyr Asn Thr Glu Lys Gly Arg Arg Pro Phe Gln Ile Gly
            100                 105                 110

Lys Ser Lys Lys Gly Gly Ser Ala Met Ala Arg Asp Ser Ser Phe Pro
        115                 120                 125

Met Asn Glu Glu Ser Pro Leu Gly Phe Ser Pro Glu Glu Met Glu Ala
    130                 135                 140

Val Ala Ser Lys Phe Arg Glu Ser Met Leu Lys Asp Gly Val Pro Ala
145                 150                 155                 160

Pro Ser Asn Thr Pro Asn Val Gln Asn
                165
```

<210> SEQ ID NO 40
<211> LENGTH: 4261
<212> TYPE: DNA
<213> ORGANISM: Artificial Sequence
<220> FEATURE:
<223> OTHER INFORMATION: Description of Artificial Sequence: Plasmid
      pTRIP-deltaU3-CMV-Hep17 deltaSP CO-WPRE
<220> FEATURE:
<221> NAME/KEY: misc_feature
<222> LOCATION: (1)..(4261)
<223> OTHER INFORMATION: Complete nucleotide sequence of the plasmid

<400> SEQUENCE: 40
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta agaagccaa     180 acaaggagag aacaccagc ttgttacaac ctgtgagcct gcatgggatg gatgacccgg     240
agagagaagt gttagagtgg aggtttgaca gccgcctagc atttcatcac ggtgcccga     300 gagctgcatc cggagtactt caagaactgc tgatatcgag cttgctacaa gggactttcc     360
gctgggggac tttccaggga ggcgtggcct gggcgggact ggggagtggc gagccctcag     420
atcctgcata taagcagctg cttttttgcct gtactgggtc tctctggtta gaccagatct     480
gagcctggga gctctctggc taactaggga acccactgct taagcctcaa taaagcttgc     540
cttgagtgct tcaagtagtg tgtgcccgtc tgttgtgtga ctctggtaac tagagatccc     600
tcagacccct ttagtcagtg tggaaaatct ctagcagtgg cgcccgaaca gggacttgaa     660
agcgaaaggg aaaccagagg agctctctcg acgcaggact cggcttgctg aagcgcgcac     720
ggcaagaggc gaggggcggc gactggtgag tacgccaaaa attttgacta gcggaggcta     780
gaaggagaga gatgggtgcg agagcgtcag tattaagcgg gggagaatta gatcgcgatg     840
ggaaaaaatt cggttaaggc cagggggaaa gaaaaaatat aaattaaaac atatagtatg     900
ggcaagcagg gagctagaac gattcgcagt taatcctggc ctgttagaaa catcagaagg     960

```
ctgtagacaa atactgggac agctacaacc atcccttcag acaggatcag aagaacttag      1020
atcattatat aatacagtag caaccctcta ttgtgtgcat caaaggatag agataaaaga      1080
caccaaggaa gctttagaca agatagagga agagcaaaac aaaagtaaga ccaccgcaca      1140
gcaagcggcc gctgatcttc agacctggag gaggagatat gagggacaat ggagaagtg      1200 aattatataa atataaagta gtaaaaattg aaccattagg agtagcaccc accaaggcaa      1260
agagaagagt ggtgcagaga gaaaaagag cagtgggaat aggagctttg ttccttgggt       1320
tcttgggagc agcaggaagc actatgggcg cagcgtcaat gacgctgacg gtacaggcca      1380
gacaattatt gtctggtata gtgcagcagc agaacaattt gctgagggct attgaggcgc      1440
aacagcatct gttgcaactc acagtctggg gcatcaagca gctccaggca agaatcctgg      1500
ctgtggaaag atacctaaag gatcaacagc tcctggggat ttggggttgc tctggaaaac      1560
tcatttgcac cactgctgtg ccttggaatg ctagttggag taataaatct ctggaacaga      1620
tttggaatca cacgacctgg atggagtggg acagagaaat taacaattac acaagcttaa      1680
tacactcctt aattgaagaa tcgcaaaacc agcaagaaaa gaatgaacaa gaattattgg      1740
aattagataa atgggcaagt ttgtggaatt ggtttaacat aacaaattgg ctgtggtata      1800
taaaattatt cataatgata gtaggaggct tggtaggttt aagaatagtt tttgctgtac      1860
tttctatagt gaatagagtt aggcagggat attcaccatt atcgtttcag acccacctcc      1920
caaccccgag gggacccgac aggcccgaag gaatagaaga agaaggtgga gagagagaca      1980
gagacagatc cattcgatta gtgaacggat ctcgacggta tcgccgaatt cacaaatggc      2040
agtattcatc cacaatttta aaagaaaagg ggggattggg gggtacagtg caggggaaag      2100
aatagtagac ataatagcaa cagacataca aactaaagaa ttacaaaaac aaattacaaa      2160
aattcaaaat tttcgggttt attacaggga cagcagagat ccactttggc tgatacgcgt      2220
ggagttccgc gttacataac ttacggtaaa tggcccgcct ggctgaccgc ccaacgaccc      2280
ccgcccattg acgtcaataa tgacgtatgt tcccatagta acgccaatag ggactttcca      2340
ttgacgtcaa tgggtggagt atttacggta aactgcccac ttggcagtac atcaagtgta      2400
tcatatgcca agtacgcccc ctattgacgt caatgacggt aaatggcccg cctggcatta      2460
tgcccagtac atgaccttat gggactttcc tacttggcag tacatctacg tattagtcat      2520
cgctattacc atggtgatgc ggttttggca gtacatcaat gggcgtggat agcggtttga      2580
ctcacgggga tttccaagtc tccaccccat tgacgtcaat gggagtttgt tttggcacca      2640
aaatcaacgg gactttccaa aatgtcgtaa caactccgcc ccattgacgc aaatgggcgg      2700
taggcgtgta cggtgggagg tctatataag cagagctcgt ttagtgaacc gtcagatcgc      2760
ctggagacgc catccacgct gttttgacct ccatagaaga caccgcgatc ggatccgcca      2820
ccatgctgtg cctggtcaac gacgcctacg gcaagaacaa gtacgggaag aacggcaagt      2880
acggcagcca gaacgtgatc aagaaacacg gcgagcccgt gatcaacgtg caggacctga      2940
tcagcgacat ggtccggaaa gaggaagaga tcgtcaagct gaccaagaac aagaagagcc      3000
tgaggaagat caacgtggcc ctggccaccg ccctgagcgt ggtgtccgcc atcctgctgg      3060
gcggagccgg cctggtcatg tacaacaccg agaagggcag aaggccttc cagatcggca       3120 agagcaagaa aggcggcagc gccatggcca gggacagcag cttccccatg aacgaggaaa      3180 gcccctggg cttcagcccc gaggaaatgg aagccgtggc cagcaagttc ggggagcagca     3240 tgctgaagga cggcgtgcct gccccccagca acacccccaa cgtgcagaac tgatgactcg      3300
```

```
agctcaagct tcgaattccc gataatcaac ctctggatta caaaatttgt gaaagattga    3360
ctggtattct taactatgtt gctccttta cgctatgtgg atacgctgct ttaatgcctt    3420
tgtatcatgc tattgcttcc cgtatggctt tcattttctc ctccttgtat aaatcctggt    3480
tgctgtctct ttatgaggag ttgtggcccg ttgtcaggca acgtggcgtg gtgtgcactg    3540
tgtttgctga cgcaaccccc actggttggg gcattgccac cacctgtcag ctcctttccg    3600
ggactttcgc tttccccctc cctattgcca cggcggaact catcgccgcc tgccttgccc    3660
gctgctggac aggggctcgg ctgttgggca ctgacaattc cgtggtgttg tcggggaagc    3720
tgacgtcctt tccatggctg ctcgcctgtg ttgccacctg gattctgcgc gggacgtcct    3780
tctgctacgt cccttcggcc ctcaatccag cggaccttcc ttcccgcggc ctgctgccgg    3840
ctctgcggcc tcttccgcgt cttcgccttc gccctcagac gagtcggatc tccctttggg    3900
ccgcctcccc gcgtcgacgc gtgaattcgg tacctttaag accaatgact acaaggcag    3960 ctgtagatct tagccacttt ttaaaagaaa aggggggact ggaagggcta attcactccc    4020
aacgaagaca agatcgtcga gagatgctgc atataagcag ctgcttttg cttgtactgg    4080 gtctctctgg ttagaccaga tctgagcctg ggagctctct ggctaactag ggaacccact    4140
gcttaagcct caataaagct tgccttgagt gcttcaagta gtgtgtgccc gtctgttgtg    4200
tgactctggt aactagagat ccctcagacc cttttagtca gtgtggaaaa tctctagcag    4260
t                                                                    4261

<210> SEQ ID NO 41
<211> LENGTH: 474
<212> TYPE: DNA
<213> ORGANISM: Artificial Sequence
<220> FEATURE:
<223> OTHER INFORMATION: Description of Artificial Sequence: Synthetic
      sequence of transgene from Hep17deltaSP CO
<220> FEATURE:
<221> NAME/KEY: CDS
<222> LOCATION: (1)..(468)

<400> SEQUENCE: 41 atg ctg tgc ctg gtc aac gac gcc tac ggc aag aac aag tac ggg aag      48
Met Leu Cys Leu Val Asn Asp Ala Tyr Gly Lys Asn Lys Tyr Gly Lys
1               5                   10                  15 aac ggc aag tac ggc agc cag aac gtg atc aag aaa cac ggc gag ccc      96
Asn Gly Lys Tyr Gly Ser Gln Asn Val Ile Lys Lys His Gly Glu Pro
            20                  25                  30 gtg atc aac gtg cag gac ctg atc agc gac atg gtc cgg aaa gag gaa     144
Val Ile Asn Val Gln Asp Leu Ile Ser Asp Met Val Arg Lys Glu Glu
        35                  40                  45 gag atc gtc aag ctg acc aag aac aag aag agc ctg agg aag atc aac     192
Glu Ile Val Lys Leu Thr Lys Asn Lys Lys Ser Leu Arg Lys Ile Asn
    50                  55                  60 gtg gcc ctg gcc acc gcc ctg agc gtg gtg tcc gcc atc ctg ctg ggc     240
Val Ala Leu Ala Thr Ala Leu Ser Val Val Ser Ala Ile Leu Leu Gly
65                  70                  75                  80 gga gcc ggc ctg gtc atg tac aac acc gag aag ggc aga agg ccc ttc     288
Gly Ala Gly Leu Val Met Tyr Asn Thr Glu Lys Gly Arg Arg Pro Phe
                85                  90                  95 cag atc ggc aag agc aag aaa ggc ggc agc gcc atg gcc agg gac agc     336
Gln Ile Gly Lys Ser Lys Lys Gly Gly Ser Ala Met Ala Arg Asp Ser
            100                 105                 110 agc ttc ccc atg aac gag gaa agc ccc ctg ggc ttc agc ccc gag gaa     384
Ser Phe Pro Met Asn Glu Glu Ser Pro Leu Gly Phe Ser Pro Glu Glu
        115                 120                 125
```

```
atg gaa gcc gtg gcc agc aag ttc cgg gag agc atg ctg aag gac ggc      432
Met Glu Ala Val Ala Ser Lys Phe Arg Glu Ser Met Leu Lys Asp Gly
    130                 135                 140 gtg cct gcc ccc agc aac acc ccc aac gtg cag aac tgatga               474
Val Pro Ala Pro Ser Asn Thr Pro Asn Val Gln Asn
145                 150                 155

<210> SEQ ID NO 42
<211> LENGTH: 156
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

Met Leu Cys Leu Val Asn Asp Ala Tyr Gly Lys Asn Lys Tyr Gly Lys
1               5                   10                  15

Asn Gly Lys Tyr Gly Ser Gln Asn Val Ile Lys Lys His Gly Glu Pro
            20                  25                  30

Val Ile Asn Val Gln Asp Leu Ile Ser Asp Met Val Arg Lys Glu Glu
        35                  40                  45

Glu Ile Val Lys Leu Thr Lys Asn Lys Ser Leu Arg Lys Ile Asn
    50                  55                  60

Val Ala Leu Ala Thr Ala Leu Ser Val Val Ser Ala Ile Leu Leu Gly
65                  70                  75                  80

Gly Ala Gly Leu Val Met Tyr Asn Thr Glu Lys Gly Arg Arg Pro Phe
                85                  90                  95

Gln Ile Gly Lys Ser Lys Lys Gly Gly Ser Ala Met Ala Arg Asp Ser
            100                 105                 110

Ser Phe Pro Met Asn Glu Glu Ser Pro Leu Gly Phe Ser Pro Glu Glu
        115                 120                 125

Met Glu Ala Val Ala Ser Lys Phe Arg Glu Ser Met Leu Lys Asp Gly
    130                 135                 140

Val Pro Ala Pro Ser Asn Thr Pro Asn Val Gln Asn
145                 150                 155

<210> SEQ ID NO 43
<211> LENGTH: 4897
<212> TYPE: DNA
<213> ORGANISM: Artificial Sequence
<220> FEATURE:
<223> OTHER INFORMATION: Description of Artificial Sequence: Plasmid
      pTRIP-DeltaU3-CMV-CSP CO WPRE

<400> SEQUENCE: 43
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180 acaaggaga gaacaccagc ttgttacaac ctgtgagcct gcatgggatg gatgacccgg      240
agagagaagt gttagagtgg aggtttgaca gccgcctagc atttcatcac ggtggcccga     300
gagctgcatc cggagtactt caagaactgc tgatatcgag cttgctacaa ggacttttcc     360
gctgggggac tttccaggga ggcgtggcct gggcgggact ggggagtggc gagccctcag     420
atcctgcata taagcagctg ctttttgcct gtactgggtc tctctggtta gaccagatct     480
gagcctggga gctctctggc taactaggga acccactgct taagcctcaa taaagcttgc     540
```

```
cttgagtgct tcaagtagtg tgtgcccgtc tgttgtgtga ctctggtaac tagagatccc    600
tcagacccct ttagtcagtg tggaaaatct ctagcagtgg cgcccgaaca gggacttgaa    660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc cagggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat ggagaagtg    1200 aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctgaaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcaggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaattta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgaagaa atgcaccatc ctggtggtgg ccagcctgct gctggtcgat agcctgctgc   2880
ccggctacgg ccagaataag agcgtgcagg cccagcggaa cctgaacgag ctgtgctaca   2940
```

| | |
|---|---|
| acgaggaaaa cgacaacaag ctgtaccacg tgctgaacag caagaacggc aagatctaca | 3000 |
| accggaacat cgtgaacagg ctgctgggcg acgctctgaa cggcaagccc gaggaaaaga | 3060 |
| aggacgaccc ccccaaggac ggcaacaagg acgacctgcc caagaagag aagaaagacg | 3120 |
| atctgcctaa agaggaaaaa aaagacgatc tcctaagga ccccaagaag gatgaccctc | 3180 |
| ctaaagaggc ccagaacaag ctgaaccagc ccgtggtggc cgacgagaac gtggatcagg | 3240 |
| gacctggcgc ccctcagggc ccaggcgctc cacaggacc cggggcaccc caggggcctg | 3300 |
| gggccccaca gggaccaggg gctcctcagg gccctggcgc acctcagggg ccaggggccc | 3360 |
| ctcaggggc tggcgctccc cagggacctg gcgcaccaca gggccctggg gctccccagg | 3420 |
| gcccaggcgc ccctcaggga ccaggcgcac cccagggacc cggcgctcct cagggacctg | 3480 |
| gggctccaca ggggccaggc gcaccacagg aacctcccca gcagcctcct cagcagccac | 3540 |
| cccagcagcc ccctcagcag cctcctcagc agccccaca gcagcctcca cagcagccta | 3600 |
| gaccccagcc cgacggcaat aacaacaaca ataataacaa cggcaacaac aacgaggaca | 3660 |
| gctacgtgcc cagcgccgag cagatcctgg aattcgtgaa gcagatcagc agccagctga | 3720 |
| ccgaagagtg gagccagtgc agcgtgacat gcggctctgg cgtgagagtg cggaagcgga | 3780 |
| agaacgtgaa caagcagccc gagaacctga ccctggaaga tatcgacacc gagatctgca | 3840 |
| agatggacaa gtgcagcagc atcttcaaca tcgtgtccaa cagcctgggc ttcgtgatcc | 3900 |
| tgctggtgct ggtgttcttc aactgatgac tcgagctcaa gcttcgaatt cccgataatc | 3960 |
| aacctctgga ttacaaaatt tgtgaaagat tgactggtat tcttaactat gttgctcctt | 4020 |
| ttacgctatg tggatacgct gctttaatgc ctttgtatca tgctattgct tcccgtatgg | 4080 |
| ctttcatttt ctcctccttg tataaatcct ggttgctgtc tctttatgag gagttgtggc | 4140 |
| ccgttgtcag gcaacgtggc gtggtgtgca ctgtgtttgc tgacgcaacc cccactggtt | 4200 |
| ggggcattgc caccacctgt cagctccttt ccgggacttt cgctttcccc ctccctattg | 4260 |
| ccacggcgga actcatcgcc gcctgccttg cccgctgctg gacaggggct cggctgttgg | 4320 |
| gcactgacaa ttccgtggtg ttgtcgggga agctgacgtc ctttccatgg ctgctcgcct | 4380 |
| gtgttgccac ctggattctg cgcgggacgt ccttctgcta cgtcccttcg ccctcaatc | 4440 |
| cagcggacct tccttcccgc ggcctgctgc cggctctgcg gcctcttccg cgtcttcgcc | 4500 |
| ttcgccctca gacgagtcgg atctcccttt gggccgcctc ccgcgtcga cgcgtgaatt | 4560 |
| cggtaccttt aagaccaatg acttacaagg cagctgagat cttagccact ttttaaaaga | 4620 |
| aaagggggga ctggaagggc taattcactc ccaacgaaga caagatcgtc gagagatgct | 4680 |
| gcatataagc agctgctttt tgcttgtact gggtctctct ggttagacca gatctgagcc | 4740 |
| tgggagctct ctggctaact agggaaccca ctgcttaagc ctcaataaag cttgccttga | 4800 |
| gtgcttcaag tagtgtgtgc ccgtctgttg tgtgactctg gtaactagag atccctcaga | 4860 |
| ccctttagt cagtgtggaa aatctctagc agtattt | 4897 |

<210> SEQ ID NO 44
<211> LENGTH: 1107
<212> TYPE: DNA
<213> ORGANISM: Artificial Sequence
<220> FEATURE:
<223> OTHER INFORMATION: Description of Artificial Sequence: Synthetic sequence of transgene for CSP-CO

<400> SEQUENCE: 44

| | |
|---|---|
| atgaagaaat gcaccatcct ggtggtggcc agcctgctgc tggtcgatag cctgctgccc | 60 |

| | |
|---|---|
| ggctacggcc agaataagag cgtgcaggcc cagcggaacc tgaacgagct gtgctacaac | 120 |
| gaggaaaacg acaacaagct gtaccacgtg ctgaacagca gaacggcaa gatctacaac | 180 |
| cggaacatcg tgaacaggct gctgggcgac gctctgaacg gcaagcccga ggaaaagaag | 240 |
| gacgaccccc ccaaggacgg caacaaggac gacctgccca agaagagaa gaaagacgat | 300 |
| ctgcctaaag aggaaaaaaa agacgatcct cctaaggacc ccaagaagga tgaccctcct | 360 |
| aaagaggccc agaacaagct gaaccagccc gtggtggccg acgagaacgt ggatcaggga | 420 |
| cctggcgccc ctcagggccc aggcgctcca cagggacccg ggcacccca ggggcctggg | 480 |
| gccccacagg gaccagggc tcctcagggc cctggcgcac ctcagggccc aggggcccct | 540 |
| caggggcctg cgctcccca gggacctggc gcaccacagg gccctgggc tccccagggc | 600 |
| ccaggcgccc ctcagggacc aggcgcaccc cagggacccg cgctcctca gggacctggg | 660 |
| gctccacagg ggccaggcgc accacaggaa cctccccagc agcctcctca gcagccaccc | 720 |
| cagcagcccc ctcagcagcc tcctcagcag ccccacagc agcctccaca gcagcctaga | 780 |
| ccccagcccg acggcaataa caacaacaat aataacaacg gcaacaacaa cgaggacagc | 840 |
| tacgtgccca cgccgagca gatcctggaa ttcgtgaagc agatcagcag ccagctgacc | 900 |
| gaagagtgga gccagtgcag cgtgacatgc ggctctggcg tgagagtgcg gaagcggaag | 960 |
| aacgtgaaca agcagcccga gaacctgacc ctggaagata tcgacaccga gatctgcaag | 1020 |
| atggacaagt gcagcagcat cttcaacatc gtgtccaaca gcctgggctt cgtgatcctg | 1080 |
| ctggtgctgg tgttcttcaa ctgatga | 1107 |

<210> SEQ ID NO 45
<211> LENGTH: 4840
<212> TYPE: DNA
<213> ORGANISM: Artificial Sequence
<220> FEATURE:
<223> OTHER INFORMATION: Description of Artificial Sequence: Plasmid
      pTRIP-deltaU3-CMV-CSP deltaSP CO-WPRE

<400> SEQUENCE: 45

| | |
|---|---|
| tggaagggct aattcactcc caacgaagac aagatatcct tgatctgtgg atctaccaca | 60 |
| cacaaggcta cttccctgat tagcagaact acacaccagg gccagggatc agatatccac | 120 |
| tgacctttgg atggtgctac aagctagtac cagttgagcc agagaagtta gaagaagcca | 180 |
| acaaaggaga gaacaccagc ttgttacaac ctgtgagcct gcatgggatg gatgacccgg | 240 |
| agagagaagt gttagagtgg aggtttgaca gccgcctagc atttcatcac ggtgcccga | 300 |
| gagctgcatc cggagtactt caagaactgc tgatatcgag cttgctacaa gggactttcc | 360 |
| gctggggac tttccaggga ggcgtggcct gggcgggact ggggagtggc gagccctcag | 420 |
| atcctgcata taagcagctg cttttgcct gtactgggtc tctctggtta gaccagatct | 480 |
| gagcctggga gctctctggc taactaggga acccactgct taagcctcaa taaagcttgc | 540 |
| cttgagtgct tcaagtagtg tgtgcccgtc tgttgtgtga ctctggtaac tagagatccc | 600 |
| tcagaccctt ttagtcagtg tggaaaatct ctagcagtgg cgcccgaaca gggacttgaa | 660 |
| agcgaaaggg aaaccagagg agctctctcg acgcaggact cggcttgctg aagcgcgcac | 720 |
| ggcaagaggc gaggggcggc gactggtgag tacgccaaaa attttgacta gcggaggcta | 780 |
| gaaggagaga gatgggtgcg agagcgtcag tattaagcgg gggagaatta gatcgcgatg | 840 |
| ggaaaaaatt cggttaaggc caggggaaa gaaaaaatat aaattaaaac atatagtatg | 900 |
| ggcaagcagg gagctagaac gattcgcagt taatcctggc ctgttagaaa catcagaagg | 960 |

| | |
|---|---|
| ctgtagacaa atactgggac agctacaacc atcccttcag acaggatcag aagaacttag | 1020 |
| atcattatat aatacagtag caaccctcta ttgtgtgcat caaaggatag agataaaaga | 1080 |
| caccaaggaa gctttagaca agatagagga agagcaaaac aaaagtaaga ccaccgcaca | 1140 |
| gcaagcggcc gctgatcttc agacctggag gaggagatat gagggacaat ggagaagtg | 1200 |
| aattatataa atataaagta gtaaaaattg aaccattagg agtagcaccc accaaggcaa | 1260 |
| agagaagagt ggtgcagaga gaaaaaagag cagtgggaat aggagctttg ttccttgggt | 1320 |
| tcttgggagc agcaggaagc actatgggcg cagcgtcaat gacgctgacg gtacaggcca | 1380 |
| gacaattatt gtctggtata gtgcagcagc agaacaattt gctgagggct attgaggcgc | 1440 |
| aacagcatct gttgcaactc acagtctggg gcatcaagca gctccaggca agaatcctgg | 1500 |
| ctgtggaaag atacctaaag gatcaacagc tcctggggat ttggggttgc tctgaaaaac | 1560 |
| tcatttgcac cactgctgtg ccttggaatg ctagttggag taataaatct ctggaacaga | 1620 |
| tttggaatca cacgacctgg atggagtggg acagagaaat taacaattac acaagcttaa | 1680 |
| tacactcctt aattgaagaa tcgcaaaacc agcaagaaaa gaatgaacaa gaattattgg | 1740 |
| aattagataa atgggcaagt ttgtggaatt ggtttaacat aacaaattgg ctgtggtata | 1800 |
| taaaattatt cataatgata gtaggaggct tggtaggttt aagaatagtt tttgctgtac | 1860 |
| tttctatagt gaatagagtt aggcagggat attcaccatt atcgtttcag acccacctcc | 1920 |
| caaccccgag gggacccgac aggcccgaag gaatagaaga agaaggtgga gagagagaca | 1980 |
| gagacagatc cattcgatta gtgaacggat ctcgacggta tcgccgaatt cacaaatggc | 2040 |
| agtattcatc cacaatttta aaagaaaagg ggggattggg gggtacagtg caggggaaag | 2100 |
| aatagtagac ataatagcaa cagacataca aactaaagaa ttacaaaaac aaattacaaa | 2160 |
| aattcaaaat tttcgggttt attacaggga cagcagagat ccactttggc tgatacgcgt | 2220 |
| ggagttccgc gttacataac ttacggtaaa tggcccgcct ggctgaccgc ccaacgaccc | 2280 |
| ccgcccattg acgtcaataa tgacgtatgt tcccatagta acgccaatag ggactttcca | 2340 |
| ttgacgtcaa tgggtggagt atttacggta aactgcccac ttggcagtac atcaagtgta | 2400 |
| tcatatgcca agtacgcccc ctattgacgt caatgacggt aaatggcccg cctggcatta | 2460 |
| tgcccagtac atgaccttat gggactttcc tacttggcag tacatctacg tattagtcat | 2520 |
| cgctattacc atggtgatgc ggttttggca gtacatcaat gggcgtggat agcggtttga | 2580 |
| ctcacgggga tttccaagtc tccaccccat tgacgtcaat gggagtttgt tttggcacca | 2640 |
| aaatcaacgg gactttccaa aatgtcgtaa caactccgcc ccattgacgc aaatgggcgg | 2700 |
| taggcgtgta cggtgggagg tctatataag cagagctcgt ttagtgaacc gtcagatcgc | 2760 |
| ctggagacgc catccacgct gttttgacct ccatagaaga caccgcgatc ggatccgcca | 2820 |
| ccatgcccgg ctacggccag aataagagcg tgcaggccca gcggaacctg aacgagctgt | 2880 |
| gctacaacga ggaaaacgac aacaagctgt accacgtgct gaacagcaag aacggcaaga | 2940 |
| tctacaaccg gaacatcgtg aacaggctgc tgggcgacgc tctgaacggc aagcccgagg | 3000 |
| aaaagaagga cgacccccc aaggacggca caaggacga cctgcccaaa gaagagaaga | 3060 |
| aagacgatct gcctaaagag gaaaaaaaag acgatcctcc taaggacccc aagaaggatg | 3120 |
| accctcctaa agaggcccag aacaagctga ccagcccgt ggtggccgac gagaacgtgg | 3180 |
| atcagggacc tggcgcccct cagggcccag gcgctccaca gggacccggg caccccagg | 3240 |
| ggcctggggc cccacaggga ccaggggctc ctcagggccc tggcgcacct caggggccag | 3300 |

```
gggcccctca ggggcctggc gctccccagg gacctggcgc accacagggc cctggggctc     3360
cccagggccc aggcgcccct cagggaccag gcgcacccca gggacccggc gctcctcagg     3420
gacctggggc tccacagggg ccaggcgcac cacaggaacc tccccagcag cctcctcagc     3480
agccacccca gcagcccct cagcagcctc ctcagcagcc cccacagcag cctccacagc      3540
agcctagacc ccagcccgac ggcaataaca acaacaataa taacaacggc aacaacaacg     3600
aggacagcta cgtgcccagc gccgagcaga tcctggaatt cgtgaagcag atcagcagcc     3660
agctgaccga agagtggagc cagtgcagcg tgacatgcgg ctctggcgtg agagtgcgga     3720
agcggaagaa cgtgaacaag cagcccgaga acctgaccct ggaagatatc gacaccgaga     3780
tctgcaagat ggacaagtgc agcagcatct tcaacatcgt gtccaacagc ctgggcttcg     3840
tgatcctgct ggtgctggtg ttcttcaact gatgactcga gctcaagctt cgaattcccg     3900
ataatcaacc tctggattac aaaatttgtg aaagattgac tggtattctt aactatgttg     3960
ctccttttac gctatgtgga tacgctgctt taatgccttt gtatcatgct attgcttccc     4020
gtatggcttt cattttctcc tccttgtata atcctggtt gctgtctctt tatgaggagt      4080
tgtggcccgt tgtcaggcaa cgtggcgtgg tgtgcactgt gtttgctgac gcaaccccca    4140
ctggttgggg cattgccacc acctgtcagc tcctttccgg gactttcgct ttcccccctcc   4200 ctattgccac ggcggaactc atcgccgcct gccttgcccg ctgctggaca ggggctcggc    4260
tgttgggcac tgacaattcc gtggtgttgt cggggaagct gacgtccttt ccatggctgc    4320
tcgcctgtgt tgccacctgg attctgcgcg gacgtccttt ctgctacgtc ccttcggccc    4380
tcaatccagc ggaccttcct tcccgcggcc tgctgccggc tctgcggcct cttccgcgtc    4440
ttcgccttcg ccctcagacg agtcggatct cccttgggc cgcctccccg cgtcgacgcg     4500
tgaattcggt acctttaaga ccaatgactt acaaggcagc tgtagatctt agccactttt    4560
taaaagaaaa gggggactg aagggctaa ttcactccca acgaagacaa gatcgtcgag       4620
agatgctgca tataagcagc tgcttttttgc ttgtactggg tctctctggt tagaccagat    4680
ctgagcctgg gagctctctg gctaactagg gaacccactg cttaagcctc aataaagctt    4740
gccttgagtg cttcaagtag tgtgtgcccg tctgttgtgt gactctggta actagagatc    4800
cctcagaccc ttttagtcag tgtggaaaat ctctagcagt                          4840
```

<210> SEQ ID NO 46
<211> LENGTH: 1053
<212> TYPE: DNA
<213> ORGANISM: Artificial Sequence
<220> FEATURE:
<223> OTHER INFORMATION: Description of Artificial Sequence: Synthetic
      sequence of transgene for CSP-deltaSP

<400> SEQUENCE: 46

```
atgcccggct acggccagaa taagagcgtg caggcccagc ggaacctgaa cgagctgtgc      60
tacaacgagg aaaacgacaa caagctgtac acgtgctga acagcaagaa cggcaagatc     120
tacaaccgga acatcgtgaa caggctgctg ggcgacgctc tgaacggcaa gcccgaggaa    180
aagaaggacg accccccaa ggacggcaac aaggacgacc tgcccaaaga agagaagaaa      240
gacgatctgc ctaaagagga aaaaaagac gatcctccta aggaccccaa gaggatgac      300 cctcctaaag aggcccagaa caagctgaac cagcccgtgg tggccgacga aacgtggat     360 cagggacctg cgcccctca gggcccaggc gctccacagg acccggggc accccagggg      420 cctggggccc cacagggacc aggggctcct cagggccctg cgcacctca ggggccaggg      480
```

```
gcccctcagg ggcctggcgc tccccaggga cctggcgcac cacagggccc tggggctccc      540
cagggcccag gcgcccctca gggaccaggc gcacccagg gacccggcgc tcctcaggga       600
cctggggctc cacaggggcc aggcgcacca caggaacctc cccagcagcc tcctcagcag      660
ccaccccagc agcccctca gcagcctcct cagcagcccc cacagcagcc tccacagcag      720
cctagacccc agcccgacgg caataacaac aacaataata caacggcaa caacaacgag      780 gacagctacg tgcccagcgc cgagcagatc ctggaattcg tgaagcagat cagcagccag      840
ctgaccgaag agtggagcca gtgcagcgtg acatgcggct ctggcgtgag agtgcggaag      900
cggaagaacg tgaacaagca gcccgagaac ctgaccctgg aagatatcga caccgagatc      960
tgcaagatgg acaagtgcag cagcatcttc aacatcgtgt ccaacagcct gggcttcgtg     1020
atcctgctgg tgctggtgtt cttcaactga tga                                  1053

<210> SEQ ID NO 47
<211> LENGTH: 4858
<212> TYPE: DNA
<213> ORGANISM: Artificial Sequence
<220> FEATURE:
<223> OTHER INFORMATION: Description of Artificial Sequence: Plasmid
      pTRIP-deltaU3-CMV-CSP deltaGPI CO-WPRE
<220> FEATURE:
<221> NAME/KEY: misc_feature
<222> LOCATION: (1)..(4858)
<223> OTHER INFORMATION: Complete nucleotide sequence of the provirus

<400> SEQUENCE: 47
tggaagggct aattcactcc caacgaagac aagatatcct tgatctgtgg atctaccaca       60
cacaaggcta cttccctgat tagcagaact acacaccagg gccagggatc agatatccac      120
tgacctttgg atggtgctac aagctagtac cagttgagcc agagaagtta gaagaagcca      180
acaaaggaga gaacaccagc ttgttacaac ctgtgagcct gcatgggatg gatgacccgg      240
agagagaagt gttagagtgg aggtttgaca gccgcctagc atttcatcac ggtggcccga      300
gagctgcatc cggagtactt caagaactgc tgatatcgag cttgctacaa gggactttcc      360 gctggggac tttccaggga ggcgtggcct gggcgggact ggggagtggc gagccctcag      420
atcctgcata taagcagctg ctttttgcct gtactgggtc tctctggtta gaccagatct      480
gagcctggga gctctctggc taactaggga acccactgct taagcctcaa taaagcttgc      540
cttgagtgct tcaagtagtg tgtgcccgtc tgttgtgtga ctctggtaac tagagatccc      600
tcagaccctt ttagtcagtg tggaaaatct ctagcagtgg cgcccgaaca gggacttgaa      660
agcgaaaggg aaaccagagg agctctctcg acgcaggact cggcttgctg aagcgcgcac      720
ggcaagaggc gaggggcggc gactggtgag tacgccaaaa attttgacta gcggaggcta      780
gaaggagaga gatgggtgcg agagcgtcag tattaagcgg gggagaatta gatcgcgatg      840
ggaaaaaatt cggttaaggc caggggggaaa gaaaaaatat aaattaaaac atatagtatg      900
ggcaagcagg gagctagaac gattcgcagt taatcctggc ctgttagaaa catcagaagg      960
ctgtagacaa atactgggac agctacaacc atcccttcag acaggatcag aagaacttag     1020
atcattatat aatacagtag caaccctcta ttgtgtgcat caaaggatag agataaaaga     1080
caccaaggaa gctttagaca agatagagga agagcaaaac aaaagtaaga ccaccgcaca     1140
gcaagcggcc gctgatcttc agacctggag gaggagatat gagggacaat tggagaagtg     1200
aattatataa atataaagta gtaaaaattg aaccattagg agtagcaccc accaaggcaa     1260
agagaagagt ggtgcagaga gaaaaaagag cagtgggaat aggagctttg ttccttgggt     1320
```

```
tcttgggagc agcaggaagc actatgggcg cagcgtcaat gacgctgacg gtacaggcca    1380
gacaattatt gtctggtata gtgcagcagc agaacaattt gctgagggct attgaggcgc    1440
aacagcatct gttgcaactc acagtctggg gcatcaagca gctccaggca agaatcctgg    1500
ctgtggaaag atacctaaag gatcaacagc tcctggggat ttggggttgc tctggaaaac    1560
tcatttgcac cactgctgtg ccttggaatg ctagttggag taataaatct ctggaacaga    1620
tttggaatca cacgacctgg atggagtggg acagagaaat taacaattac acaagcttaa    1680
tacactcctt aattgaagaa tcgcaaaacc agcaagaaaa gaatgaacaa gaattattgg    1740
aattagataa atgggcaagt ttgtggaatt ggtttaacat aacaaattgg ctgtggtata    1800
taaaattatt cataatgata gtaggaggct tggtaggttt aagaatagtt tttgctgtac    1860
tttctatagt gaatagagtt aggcagggat attcaccatt atcgtttcag acccacctcc    1920
caaccccgag gggacccgac aggcccgaag gaatagaaga agaaggtgga gagagagaca    1980
gagacagatc cattcgatta gtgaacggat ctcgacggta tcgccgaatt cacaaatggc    2040
agtattcatc cacaatttta aaagaaaagg ggggattggg gggtacagtg caggggaaag    2100
aatagtagac ataatagcaa cagacataca aactaaagaa ttacaaaaac aaattacaaa    2160
aattcaaaat tttcgggttt attacaggga cagcagagat ccactttggc tgatacgcgt    2220
ggagttccgc gttacataac ttacggtaaa tggcccgcct ggctgaccgc ccaacgaccc    2280
ccgcccattg acgtcaataa tgacgtatgt tcccatagta acgccaatag ggactttcca    2340
ttgacgtcaa tgggtggagt atttacggta aactgcccac ttggcagtac atcaagtgta    2400
tcatatgcca agtacgcccc ctattgacgt caatgacggt aaatggcccg cctggcatta    2460
tgcccagtac atgaccttat gggactttcc tacttggcag tacatctacg tattagtcat    2520
cgctattacc atggtgatgc ggttttggca gtacatcaat gggcgtggat agcggtttga    2580
ctcacgggga tttccaagtc tccaccccat tgacgtcaat gggagtttgt tttggcacca    2640
aaatcaacgg gactttccaa aatgtcgtaa caactccgcc ccattgacgc aaatgggcgg    2700
taggcgtgta cggtgggagg tctatataag cagagctcgt ttagtgaacc gtcagatcgc    2760
ctggagacgc catccacgct gttttgacct ccatagaaga caccgcgatc ggatccgcca    2820
ccatgaagaa atgcaccatc ctggtggtgg ccagcctgct gctggtcgat agcctgctgc    2880
ccggctacgg ccagaataag agcgtgcagg cccagcggaa cctgaacgag ctgtgctaca    2940
acgaggaaaa cgacaacaag ctgtaccacg tgctgaacag caagaacggc aagatctaca    3000
accggaacat cgtgaacagg ctgctgggcg acgtctgaa cggcaagccc gaggaaaaga    3060
aggacgaccc ccccaaggac ggcaacaagg acgacctgcc caagaagag aagaaagacg    3120
atctgcctaa agaggaaaaa aaagacgatc ctcctaagga ccccaagaag gatgaccctc    3180
ctaaagaggc ccagaacaag ctgaaccagc ccgtggtggc cgacgagaac gtggatcagg    3240
gacctggcgc ccctcagggc ccaggcgctc cacaggggacc cggggcaccc cagggggcctg    3300
gggccccaca gggaccaggg gctcctcagg gccctggcgc acctcagggg ccaggggccc    3360
ctcaggggcc tggcgctccc cagggacctg gcgcaccaca gggccctggg gctccccagg    3420
gcccaggcgc ccctcaggga ccaggcgcac cccaggaccc ggcgctcct cagggacctg    3480
gggctccaca ggggccaggc gcaccacagg aacctcccca gcagcctcct cagcagccac    3540
cccagcagcc ccctcagcag cctcctcagc agccccaca gcagcctcca cagcagccta    3600
gaccccagcc cgacggcaat aacaacaaca ataataacaa cggcaacaac aacgaggaca    3660
gctacgtgcc cagcgccgag cagatcctgg aattcgtgaa gcagatcagc agccagctga    3720
```

| | |
|---|---|
| ccgaagagtg gagccagtgc agcgtgacat gcggctctgg cgtgagagtg cggaagcgga | 3780 |
| agaacgtgaa caagcagccc gagaacctga ccctggaaga tatcgacacc gagatctgca | 3840 |
| agatggacaa gtgcagcagc atcttcaaca tcgtgtccaa cagcctgtga tgactcgagc | 3900 |
| tcaagcttcg aattcccgat aatcaacctc tggattacaa aatttgtgaa agattgactg | 3960 |
| gtattcttaa ctatgttgct ccttttacgc tatgtggata cgctgcttta atgcctttgt | 4020 |
| atcatgctat tgcttcccgt atggctttca ttttctcctc cttgtataaa tcctggttgc | 4080 |
| tgtctcttta tgaggagttg tggcccgttg tcaggcaacg tggcgtggtg tgcactgtgt | 4140 |
| ttgctgacgc aaccccact ggttggggca ttgccaccac ctgtcagctc ctttccggga | 4200 |
| cttttcgcttt cccctccct attgccacgg cggaactcat cgccgcctgc cttgcccgct | 4260 |
| gctggacagg ggctcggctg ttgggcactg acaattccgt ggtgttgtcg gggaagctga | 4320 |
| cgtcctttcc atggctgctc gcctgtgttg ccacctggat tctgcgcggg acgtccttct | 4380 |
| gctacgtccc ttcggccctc aatccagcgg accttccttc ccgcgcctg ctgccggctc | 4440 |
| tgcggcctct tccgcgtctt cgccttcgcc ctcagacgag tcggatctcc ctttgggccg | 4500 |
| cctccccgcg tcgacgcgtg aattcggtac ctttaagacc aatgacttac aaggcagctg | 4560 |
| tagatcttag ccactttta aagaaaagg ggggactgga agggctaatt cactcccaac | 4620 |
| gaagacaaga tcgtcgagag atgctgcata taagcagctg cttttgctt gtactgggtc | 4680 |
| tctctggtta gaccagatct gagcctggga gctctctggc taactaggga acccactgct | 4740 |
| taagcctcaa taaagcttgc cttgagtgct tcaagtagtg tgtgcccgtc tgttgtgtga | 4800 |
| ctctggtaac tagagatccc tcagaccctt ttagtcagtg tggaaaatct ctagcagt | 4858 |

<210> SEQ ID NO 48
<211> LENGTH: 1071
<212> TYPE: DNA
<213> ORGANISM: Artificial Sequence
<220> FEATURE:
<223> OTHER INFORMATION: Description of Artificial Sequence: Synthetic
      sequence of transgene for CSP-delta GPI CO

<400> SEQUENCE: 48

| | |
|---|---|
| atgaagaaat gcaccatcct ggtggtggcc agcctgctgc tggtcgatag cctgctgccc | 60 |
| ggctacggcc agaataagag cgtgcaggcc cagcggaacc tgaacgagct gtgctacaac | 120 |
| gaggaaaacg acaacaagct gtaccacgtg ctgaacagca gaacggcaa gatctacaac | 180 |
| cggaacatcg tgaacaggct gctgggcgac gctctgaacg gcaagcccga ggaaaagaag | 240 |
| gacgaccccc ccaaggacgg caacaaggac gacctgccca agaagagaaa gaagacgat | 300 |
| ctgcctaaag aggaaaaaaa agacgatcct cctaaggacc caagaagga tgaccctcct | 360 |
| aaagaggccc agaacaagct gaaccagccc gtggtggccg acgagaacgt ggatcaggga | 420 |
| cctggcgccc ctcagggccc aggcgctcca cagggacccg ggcaccccca ggggcctggg | 480 |
| gccccacagg gaccaggggc tcctcagggc cctggcgcac tcagggggcc aggggcccct | 540 |
| caggggcctg gcgctcccca gggacctggc gcaccacagg gcctggggc tccccagggc | 600 |
| ccaggcgccc tcagggacc aggcgcaccc caggacccg cgctcctca gggacctggg | 660 |
| gctccacagg ggcaggcgc accacaggaa cctccccagc agcctcctca gcagccaccc | 720 |
| cagcagcccc tcagcagcc tcctcagcag ccccacagc agcctccaca gcagcctaga | 780 |
| ccccagcccg acggcaataa caacaacaat aataacaacg caacaacaa cgaggacagc | 840 |
| tacgtgccca gcgccgagca gatcctggaa ttcgtgaagc agatcagcag ccagctgacc | 900 |

```
gaagagtgga gccagtgcag cgtgacatgc ggctctggcg tgagagtgcg gaagcggaag    960
aacgtgaaca agcagcccga gaacctgacc ctggaagata tcgacaccga gatctgcaag   1020
atggacaagt gcagcagcat cttcaacatc gtgtccaaca gcctgtgatg a            1071
```

<210> SEQ ID NO 49
<211> LENGTH: 442
<212> TYPE: PRT
<213> ORGANISM: Plasmodium falciparum
<220> FEATURE:
<221> NAME/KEY: MISC_FEATURE
<222> LOCATION: (1)..(442)
<223> OTHER INFORMATION: CSP protein
<300> PUBLICATION INFORMATION:
<308> DATABASE ACCESSION NUMBER: GenBank Accession Number: M15505.1

<400> SEQUENCE: 49

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asp Asn
65                  70                  75                  80

Asp Asn Gly Asn Asn Asn Gly Asn Asn Asn Gly Asp Asn Gly
                85                  90                  95

Arg Glu Gly Lys Asp Glu Asp Lys Arg Asp Gly Asn Asn Glu Asp Asn
            100                 105                 110

Glu Lys Leu Arg Lys Pro Lys His Lys Lys Leu Lys Gln Pro Gly Asp
        115                 120                 125

Gly Asn Pro Asp Pro Asn Ala Asn Pro Asn Val Asp Pro Asn Ala Asn
    130                 135                 140

Pro Asn Val Asp Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
        195                 200                 205

Pro Asn Val Asp Pro Asn Ala Asn Pro Asn Ala Asn Pro Asn Ala Asn
    210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Ala Asn Pro Asn Ala Asn
                245                 250                 255

Pro Asn Ala Asn Pro Asn Ala Asn Pro Asn Ala Asn Pro Asn Ala Asn
            260                 265                 270

Pro Asn Ala Asn Pro Asn Ala Asn Pro Asn Ala Asn Pro Asn Ala Asn
        275                 280                 285

Pro Asn Ala Asn Pro Asn Ala Asn Pro Asn Ala Asn Pro Asn Ala Asn
    290                 295                 300

Pro Asn Ala Asn Pro Asn Ala Asn Pro Asn Ala Asn Pro Asn Lys Asn
```

| 305 | | | 310 | | | 315 | | | 320 | |
|---|---|---|---|---|---|---|---|---|---|---|
| Asn | Gln | Gly | Asn | Gly | Gln | Gly | His | Asn | Met | Pro | Asn | Asp | Pro | Asn | Arg |
| | | | | 325 | | | | | 330 | | | | | 335 | |

Asn Val Asp Glu Asn Ala Asn Ala Asn Asn Ala Val Lys Asn Asn Asn
            340                 345                 350

Asn Glu Glu Pro Ser Asp Lys His Ile Glu Gln Tyr Leu Lys Lys Ile
            355                 360                 365

Gln Asn Ser Leu Ser Thr Glu Trp Ser Pro Cys Ser Val Thr Cys Gly
            370                 375                 380

Asn Gly Ile Gln Val Arg Ile Lys Pro Gly Ser Ala Asp Lys Pro Lys
385                 390                 395                 400

Asp Gln Leu Asp Tyr Glu Asn Asp Ile Glu Lys Lys Ile Cys Lys Met
            405                 410                 415

Glu Lys Cys Ser Ser Val Phe Asn Val Val Asn Ser Ser Ile Gly Leu
            420                 425                 430

Ile Met Val Leu Ser Phe Leu Phe Leu Asn
            435                 440

```
<210> SEQ ID NO 50
<211> LENGTH: 1669
<212> TYPE: DNA
<213> ORGANISM: Plasmodium falciparum
<220> FEATURE:
<221> NAME/KEY: misc_feature
<222> LOCATION: (1)..(1669)
<223> OTHER INFORMATION: CSP gene
<300> PUBLICATION INFORMATION:
<308> DATABASE ACCESSION NUMBER: GenBank Accession Number: M15505.1

<400> SEQUENCE: 50
gtagaaacca cgtaatatta taaattacaa ttcatgatga gaaaattagc tattttatct      60
gtttcttcct ttttatttgt tgaggcctta ttccaggaat accagtgcta tggaagttcg     120
tcaaacacaa gggttctaaa tgaattaaat tatgataatg caggcactaa tttatataat     180
gaattagaaa tgaattatta tgggaaacag gaaaattggt atagtcttaa aaaaaatagt     240
agatcacttg gagaaaatga tgatggagat aatgataatg gaataataa taatggaaat      300 aataataatg gagataatgg tcgtgaaggt aaagatgaag ataaagaga tggaaataac      360 gaagacaacg agaaattaag gaaaccaaaa cataaaaaat taaagcaacc aggggatggt     420
aatcctgatc caaatgccaa cccaaatgta gatccaaatg ccaacccaaa tgtagatcca     480
aatgcaaacc caaatgcaaa cccaaatgca acccaaatg caaacccaaa tgcaaaccca     540
aatgcaaacc caaatgcaaa cccaaatgca acccaaatg caaacccaaa tgcaaaccca     600
aatgcaaacc caaatgcaaa cccaaatgca acccaaatg caaacccaaa tgcaaaccca     660
aacgtagatc ctaatgcaaa tccaaatgca acccaaatg caaacccaaa cgcaaaccca     720
aatgcaaatc ctaatgcaaa tcctaatgca aatcctaatg ccaatccaaa tgcaaatcca     780
aatgcaaacc caaacgcaaa ccccaatgca aatcctaatg ccaatccaaa tgcaaatcca     840
aatgcaaacc caaacgcaaa ccccaatgca aatcctaatg ccaatccaaa tgcaaatcca     900
aatgcaaacc ccaatgcaaa tcctaatgcc aatccaaatg caaatccaaa tgcaaaccca     960
aatgcaaacc caaatgcaaa tcctaataaa acaatcaag gtaatggaca aggtcacaat     1020
atgccaaatg acccaaaccg aaatgtagat gaaaatgcta atgccaacaa tgctgtaaaa     1080
aataataata cgaagaacc aagtgataag cacatagaac aatatttaa gaaaatacaa      1140 aattctcttt caactgaatg gtccccatgt agtgtaactt gtggaaatgg tattcaagtt     1200
```

```
agaataaagc ctggctctgc tgataaacct aaagaccaat tagattatga aaatgatatt    1260
gaaaaaaaaa tttgtaaaat ggaaaaatgt tccagtgtgt ttaatgtcgt aaatagttca    1320
ataggattaa taatggtatt atccttcttg ttccttaatt agataaagaa cacatcttag    1380
tttgagttgt acaatattta taaaatata tactactttt tttcttaatt ttcattttc     1440 tttatatttt cctatttaat ttattttttt gtgaatattt aattatgttt gcgattaatt    1500
gtagaaatat atatgtatat actatattta tagaatgtgt tattctcaaa aacaacaaca    1560
aaaaaaaaaa aaaaaaaaa aaaaagaaa aaggattaa aagtaaaata gttataaata     1620
ttttcaaaaa tatttataac acaaaaaata cttcgaagtt catttaaca               1669
```

<210> SEQ ID NO 51
<211> LENGTH: 388
<212> TYPE: PRT
<213> ORGANISM: Plasmodium reichenowi
<220> FEATURE:
<221> NAME/KEY: MISC_FEATURE
<222> LOCATION: (1)..(388)
<223> OTHER INFORMATION: CSP protein
<300> PUBLICATION INFORMATION:
<308> DATABASE ACCESSION NUMBER: GenBank Accession Number: M60972.1

<400> SEQUENCE: 51

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Ala Asp Asn
65                  70                  75                  80

Gly Asp Ala Asp Asn Gly Asp Glu Gly Ile Asp Glu Asn Arg Arg His
                85                  90                  95

Arg Asn Lys Glu Gly Lys Glu Lys Leu Lys Pro Lys His Asn Lys
            100                 105                 110

Leu Lys Gln Pro Gly Asn Asp Asn Val Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Val Asp Pro Asn Ala Asn Pro Asn
145                 150                 155                 160

Val Asn Pro Asn Ala Asn Pro Asn Val Asp Pro Asn Ala Asn Pro Asn
                165                 170                 175

Val Asn Pro Asn Ala Asn Pro Asn Val Asn Pro Asn Ala Asn Pro Asn
            180                 185                 190

Val Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255
```

```
Ala Asn Pro Asn Ala Asn Pro Asn Arg Asn Asn Glu Ala Asn Gly Gln
            260                 265                 270

Gly His Asn Lys Pro Asn Asp Gln Asn Arg Asn Val Asn Glu Asn Ala
            275                 280                 285

Asn Ala Asn Asn Ala Gly Arg Asn Asn Asn Glu Glu Pro Ser Asp
        290                 295                 300

Lys His Ile Glu Glu Phe Leu Lys Gln Ile Gln Asn Asn Leu Ser Thr
305                 310                 315                 320

Glu Trp Ser Pro Cys Ser Val Thr Cys Gly Asn Gly Ile Gln Val Arg
                325                 330                 335

Ile Lys Pro Gly Ser Ala Gly Lys Pro Lys Asp Gln Leu Asp Tyr Glu
            340                 345                 350

Asn Asp Leu Glu Lys Lys Ile Cys Lys Met Glu Lys Cys Ser Ser Val
            355                 360                 365

Phe Asn Val Val Asn Ser Ser Ile Gly Leu Ile Met Val Leu Ser Phe
            370                 375                 380

Leu Phe Leu Asn
385

<210> SEQ ID NO 52
<211> LENGTH: 1167
<212> TYPE: DNA
<213> ORGANISM: Plasmodium reichenowi
<220> FEATURE:
<221> NAME/KEY: misc_feature
<222> LOCATION: (1)..(1167)
<223> OTHER INFORMATION: CSP gene
<300> PUBLICATION INFORMATION:
<308> DATABASE ACCESSION NUMBER: GenBank Accession Number: M60972.1

<400> SEQUENCE: 52
atgatgagaa aattagctat tttatctgtt tcttcctttt tatttgttga ggccttattc      60
caggaatatc agtgctatgg aagttcgtca aacacaaggg ttctaaatga attaaattat     120
gataatgcag gcactaattt atataatgaa ttagaaatga attattatgg aaacaggaa      180
aattggtata gccttaaaaa aaatagtaga tcacttggag aaaatgatga tgcagataat     240
ggtgatgcag ataatggtga tgaaggtata gatgaaaata gaagacatag aaataaagaa     300
ggcaaagaga aattaaagaa accaaaacat aataaattaa agcaaccagg gaatgataat     360
gttgatccaa atgccaaccc aaatgtagat ccaaatgcca acccaaatgt agatcccaat     420
gcaaacccaa atgtagatcc caatgcaaac ccaaatgtag atcctaatgc aaacccaaat     480
gtaaatccca atgcaaaccc aaatgtagat cctaatgcaa cccaaatgt aaatcccaat     540
gcaaacccaa atgtaaatcc caatgcaaac ccaaatgtaa atcccaatgc aaacccaaat     600
gcaaatccta atgcaaatcc caatgcaaat cccaatgcaa acccaaatgc aaatcctaat     660
gcaaatccca atgcaaatcc caatgcaaac ccaaatgcaa atcctaatgc aaatcctaat     720
gcaaatccta atgcaaatcc taatgcaaat cctaatgcca tccaaacgc aaacccaaat     780
gcaaatccta atagaaacaa tgaagctaat ggacaaggtc acaataagcc aaatgaccaa     840
aaccgaaatg taaatgaaaa tgctaatgcc aacaatgctg gaagaaataa taataacgaa     900
gaaccaagtg ataagcacat agaagaattt ttaaagcaaa tacaaaataa tctttcaact     960
gaatggtccc catgtagtgt aacttgtgga aatggtattc aagttagaat aaagcctggc    1020
tctgctggta aacctaaaga ccaattagat tatgaaaatg accttgaaaa aaaaatttgt    1080
aaaatggaaa aatgttccag tgtgttcaat gtcgtaaata gttcaatagg attaataatg    1140
```
gtattatcct tcttgttcct taattag       1167

<210> SEQ ID NO 53
<211> LENGTH: 367
<212> TYPE: PRT
<213> ORGANISM: Plasmodium yoelii
<220> FEATURE:
<221> NAME/KEY: MISC_FEATURE
<222> LOCATION: (1)..(367)
<223> OTHER INFORMATION: CSP protein
<300> PUBLICATION INFORMATION:
<308> DATABASE ACCESSION NUMBER: GenBank Accession Number: J02695.1

<400> SEQUENCE: 53

```
Met Lys Lys Cys Thr Ile Leu Val Val Ala Ser Leu Leu Leu Val Asp
1               5                   10                  15

Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Pro Gln Gln Pro Gln Gln Pro Gln Pro
225                 230                 235                 240

Gln Gln Pro Pro Gln Gln Pro Gln Gln Pro Pro Gln Gln Pro Pro
                245                 250                 255

Gln Gln Pro Arg Pro Gln Pro Asp Gly Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335
```

Glu Ile Cys Lys Met Asp Lys Cys Ser Ser Ile Phe Asn Ile Val Ser
            340                 345                 350

Asn Ser Leu Gly Phe Val Ile Leu Leu Val Leu Val Phe Phe Asn
            355                 360                 365

<210> SEQ ID NO 54
<211> LENGTH: 1580
<212> TYPE: DNA
<213> ORGANISM: Plasmodium yoelii
<220> FEATURE:
<221> NAME/KEY: misc_feature
<222> LOCATION: (1)..(1580)
<223> OTHER INFORMATION: CSP gene
<300> PUBLICATION INFORMATION:
<308> DATABASE ACCESSION NUMBER: GenBank Accession Number: J02695.1

<400> SEQUENCE: 54

| | | | | |
|---|---|---|---|---|
| aaaatgaaga | agtgtaccat | tttagttgta | gcgtcacttt | tattagttga | ttctctactt | 60 |
| ccaggatatg | gacaaaataa | aagtgtccaa | gcccaaagaa | acttaaacga | gctatgttac | 120 |
| aatgaagaaa | atgataataa | attgtatcac | gtccttaact | cgaagaatgg | aaaaatatac | 180 |
| aatcgaaata | tagtcaacag | attacttggc | gatgctctca | acggaaaacc | agaagaaaaa | 240 |
| aaagatgatc | cccaaaaga | tggcaacaaa | gatgatcttc | caaagaaga | aaaaaaagat | 300 |
| gatcttccaa | aagaagaaaa | aaaagatgat | ccccaaaag | atcctaaaaa | agatgatcca | 360 |
| ccaaaagagg | ctcaaaataa | attgaatcaa | ccagtagtgg | cagatgaaaa | tgtagatcaa | 420 |
| gggccaggag | caccacaagg | gccaggagca | ccacaaggac | caggagcacc | acagggtcca | 480 |
| ggagcaccac | aaggaccagg | agcaccacaa | ggaccaggag | caccacaagg | tccaggagca | 540 |
| ccacagggtc | caggagcacc | acagggtcca | ggagcaccac | aaggaccagg | agcaccacag | 600 |
| gggccaggag | caccacaagg | accaggagca | ccacaaggac | caggagcacc | acaggggcca | 660 |
| ggagcaccac | aagggccagg | agcaccacaa | gaaccacccc | aacaaccacc | ccaacaacca | 720 |
| ccacaacagc | caccacaaca | gccaccacaa | cagccaccac | aacagccacc | acaacaacca | 780 |
| cgcccacagc | cagatggtaa | taacaacaat | aacaataata | atggtaataa | taatgaagat | 840 |
| tcttatgtcc | caagcgcgga | acaaatacta | gaatttgtta | aacagataag | tagtcaactc | 900 |
| acagaggaat | ggtctcaatg | tagtgtaacc | tgtggttctg | gtgtaagagt | tagaaaacga | 960 |
| aaaaatgtaa | acaagcaacc | agaaaatttg | accttagagg | atattgatac | tgaaatttgt | 1020 |
| aaaatggata | aatgttcaag | tatatttaat | attgtaagca | attcattagg | atttgtaata | 1080 |
| ttattagtat | tagtattctt | taattaaata | aacattacac | attattataa | atatttatat | 1140 |
| attatataaa | tatttaatat | acatataatg | tgtgtagact | ttattttttg | tattgtgaac | 1200 |
| tttcctcatt | tattacgatt | atttttatat | atatacatat | ttaatatgta | aattaaaaga | 1260 |
| aaaaagaaat | aatagaaatc | ttattatatt | tatgatataa | attaaaaaa | taaaatatat | 1320 |
| atacattaca | aaatttactt | ttttagttt | atttttttcg | tgtttattat | atatgtaatt | 1380 |
| aacttgttat | gacgatatcg | aaactttatt | tttgagaata | tattttatg | aattagaata | 1440 |
| ttaataatta | ttatggttat | ttgtttggga | atttatataa | tttacaatat | tatttaaggg | 1500 |
| caatctaaaa | atattttatt | gttatgatat | ttgaaacatt | ttatgtagct | atccaaatta | 1560 |
| tttatttgtg | taaaatattt | | | | | 1580 |

<210> SEQ ID NO 55
<211> LENGTH: 341
<212> TYPE: PRT
<213> ORGANISM: Plasmodium coateneyi

```
<220> FEATURE:
<221> NAME/KEY: MISC_FEATURE
<222> LOCATION: (1)..(341)
<223> OTHER INFORMATION: CSP Protein
<300> PUBLICATION INFORMATION:
<308> DATABASE ACCESSION NUMBER: GenBank Accession Number: AY135360.1

<400> SEQUENCE: 55
```

Met Lys Asn Phe Ile Leu Leu Ala Val Ser Ser Ile Leu Leu Val Asp
1               5                   10                  15

Leu Phe Pro Thr His Phe Gly His Asn Val Asp Leu Ser Arg Ala Ile
            20                  25                  30

Asn Leu Asn Gly Val Ser Phe Asn Asn Val Asp Thr Ser Leu Leu Gly
        35                  40                  45

Ala Ala Gln Val Arg Gln Ser Ala Ser Arg Gly Arg Gly Leu Gly Glu
    50                  55                  60

Lys Pro Lys Lys Lys Ala Glu Lys Lys Glu Glu Pro Lys Lys Pro
65              70                  75                  80

Asn Glu Asn Lys Leu Lys Gln Pro Val Asp Gly Ala Arg Asp Gly Pro
                85                  90                  95

Ala Pro Ala Ala Asp Gly Ala Arg Asp Gly Pro Ala Pro Ala Ala Asp
            100                 105                 110

Gly Ala Arg Asp Gly Pro Ala Pro Ala Ala Asp Gly Ala Arg Asp Gly
        115                 120                 125

Pro Ala Pro Ala Ala Asp Gly Ala Arg Asp Gly Pro Ala Pro Ala Ala
    130                 135                 140

Asp Gly Ala Arg Asp Gly Pro Ala Pro Ala Ala Asp Gly Ala Arg Asp
145                 150                 155                 160

Gly Pro Ala Pro Ala Ala Asp Gly Ala Arg Asp Gly Pro Ala Pro Pro
                165                 170                 175

Ala Asp Gly Ala Arg Asp Gly Pro Ala Pro Pro Ala Ala Asp Gly Ala
            180                 185                 190

Arg Asp Gly Pro Ala Pro Pro Ala Ala Asp Gly Ala Arg Asp Gly Pro
        195                 200                 205

Ala Pro Pro Ala Gly Gln Gly Gly Asn Ala Ala Gly Gln Ala Gln
    210                 215                 220

Gly Gly Gly Asn Ala Gly Asn Lys Lys Ala Gly Asp Ala Ala Gly Asn
225                 230                 235                 240

Ala Gly Ala Ala Lys Gly Gln Gly Gln Asn Asn Glu Gly Ala Asn Val
                245                 250                 255

Pro Asn Glu Lys Val Val Asn Asp Tyr Leu Gln Lys Ile Arg Ser Thr
            260                 265                 270

Val Thr Thr Glu Trp Thr Pro Cys Ser Val Thr Cys Gly Asn Gly Val
        275                 280                 285

Arg Leu Arg Arg Lys Ala His Ala Glu Lys Lys Pro Glu Asp Leu
    290                 295                 300

Thr Met Asp Asp Leu Asp Val Glu Val Cys Ala Met Asp Lys Cys Ala
305                 310                 315                 320

Gly Ile Phe Asn Phe Val Ser Asn Ser Leu Gly Leu Val Ile Leu Leu
                325                 330                 335

Val Leu Ala Phe Asn
            340

```
<210> SEQ ID NO 56
<211> LENGTH: 1049
<212> TYPE: DNA
```

<213> ORGANISM: Plasmodium coatneyi
<220> FEATURE:
<221> NAME/KEY: misc_feature
<222> LOCATION: (1)..(1049)
<223> OTHER INFORMATION: CSP gene
<300> PUBLICATION INFORMATION:
<308> DATABASE ACCESSION NUMBER: GenBank Accession Number: AY135360.1

<400> SEQUENCE: 56

```
atgaagaact tcattctctt ggctgtttct tccatcctgt tggtggactt gttccccacg      60
cacttcggac ataatgtaga tctctccagg gccataaatt taaatggagt aagcttcaat    120
aatgtagaca ccagtttact tggcgcagca caggtaagac aaagtgctag ccgaggcaga    180
ggacttggtg agaaaccaaa aaaaaaggcg aaaaaaaag aagaagaacc aaaaaagcca     240
aatgaaaata agctgaagca accagtagat ggagcacgag atgggccagc accagcagca    300
gatggagcaa gagatggacc agcaccagca gcagatggag cacgagatgg accagcacca    360
gcagcagatg gagcaagaga tggaccagca ccagcagcag atggagcaag agatggacca    420
gcaccagcag cagatggagc aagagatgga ccagcaccag cagatgg agcacgagat       480
ggaccagcac cagcagcaga tggagcaaga gatgggccag caccaccagc cgatggagca    540
agagatgggc cagcaccacc agcagcagat ggagcacgag atggaccagc accaccagca    600
gcagatggag cacgagatgg ccagcacca ccagcaggac aaggaggagg aaatgcagca     660
ggccaagcac aaggaggagg aaatgccgga acaaaaaag caggagacgc agctggaaac    720
gcaggagcag caaaaggaca gggacaaaat aatgaaggtg cgaatgtccc aaatgagaaa    780
gttgtgaatg attacctaca gaaaattaga tctaccgtta ccaccgaatg gactccatgc    840
agtgtaacct gtggaaatgg tgtaagactt agaagaaaag ctcatgcaga aagaaaaaa     900
ccagaggacc ttaccatgga tgaccttgac gtggaagttt gtgcaatgga taagtgcgct    960
ggcatattta actttgtgag taattcatta gggctagtca tattgttagt cctagcattc   1020
aattaagtag ctgacatcca ttattttcg                                     1049
```

<210> SEQ ID NO 57
<211> LENGTH: 371
<212> TYPE: PRT
<213> ORGANISM: Plasmodium knowlesi
<220> FEATURE:
<221> NAME/KEY: MISC_FEATURE
<222> LOCATION: (1)..(371)
<223> OTHER INFORMATION: CSP protein
<300> PUBLICATION INFORMATION:
<308> DATABASE ACCESSION NUMBER: GenBank Accession Number: DQ350294.2

<400> SEQUENCE: 57

```
Met Arg Asn Phe Ile Leu Leu Ala Val Ser Ser Ile Leu Leu Val Asp
1               5                   10                  15

Leu Leu Pro Thr His Phe Glu His Asn Val Asp Leu Ser Arg Ala Ile
            20                  25                  30

Asn Val Asn Gly Val Ser Phe Asn Asn Val Asp Thr Ser Ser Leu Gly
        35                  40                  45

Ala Ala Gln Val Arg Gln Ser Ala Ser Arg Gly Arg Gly Leu Gly Glu
    50                  55                  60

Lys Arg Lys Glu Gly Ala Asp Lys Glu Lys Lys Glu Lys Glu Glu
65                  70                  75                  80

Glu Pro Lys Lys Pro Asn Glu Asn Lys Leu Lys Gln Pro Asn Pro Gly
                85                  90                  95

Gln Pro Gln Ala Gln Gly Asp Gly Ala Asn Ala Gly Gln Pro Gln Ala
```

```
            100                 105                 110
Gln Gly Asp Gly Ala Asn Ala Gly Gln Pro Gln Ala Gln Gly Asp Gly
        115                 120                 125

Ala Asn Ala Gly Gln Pro Gln Ala Gln Gly Asp Gly Ala Asn Ala Gly
    130                 135                 140

Gln Pro Gln Ala Gln Gly Asp Gly Ala Asn Ala Gly Gln Pro Gln Ala
145                 150                 155                 160

Gln Gly Asp Gly Ala Asn Ala Gly Gln Pro Gln Ala Gln Gly Asp Gly
        165                 170                 175

Ala Asn Ala Gly Gln Pro Gln Ala Gln Gly Asp Gly Ala Asn Ala Gly
    180                 185                 190

Gln Pro Gln Ala Gln Gly Asp Gly Ala Asn Ala Gly Gln Pro Gln Ala
    195                 200                 205

Gln Gly Asp Gly Ala Asn Ala Gly Gln Pro Gln Ala Gln Gly Asp Gly
    210                 215                 220

Ala Asn Ala Gly Gln Pro Gln Ala Gln Gly Asp Arg Ala Asn Ala Gly
225                 230                 235                 240

Gln Pro Gln Ala Gln Gly Asp Gly Ala Asn Val Pro Arg Gln Gly Arg
            245                 250                 255

Asn Gly Gly Gly Ala Pro Ala Gly Gly Asn Glu Gly Asn Lys Gln Ala
            260                 265                 270

Gly Lys Gly Gln Gly Gln Asn Asn Gln Gly Ala Asn Ala Pro Asn Glu
        275                 280                 285

Lys Val Val Asn Asp Tyr Leu His Lys Ile Arg Ser Ser Val Thr Thr
    290                 295                 300

Glu Trp Thr Pro Cys Ser Val Thr Cys Gly Asn Gly Val Arg Ile Arg
305                 310                 315                 320

Arg Lys Ala His Ala Gly Asn Lys Lys Ala Glu Asp Leu Thr Met Asp
            325                 330                 335

Asp Leu Glu Val Glu Ala Cys Val Met Asp Lys Cys Ala Gly Ile Phe
        340                 345                 350

Asn Val Val Ser Asn Ser Leu Gly Leu Val Ile Leu Leu Val Leu Ala
    355                 360                 365

Leu Phe Asn
    370

<210> SEQ ID NO 58
<211> LENGTH: 1113
<212> TYPE: DNA
<213> ORGANISM: Plasmodium knowlesi
<220> FEATURE:
<221> NAME/KEY: misc_feature
<222> LOCATION: (1)..(1113)
<223> OTHER INFORMATION: CSP gene
<300> PUBLICATION INFORMATION:
<308> DATABASE ACCESSION NUMBER: GenBank Accession Number: DQ350294.2

<400> SEQUENCE: 58
atgaggaact tcattctctt ggccgtctcc tccatcctgc tggtggactt gctccccaca      60
cacttcgaac ataatgtaga tctctccagg gccataaatg taaatggagt aagcttcaat     120
aatgtagaca ccagttcact tggcgcagca caggtaagac aaagtgctag ccgaggcaga     180
ggacttggtg agaagcgaaa agaaggagct gataagaaa gaaaaaaga aaagaagaa        240 gaaccaaaga agccaaatga aaataagctg aacaaccga atccaggaca accacaagca     300
caaggagatg gagcaaatgc aggacaacca caagcacaag gagatggagc aaatgcagga     360
```

```
caaccacaag cacagggtga tggagcaaat gcaggacaac cacaagcaca aggagatgga    420
gcaaatgcag gacaaccaca agcacagggt gatggagcaa atgcaggaca accacaagca    480
caaggagatg gagcaaatgc aggacaacca caagcacagg gtgatggagc aaatgcagga    540
caaccacaag cacaaggaga tggagcaaat gcaggacaac cacaagcaca gggtgatgga    600
gcaaatgcag gacaaccaca agcacagggt gatggagcaa atgcaggaca accacaagca    660
cagggtgatg gagcaaatgc aggacaacca caagcacagg gtgatagggc gaatgcagga    720
caaccacaag cacaaggaga tggggcaaat gtaccacgac aaggaagaaa cggggggaggt    780 gcaccagcag gaggaaatga ggggaataaa caagcaggaa aaggacaggg acaaaacaat    840
cagggtgcga atgccccaaa tgaaaaagtt gtgaatgatt acctacacaa aattagatct    900
agcgttacca ccgagtggac tccatgcagt gtaacctgtg gaaatggtgt aagaattaga    960
agaaaagctc atgcaggtaa taaaaaggca gaggaccttta ctatggatga ccttgaggtg   1020
gaagcttgtg taatggataa gtgcgctggc atatttaacg ttgtgagtaa ttcattaggg   1080
ttagtcatat tgttagtcct agcattattc aat                                 1113
```

<210> SEQ ID NO 59
<211> LENGTH: 332
<212> TYPE: PRT
<213> ORGANISM: Plasmodium berghei
<220> FEATURE:
<221> NAME/KEY: MISC_FEATURE
<222> LOCATION: (1)..(332)
<223> OTHER INFORMATION: CSP protein
<300> PUBLICATION INFORMATION:
<308> DATABASE ACCESSION NUMBER: GenBank Accession Number: M28887.1

<400> SEQUENCE: 59

Met Lys Lys Cys Thr Ile Leu Val Val Ala Ser Leu Leu Val Asn
1               5                   10                  15

Ser Leu Leu Pro Gly Tyr Gly Gln Asn Lys Ile Ile Gln Ala Gln Arg
            20                  25                  30

Asn Leu Asn Glu Leu Cys Tyr Asn Glu Gly Asn Asp Asn Lys Leu Tyr
        35                  40                  45

His Val Leu Asn Ser Lys Asn Gly Lys Ile Tyr Asn Arg Asn Thr Val
    50                  55                  60

Asn Arg Leu Leu Ala Asp Ala Pro Glu Gly Lys Lys Asn Glu Lys Lys
65                  70                  75                  80

Asn Glu Lys Ile Glu Arg Asn Asn Lys Leu Lys Gln Pro Pro Pro Pro
                85                  90                  95

Pro Asn Pro Asn Asp Pro Pro Pro Asn Pro Asn Asp Pro Pro Pro
            100                 105                 110

Pro Asn Pro Asn Asp Pro Pro Pro Asn Pro Asn Asp Pro Ala Pro
            115                 120                 125

Pro Asn Ala Asn Asp Pro Ala Pro Pro Asn Ala Asn Asp Pro Ala Pro
        130                 135                 140

Pro Asn Ala Asn Asp Pro Ala Pro Pro Asn Ala Asn Asp Pro Ala Pro
145                 150                 155                 160

Pro Asn Ala Asn Asp Pro Ala Pro Pro Asn Ala Asn Asp Pro Ala Pro
                165                 170                 175

Pro Asn Ala Asn Asp Pro Pro Pro Pro Asn Pro Asn Asp Pro Ala Pro
            180                 185                 190

Pro Gln Gly Asn Asn Asn Pro Gln Pro Gln Pro Arg Pro Gln Pro Gln
            195                 200                 205

Pro Gln Pro Gln Pro Gln Pro Gln Pro Gln Pro Gln Pro Arg
    210                 215                 220

Pro Gln Pro Gln Pro Gln Pro Gly Gly Asn Asn Asn Lys Asn Asn
225                 230                 235                 240

Asn Asn Asp Asp Ser Tyr Ile Pro Ser Ala Glu Lys Ile Leu Glu Phe
            245                 250                 255

Val Lys Gln Ile Arg Asp Ser Ile Thr Glu Glu Trp Ser Gln Cys Asn
                260                 265                 270

Val Thr Cys Gly Ser Gly Ile Arg Val Arg Lys Arg Lys Gly Ser Asn
            275                 280                 285

Lys Lys Ala Glu Asp Leu Thr Leu Glu Asp Ile Asp Thr Glu Ile Cys
290                 295                 300

Lys Met Asp Lys Cys Ser Ser Ile Phe Asn Ile Val Ser Asn Ser Leu
305                 310                 315                 320

Gly Phe Val Ile Leu Leu Val Leu Val Phe Phe Asn
            325                 330

<210> SEQ ID NO 60
<211> LENGTH: 999
<212> TYPE: DNA
<213> ORGANISM: Plasmodium berghei
<220> FEATURE:
<221> NAME/KEY: misc_feature
<222> LOCATION: (1)..(999)
<223> OTHER INFORMATION: CSP gene
<300> PUBLICATION INFORMATION:
<308> DATABASE ACCESSION NUMBER: GenBank Accession Number: M28887.1

<400> SEQUENCE: 60
atgaagaagt gtaccatttt agttgtagcg tcacttttat tagttaattc tctacttcca      60
ggatatggac aaaataaaat catccaagcc caaggaact taaacgagct atgttacaat      120
gaaggaaatg ataataaatt gtatcacgtg cttaactcta agaatggaaa aatatacaat      180
cgaaatacag tcaacagatt acttgccgat gctcccgaag gaaaaaaaaa tgagaaaaaa      240
aacgaaaaaa tagagcgtaa taataaattg aaacaaccac caccaccacc aaacccaaat      300
gacccaccac caccaaaccc aaatgaccca ccaccaccaa acccaaatga cccaccacca      360
ccaaacccaa atgacccagc accaccaaac gcaaatgacc cagcaccacc aaacgcaaat      420
gacccagcac caccaaacgc aaatgaccca gcaccaccaa acgcaaatga cccagcacca      480
ccaaacgcaa atgacccagc accaccaaac gcaaatgacc cagcaccacc aaacgcaaat      540
gacccaccac caccaaaccc aaatgaccca gcaccaccac aaggaaataa caatccacaa      600
ccacagccac ggccgcagcc acaaccacag ccacagccac aaccacagcc acagccacaa      660
ccacagccac gaccacagcc acaaccacag ccaggtggta ataacaataa caaaaataat      720
aataatgacg attcttatat cccaagcgcg gaaaaaatac tagaatttgt taaacagatc      780
agggatagta tcacagagga atggtctcaa tgtaacgtaa catgtggttc tggtataaga      840
gttagaaaac gaaaaggttc aaataagaaa gcagaagatt tgaccttaga agatattgat      900
actgaaattt gtaaaatgga taaatgttca agtatattta atattgtaag caattcatta      960
ggatttgtaa tattattagt attagtattc tttaattaa                             999

<210> SEQ ID NO 61
<211> LENGTH: 322
<212> TYPE: PRT
<213> ORGANISM: Plasmodium vivax
<220> FEATURE:
<221> NAME/KEY: MISC_FEATURE

```
<222> LOCATION: (1)..(322)
<223> OTHER INFORMATION: CSP protein
<300> PUBLICATION INFORMATION:
<308> DATABASE ACCESSION NUMBER: GenBank Accession Number: AY674050.1

<400> SEQUENCE: 61
```

Lys Ala Ile Asn Leu Asn Gly Val Asn Phe Asn Asn Val Asp Ala Ser
1               5                   10                  15

Ser Leu Gly Ala Ala His Val Gly Gln Ser Ala Ser Arg Gly Arg Gly
            20                  25                  30

Leu Gly Glu Asn Pro Asp Asp Glu Gly Asp Ala Lys Lys Lys
        35                  40                  45

Asp Gly Lys Lys Ala Glu Pro Lys Asn Pro Arg Glu Asn Lys Leu Lys
    50                  55                  60

Gln Pro Gly Asp Arg Ala Asp Gly Gln Pro Ala Gly Asp Arg Ala Asp
65                  70                  75                  80

Gly Gln Pro Ala Gly Asp Arg Ala Asp Gly Gln Pro Ala Gly Asp Arg
            85                  90                  95

Ala Ala Gly Gln Pro Ala Gly Asp Arg Ala Asp Gly Gln Pro Ala Gly
            100                 105                 110

Asp Arg Ala Ala Gly Gln Pro Ala Gly Asp Arg Ala Asp Gly Gln Pro
            115                 120                 125

Ala Gly Asp Arg Ala Ala Gly Gln Pro Ala Gly Asp Arg Ala Asp Gly
        130                 135                 140

Gln Pro Ala Gly Asp Arg Ala Ala Gly Gln Pro Ala Gly Asp Arg Ala
145                 150                 155                 160

Asp Gly Gln Pro Ala Gly Asp Arg Ala Ala Gly Gln Pro Ala Gly Asp
            165                 170                 175

Arg Ala Ala Gly Gln Pro Ala Gly Asp Arg Ala Asp Gly Gln Pro Ala
            180                 185                 190

Gly Asp Arg Ala Ala Gly Gln Pro Ala Gly Asp Arg Ala Ala Gly Gln
            195                 200                 205

Pro Ala Gly Asp Arg Ala Ala Gly Gln Pro Ala Gly Asn Gly Ala Gly
        210                 215                 220

Gly Gln Ala Ala Gly Gly Asn Ala Ala Asn Lys Lys Ala Glu Asp Ala
225                 230                 235                 240

Gly Gly Asn Ala Gly Gly Gln Gly Gln Asn Asn Glu Gly Ala Asn Ala
            245                 250                 255

Pro Asn Glu Lys Ser Val Lys Glu Tyr Leu Asp Lys Val Arg Ala Thr
        260                 265                 270

Val Gly Thr Glu Trp Thr Pro Cys Ser Val Thr Cys Gly Val Gly Val
        275                 280                 285

Arg Val Arg Arg Arg Val Asn Ala Ala Asn Lys Lys Pro Glu Asp Leu
        290                 295                 300

Thr Leu Asn Asp Leu Glu Thr Asp Val Cys Thr Met Asp Lys Cys Ala
305                 310                 315                 320

Gly Ile

```
<210> SEQ ID NO 62
<211> LENGTH: 968
<212> TYPE: DNA
<213> ORGANISM: Plasmodium vivax
<220> FEATURE:
<221> NAME/KEY: misc_feature
<222> LOCATION: (1)..(968)
<223> OTHER INFORMATION: CSP gene
<300> PUBLICATION INFORMATION:
```

<308> DATABASE ACCESSION NUMBER: GenBank Accession Number: AY674050.1

<400> SEQUENCE: 62

```
ccaaggccat aaatttaaat ggagtaaact tcaataatgt agacgccagt tcacttggcg      60
cggcacacgt aggacaaagt gctagccgag gcagaggact tggtgagaac ccagatgacg     120
aggaaggaga tgctaaaaaa aaaaaggatg gaaagaaagc agaaccaaaa aatccacgtg     180
aaaataagct gaaacaacca ggagacagag cagatggaca gccagcagga gacagagcag     240
atggacagcc agcaggagac agagcagatg gacagccagc aggtgataga gcagctggac     300
aaccagcagg tgatagagca gatggacagc cagcaggcga tagagcagct ggacagccag     360
caggcgatag agcagatgga cagccagcag gagatagagc agctggacag ccagcaggcg     420
atagagcaga tggacagcca gcaggagata gagcagctgg acagccagca ggcgatagag     480
cagatggaca gccagcagga gatagagcag ctggacaacc agcaggtgat agagcagctg     540
gacaaccagc aggagataga gcagatggac aaccagcagg agatagagca gctggacagc     600
cagcaggaga tagagcagct ggacagccag caggagatag agcagctgga cagccagcag     660
gaaatggtgc aggtggacag gcagcaggag gaaatgcggc aaacaagaag gcagaagacg     720
caggaggaaa cgcaggagga cagggacaaa ataatgaagg tgcgaatgcc ccaaatgaaa     780
agtctgtgaa agaataccta gataaagtta gagctaccgt tggcaccgaa tggactccat     840
gcagtgtaac ctgtggagtg ggtgtaagag tcagaagaag agttaatgca gctaacaaaa     900
aaccagagga tcttactttg aatgaccttg agactgatgt ttgtacaatg gataagtgtg     960
ctggcata                                                             968
```

<210> SEQ ID NO 63
<211> LENGTH: 429
<212> TYPE: PRT
<213> ORGANISM: Plasmodium malariae
<220> FEATURE:
<221> NAME/KEY: MISC_FEATURE
<222> LOCATION: (1)..(429)
<223> OTHER INFORMATION: CSP protein
<300> PUBLICATION INFORMATION:
<308> DATABASE ACCESSION NUMBER: GenBank Accession Number: J03992.1

<400> SEQUENCE: 63

```
Met Lys Lys Leu Ser Val Leu Ala Ile Ser Ser Phe Leu Ile Val Asp
1               5                   10                  15

Phe Leu Phe Pro Gly Tyr His His Asn Ser Asn Ser Thr Lys Ser Arg
                20                  25                  30

Asn Leu Ser Glu Leu Cys Tyr Asn Asn Val Asp Thr Lys Leu Phe Asn
            35                  40                  45

Glu Leu Glu Val Arg Tyr Ser Thr Asn Gln Asp His Phe Tyr Asn Tyr
        50                  55                  60

Asn Lys Thr Ile Arg Leu Leu Asn Glu Asn Asn Glu Lys Asp Gly
65                  70                  75                  80

Asn Val Thr Asn Glu Arg Lys Lys Lys Pro Thr Lys Ala Val Glu Asn
                85                  90                  95

Lys Leu Lys Gln Pro Pro Gly Asp Asp Asp Gly Ala Gly Asn Asp Ala
                100                 105                 110

Gly Asn Asp Ala Gly Asn Asp Ala Gly Asn Ala Ala Gly Asn Ala Ala
            115                 120                 125

Gly Asn Ala Ala Gly Asn Ala Ala Gly Asn Ala Ala Gly Asn Ala Ala
        130                 135                 140
```

Gly Asn Ala Ala Gly Asn Ala Ala Gly Asn Ala Ala Gly Asn Ala Ala
145                 150                 155                 160

Gly Asn Asp Ala Gly Asn Ala Ala Gly Asn Ala Ala Gly Asn Ala Ala
            165                 170                 175

Gly Asn Ala Ala Gly Asn Ala Ala Gly Asn Asp Ala Gly Asn Ala Ala
        180                 185                 190

Gly Asn Ala Ala Gly Asn Ala Ala Gly Asn Ala Ala Gly Asn Ala Ala
    195                 200                 205

Gly Asn Ala Ala Gly Asn Ala Ala Gly Asn Ala Ala Gly Asn Ala Ala
210                 215                 220

Gly Asn Ala Ala Gly Asn Asp Ala Gly Asn Ala Ala Gly Asn Ala Ala
225                 230                 235                 240

Gly Asn Ala Ala Gly Asn Ala Ala Gly Asn Ala Ala Gly Asn Ala Ala
            245                 250                 255

Gly Asn Ala Ala Gly Asn Ala Ala Gly Asn Ala Ala Gly Asn Ala Ala
        260                 265                 270

Gly Asn Ala Ala Gly Asn Ala Ala Gly Asn Ala Ala Gly Asn Ala Ala
    275                 280                 285

Gly Asn Ala Ala Gly Asn Ala Ala Gly Asn Ala Ala Gly Asn Ala Ala
290                 295                 300

Gly Asn Ala Ala Gly Asn Ala Ala Gly Asn Glu Lys Ala Lys Asn Lys
305                 310                 315                 320

Asp Asn Lys Val Asp Ala Asn Thr Asn Lys Lys Asp Asn Gln Glu Glu
            325                 330                 335

Asn Asn Asp Ser Ser Asn Gly Pro Ser Glu Glu His Ile Lys Asn Tyr
        340                 345                 350

Leu Glu Ser Ile Arg Asn Ser Ile Thr Glu Glu Trp Ser Pro Cys Ser
    355                 360                 365

Val Thr Cys Gly Ser Gly Ile Arg Ala Arg Arg Lys Val Gly Ala Lys
370                 375                 380

Asn Lys Lys Pro Ala Glu Leu Val Leu Ser Asp Leu Glu Thr Glu Ile
385                 390                 395                 400

Cys Ser Leu Asp Lys Cys Ser Ser Ile Phe Asn Val Val Ser Asn Ser
            405                 410                 415

Leu Gly Ile Val Leu Val Leu Val Leu Ile Leu Phe His
        420                 425

<210> SEQ ID NO 64
<211> LENGTH: 1545
<212> TYPE: DNA
<213> ORGANISM: Plasmodium malariae

<400> SEQUENCE: 64
tttcacatac ataatttgct gaatattaaa aaaaaataaa taataagtaa ataataaaaa     60
cacaaaaaag tatatataaa tatagacttg ctccaacatg aagaagttat ctgtcttagc    120
aatatcctct tttttaattg ttgatttcct cttccctgga tatcatcaca actcaaattc    180
caccaagtca agaaatttaa gtgagttgtg ttacaataat gtggacacta aattatttaa    240
tgagttagaa gtcagatata gcacgaatca agatcatttc tataactata ataagacaat    300
cagattactt aatgaaaata caatgaaaaa agatggaaat gtgaccaatg aaagaaaaaa    360
aaaacccaca aaagctgttt aaaataaatt gaacaacccc cccggagatg atgatggcgc    420
aggaaatgat gcaggaaatg atgcaggaaa tgatgcagga aatgcagcag gaaatgcagc    480
aggaaatgca gcaggaaatg cagcaggtaa cgcagcaggt aacgcagcag gaaatgcagc    540

```
aggaaatgca gcaggtaacg cagcaggaaa tgcagcagga aatgatgcag gaaatgcagc    600
aggtaacgca gcaggaaatg cagcaggaaa tgcagcagga aatgcagcag gaaatgatgc    660
aggaaatgca gcaggaaatg cagcaggaaa tgcagcaggt aacgcagcag gaaatgcagc    720
aggaaatgca gcaggtaacg cagcaggtaa cgcagcagga aatgcagcag gaaatgcagc    780
aggaaatgat gcaggaaatg cagcaggtaa cgcagcagga aatgcagcag gaaatgcagc    840
aggtaacgca gcaggtaacg cagcaggaaa tgcagcagga aatgcagcag gtaacgcagc    900
aggaaatgca gcaggaaatg cagcaggtaa cgcagcaggt aacgcagcag gaaatgcagc    960
aggaaatgca gcaggtaacg cagcaggaaa tgcagcagga aatgcagcag gtaacgcagc   1020
aggaaatgca gcaggaaatg aaaaagcgaa aataaggat aataaagtgg atgcaaatac    1080
gaataaaaag gacaaccagg aagaaaataa tgattcgtct aatggtccat ctgaagaaca   1140
tataaagaat tatttagaaa gtattcgtaa tagtattacg gaggaatggt caccatgtag   1200
tgtaacttgt ggaagtggta taagggctag aagaaaggtt ggtgcaaaaa ataagaaacc   1260
tgcagaatta gttttaagtg accttgaaac tgaaatttgt tcactagata aatgctccag   1320
tatatttaat gtcgtaagta attcgttagg aatagtatta gttttagtct taatactctt   1380
tcactaaata aatagcatgt atctttcgaa atattatata catatatatt tatatatatt   1440
ttttctttct tttttctttt ttttgtgaat gattactaat gtttgcactt aattgtatat   1500
atattatata tattcaatat ataattctaa aaattaccag tattt                   1545

<210> SEQ ID NO 65
<211> LENGTH: 388
<212> TYPE: PRT
<213> ORGANISM: Plasmodium gallinaceum

<400> SEQUENCE: 65

Met Lys Lys Leu Ala Ile Leu Ser Ala Ser Ser Phe Leu Phe Ala Asp
1               5                   10                  15

Phe Leu Phe Gln Glu Tyr Gln His Asn Gly Asn Tyr Lys Asn Phe Arg
            20                  25                  30

Leu Leu Asn Glu Val Cys Tyr Asn Asn Met Asn Ile Gln Leu Tyr Asn
        35                  40                  45

Glu Leu Glu Met Glu Asn Tyr Met Ser Asn Thr Tyr Phe Tyr Asn Asn
    50                  55                  60

Lys Lys Thr Ile Arg Leu Leu Gly Glu Asn Asp Asn Glu Ala Asn Val
65                  70                  75                  80

Asn Arg Ala Asn Asn Val Ala Asn Asp Asn Arg Ala Asn Gly Asn
                85                  90                  95

Arg Gly Asn Val Asn Arg Ala Asn Asp Arg Asn Ile Pro Tyr Phe Arg
            100                 105                 110

Glu Asn Val Val Asn Leu Asn Gln Pro Val Gly Gly Asn Gly Gly Val
        115                 120                 125

Gln Pro Ala Gly Gly Asn Gly Gly Val Gln Pro Ala Gly Gly Asn Gly
    130                 135                 140

Gly Val Gln Pro Ala Gly Gly Asn Gly Gly Val Gln Pro Ala Gly Gly
145                 150                 155                 160

Asn Gly Gly Val Gln Pro Ala Gly Gly Asn Gly Gly Val Gln Pro Ala
                165                 170                 175

Gly Gly Asn Gly Gly Val Gln Pro Ala Gly Gly Asn Gly Gly Ala Gln
            180                 185                 190
```

```
Pro Val Ala Ala Gly Gly Ala Gln Pro Val Ala Asp Gly Gly
        195                 200                 205

Val Gln Pro Leu Arg Gln Glu Gly Asp Ala Glu Asp Gly Gly Asn
    210                 215                 220

Gly Gly Ala Gln Pro Ala Gly Asn Gly Gly Ala Gln Pro Ala Gly
225                 230                 235                 240

Gly Asn Gly Gly Ala Gln Pro Ala Gly Asn Gly Gly Ala Gln Pro
                245                 250                 255

Ala Gly Gly Asn Gly Gly Ala Gln Pro Ala Gly Asn Asp Ala Ala
                260                 265                 270

Lys Pro Asp Gly Gly Asn Asp Asp Lys Pro Glu Gly Gly Asp Glu
                275                 280                 285

Lys Ser Glu Glu Glu Lys Glu Asp Glu Pro Ile Pro Asp Pro Thr Gln
    290                 295                 300

Glu Glu Ile Asp Lys Tyr Leu Lys Ser Ile Leu Gly Asn Val Thr Ser
305                 310                 315                 320

Glu Trp Thr Asn Cys Asn Val Thr Cys Gly Lys Gly Ile Gln Ala Lys
                325                 330                 335

Ile Lys Ser Thr Ser Ala Asn Lys Lys Arg Glu Glu Ile Thr Pro Asn
                340                 345                 350

Asp Val Glu Val Lys Ile Cys Glu Leu Glu Arg Cys Ser Phe Ser Ile
                355                 360                 365

Phe Asn Val Ile Ser Asn Ser Leu Gly Leu Ala Ile Ile Leu Thr Phe
    370                 375                 380

Leu Phe Phe Tyr
385

<210> SEQ ID NO 66
<211> LENGTH: 1260
<212> TYPE: DNA
<213> ORGANISM: Plasmodium gallinaceum
<220> FEATURE:
<221> NAME/KEY: misc_feature
<222> LOCATION: (1)..(1260)
<223> OTHER INFORMATION: CSP gene
<300> PUBLICATION INFORMATION:
<308> DATABASE ACCESSION NUMBER: GenBank Accession Number: U65959.1

<400> SEQUENCE: 66
tgatttcact aaaaatttta atatatataa tataatagtt taaaatagtg aagaatatat      60
ataggtgtac ttcaaaatga agaaattagc cattttatcg gcatcttcgt ttttatttgc     120
tgactttcta tttcaagagt atcaacacaa tggaaactac aaaaatttta gactttaaa     180 tgaggtgtgt tataataata tgaatattca attatataat gaattggaaa tggaaaatta     240
catgagtaac acatatttct ataataataa aaaaaccatt agattacttg agaaaatga     300 taatgaagca aatgttaata gagcaaataa taatgtagca aatgataata gagcaaatgg     360
taatagagga aatgttaata gagcaaatga tagaaatata ccatattta gagaaaatgt     420 tgtgaatctt aatcaaccag ttggaggaaa tggtggtgtt caacctgctg gaggaaatgg     480
tggtgttcaa cctgctggag gaaatggtgg tgttcaacct gctggaggta atggtggtgt     540
tcaacctgct ggaggaaatg gtggtgttca acctgctgga ggaaatggtg gtgttcaacc     600
tgctggaggt aatggtggtg ttcaacctgc tggaggcaat ggtggtgctc aaccagttgc     660
agcaggtggt ggtgctcaac cagttgtagc agatggtggt gttcagcctc ttagacaaga     720
aggtgatgct gaagaggatg gaggaaatgg tggtgcccaa ccagctggag gaaatggtgg     780
```

```
tgctcaacca gctggaggaa atggtggtgc tcaaccagct ggaggaaatg gtggtgccca    840
acctgctgga ggaaatggtg gtgctcaacc tgctggagga atgatgctg ctaaacctga    900 tggaggaaat gatgatgaca aacctgaagg aggagatgaa aaatctgaag aagaaaagga    960
ggatgaacca ataccagatc caactcaaga gaaatagat aaatatttaa aaagcatact   1020
tggtaatgtt acatctgaat ggactaattg caatgtaaca tgtgggaaag gtatacaagc   1080
taaaataaaa tctacatctg ctaataagaa aagagaagaa attactccaa atgatgttga   1140
agtaaaaatt tgcgaactag aaagatgttc ttttagcata tttaatgtta taagcaattc   1200
gttaggttta gctataattt taaccttttt attttttat taaataaata ttataaaatt   1260
```

<210> SEQ ID NO 67
<211> LENGTH: 388
<212> TYPE: PRT
<213> ORGANISM: Plasmodium reichenowi
<220> FEATURE:
<221> NAME/KEY: MISC_FEATURE
<222> LOCATION: (1)..(388)
<223> OTHER INFORMATION: CSP protein
<300> PUBLICATION INFORMATION:
<308> DATABASE ACCESSION NUMBER: GenBank Accession Number: U65959.1

<400> SEQUENCE: 67

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Ala Asp Asn
65                  70                  75                  80

Gly Asp Ala Asp Asn Gly Asp Glu Gly Ile Asp Glu Asn Arg Arg His
                85                  90                  95

Arg Asn Lys Glu Gly Lys Glu Lys Leu Lys Lys Pro Lys His Asn Lys
            100                 105                 110

Leu Lys Gln Pro Gly Asn Asp Asn Val Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Val Asp Pro Asn Ala Asn Pro Asn
145                 150                 155                 160

Val Asn Pro Asn Ala Asn Pro Asn Val Asp Pro Asn Ala Asn Pro Asn
                165                 170                 175

Val Asn Pro Asn Ala Asn Pro Asn Val Asn Pro Asn Ala Asn Pro Asn
            180                 185                 190

Val Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Arg Asn Asn Glu Ala Asn Gly Gln
```

```
                  260               265               270
Gly His Asn Lys Pro Asn Asp Gln Asn Arg Asn Val Asn Glu Asn Ala
                275               280               285

Asn Ala Asn Ala Gly Arg Asn Asn Asn Glu Glu Pro Ser Asp
        290               295               300

Lys His Ile Glu Glu Phe Leu Lys Gln Ile Gln Asn Asn Leu Ser Thr
305               310               315               320

Glu Trp Ser Pro Cys Ser Val Thr Cys Gly Asn Gly Ile Gln Val Arg
                325               330               335

Ile Lys Pro Gly Ser Ala Gly Lys Pro Lys Asp Gln Leu Asp Tyr Glu
                340               345               350

Asn Asp Leu Glu Lys Lys Ile Cys Lys Met Glu Lys Cys Ser Ser Val
                355               360               365

Phe Asn Val Val Asn Ser Ser Ile Gly Leu Ile Met Val Leu Ser Phe
                370               375               380

Leu Phe Leu Asn
385

<210> SEQ ID NO 68
<211> LENGTH: 1167
<212> TYPE: DNA
<213> ORGANISM: Plasmodium reichenowi

<400> SEQUENCE: 68
atgatgagaa aattagctat tttatctgtt tcttcctttt tatttgttga ggccttattc      60
caggaatatc agtgctatgg aagttcgtca aacacaaggg ttctaaatga attaaattat     120
gataatgcag gcactaattt atataatgaa ttagaaatga attattatgg gaaacaggaa     180
aattggtata gccttaaaaa aaatagtaga tcacttggag aaaatgatga tgcagataat     240
ggtgatgcag ataatggtga tgaaggtata gatgaaaata aagacatag aaataaagaa      300 ggcaaagaga aattaaagaa accaaaacat aataaattaa agcaaccagg aatgataat      360 gttgatccaa atgccaaccc aaatgtagat ccaaatgcca acccaaatgt agatcccaat     420
gcaaacccaa atgtagatcc caatgcaaac ccaaatgtag atcctaatgc aaacccaaat     480
gtaaatccca atgcaaaccc aaatgtagat cctaatgcaa acccaaatgt aaatcccaat     540
gcaaacccaa atgtaaatcc aatgcaaac ccaaatgtaa atcccaatgc aaacccaaat      600
gcaaatccta atgcaaatcc caatgcaaat cccaatgcaa acccaaatgc aaatcctaat     660
gcaaatccca atgcaaatcc caatgcaaac ccaaatgcaa atcctaatgc aaatcctaat     720
gcaaatccta atgcaaatcc taatgcaaat cctaatgcca atccaaacgc aaacccaaat     780
gcaaatccta atagaaacaa tgaagctaat ggacaaggtc acaataagcc aaatgaccaa     840
aaccgaaatg taaatgaaaa tgctaatgcc aacaatgctg gaagaaataa taataacgaa     900
gaaccaagtg ataagcacat agaagaattt ttaaagcaaa tacaaaataa tctttcaact     960
gaatggtccc catgtagtgt aacttgtgga atggtattc aagttagaat aaagcctggc     1020
tctgctggta aacctaaaga ccaattagat tatgaaaatg accttgaaaa aaaaatttgt     1080
aaaatggaaa aatgttccag tgtgttcaat gtcgtaaata gttcaatagg attaataatg     1140
gtattatcct tcttgttcct taattag                                         1167

<210> SEQ ID NO 69
<211> LENGTH: 200
<212> TYPE: DNA
<213> ORGANISM: Artificial Sequence
```

<220> FEATURE:
<223> OTHER INFORMATION: Description of Artificial Sequence: Synthetic
      DNA FLAP of CAEV

<400> SEQUENCE: 69
gttccagcca caatttgtcg ctgtagaatc agccatagca gcagccctag tcgccataaa    60
tataaaaaga aagggtgggc tggggacaag ccctatggat atttttatat ataataaaga   120
acagaaaaga ataaataata aatataataa aaattctcaa aaattcaat tctgttatta    180 cagaataagg aaaagaggac                                              200

<210> SEQ ID NO 70
<211> LENGTH: 200
<212> TYPE: DNA
<213> ORGANISM: Artificial Sequence
<220> FEATURE:
<223> OTHER INFORMATION: Description of Artificial Sequence: Synthetic
      DNA FLAP of EIAV

<400> SEQUENCE: 70
cttgtaacaa agggagggaa agtatgggag acagacacc atggaagta tttatcacta      60 atcaagcaca agtaatacat gagaaacttt tactacagca agcacaatcc tccaaaaaat   120
tttgttttta caaatcccct ggtgaacatg attggaaggg acctactagg gtgctgtgga   180
agggtgatgg tgcagtagta                                              200

<210> SEQ ID NO 71
<211> LENGTH: 200
<212> TYPE: DNA
<213> ORGANISM: Artificial Sequence
<220> FEATURE:
<223> OTHER INFORMATION: Description of Artificial Sequence: Synthetic
      DNA FLAP of VISNA

<400> SEQUENCE: 71
ggaccctcat tactctaaat ataaaaagaa agggtgggct agggacaagc cctatggata    60 tattttatatt taataaggaa caacaaagaa tacagcaaca aagtaaatca aaacaagaaa   120
aaattcgatt ttgttattac agaacaagaa aaagagggca tccaggagag tggcaaggac   180
caacacaggt actttggggc                                              200

<210> SEQ ID NO 72
<211> LENGTH: 200
<212> TYPE: DNA
<213> ORGANISM: Artificial Sequence
<220> FEATURE:
<223> OTHER INFORMATION: Description of Artificial Sequence: Synthetic
      DNA FLAP of VISNA

<400> SEQUENCE: 72
tactgatggc ttgcatactt cacaatttta aagaaaggg aggaataggg ggacagactt     60
cagcagagag actaattaat ataataacaa cacaattaga aatacaacat ttacaaacca   120
aaattcaaaa aatttttaaat tttagagtct actacagaga agggagagac cctgtgtgga   180
aaggaccggc acaattaatc                                              200

<210> SEQ ID NO 73
<211> LENGTH: 200
<212> TYPE: DNA
<213> ORGANISM: Artificial Sequence
<220> FEATURE:
<223> OTHER INFORMATION: Description of Artificial Sequence: Synthetic
      DNA FLAP of HIV-2 ROD

<400> SEQUENCE: 73

```
tgcatgaatt ttaaaagaag gggggaata ggggatatga ctccatcaga aagattaatc    60
aatatgatca ccacagaaca agagatacaa ttcctccaag ccaaaaattc aaaattaaaa   120
gattttcggg tctatttcag agaaggcaga gatcagttgt ggaaaggacc tggggaacta   180
ctgtggaaag gagaaggagc                                               200
```

<210> SEQ ID NO 74
<211> LENGTH: 200
<212> TYPE: DNA
<213> ORGANISM: Artificial Sequence
<220> FEATURE:
<223> OTHER INFORMATION: Description of Artificial Sequence: Synthetic
DNA FLAP of HIV-1 LAI

<400> SEQUENCE: 74

```
cagtattcat ccacaatttt aaaagaaaag ggggattgg ggggtacagt gcaggggaaa    60
gaatagtaga cataatagca acagacatac aaactaaaga attacaaaaa caaattacaa   120
aaattcaaaa ttttcgggtt tattacaggg acagcagaga tccactttgg aaaggaccag   180
caaagctcct ctggaaaggt                                               200
```

<210> SEQ ID NO 75
<211> LENGTH: 119
<212> TYPE: DNA
<213> ORGANISM: Artificial Sequence
<220> FEATURE:
<223> OTHER INFORMATION: Description of Artificial Sequence: Synthetic
DNA FLAP of HIV-1

<400> SEQUENCE: 75

```
ttttaaaaga aaagggggga ttgggggggta cagtgcaggg gaaagaatag tagacataat    60
agcaacagac atacaaacta agaattaca aaaacaaatt acaaaaattc aaaattttc    119
```

<210> SEQ ID NO 76
<211> LENGTH: 1578
<212> TYPE: DNA
<213> ORGANISM: Artificial Sequence
<220> FEATURE:
<223> OTHER INFORMATION: Description of Artificial Sequence: Synthetic
VSV-G Indiana optimized

<400> SEQUENCE: 76

```
ctcggatcct gatcagccac catgaaatgc ctgctctatc tggccttcct ctttatcggc    60
gtgaactgta agttcacgat cgtgtttccc cacaatcaga agggaaactg gaagaacgtc   120
ccgagcaact accactactg ccctagctca agcgacctga actggcacaa cgacctgatc   180
ggcaccgcta tccaggtgaa gatgccaaag agccacaagg ccatccaagc cgacggctgg   240
atgtgtcacg ccagcaaatg ggtgacgacg tgcgattttc gctggtatgg ccccaagtac   300
atcacccaat caatccgctc atttacaccc agcgtggagc aatgtaagga gagcatcgag   360
cagaccaagc aggggacctg gctcaacccc ggcttcccac cgcaaagctg cggatacgcc   420
accgtgaccg acgctgaggc cgtcatcgtg caggtgaccc cgcaccacgt gctggtggac   480
gagtacaccg gcgagtgggt ggattcacag tttatcaacg gaaagtgtag caattacatc   540
tgcccccaccg tgcacaacag caccacctgg cactcagact ataaggtgaa gggcctctgc   600
gacagcaatg tgatctcaat ggacatcacc ttctttagcg aagacggcga actctcaagc   660
ctcgggaagg aaggcaccgg gttccgcagc aattactttg cttacgaaac cggcggcaag   720
```

```
gcctgcaaga tgcaatactg caagcactgg ggcgtgcgcc tgccaagcgg cgtgtggttt      780
gagatggctg ataaggacct gttcgccgct gcccgcttcc cggaatgccc cgagggagc      840 agcatcagcg cccccagcca gacatcagtg gacgtgagcc tgatccagga tgtggaacgc      900
atcctggact acagcctgtg tcaggaaacg tggagcaaga tccgcgccgg actgcctatc      960
agccccgtgg atctcagcta cctggcccca aagaacccag gcaccggacc cgcctttaca     1020
atcatcaacg gcaccctgaa gtactttgaa acacgctaca tccgcgtcga catcgccgct     1080
cccatcctct cacgcatggt gggcatgatc tcagggacga ccacggagcg cgagctgtgg     1140
gatgactggg ccccgtatga agatgtggag atcggaccta acggcgtgct gcgcacatca     1200
agcgggtaca agttcccgct gtacatgatc ggccacggca tgctggacag cgacctgcac     1260
ctcagctcaa aggcccaggt ctttgagcac ccacacatcc aggacgctgc cagccagctc     1320
cccgacgacg aaagcctgtt ctttggagat acagggctca gcaagaaccc catcgagctg     1380
gtcgagggct ggttctcaag ctggaagagc agcatcgctt cattttttt catcatcggc     1440 ctcatcatcg ggctgtttct ggtgctgcgc gtcggcatcc acctgtgcat caagctgaag     1500
cacaccaaga agcgccagat ctataccgac atcgagatga tcgcctgggg aagtaagaa      1560 ttctgcagat atccagca                                                   1578
```

<210> SEQ ID NO 77
<211> LENGTH: 511
<212> TYPE: PRT
<213> ORGANISM: Artificial Sequence
<220> FEATURE:
<223> OTHER INFORMATION: Description of Artificial Sequence: Synthetic
      VSV-G Indiana

<400> SEQUENCE: 77

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Ile Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp

```
                195                 200                 205
Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 78
<211> LENGTH: 1597
<212> TYPE: DNA
<213> ORGANISM: Artificial Sequence
<220> FEATURE:
<223> OTHER INFORMATION: Description of Artificial Sequence: Synthetic
      VSV-G New Jersey optimized

<400> SEQUENCE: 78
taccgagctc ggatcctgat cagccaccat gctgtcatat ctgatctttg ccctggctgt    60
gagcccaatc ctcggaaaga tcgaaatcgt gttcccacaa cacaccacag gggactggaa   120
gcgcgtgccc cacgagtaca actactgccc gacctcagcc gacaagaata gccacggcac   180
gcagaccggc atccctgtgg agctgaccat gcccaagggg ctcacaacgc accaagtcga   240
aggcttcatg tgccacagcg ctctctggat gacaacctgc gattttcgct ggtatggccc   300
```

```
caagtacatc acgcacagca tccacaatga ggaaccaacc gactaccagt gcctcgaagc    360
catcaagtca taaaggatg gggtgagctt caaccccggc ttcccgcccc aatcatgtgg    420
ctacggcacc gtgaccgacg ccgaggccca catcgtgacc gtgacacccc actcagtcaa    480
ggtgacgag tacacaggcg aatggatcga ccccacttc atcggggggcc gctgtaaggg    540
ccaaatctgc gagaccgtgc acaacagcac caagtggttt acgtcatcag acggcaaag    600
cgtgtgcagc caactgttta cgctcgtggg cggcatcttc tttagcgaca gcaggagat    660
caccagcatg ggcctcccgg agacaggaat ccgcagcaac tactttccgt acatcagcac    720
cgagggaatc tgtaagatgc ttttttgccg caagcaggga tataagctga agaatgacct    780
gtggttccag atcatggacc cggacctgga caagaccgtc cgcgatctgc cccacatcaa    840
ggactgtgat ctgtcatcaa gcatcatcac ccccggagaa cacgccacgg acatcagcct    900
catcagcgat gtggagcgca tcctcgacta cgctctctgc cagaacacat ggagcaagat    960
cgaaagcggc gaacccatca ccccagtgga cctgagctat ctcggcccaa agaacccgg    1020
cgtggggccc gtgttcacca tcatcaacgg gagcctgcac tactttacaa gcaagtatct    1080
gcgcgtggag ctcgaaagcc cagtcatccc ccgcatggag gggaaggtgg ccgggacccg    1140
catcgtgcgc cagctgtggg accagtggtt ccctttttggc gaggtggaaa tcggccccaa    1200
cggcgtgctg aagaccaagc aaggatataa gttcccgctg cacatcatcg ggacgggcga    1260
agtggacagc gatatcaaga tggagcgcgt ggtcaagcac tgggagcacc cacacatcga    1320
ggctgctcag acctttctca agaaggacga taccggcgaa gtcctgtatt acggggatac    1380
gggagtgagc aagaaccctg tggagctggt ggaaggctgg ttcagcggat ggcgctcaag    1440
cctgatgggc gtgctggccg tcatcatcgg atttgtgatc ctgatgttcc tcatcaagct    1500
gatcggcgtg ctgtcaagcc tgttccgccc taagcgccgc ccaatctaca agagcgacgt    1560
cgagatggcc cactttcgct aagaattctg cagatat                            1597
```

<210> SEQ ID NO 79
<211> LENGTH: 1563
<212> TYPE: DNA
<213> ORGANISM: Artificial Sequence
<220> FEATURE:
<223> OTHER INFORMATION: Description of Artificial Sequence: Synthetic fusion VSV-G Ghandipura / Indiana
<220> FEATURE:
<221> NAME/KEY: CDS
<222> LOCATION: (1)..(1560)

<400> SEQUENCE: 79

```
atg acc agc agc gtg acc atc agc gtg gtg ctg ctg atc agc ttc atc     48
Met Thr Ser Ser Val Thr Ile Ser Val Val Leu Leu Ile Ser Phe Ile
1               5                   10                  15 acc ccc ctg tac agc tac ctg agc att gcc ttc ccc gag aac acc aag     96
Thr Pro Leu Tyr Ser Tyr Leu Ser Ile Ala Phe Pro Glu Asn Thr Lys
            20                  25                  30 ctg gac tgg aag ccc gtg acc aag aac acc cgg tac tgc ccc atg ggc    144
Leu Asp Trp Lys Pro Val Thr Lys Asn Thr Arg Tyr Cys Pro Met Gly
        35                  40                  45 ggc gag tgg ttt ctg gaa ccc ggc ctg cag gaa gag agc ttc ctg agc    192
Gly Glu Trp Phe Leu Glu Pro Gly Leu Gln Glu Glu Ser Phe Leu Ser
    50                  55                  60 agc acc ccc atc ggc gcc acc ccc agc aag agc gac ggc ttc ctg tgc    240
Ser Thr Pro Ile Gly Ala Thr Pro Ser Lys Ser Asp Gly Phe Leu Cys
65                  70                  75                  80
```

```
cac gcc gcc aag tgg gtg acc acc tgc gac ttc cgg tgg tac ggc ccc       288
His Ala Ala Lys Trp Val Thr Thr Cys Asp Phe Arg Trp Tyr Gly Pro
             85                  90                  95 aag tac atc acc cac agc atc cac aac atc aag ccc acc aga agc gac       336
Lys Tyr Ile Thr His Ser Ile His Asn Ile Lys Pro Thr Arg Ser Asp
            100                 105                 110 tgc gac aca gcc ctg gcc tct tac aag agc ggc acc ctg gtg tcc ctg       384
Cys Asp Thr Ala Leu Ala Ser Tyr Lys Ser Gly Thr Leu Val Ser Leu
        115                 120                 125 ggc ttc cct ccc gag agc tgc ggc tac gcc agc gtg acc gac agc gag       432
Gly Phe Pro Pro Glu Ser Cys Gly Tyr Ala Ser Val Thr Asp Ser Glu
    130                 135                 140 ttc ctg gtg att atg att acc ccc cac cac gtg ggc gtg gac gac tac       480
Phe Leu Val Ile Met Ile Thr Pro His His Val Gly Val Asp Asp Tyr
145                 150                 155                 160 cgg ggc cac tgg gtg gac cct ctg ttc gtg gga ggg gaa tgc gac cag       528
Arg Gly His Trp Val Asp Pro Leu Phe Val Gly Gly Glu Cys Asp Gln
                165                 170                 175 agc tac tgc gat acc atc cac aac tcc agc gtg tgg att ccc gcc gac       576
Ser Tyr Cys Asp Thr Ile His Asn Ser Ser Val Trp Ile Pro Ala Asp
            180                 185                 190 cag acc aag aag aac atc tgc ggc cag agc ttc acc cct ctg acc gtg       624
Gln Thr Lys Lys Asn Ile Cys Gly Gln Ser Phe Thr Pro Leu Thr Val
        195                 200                 205 acc gtg gcc tac gac aag acc aaa gag att gcc gcc gga ggg atc gtg       672
Thr Val Ala Tyr Asp Lys Thr Lys Glu Ile Ala Ala Gly Gly Ile Val
    210                 215                 220 ttc aag agc aag tac cac agc cac atg gaa ggc gcc agg acc tgc aga       720
Phe Lys Ser Lys Tyr His Ser His Met Glu Gly Ala Arg Thr Cys Arg
225                 230                 235                 240 ctg tcc tac tgc ggc cgg aac ggc atc aag ttc ccc aac ggc gag tgg       768
Leu Ser Tyr Cys Gly Arg Asn Gly Ile Lys Phe Pro Asn Gly Glu Trp
                245                 250                 255 gtg tcc ctg atg ctg aag ctg cgg agc aag cgg aac ctg tac ttc ccc       816
Val Ser Leu Met Leu Lys Leu Arg Ser Lys Arg Asn Leu Tyr Phe Pro
            260                 265                 270 tgc ctg aag atg tgc ccc acc ggc atc cgg ggc gag atc tac ccc agc       864
Cys Leu Lys Met Cys Pro Thr Gly Ile Arg Gly Glu Ile Tyr Pro Ser
        275                 280                 285 atc aga tgg gcc cag gtg ctg acc agc gag atc cag aga atc ctg gac       912
Ile Arg Trp Ala Gln Val Leu Thr Ser Glu Ile Gln Arg Ile Leu Asp
    290                 295                 300 tac agc ctg tgc cag aac acc tgg gac aag gtg gag cgg aaa gag ccc       960
Tyr Ser Leu Cys Gln Asn Thr Trp Asp Lys Val Glu Arg Lys Glu Pro
305                 310                 315                 320 ctg agc ccc ctg gac ctg agc tac ctg gcc agc aag tcc ccc ggc aag      1008
Leu Ser Pro Leu Asp Leu Ser Tyr Leu Ala Ser Lys Ser Pro Gly Lys
                325                 330                 335 ggc ctg gcc tac acc gtg atc aac ggc acc ctg agc ttc gcc cac acc      1056
Gly Leu Ala Tyr Thr Val Ile Asn Gly Thr Leu Ser Phe Ala His Thr
            340                 345                 350 aga tac gtg cgg atg tgg atc gac ggc ccc gtg ctg aaa gag ccc aag      1104
Arg Tyr Val Arg Met Trp Ile Asp Gly Pro Val Leu Lys Glu Pro Lys
        355                 360                 365 ggc aag aga gag agc ccc agc ggc atc agc agc gac atc tgg acc cag      1152
Gly Lys Arg Glu Ser Pro Ser Gly Ile Ser Ser Asp Ile Trp Thr Gln
    370                 375                 380 tgg ttc aag tac ggc gac atg gaa atc ggc ccc aac ggc ctg ctg aaa      1200
Trp Phe Lys Tyr Gly Asp Met Glu Ile Gly Pro Asn Gly Leu Leu Lys
385                 390                 395                 400
```

```
aca gcc ggc gga tac aag ttt cct tgg cac ctg atc ggc atg ggc atc    1248
Thr Ala Gly Gly Tyr Lys Phe Pro Trp His Leu Ile Gly Met Gly Ile
                405                 410                 415 gtg gac aac gag ctg cac gag ctg tcc gag gcc aac ccc ctg gat cac    1296
Val Asp Asn Glu Leu His Glu Leu Ser Glu Ala Asn Pro Leu Asp His
            420                 425                 430 ccc cag ctg ccc cac gcc cag agc att gcc gac gac agc gag gaa atc    1344
Pro Gln Leu Pro His Ala Gln Ser Ile Ala Asp Asp Ser Glu Glu Ile
        435                 440                 445 ttc ttc ggc gac acc ggc gtg agc aag aac ccc gtg gaa ctg gtg aca    1392
Phe Phe Gly Asp Thr Gly Val Ser Lys Asn Pro Val Glu Leu Val Thr
450                 455                 460 ggc tgg ttc acc agc tgg aaa agc agc atc gct tca ttt ttt ttc atc    1440
Gly Trp Phe Thr Ser Trp Lys Ser Ser Ile Ala Ser Phe Phe Phe Ile
465                 470                 475                 480 atc ggc ctc atc atc ggg ctg ttt ctg gtg ctg cgc gtc ggc atc cac    1488
Ile Gly Leu Ile Ile Gly Leu Phe Leu Val Leu Arg Val Gly Ile His
                485                 490                 495 ctg tgc atc aag ctg aag cac acc aag aag cgc cag atc tat acc gac    1536
Leu Cys Ile Lys Leu Lys His Thr Lys Lys Arg Gln Ile Tyr Thr Asp
            500                 505                 510 atc gag atg aat cgc ctg ggg aag taa                                 1563
Ile Glu Met Asn Arg Leu Gly Lys
        515                 520

<210> SEQ ID NO 80
<211> LENGTH: 520
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 80

Met Thr Ser Ser Val Thr Ile Ser Val Val Leu Leu Ile Ser Phe Ile
1               5                   10                  15

Thr Pro Leu Tyr Ser Tyr Leu Ser Ile Ala Phe Pro Glu Asn Thr Lys
            20                  25                  30

Leu Asp Trp Lys Pro Val Thr Lys Asn Thr Arg Tyr Cys Pro Met Gly
        35                  40                  45

Gly Glu Trp Phe Leu Glu Pro Gly Leu Gln Glu Glu Ser Phe Leu Ser
    50                  55                  60

Ser Thr Pro Ile Gly Ala Thr Pro Ser Lys Ser Asp Gly Phe Leu Cys
65                  70                  75                  80

His Ala Ala Lys Trp Val Thr Thr Cys Asp Phe Arg Trp Tyr Gly Pro
                85                  90                  95

Lys Tyr Ile Thr His Ser Ile His Asn Ile Lys Pro Thr Arg Ser Asp
            100                 105                 110

Cys Asp Thr Ala Leu Ala Ser Tyr Lys Ser Gly Thr Leu Val Ser Leu
        115                 120                 125

Gly Phe Pro Pro Glu Ser Cys Gly Tyr Ala Ser Val Thr Asp Ser Glu
    130                 135                 140

Phe Leu Val Ile Met Ile Thr Pro His Val Gly Val Asp Asp Tyr
145                 150                 155                 160

Arg Gly His Trp Val Asp Pro Leu Phe Val Gly Gly Glu Cys Asp Gln
                165                 170                 175

Ser Tyr Cys Asp Thr Ile His Asn Ser Ser Val Trp Ile Pro Ala Asp
            180                 185                 190
```

```
Gln Thr Lys Lys Asn Ile Cys Gly Gln Ser Phe Thr Pro Leu Thr Val
            195                 200                 205

Thr Val Ala Tyr Asp Lys Thr Lys Glu Ile Ala Ala Gly Gly Ile Val
210                 215                 220

Phe Lys Ser Lys Tyr His Ser His Met Glu Gly Ala Arg Thr Cys Arg
225                 230                 235                 240

Leu Ser Tyr Cys Gly Arg Asn Gly Ile Lys Phe Pro Asn Gly Glu Trp
                245                 250                 255

Val Ser Leu Met Leu Lys Leu Arg Ser Lys Arg Asn Leu Tyr Phe Pro
            260                 265                 270

Cys Leu Lys Met Cys Pro Thr Gly Ile Arg Gly Glu Ile Tyr Pro Ser
            275                 280                 285

Ile Arg Trp Ala Gln Val Leu Thr Ser Glu Ile Gln Arg Ile Leu Asp
            290                 295                 300

Tyr Ser Leu Cys Gln Asn Thr Trp Asp Lys Val Glu Arg Lys Glu Pro
305                 310                 315                 320

Leu Ser Pro Leu Asp Leu Ser Tyr Leu Ala Ser Lys Ser Pro Gly Lys
                325                 330                 335

Gly Leu Ala Tyr Thr Val Ile Asn Gly Thr Leu Ser Phe Ala His Thr
            340                 345                 350

Arg Tyr Val Arg Met Trp Ile Asp Gly Pro Val Leu Lys Glu Pro Lys
            355                 360                 365

Gly Lys Arg Glu Ser Pro Ser Gly Ile Ser Ser Asp Ile Trp Thr Gln
            370                 375                 380

Trp Phe Lys Tyr Gly Asp Met Glu Ile Gly Pro Asn Gly Leu Leu Lys
385                 390                 395                 400

Thr Ala Gly Gly Tyr Lys Phe Pro Trp His Leu Ile Gly Met Gly Ile
                405                 410                 415

Val Asp Asn Glu Leu His Glu Leu Ser Glu Ala Asn Pro Leu Asp His
            420                 425                 430

Pro Gln Leu Pro His Ala Gln Ser Ile Ala Asp Ser Glu Glu Ile
            435                 440                 445

Phe Phe Gly Asp Thr Gly Val Ser Lys Asn Pro Val Glu Leu Val Thr
            450                 455                 460

Gly Trp Phe Thr Ser Trp Lys Ser Ser Ile Ala Ser Phe Phe Phe Ile
465                 470                 475                 480

Ile Gly Leu Ile Ile Gly Leu Phe Leu Val Leu Arg Val Gly Ile His
                485                 490                 495

Leu Cys Ile Lys Leu Lys His Thr Lys Lys Arg Gln Ile Tyr Thr Asp
            500                 505                 510

Ile Glu Met Asn Arg Leu Gly Lys
            515                 520

<210> SEQ ID NO 81
<211> LENGTH: 1539
<212> TYPE: DNA
<213> ORGANISM: Artificial Sequence
<220> FEATURE:
<223> OTHER INFORMATION: Description of Artificial Sequence: Synthetic
      fusion VSV-G Cocal / Indiana
<220> FEATURE:
<221> NAME/KEY: CDS
<222> LOCATION: (1)..(1536)

<400> SEQUENCE: 81 atg aac ttt ctg ctg ctg aca ttc atc gtg ctg cct ctg tgc agc cac      48
```

```
                Met Asn Phe Leu Leu Thr Phe Ile Val Leu Pro Leu Cys Ser His
                1               5                  10                 15 gcc aag ttc agc atc gtg ttc ccc cag agc cag aag ggc aac tgg aag         96
Ala Lys Phe Ser Ile Val Phe Pro Gln Ser Gln Lys Gly Asn Trp Lys
                20                  25                  30 aac gtg ccc agc agc tac cac tac tgc ccc agc agc agc gac cag aac        144
Asn Val Pro Ser Ser Tyr His Tyr Cys Pro Ser Ser Ser Asp Gln Asn
            35                  40                  45 tgg cac aac gac ctg ctg ggc atc acc atg aag gtg aaa atg ccc aag        192
Trp His Asn Asp Leu Leu Gly Ile Thr Met Lys Val Lys Met Pro Lys
        50                  55                  60 acc cac aag gcc att cag gct gac ggc tgg atg tgc cac gcc gcc aag        240
Thr His Lys Ala Ile Gln Ala Asp Gly Trp Met Cys His Ala Ala Lys
65                  70                  75                  80 tgg atc acc acc tgc gac ttc cgg tgg tac ggc ccc aag tac atc acc        288
Trp Ile Thr Thr Cys Asp Phe Arg Trp Tyr Gly Pro Lys Tyr Ile Thr
                85                  90                  95 cac agc atc cac tcc atc cag ccc acc tcc gag cag tgc aaa gag agc        336
His Ser Ile His Ser Ile Gln Pro Thr Ser Glu Gln Cys Lys Glu Ser
            100                 105                 110 atc aag cag acc aag cag ggc acc tgg atg agc ccc ggc ttc cca ccc        384
Ile Lys Gln Thr Lys Gln Gly Thr Trp Met Ser Pro Gly Phe Pro Pro
        115                 120                 125 cag aac tgc ggc tac gcc acc gtg acc gac agc gtg gcc gtg gtg gtg        432
Gln Asn Cys Gly Tyr Ala Thr Val Thr Asp Ser Val Ala Val Val Val
130                 135                 140 cag gcc acc ccc cac cac gtg ctg gtc gac gag tac acc ggc gag tgg        480
Gln Ala Thr Pro His His Val Leu Val Asp Glu Tyr Thr Gly Glu Trp
145                 150                 155                 160 atc gac agc cag ttc ccc aac ggc aag tgc gag aca gag gaa tgc gag        528
Ile Asp Ser Gln Phe Pro Asn Gly Lys Cys Glu Thr Glu Glu Cys Glu
                165                 170                 175 aca gtg cac aac agc acc gtg tgg tac agc gac tac aag gtg acc ggc        576
Thr Val His Asn Ser Thr Val Trp Tyr Ser Asp Tyr Lys Val Thr Gly
            180                 185                 190 ctg tgc gac gcc acc ctg gtg gac acc gag atc acc ttt ttc agc gag        624
Leu Cys Asp Ala Thr Leu Val Asp Thr Glu Ile Thr Phe Phe Ser Glu
        195                 200                 205 gac ggc aag aaa gag tcc atc ggc aag ccc aac acc ggc tac aga agc        672
Asp Gly Lys Lys Glu Ser Ile Gly Lys Pro Asn Thr Gly Tyr Arg Ser
210                 215                 220 aac tac ttc gcc tac gag aag ggc gac aaa gtg tgc aag atg aac tac        720
Asn Tyr Phe Ala Tyr Glu Lys Gly Asp Lys Val Cys Lys Met Asn Tyr
225                 230                 235                 240 tgc aag cat gcc gga gtg agg ctg cct agc ggc gtg tgg ttc gag ttc        768
Cys Lys His Ala Gly Val Arg Leu Pro Ser Gly Val Trp Phe Glu Phe
                245                 250                 255 gtg gac cag gac gtg tac gcc gcc gcc aag ctg ccc gag tgc ccc gtg        816
Val Asp Gln Asp Val Tyr Ala Ala Ala Lys Leu Pro Glu Cys Pro Val
            260                 265                 270 ggc gcc acc atc agc gcc ccc acc cag acc agc gtg gac gtg agc ctg        864
Gly Ala Thr Ile Ser Ala Pro Thr Gln Thr Ser Val Asp Val Ser Leu
        275                 280                 285 atc ctg gac gtg gag aga atc ctg gac tac tct ctg tgt cag gaa acc        912
Ile Leu Asp Val Glu Arg Ile Leu Asp Tyr Ser Leu Cys Gln Glu Thr
290                 295                 300 tgg tcc aag atc aga tcc aag cag ccc gtg agc cct gtg gac ctg agc        960
Trp Ser Lys Ile Arg Ser Lys Gln Pro Val Ser Pro Val Asp Leu Ser
305                 310                 315                 320
```

```
tac ctg gcc cct aag aac ccc ggc acc ggc cct gcc ttc acc atc atc    1008
Tyr Leu Ala Pro Lys Asn Pro Gly Thr Gly Pro Ala Phe Thr Ile Ile
                325                 330                 335 aac ggc acc ctg aag tac ttc gag aca cgg tac atc cgg atc gac atc    1056
Asn Gly Thr Leu Lys Tyr Phe Glu Thr Arg Tyr Ile Arg Ile Asp Ile
            340                 345                 350 gac aac ccc atc atc agc aag atg gtg ggc aag atc agc ggc agc cag    1104
Asp Asn Pro Ile Ile Ser Lys Met Val Gly Lys Ile Ser Gly Ser Gln
        355                 360                 365 acc gag cgg gag ctg tgg acc gag tgg ttc ccc tac gag ggc gtg gag    1152
Thr Glu Arg Glu Leu Trp Thr Glu Trp Phe Pro Tyr Glu Gly Val Glu
    370                 375                 380 atc ggc ccc aat ggc atc ctg aaa acc cct acc ggc tac aag ttc ccc    1200
Ile Gly Pro Asn Gly Ile Leu Lys Thr Pro Thr Gly Tyr Lys Phe Pro
385                 390                 395                 400 ctg ttc atg atc ggc cac ggc atg ctg gac agc gac ctg cac aag acc    1248
Leu Phe Met Ile Gly His Gly Met Leu Asp Ser Asp Leu His Lys Thr
                405                 410                 415 tcc cag gcc gag gtg ttc gag cac ccc cac ctg gcc gag gcc ccc aag    1296
Ser Gln Ala Glu Val Phe Glu His Pro His Leu Ala Glu Ala Pro Lys
            420                 425                 430 cag ctg ccc gaa gag gaa acc ctg ttc ttc ggc gac acc ggc atc tcc    1344
Gln Leu Pro Glu Glu Glu Thr Leu Phe Phe Gly Asp Thr Gly Ile Ser
        435                 440                 445 aag aac cct gtg gag ctg atc gag ggc tgg ttc agc agc tgg aag agc    1392
Lys Asn Pro Val Glu Leu Ile Glu Gly Trp Phe Ser Ser Trp Lys Ser
    450                 455                 460 agc atc gct tca ttt ttt ttc atc atc ggc ctc atc atc ggg ctg ttt    1440
Ser Ile Ala Ser Phe Phe Phe Ile Ile Gly Leu Ile Ile Gly Leu Phe
465                 470                 475                 480 ctg gtg ctg cgc gtc ggc atc cac ctg tgc atc aag ctg aag cac acc    1488
Leu Val Leu Arg Val Gly Ile His Leu Cys Ile Lys Leu Lys His Thr
                485                 490                 495 aag aag cgc cag atc tat acc gac atc gag atg aat cgc ctg ggg aag    1536
Lys Lys Arg Gln Ile Tyr Thr Asp Ile Glu Met Asn Arg Leu Gly Lys
            500                 505                 510 taa                                                                1539

<210> SEQ ID NO 82
<211> LENGTH: 512
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 82

Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
            20                  25                  30

Asn Val Pro Ser Ser Tyr His Tyr Cys Pro Ser Ser Ser Asp Gln Asn
        35                  40                  45

Trp His Asn Asp Leu Leu Gly Ile Thr Met Lys Val Lys Met Pro Lys
    50                  55                  60

Thr His Lys Ala Ile Gln Ala Asp Gly Trp Met Cys His Ala Ala Lys
65                  70                  75                  80

Trp Ile Thr Thr Cys Asp Phe Arg Trp Tyr Gly Pro Lys Tyr Ile Thr
                85                  90                  95
```

```
His Ser Ile His Ser Ile Gln Pro Thr Ser Glu Gln Cys Lys Glu Ser
                100                 105                 110
Ile Lys Gln Thr Lys Gln Gly Thr Trp Met Ser Pro Gly Phe Pro Pro
            115                 120                 125
Gln Asn Cys Gly Tyr Ala Thr Val Thr Asp Ser Val Ala Val Val Val
        130                 135                 140
Gln Ala Thr Pro His His Val Leu Val Asp Glu Tyr Thr Gly Glu Trp
145                 150                 155                 160
Ile Asp Ser Gln Phe Pro Asn Gly Lys Cys Glu Thr Glu Glu Cys Glu
                165                 170                 175
Thr Val His Asn Ser Thr Val Trp Tyr Ser Asp Tyr Lys Val Thr Gly
            180                 185                 190
Leu Cys Asp Ala Thr Leu Val Asp Thr Glu Ile Thr Phe Phe Ser Glu
        195                 200                 205
Asp Gly Lys Lys Glu Ser Ile Gly Lys Pro Asn Thr Gly Tyr Arg Ser
    210                 215                 220
Asn Tyr Phe Ala Tyr Glu Lys Gly Asp Lys Val Cys Lys Met Asn Tyr
225                 230                 235                 240
Cys Lys His Ala Gly Val Arg Leu Pro Ser Gly Val Trp Phe Glu Phe
                245                 250                 255
Val Asp Gln Asp Val Tyr Ala Ala Lys Leu Pro Glu Cys Pro Val
            260                 265                 270
Gly Ala Thr Ile Ser Ala Pro Thr Gln Thr Ser Val Asp Val Ser Leu
        275                 280                 285
Ile Leu Asp Val Glu Arg Ile Leu Asp Tyr Ser Leu Cys Gln Glu Thr
    290                 295                 300
Trp Ser Lys Ile Arg Ser Lys Gln Pro Val Ser Pro Val Asp Leu Ser
305                 310                 315                 320
Tyr Leu Ala Pro Lys Asn Pro Gly Thr Gly Pro Ala Phe Thr Ile Ile
                325                 330                 335
Asn Gly Thr Leu Lys Tyr Phe Glu Thr Arg Tyr Ile Arg Ile Asp Ile
            340                 345                 350
Asp Asn Pro Ile Ile Ser Lys Met Val Gly Lys Ile Ser Gly Ser Gln
        355                 360                 365
Thr Glu Arg Glu Leu Trp Thr Glu Trp Phe Pro Tyr Glu Gly Val Glu
    370                 375                 380
Ile Gly Pro Asn Gly Ile Leu Lys Thr Pro Thr Gly Tyr Lys Phe Pro
385                 390                 395                 400
Leu Phe Met Ile Gly His Gly Met Leu Asp Ser Asp Leu His Lys Thr
                405                 410                 415
Ser Gln Ala Glu Val Phe Glu His Pro His Leu Ala Glu Ala Pro Lys
            420                 425                 430
Gln Leu Pro Glu Glu Glu Thr Leu Phe Phe Gly Asp Thr Gly Ile Ser
        435                 440                 445
Lys Asn Pro Val Glu Leu Ile Glu Gly Trp Phe Ser Ser Trp Lys Ser
    450                 455                 460
Ser Ile Ala Ser Phe Phe Phe Ile Ile Gly Leu Ile Ile Gly Leu Phe
465                 470                 475                 480
Leu Val Leu Arg Val Gly Ile His Leu Cys Ile Lys Leu Lys His Thr
                485                 490                 495
Lys Lys Arg Gln Ile Tyr Thr Asp Ile Glu Met Asn Arg Leu Gly Lys
            500                 505                 510
```

```
<210> SEQ ID NO 83
<211> LENGTH: 1518
<212> TYPE: DNA
<213> ORGANISM: Artificial Sequence
<220> FEATURE:
<223> OTHER INFORMATION: Description of Artificial Sequence: Synthetic
      Fusion VSV-G Piry / Indiana
<220> FEATURE:
<221> NAME/KEY: CDS
<222> LOCATION: (1)..(1515)

<400> SEQUENCE: 83 atg acc gat aca gtg ctg ggc aag ttc cag atc gtg ttc ccc gac cag    48
Met Thr Asp Thr Val Leu Gly Lys Phe Gln Ile Val Phe Pro Asp Gln
1               5                   10                  15 aac gag ctg gaa tgg acc ccc gtc gtg ggc gac agc cgg cat tgc cct    96
Asn Glu Leu Glu Trp Thr Pro Val Val Gly Asp Ser Arg His Cys Pro
                20                  25                  30 cag tcc agc gag atg cag ttc gac ggc agc aga agc cag acc atc ctg   144
Gln Ser Ser Glu Met Gln Phe Asp Gly Ser Arg Ser Gln Thr Ile Leu
            35                  40                  45 acc ggc aag gcc ccc gtg ggc atc aca ccc agc aag agc gac ggc ttc   192
Thr Gly Lys Ala Pro Val Gly Ile Thr Pro Ser Lys Ser Asp Gly Phe
50                  55                  60 atc tgc cac gcc gcc aag tgg gtg acc acc tgc gac ttc cgg tgg tac   240
Ile Cys His Ala Ala Lys Trp Val Thr Thr Cys Asp Phe Arg Trp Tyr
65                  70                  75                  80 ggc ccc aag tac atc acc cac agc atc cac cac ctg cgg ccc acc acc   288
Gly Pro Lys Tyr Ile Thr His Ser Ile His His Leu Arg Pro Thr Thr
                85                  90                  95 tcc gac tgc gag aca gcc ctg cag cgg tac aag gac ggc agc ctg atc   336
Ser Asp Cys Glu Thr Ala Leu Gln Arg Tyr Lys Asp Gly Ser Leu Ile
            100                 105                 110 aac ctg ggc ttc cct ccc gag agc tgc ggc tac gcc acc gtg aca gac   384
Asn Leu Gly Phe Pro Pro Glu Ser Cys Gly Tyr Ala Thr Val Thr Asp
        115                 120                 125 agc gag gcc atg ctg gtg cag gtg acc ccc cac cac gtg ggc gtg gac   432
Ser Glu Ala Met Leu Val Gln Val Thr Pro His His Val Gly Val Asp
130                 135                 140 gac tac cgg ggc cac tgg atc gac ccc ctg ttc cct ggc ggc gag tgc   480
Asp Tyr Arg Gly His Trp Ile Asp Pro Leu Phe Pro Gly Gly Glu Cys
145                 150                 155                 160 agc acc aat ttc tgc gat acc gtg cac aac agc agc gtg tgg att ccc   528
Ser Thr Asn Phe Cys Asp Thr Val His Asn Ser Ser Val Trp Ile Pro
                165                 170                 175 aag agc cag aaa acc gac atc tgc gcc cag agc ttc aag aac atc aag   576
Lys Ser Gln Lys Thr Asp Ile Cys Ala Gln Ser Phe Lys Asn Ile Lys
            180                 185                 190 atg acc gcc agc tac ccc agc gag gga gcc ctg gtg tcc gac cgg ttc   624
Met Thr Ala Ser Tyr Pro Ser Glu Gly Ala Leu Val Ser Asp Arg Phe
        195                 200                 205 gcc ttc cac agc gcc tac cac ccc aac atg ccc ggc agc acc gtg tgc   672
Ala Phe His Ser Ala Tyr His Pro Asn Met Pro Gly Ser Thr Val Cys
210                 215                 220 atc atg gat ttc tgc gag cag aag ggc ctg cgg ttc acc aac ggc gag   720
Ile Met Asp Phe Cys Glu Gln Lys Gly Leu Arg Phe Thr Asn Gly Glu
225                 230                 235                 240 tgg atg ggc ctg aac gtg gag cag agc atc cgg gag aag aag atc agc   768
Trp Met Gly Leu Asn Val Glu Gln Ser Ile Arg Glu Lys Lys Ile Ser
                245                 250                 255 gcc atc ttc ccc aac tgc gtg gcc ggc acc gag atc cgg gcc acc ctg   816
Ala Ile Phe Pro Asn Cys Val Ala Gly Thr Glu Ile Arg Ala Thr Leu
```

```
gaa tcc gag ggc gcc agg acc ctg acc tgg gag aca cag cgg atg ctg      864
Glu Ser Glu Gly Ala Arg Thr Leu Thr Trp Glu Thr Gln Arg Met Leu
        275                 280                 285 gac tac agc ctg tgc cag aac acc tgg gac aag gtg tcc cgg aaa gag      912
Asp Tyr Ser Leu Cys Gln Asn Thr Trp Asp Lys Val Ser Arg Lys Glu
    290                 295                 300 cct ctg tcc ccc ctg gac ctg agc tac ctg agc cct aga gcc cct ggc      960
Pro Leu Ser Pro Leu Asp Leu Ser Tyr Leu Ser Pro Arg Ala Pro Gly
305                 310                 315                 320 aag ggc atg gcc tac acc gtg atc aac ggc acc ctg cac agc gcc cac     1008
Lys Gly Met Ala Tyr Thr Val Ile Asn Gly Thr Leu His Ser Ala His
                325                 330                 335 gcc aag tat atc cgg acc tgg atc gac tac ggc gag atg aaa gag atc     1056
Ala Lys Tyr Ile Arg Thr Trp Ile Asp Tyr Gly Glu Met Lys Glu Ile
            340                 345                 350 aag ggc ggc agg ggc gag tac agc aag gcc cct gag ctg ctg tgg agc     1104
Lys Gly Gly Arg Gly Glu Tyr Ser Lys Ala Pro Glu Leu Leu Trp Ser
        355                 360                 365 cag tgg ttc gac ttc ggc ccc ttc aag atc ggc ccc aac ggc ctg ctg     1152
Gln Trp Phe Asp Phe Gly Pro Phe Lys Ile Gly Pro Asn Gly Leu Leu
    370                 375                 380 cac acc ggc aag acc ttc aag ttc cct ctg tat ctg atc gga gcc ggc     1200
His Thr Gly Lys Thr Phe Lys Phe Pro Leu Tyr Leu Ile Gly Ala Gly
385                 390                 395                 400 atc atc gac gag gac ctg cac gag ctg gac gaa gcc gcc cct atc gac     1248
Ile Ile Asp Glu Asp Leu His Glu Leu Asp Glu Ala Ala Pro Ile Asp
                405                 410                 415 cac ccc cag atg ccc gac gcc aag agc gtg ctg ccc gag gac gag gaa     1296
His Pro Gln Met Pro Asp Ala Lys Ser Val Leu Pro Glu Asp Glu Glu
            420                 425                 430 atc ttc ttc ggc gac acc ggc gtg agc aag aac ccc atc gag ctg atc     1344
Ile Phe Phe Gly Asp Thr Gly Val Ser Lys Asn Pro Ile Glu Leu Ile
        435                 440                 445 cag ggc tgg ttc agc aac tgg cgg agc agc atc gct tca ttt ttt ttc     1392
Gln Gly Trp Phe Ser Asn Trp Arg Ser Ser Ile Ala Ser Phe Phe Phe
    450                 455                 460 atc atc ggc ctc atc atc ggg ctg ttt ctg gtg ctg cgc gtc ggc atc     1440
Ile Ile Gly Leu Ile Ile Gly Leu Phe Leu Val Leu Arg Val Gly Ile
465                 470                 475                 480 cac ctg tgc atc aag ctg aag cac acc aag aag cgc cag atc tat acc     1488
His Leu Cys Ile Lys Leu Lys His Thr Lys Lys Arg Gln Ile Tyr Thr
                485                 490                 495 gac atc gag atg aat cgc ctg ggg aag taa                              1518
Asp Ile Glu Met Asn Arg Leu Gly Lys
            500                 505
```

<210> SEQ ID NO 84
<211> LENGTH: 505
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 84

Met Thr Asp Thr Val Leu Gly Lys Phe Gln Ile Val Phe Pro Asp Gln
1               5                   10                  15

Asn Glu Leu Glu Trp Thr Pro Val Val Gly Asp Ser Arg His Cys Pro
            20                  25                  30

```
Gln Ser Ser Glu Met Gln Phe Asp Gly Ser Arg Ser Gln Thr Ile Leu
         35                  40                  45

Thr Gly Lys Ala Pro Val Gly Ile Thr Pro Ser Lys Ser Asp Gly Phe
 50                  55                  60

Ile Cys His Ala Ala Lys Trp Val Thr Thr Cys Asp Phe Arg Trp Tyr
 65                  70                  75                  80

Gly Pro Lys Tyr Ile Thr His Ser Ile His His Leu Arg Pro Thr Thr
                 85                  90                  95

Ser Asp Cys Glu Thr Ala Leu Gln Arg Tyr Lys Asp Gly Ser Leu Ile
             100                 105                 110

Asn Leu Gly Phe Pro Pro Glu Ser Cys Gly Tyr Ala Thr Val Thr Asp
             115                 120                 125

Ser Glu Ala Met Leu Val Gln Val Thr Pro His His Val Gly Val Asp
 130                 135                 140

Asp Tyr Arg Gly His Trp Ile Asp Pro Leu Phe Pro Gly Gly Glu Cys
 145                 150                 155                 160

Ser Thr Asn Phe Cys Asp Thr Val His Asn Ser Ser Val Trp Ile Pro
                 165                 170                 175

Lys Ser Gln Lys Thr Asp Ile Cys Ala Gln Ser Phe Lys Asn Ile Lys
             180                 185                 190

Met Thr Ala Ser Tyr Pro Ser Glu Gly Ala Leu Val Ser Asp Arg Phe
             195                 200                 205

Ala Phe His Ser Ala Tyr His Pro Asn Met Pro Gly Ser Thr Val Cys
         210                 215                 220

Ile Met Asp Phe Cys Glu Gln Lys Gly Leu Arg Phe Thr Asn Gly Glu
225                 230                 235                 240

Trp Met Gly Leu Asn Val Glu Gln Ser Ile Arg Glu Lys Lys Ile Ser
                 245                 250                 255

Ala Ile Phe Pro Asn Cys Val Ala Gly Thr Glu Ile Arg Ala Thr Leu
             260                 265                 270

Glu Ser Glu Gly Ala Arg Thr Leu Thr Trp Glu Thr Gln Arg Met Leu
             275                 280                 285

Asp Tyr Ser Leu Cys Gln Asn Thr Trp Asp Lys Val Ser Arg Lys Glu
         290                 295                 300

Pro Leu Ser Pro Leu Asp Leu Ser Tyr Leu Ser Pro Arg Ala Pro Gly
305                 310                 315                 320

Lys Gly Met Ala Tyr Thr Val Ile Asn Gly Thr Leu His Ser Ala His
                 325                 330                 335

Ala Lys Tyr Ile Arg Thr Trp Ile Asp Tyr Gly Glu Met Lys Glu Ile
             340                 345                 350

Lys Gly Gly Arg Gly Glu Tyr Ser Lys Ala Pro Glu Leu Leu Trp Ser
             355                 360                 365

Gln Trp Phe Asp Phe Gly Pro Phe Lys Ile Gly Pro Asn Gly Leu Leu
         370                 375                 380

His Thr Gly Lys Thr Phe Lys Phe Pro Leu Tyr Leu Ile Gly Ala Gly
385                 390                 395                 400

Ile Ile Asp Glu Asp Leu His Glu Leu Asp Glu Ala Ala Pro Ile Asp
             405                 410                 415

His Pro Gln Met Pro Asp Ala Lys Ser Val Leu Pro Glu Asp Glu Glu
             420                 425                 430

Ile Phe Phe Gly Asp Thr Gly Val Ser Lys Asn Pro Ile Glu Leu Ile
             435                 440                 445

Gln Gly Trp Phe Ser Asn Trp Arg Ser Ser Ile Ala Ser Phe Phe Phe
```

```
                450                 455                 460
Ile Ile Gly Leu Ile Ile Gly Leu Phe Leu Val Leu Arg Val Gly Ile
465                 470                 475                 480

His Leu Cys Ile Lys Leu Lys His Thr Lys Lys Arg Gln Ile Tyr Thr
                485                 490                 495

Asp Ile Glu Met Asn Arg Leu Gly Lys
                500                 505

<210> SEQ ID NO 85
<211> LENGTH: 1560
<212> TYPE: DNA
<213> ORGANISM: Artificial Sequence
<220> FEATURE:
<223> OTHER INFORMATION: Description of Artificial Sequence: Synthetic
      Fusion VSV-G Isfahan / Indiana
<220> FEATURE:
<221> NAME/KEY: CDS
<222> LOCATION: (1)..(1557)

<400

```
                  210                 215                 220
aag agc aag ttc cac gcc cac atg aag ggc gac aga gtg tgc aag atg      720
Lys Ser Lys Phe His Ala His Met Lys Gly Asp Arg Val Cys Lys Met
225                 230                 235                 240 aag ttc tgc aac aag aac ggc ctg cgg ctg ggc aac ggc gag tgg atc      768
Lys Phe Cys Asn Lys Asn Gly Leu Arg Leu Gly Asn Gly Glu Trp Ile
                245                 250                 255 gaa gtg ggc gac gag gtg atg ctg gac aac agc aag ctg ctg tcc ctg      816
Glu Val Gly Asp Glu Val Met Leu Asp Asn Ser Lys Leu Leu Ser Leu
            260                 265                 270 ttc ccc gac tgc ctg gtg ggc agc gtg gtg aag agc acc ctg ctg tcc      864
Phe Pro Asp Cys Leu Val Gly Ser Val Val Lys Ser Thr Leu Leu Ser
        275                 280                 285 gag ggc gtg cag acc gcc ctg tgg gag aca gac cgg ctg ctg gac tac      912
Glu Gly Val Gln Thr Ala Leu Trp Glu Thr Asp Arg Leu Leu Asp Tyr
    290                 295                 300 agc ctg tgc cag aac acc tgg gag aag atc gac cgg aaa gag ccc ctg      960
Ser Leu Cys Gln Asn Thr Trp Glu Lys Ile Asp Arg Lys Glu Pro Leu
305                 310                 315                 320 agc gcc gtc gac ctg agc tac ctg gcc cct aga agc ccc ggc aag ggc     1008
Ser Ala Val Asp Leu Ser Tyr Leu Ala Pro Arg Ser Pro Gly Lys Gly
                325                 330                 335 atg gcc tac atc gtg gcc aac ggc agc ctg atg agc gcc cct gcc cgg     1056
Met Ala Tyr Ile Val Ala Asn Gly Ser Leu Met Ser Ala Pro Ala Arg
            340                 345                 350 tac atc aga gtg tgg atc gac agc ccc atc ctg aaa gag atc aag ggc     1104
Tyr Ile Arg Val Trp Ile Asp Ser Pro Ile Leu Lys Glu Ile Lys Gly
        355                 360                 365 aag aaa gag agc gcc agc ggc atc gac acc gtg ctg tgg gag cag tgg     1152
Lys Lys Glu Ser Ala Ser Gly Ile Asp Thr Val Leu Trp Glu Gln Trp
    370                 375                 380 ctg ccc ttc aac ggc atg gaa ctg ggc ccc aac ggc ctg atc aag acc     1200
Leu Pro Phe Asn Gly Met Glu Leu Gly Pro Asn Gly Leu Ile Lys Thr
385                 390                 395                 400 aag agc ggc tac aag ttc ccc ctg tac ctg ctg ggc atg ggc atc gtg     1248
Lys Ser Gly Tyr Lys Phe Pro Leu Tyr Leu Leu Gly Met Gly Ile Val
                405                 410                 415 gac cag gac ctg cag gaa ctg agc agc gtc aac ccc gtg gac cac ccc     1296
Asp Gln Asp Leu Gln Glu Leu Ser Ser Val Asn Pro Val Asp His Pro
            420                 425                 430 cac gtg cct atc gcc cag gcc ttc gtg agc gag ggc gag gaa gtg ttc     1344
His Val Pro Ile Ala Gln Ala Phe Val Ser Glu Gly Glu Glu Val Phe
        435                 440                 445 ttc ggc gac acc ggc gtg agc aag aac ccc atc gag ctg atc agc ggc     1392
Phe Gly Asp Thr Gly Val Ser Lys Asn Pro Ile Glu Leu Ile Ser Gly
    450                 455                 460 tgg ttc agc gac tgg aaa agc agc atc gct tca ttt ttt ttc atc atc     1440
Trp Phe Ser Asp Trp Lys Ser Ser Ile Ala Ser Phe Phe Phe Ile Ile
465                 470                 475                 480 ggc ctc atc atc ggg ctg ttt ctg gtg ctg cgc gtc ggc atc cac ctg     1488
Gly Leu Ile Ile Gly Leu Phe Leu Val Leu Arg Val Gly Ile His Leu
                485                 490                 495 tgc atc aag ctg aag cac acc aag aag cgc cag atc tat acc gac atc     1536
Cys Ile Lys Leu Lys His Thr Lys Lys Arg Gln Ile Tyr Thr Asp Ile
            500                 505                 510 gag atg aat cgc ctg ggg aag taa                                     1560
Glu Met Asn Arg Leu Gly Lys
                515
```

<210> SEQ ID NO 86
<211> LENGTH: 519
<212> TYPE: PRT
<213> ORGANISM: Artificial Sequence
<220> FEATURE:
<223> OTHER INFORMATION: Description of Artificial Sequence: Synthetic construct

<400> SEQUENCE: 86

```
Met Thr Ser Val Leu Phe Met Val Gly Val Leu Leu Gly Ala Phe Gly
1               5                   10                  15

Ser Thr His Cys Ser Ile Gln Ile Val Phe Pro Ser Glu Thr Lys Leu
            20                  25                  30

Val Trp Lys Pro Val Leu Lys Gly Thr Arg Tyr Cys Pro Gln Ser Ala
        35                  40                  45

Glu Leu Asn Leu Glu Pro Asp Leu Lys Thr Met Ala Phe Asp Ser Lys
    50                  55                  60

Val Pro Ile Gly Ile Thr Pro Ser Asn Ser Asp Gly Tyr Leu Cys His
65                  70                  75                  80

Ala Ala Lys Trp Val Thr Thr Cys Asp Phe Arg Trp Tyr Gly Pro Lys
                85                  90                  95

Tyr Ile Thr His Ser Val His Ser Leu Arg Pro Thr Val Ser Asp Cys
            100                 105                 110

Lys Ala Ala Val Glu Ala Tyr Asn Ala Gly Thr Leu Met Tyr Pro Gly
        115                 120                 125

Phe Pro Pro Glu Ser Cys Gly Tyr Ala Ser Ile Thr Asp Ser Glu Phe
    130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
                165                 170                 175

Phe Cys Glu Thr Val His Asn Ala Thr Met Trp Ile Pro Lys Asp Leu
            180                 185                 190

Lys Thr His Asp Val Cys Ser Gln Asp Phe Gln Thr Ile Arg Val Ser
        195                 200                 205

Val Met Tyr Pro Gln Thr Lys Pro Thr Lys Gly Ala Asp Leu Thr Leu
    210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
            260                 265                 270

Phe Pro Asp Cys Leu Val Gly Ser Val Val Lys Ser Thr Leu Leu Ser
        275                 280                 285

Glu Gly Val Gln Thr Ala Leu Trp Glu Thr Asp Arg Leu Leu Asp Tyr
    290                 295                 300

Ser Leu Cys Gln Asn Thr Trp Glu Lys Ile Asp Arg Lys Glu Pro Leu
305                 310                 315                 320

Ser Ala Val Asp Leu Ser Tyr Leu Ala Pro Arg Ser Pro Gly Lys Gly
                325                 330                 335

Met Ala Tyr Ile Val Ala Asn Gly Ser Leu Met Ser Ala Pro Ala Arg
            340                 345                 350

Tyr Ile Arg Val Trp Ile Asp Ser Pro Ile Leu Lys Glu Ile Lys Gly
        355                 360                 365
```

-continued

```
Lys Lys Glu Ser Ala Ser Gly Ile Asp Thr Val Leu Trp Glu Gln Trp
    370                 375                 380
Leu Pro Phe Asn Gly Met Glu Leu Gly Pro Asn Gly Leu Ile Lys Thr
385                 390                 395                 400
Lys Ser Gly Tyr Lys Phe Pro Leu Tyr Leu Leu Gly Met Gly Ile Val
                405                 410                 415
Asp Gln Asp Leu Gln Glu Leu Ser Ser Val Asn Pro Val Asp His Pro
            420                 425                 430
His Val Pro Ile Ala Gln Ala Phe Val Ser Glu Gly Glu Val Phe
        435                 440                 445
Phe Gly Asp Thr Gly Val Ser Lys Asn Pro Ile Glu Leu Ile Ser Gly
    450                 455                 460
Trp Phe Ser Asp Trp Lys Ser Ser Ile Ala Ser Phe Phe Ile Ile
465                 470                 475                 480
Gly Leu Ile Ile Gly Leu Phe Leu Val Leu Arg Val Gly Ile His Leu
                485                 490                 495
Cys Ile Lys Leu Lys His Thr Lys Arg Gln Ile Tyr Thr Asp Ile
            500                 505                 510
Glu Met Asn Arg Leu Gly Lys
        515
```

<210> SEQ ID NO 87
<211> LENGTH: 1536
<212> TYPE: DNA
<213> ORGANISM: Artificial Sequence
<220> FEATURE:
<223> OTHER INFORMATION: Description of Artificial Sequence: Synthetic
      Fusion VSV-G New Jersey / Indiana
<220> FEATURE:
<221> NAME/KEY: CDS
<222> LOCATION: (1)..(1533)

<400> SEQUENCE: 87

```
atg agc atc atc agc tat atc gcc ttt ctg ctg ctg atc gac agc acc        48
Met Ser Ile Ile Ser Tyr Ile Ala Phe Leu Leu Leu Ile Asp Ser Thr
1               5                   10                  15 ctg ggc atc ccc atc ttc gtg ccc agc ggc cag aac atc agc tgg cag        96
Leu Gly Ile Pro Ile Phe Val Pro Ser Gly Gln Asn Ile Ser Trp Gln
            20                  25                  30 ccc gtg atc cag ccc ttc gac tac cag tgc ccc atc cac ggc aac ctg       144
Pro Val Ile Gln Pro Phe Asp Tyr Gln Cys Pro Ile His Gly Asn Leu
        35                  40                  45 ccc aac acc atg ggc ctg agc gcc acc aag ctg acc atc aag agc ccc       192
Pro Asn Thr Met Gly Leu Ser Ala Thr Lys Leu Thr Ile Lys Ser Pro
    50                  55                  60 agc gtg ttc agc acc gac aag gtg tcc ggc tgg atc tgc cac gcc gcc       240
Ser Val Phe Ser Thr Asp Lys Val Ser Gly Trp Ile Cys His Ala Ala
65                  70                  75                  80 gag tgg aaa acc acc tgc gac tac cgg tgg tac ggc ccc cag tac atc       288
Glu Trp Lys Thr Thr Cys Asp Tyr Arg Trp Tyr Gly Pro Gln Tyr Ile
                85                  90                  95 acc cac agc atc cac ccc atc agc ccc acc atc gac gag tgc aag cgg       336
Thr His Ser Ile His Pro Ile Ser Pro Thr Ile Asp Glu Cys Lys Arg
            100                 105                 110 atc atc agc cgg atc gcc agc ggc acc gac gag gac ctg ggc ttc cca       384
Ile Ile Ser Arg Ile Ala Ser Gly Thr Asp Glu Asp Leu Gly Phe Pro
        115                 120                 125 ccc cag agc tgc ggc tgg gcc agc gtg acc acc gtg agc aac acc aac       432
Pro Gln Ser Cys Gly Trp Ala Ser Val Thr Thr Val Ser Asn Thr Asn
    130                 135                 140
```

```
tac aag gtg gtg ccc cac agc gtg cac ctg gaa ccc tac ggc ggc cac       480
Tyr Lys Val Val Pro His Ser Val His Leu Glu Pro Tyr Gly Gly His
145                 150                 155                 160 tgg atc gac cac gac ttc aac ggc ggc gag tgc cgg gag aaa gtg tgc       528
Trp Ile Asp His Asp Phe Asn Gly Gly Glu Cys Arg Glu Lys Val Cys
                165                 170                 175 gag atg aag ggc aac cac agc atc tgg atc acc gac gag aca gtg cag       576
Glu Met Lys Gly Asn His Ser Ile Trp Ile Thr Asp Glu Thr Val Gln
            180                 185                 190 cac gag tgc gag aag cac atc gag gaa gtg gag ggc atc atg tac ggc       624
His Glu Cys Glu Lys His Ile Glu Glu Val Glu Gly Ile Met Tyr Gly
        195                 200                 205 aac gcc ccc agg ggc gac gcc atc tac atc aac aac ttc atc atc gac       672
Asn Ala Pro Arg Gly Asp Ala Ile Tyr Ile Asn Asn Phe Ile Ile Asp
210                 215                 220 aag cac cac cgg gtg tac cgg ttc ggc ggc tcc tgc cgg atg aag ttc       720
Lys His His Arg Val Tyr Arg Phe Gly Gly Ser Cys Arg Met Lys Phe
225                 230                 235                 240 tgc aac aag gac ggc atc aag ttc acc aga ggc gac tgg gtg gag aaa       768
Cys Asn Lys Asp Gly Ile Lys Phe Thr Arg Gly Asp Trp Val Glu Lys
                245                 250                 255 acc gcc ggc acc ctg acc aac atc tac gag aac atc ccc gag tgc gcc       816
Thr Ala Gly Thr Leu Thr Asn Ile Tyr Glu Asn Ile Pro Glu Cys Ala
            260                 265                 270 gac ggc aca ctg gtg tcc ggc cac aga ccc ggc ctg gac ctg atc gac       864
Asp Gly Thr Leu Val Ser Gly His Arg Pro Gly Leu Asp Leu Ile Asp
        275                 280                 285 acc gtg ttc aac ctg gaa aac gtg gtg gag tac acc ctg tgc gag ggc       912
Thr Val Phe Asn Leu Glu Asn Val Val Glu Tyr Thr Leu Cys Glu Gly
290                 295                 300 acc aag cgg aag atc aac aag cag gaa aag ctg acc agc gtc gac ctg       960
Thr Lys Arg Lys Ile Asn Lys Gln Glu Lys Leu Thr Ser Val Asp Leu
305                 310                 315                 320 agc tac ctg gcc ccc agg atc ggc ggc ttc ggc agc gtg ttc cgc gtg      1008
Ser Tyr Leu Ala Pro Arg Ile Gly Gly Phe Gly Ser Val Phe Arg Val
                325                 330                 335 cgg aat ggg acc ctg gaa aga gga agc aca aca tac att cgg atc gaa      1056
Arg Asn Gly Thr Leu Glu Arg Gly Ser Thr Thr Tyr Ile Arg Ile Glu
            340                 345                 350 gtg gaa ggc ccc gtg gtg gac agc ctg aac ggc atc gac ccc cgg acc      1104
Val Glu Gly Pro Val Val Asp Ser Leu Asn Gly Ile Asp Pro Arg Thr
        355                 360                 365 aac gcc agc cgg gtg ttc tgg gac gac tgg gag ctg gac ggc aac atc      1152
Asn Ala Ser Arg Val Phe Trp Asp Asp Trp Glu Leu Asp Gly Asn Ile
370                 375                 380 tac cag ggc ttc aat ggc gtg tac aag ggc aag gat ggc aag atc cac      1200
Tyr Gln Gly Phe Asn Gly Val Tyr Lys Gly Lys Asp Gly Lys Ile His
385                 390                 395                 400 atc ccc ctg aac atg atc gag agc ggc atc atc gac gac gag ctg cag      1248
Ile Pro Leu Asn Met Ile Glu Ser Gly Ile Ile Asp Asp Glu Leu Gln
                405                 410                 415 cac gcc ttc cag gcc gac atc atc ccc cac ccc cac tac gac gac gac      1296
His Ala Phe Gln Ala Asp Ile Ile Pro His Pro His Tyr Asp Asp Asp
            420                 425                 430 gag atc cgg gag gac gac atc ttc ttc gac aac acc ggc gag aac ggc      1344
Glu Ile Arg Glu Asp Asp Ile Phe Phe Asp Asn Thr Gly Glu Asn Gly
        435                 440                 445 aac ccc gtg gac gcc gtg gtg gaa tgg gtg tcc gga tgg ggc agc agc      1392
Asn Pro Val Asp Ala Val Val Glu Trp Val Ser Gly Trp Gly Ser Ser
```

```
           450                 455                 460
atc gct tca ttt ttt ttc atc atc ggc ctc atc atc ggg ctg ttt ctg    1440
Ile Ala Ser Phe Phe Phe Ile Ile Gly Leu Ile Ile Gly Leu Phe Leu
465                 470                 475                 480 gtg ctg cgc gtc ggc atc cac ctg tgc atc aag ctg aag cac acc aag    1488
Val Leu Arg Val Gly Ile His Leu Cys Ile Lys Leu Lys His Thr Lys
                485                 490                 495 aag cgc cag atc tat acc gac atc gag atg aat cgc ctg ggg aag taa    1536
Lys Arg Gln Ile Tyr Thr Asp Ile Glu Met Asn Arg Leu Gly Lys
                500                 505                 510
```

<210> SEQ ID NO 88
<211> LENGTH: 511
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 88

```
Met Ser Ile Ile Ser Tyr Ile Ala Phe Leu Leu Ile Asp Ser Thr
1               5                   10                  15

Leu Gly Ile Pro Ile Phe Val Pro Ser Gly Gln Asn Ile Ser Trp Gln
                20                  25                  30

Pro Val Ile Gln Pro Phe Asp Tyr Gln Cys Pro Ile His Gly Asn Leu
            35                  40                  45

Pro Asn Thr Met Gly Leu Ser Ala Thr Lys Leu Thr Ile Lys Ser Pro
        50                  55                  60

Ser Val Phe Ser Thr Asp Lys Val Ser Gly Trp Ile Cys His Ala Ala
65                  70                  75                  80

Glu Trp Lys Thr Thr Cys Asp Tyr Arg Trp Tyr Gly Pro Gln Tyr Ile
                85                  90                  95

Thr His Ser Ile His Pro Ile Ser Pro Thr Ile Asp Glu Cys Lys Arg
            100                 105                 110

Ile Ile Ser Arg Ile Ala Ser Gly Thr Asp Glu Asp Leu Gly Phe Pro
        115                 120                 125

Pro Gln Ser Cys Gly Trp Ala Ser Val Thr Thr Val Ser Asn Thr Asn
    130                 135                 140

Tyr Lys Val Val Pro His Ser Val His Leu Glu Pro Tyr Gly Gly His
145                 150                 155                 160

Trp Ile Asp His Asp Phe Asn Gly Gly Glu Cys Arg Glu Lys Val Cys
                165                 170                 175

Glu Met Lys Gly Asn His Ser Ile Trp Ile Thr Asp Glu Thr Val Gln
            180                 185                 190

His Glu Cys Glu Lys His Ile Glu Val Glu Gly Ile Met Tyr Gly
        195                 200                 205

Asn Ala Pro Arg Gly Asp Ala Ile Tyr Ile Asn Asn Phe Ile Ile Asp
    210                 215                 220

Lys His His Arg Val Tyr Arg Phe Gly Gly Ser Cys Arg Met Lys Phe
225                 230                 235                 240

Cys Asn Lys Asp Gly Ile Lys Phe Thr Arg Gly Asp Trp Val Glu Lys
                245                 250                 255

Thr Ala Gly Thr Leu Thr Asn Ile Tyr Glu Asn Ile Pro Glu Cys Ala
            260                 265                 270

Asp Gly Thr Leu Val Ser Gly His Arg Pro Gly Leu Asp Leu Ile Asp
        275                 280                 285
```

```
Thr Val Phe Asn Leu Glu Asn Val Val Glu Tyr Thr Leu Cys Glu Gly
    290                 295                 300

Thr Lys Arg Lys Ile Asn Lys Gln Glu Lys Leu Thr Ser Val Asp Leu
305                 310                 315                 320

Ser Tyr Leu Ala Pro Arg Ile Gly Gly Phe Gly Ser Val Phe Arg Val
                325                 330                 335

Arg Asn Gly Thr Leu Glu Arg Gly Ser Thr Thr Tyr Ile Arg Ile Glu
                340                 345                 350

Val Glu Gly Pro Val Val Asp Ser Leu Asn Gly Ile Asp Pro Arg Thr
            355                 360                 365

Asn Ala Ser Arg Val Phe Trp Asp Asp Trp Glu Leu Asp Gly Asn Ile
370                 375                 380

Tyr Gln Gly Phe Asn Gly Val Tyr Lys Gly Lys Asp Gly Lys Ile His
385                 390                 395                 400

Ile Pro Leu Asn Met Ile Glu Ser Gly Ile Ile Asp Asp Glu Leu Gln
                405                 410                 415

His Ala Phe Gln Ala Asp Ile Ile Pro His Pro His Tyr Asp Asp Asp
                420                 425                 430

Glu Ile Arg Glu Asp Asp Ile Phe Phe Asp Asn Thr Gly Glu Asn Gly
            435                 440                 445

Asn Pro Val Asp Ala Val Val Glu Trp Val Ser Gly Trp Gly Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
                500                 505                 510

<210> SEQ ID NO 89
<211> LENGTH: 1557
<212> TYPE: DNA
<213> ORGANISM: Artificial Sequence
<220> FEATURE:
<223> OTHER INFORMATION: Description of Artificial Sequence: Synthetic
      Fusion VSV-G New Jersey / Indiana
<220> FEATURE:
<221> NAME/KEY: CDS
<222> LOCATION: (1)..(1554)

<400> SEQUENCE: 89 atg ctg tca tat ctg atc ttt gcc ctg gct gtg agc cca atc ctc gga      48
Met Leu Ser Tyr Leu Ile Phe Ala Leu Ala Val Ser Pro Ile Leu Gly
1               5                   10                  15 aag atc gaa atc gtg ttc cca caa cac acc aca ggg gac tgg aag cgc      96
Lys Ile Glu Ile Val Phe Pro Gln His Thr Thr Gly Asp Trp Lys Arg
                20                  25                  30 gtg ccc cac gag tac aac tac tgc ccg acc tca gcc gac aag aat agc     144
Val Pro His Glu Tyr Asn Tyr Cys Pro Thr Ser Ala Asp Lys Asn Ser
            35                  40                  45 cac ggc acg cag acc ggc atc cct gtg gag ctg acc atg ccc aag ggg     192
His Gly Thr Gln Thr Gly Ile Pro Val Glu Leu Thr Met Pro Lys Gly
        50                  55                  60 ctc aca acg cac caa gtc gaa ggc ttc atg tgc cac agc gct ctc tgg     240
Leu Thr Thr His Gln Val Glu Gly Phe Met Cys His Ser Ala Leu Trp
65                  70                  75                  80 atg aca acc tgc gat ttt cgc tgg tat ggc ccc aag tac atc acg cac     288
Met Thr Thr Cys Asp Phe Arg Trp Tyr Gly Pro Lys Tyr Ile Thr His
                85                  90                  95
```

| | | |
|---|---|---|
| agc atc cac aat gag gaa cca acc gac tac cag tgc ctc gaa gcc atc<br>Ser Ile His Asn Glu Glu Pro Thr Asp Tyr Gln Cys Leu Glu Ala Ile<br>            100                        105                    110 | 336 | |
| aag tca tac aag gat ggg gtg agc ttc aac ccc ggc ttc ccg ccc caa<br>Lys Ser Tyr Lys Asp Gly Val Ser Phe Asn Pro Gly Phe Pro Pro Gln<br>            115                        120                    125 | 384 | |
| tca tgt ggc tac ggc acc gtg acc gac gcc gag gcc cac atc gtg acc<br>Ser Cys Gly Tyr Gly Thr Val Thr Asp Ala Glu Ala His Ile Val Thr<br>130                          135                    140 | 432 | |
| gtg aca ccc cac tca gtc aag gtg gac gag tac aca ggc gaa tgg atc<br>Val Thr Pro His Ser Val Lys Val Asp Glu Tyr Thr Gly Glu Trp Ile<br>145                          150                    155                  160 | 480 | |
| gac ccc cac ttc atc ggg ggc cgc tgt aag ggc caa atc tgc gag acc<br>Asp Pro His Phe Ile Gly Gly Arg Cys Lys Gly Gln Ile Cys Glu Thr<br>                      165                        170                    175 | 528 | |
| gtg cac aac agc acc aag tgg ttt acg tca tca gac ggc gaa agc gtg<br>Val His Asn Ser Thr Lys Trp Phe Thr Ser Ser Asp Gly Glu Ser Val<br>                      180                        185                    190 | 576 | |
| tgc agc caa ctg ttt acg ctc gtg ggc ggc atc ttc ttt agc gac agc<br>Cys Ser Gln Leu Phe Thr Leu Val Gly Gly Ile Phe Phe Ser Asp Ser<br>            195                        200                    205 | 624 | |
| gag gag atc acc agc atg ggc ctc ccg gag aca gga atc cgc agc aac<br>Glu Glu Ile Thr Ser Met Gly Leu Pro Glu Thr Gly Ile Arg Ser Asn<br>210                          215                    220 | 672 | |
| tac ttt ccg tac atc agc acc gag gga atc tgt aag atg cct ttt tgc<br>Tyr Phe Pro Tyr Ile Ser Thr Glu Gly Ile Cys Lys Met Pro Phe Cys<br>225                          230                    235                  240 | 720 | |
| cgc aag cag gga tat aag ctg aag aat gac ctg tgg ttc cag atc atg<br>Arg Lys Gln Gly Tyr Lys Leu Lys Asn Asp Leu Trp Phe Gln Ile Met<br>                      245                        250                    255 | 768 | |
| gac ccg gac ctg gac aag acc gtc cgc gat ctg ccc cac atc aag gac<br>Asp Pro Asp Leu Asp Lys Thr Val Arg Asp Leu Pro His Ile Lys Asp<br>            260                        265                    270 | 816 | |
| tgt gat ctg tca tca agc atc atc acc ccc gga gaa cac gcc acg gac<br>Cys Asp Leu Ser Ser Ser Ile Ile Thr Pro Gly Glu His Ala Thr Asp<br>275                          280                    285 | 864 | |
| atc agc ctc atc agc gat gtg gag cgc atc ctc gac tac gct ctc tgc<br>Ile Ser Leu Ile Ser Asp Val Glu Arg Ile Leu Asp Tyr Ala Leu Cys<br>290                          295                    300 | 912 | |
| cag aac aca tgg agc aag atc gaa agc ggc gaa ccc atc acc cca gtg<br>Gln Asn Thr Trp Ser Lys Ile Glu Ser Gly Glu Pro Ile Thr Pro Val<br>305                          310                    315                  320 | 960 | |
| gac ctg agc tat ctc ggc cca aag aac ccc ggc gtg ggg ccc gtg ttc<br>Asp Leu Ser Tyr Leu Gly Pro Lys Asn Pro Gly Val Gly Pro Val Phe<br>                      325                        330                    335 | 1008 | |
| acc atc atc aac ggg agc ctg cac tac ttt aca agc aag tat ctg cgc<br>Thr Ile Ile Asn Gly Ser Leu His Tyr Phe Thr Ser Lys Tyr Leu Arg<br>                340                        345                    350 | 1056 | |
| gtg gag ctc gaa agc cca gtc atc ccc cgc atg gag ggg aag gtg gcc<br>Val Glu Leu Glu Ser Pro Val Ile Pro Arg Met Glu Gly Lys Val Ala<br>            355                        360                    365 | 1104 | |
| ggg acc cgc atc gtg cgc cag ctg tgg gac cag tgg ttc cct ttt ggc<br>Gly Thr Arg Ile Val Arg Gln Leu Trp Asp Gln Trp Phe Pro Phe Gly<br>370                          375                    380 | 1152 | |
| gag gtg gaa atc ggc ccc aac ggc gtg ctg aag acc aag caa gga tat<br>Glu Val Glu Ile Gly Pro Asn Gly Val Leu Lys Thr Lys Gln Gly Tyr<br>385                          390                    395                  400 | 1200 | |
| aag ttc ccg ctg cac atc atc ggg acg ggc gaa gtg gac agc gat atc<br>Lys Phe Pro Leu His Ile Ile Gly Thr Gly Glu Val Asp Ser Asp Ile | 1248 | |

```
aag atg gag cgc gtg gtc aag cac tgg gag cac cca cac atc gag gct    1296
Lys Met Glu Arg Val Val Lys His Trp Glu His Pro His Ile Glu Ala
        420                 425                 430 gct cag acc ttt ctc aag aag gac gat acc ggc gaa gtc ctg tat tac    1344
Ala Gln Thr Phe Leu Lys Lys Asp Asp Thr Gly Glu Val Leu Tyr Tyr
                435                 440                 445 ggg gat acg gga gtg agc aag aac cct gtg gag ctg gtg gaa ggc tgg    1392
Gly Asp Thr Gly Val Ser Lys Asn Pro Val Glu Leu Val Glu Gly Trp
450                 455                 460 ttc agc gga tgg cgc agc agc atc gct tca ttt ttt ttc atc atc ggc    1440
Phe Ser Gly Trp Arg Ser Ser Ile Ala Ser Phe Phe Phe Ile Ile Gly
465                 470                 475                 480 ctc atc atc ggg ctg ttt ctg gtg ctg cgc gtc ggc atc cac ctg tgc    1488
Leu Ile Ile Gly Leu Phe Leu Val Leu Arg Val Gly Ile His Leu Cys
                485                 490                 495 atc aag ctg aag cac acc aag aag cgc cag atc tat acc gac atc gag    1536
Ile Lys Leu Lys His Thr Lys Lys Arg Gln Ile Tyr Thr Asp Ile Glu
                500                 505                 510 atg aat cgc ctg ggg aag taa                                         1557
Met Asn Arg Leu Gly Lys
            515

<210> SEQ ID NO 90
<211> LENGTH: 518
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 90

Met Leu Ser Tyr Leu Ile Phe Ala Leu Ala Val Ser Pro Ile Leu Gly
1               5                   10                  15

Lys Ile Glu Ile Val Phe Pro Gln His Thr Thr Gly Asp Trp Lys Arg
            20                  25                  30

Val Pro His Glu Tyr Asn Tyr Cys Pro Thr Ser Ala Asp Lys Asn Ser
        35                  40                  45

His Gly Thr Gln Thr Gly Ile Pro Val Glu Leu Thr Met Pro Lys Gly
    50                  55                  60

Leu Thr Thr His Gln Val Glu Gly Phe Met Cys His Ser Ala Leu Trp
65                  70                  75                  80

Met Thr Thr Cys Asp Phe Arg Trp Tyr Gly Pro Lys Tyr Ile Thr His
                85                  90                  95

Ser Ile His Asn Glu Glu Pro Thr Asp Tyr Gln Cys Leu Glu Ala Ile
            100                 105                 110

Lys Ser Tyr Lys Asp Gly Val Ser Phe Asn Pro Gly Phe Pro Pro Gln
        115                 120                 125

Ser Cys Gly Tyr Gly Thr Val Thr Asp Ala Glu Ala His Ile Val Thr
    130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Gln Ile Cys Glu Thr
                165                 170                 175

Val His Asn Ser Thr Lys Trp Phe Thr Ser Ser Asp Gly Glu Ser Val
            180                 185                 190

Cys Ser Gln Leu Phe Thr Leu Val Gly Gly Ile Phe Phe Ser Asp Ser
        195                 200                 205
```

```
Glu Glu Ile Thr Ser Met Gly Leu Pro Glu Thr Gly Ile Arg Ser Asn
    210             215             220

Tyr Phe Pro Tyr Ile Ser Thr Glu Gly Ile Cys Lys Met Pro Phe Cys
225             230             235             240

Arg Lys Gln Gly Tyr Lys Leu Lys Asn Asp Leu Trp Phe Gln Ile Met
            245             250             255

Asp Pro Asp Leu Asp Lys Thr Val Arg Asp Leu Pro His Ile Lys Asp
            260             265             270

Cys Asp Leu Ser Ser Ser Ile Ile Thr Pro Gly Glu His Ala Thr Asp
        275             280             285

Ile Ser Leu Ile Ser Asp Val Glu Arg Ile Leu Asp Tyr Ala Leu Cys
    290             295             300

Gln Asn Thr Trp Ser Lys Ile Glu Ser Gly Glu Pro Ile Thr Pro Val
305             310             315             320

Asp Leu Ser Tyr Leu Gly Pro Lys Asn Pro Gly Val Gly Pro Val Phe
            325             330             335

Thr Ile Ile Asn Gly Ser Leu His Tyr Phe Thr Ser Lys Tyr Leu Arg
            340             345             350

Val Glu Leu Glu Ser Pro Val Ile Pro Arg Met Glu Gly Lys Val Ala
            355             360             365

Gly Thr Arg Ile Val Arg Gln Leu Trp Asp Gln Trp Phe Pro Phe Gly
    370             375             380

Glu Val Glu Ile Gly Pro Asn Gly Val Leu Lys Thr Lys Gln Gly Tyr
385             390             395             400

Lys Phe Pro Leu His Ile Ile Gly Thr Gly Glu Val Asp Ser Asp Ile
            405             410             415

Lys Met Glu Arg Val Val Lys His Trp Glu His Pro His Ile Glu Ala
            420             425             430

Ala Gln Thr Phe Leu Lys Lys Asp Asp Thr Gly Glu Val Leu Tyr Tyr
        435             440             445

Gly Asp Thr Gly Val Ser Lys Asn Pro Val Glu Leu Val Glu Gly Trp
    450             455             460

Phe Ser Gly Trp Arg Ser Ser Ile Ala Ser Phe Phe Phe Ile Ile Gly
465             470             475             480

Leu Ile Ile Gly Leu Phe Leu Val Leu Arg Val Gly Ile His Leu Cys
            485             490             495

Ile Lys Leu Lys His Thr Lys Lys Arg Gln Ile Tyr Thr Asp Ile Glu
            500             505             510

Met Asn Arg Leu Gly Lys
            515
```

LENTIVIRAL VECTOR BASED IMMUNOLOGICAL COMPOUNDS AGAINST MALARIA

Sequence Listing: The instant application contains a Sequence Listing which has been filed electronically in ASCII format and is hereby incorporated by reference in its entirety. Said ASCII copy, created on Aug. 11, 2015, is named B08621A_SL.txt and is 250,951 bytes in size.

The invention relates to a lentiviral vector based immunological compounds against malaria.

In view of the impediments which have been observed in the design of vaccine strategies, many diseases that lead to high mortality and morbidity such as malaria still necessitate the development of new vaccine platforms capable of eliciting strong T-cell mediated immunity and advantageously potent humoral immune responses. Among parasitic infections affecting humans, malaria is a disease for which numerous attempts for such vaccines have been proposed.

However, concerning malaria, only vaccines containing radiation attenuated sporozoites consistently induce sterile immunity in rodents (Nussenzweig R. S. et al, Nature 216, 160-162 (1967)), monkeys (Gwadz; R. W. et al, Bull World Health Organ 57 Suppl 1, 165-173 (1979)) and humans (Clyde, D. F. et al, Am J. Med Sci 266, 169-177 (1973). Albeit very interesting, the irradiated sporozoite vaccine approach still needs to overcome numerous challenges, in particular related to safety, production, storage and distribution, before it can be considered promising for mass vaccination.

In a Review Article, Limbach K. J. & Richie T. L. (Parasit immunology, 2009, 31, 501-519) have considered different available vaccine platforms against malaria, which are based on the use of viral vectors as delivery means for the antigens eliciting an immune response. Such platforms include vaccines designed on the basis of poxvirus-vectored malaria antigens, or adenovirus-vectored malaria antigens, both types of vectors being inter alia proposed in approaches involving heterologous prime-boost regimens for administration. Apart from these poxvirus or adenovirus based technologies, the authors of the review disclose that novel vector systems may be promising in animal models considering accordingly yellow fever vectored strategies or alpha virus replicon vectored strategies. They also envisage various potentially interesting ways to overcome the persisting difficulties in designing vaccine vectors that may be efficient in providing long-lasting immunity in mammalian hosts and fulfil the requirements of safety for administration to human hosts. Such ways would include combination of heterologous delivery means for the antigens, use of adjuvants or immunomodulatory components.

In an attempt to overcome at least some of the drawbacks observed when assaying the proposed vaccine compositions of the prior art, the inventors have considered the approach of lentiviral vectors as a basis for a new vaccination platform with a view to develop prophylactic vaccines against malaria.

Malaria is a pathology which is transmitted to the host by *Anophele* mosquitoes and is endemic in many countries where it generates the death of many millions of people each year. Apart from mortality, malaria causes morbidity in a large proportion of the population in countries where it is endemic, thereby causing medical and economic major concerns for these countries.

Five species of *Plasmodium* parasites are known to infect human: *Plasmodium vivax, Plasmodium ovale, Plasmodium malariae, Plasmodium knowlesi* (17) and *Plasmodium falciparum*, the latter being the agent of malaria which causes almost all mortality cases. Infection in humans begins with inoculation of sporozoites forms of the parasite that originate from female mosquitoes. These forms of the parasite are rapidly transferred from the blood flow to the liver of the human host where they proceed with invasion of hepatocytes. Depending on the strain of *Plasmodium*, the duration of the intra-hepatic cycle of the parasite is from 5 to 15 days, the shorter (around 5.5 days) being for *P. falciparum*. The parasite amplifies in the liver as a result of asexual replication in the infected cells, giving rise to merozoite forms of the parasite. After the merozoites have been liberated from the hepatocytes, they progress toward a blood-stage infection which corresponds to the symptomatic phase of the infection in the human host. Accordingly, the merozoites rapidly penetrate into red blood cells (erythrocytes) through a specific membrane receptor. The merozoite invasion of the erythrocytes corresponds to the erythrocytic stage of the cycle which lasts for 48 to 72 hours depending on the strain of *Plasmodium*. During this stage, merozoites undergo multiple nuclear divisions, giving rise to the liberation of further merozoites, which are able to perform invasion of additional red blood cells and thus to repeat the cycle. In humans, the symptomatic disease is the result of the effects of invasion of erythrocytes, of their destruction and of the response of the hosts. During the infection, some of the parasital forms differenciate as gametocytes which are then ingested by mosquitoes where they undergo a sporogonic cycle, giving rise to sporozoites which then infect humans.

Due to the cycle of the infection encompassing distinct stages in the human body, and different forms of the parasite, various strategies have been proposed in order to deliver vaccine principles and various antigens of *Plasmodium* have been proposed as targets for the immune response, especially when addressing humoral antibody response.

Target candidates suitable for causing or improving the immune response may encompass various antigens with a view to design a vaccine and accordingly encompass "liver-stage antigens" (also designated as "pre-erythrocytic stage antigens") and/or "blood-stage antigens".

Within the frame of the present invention, the inventors have primarily considered that pre-erythrocytic stage antigens of malaria parasite may be advantageously used to elicit a protective immune response which would be uniformly effective at the level of a population, because they show less variability than antigens appearing at a later stage in the cycle of the parasite in humans. The inventors have also considered that for a long-term protection against malaria, means suitable to elicit cellular responses would be necessary, and would advantageously be supplemented by humoral responses.

The inventors have accordingly determined that a protective immune response would require the onset and development of efficient effector cells and memory cells and that said response should be strong enough to outperform the efficiency of the immune response which has been observed to natural infection.

The invention thus provides a novel lentiviral-based vector, as a new platform for the preparation or development of malaria vaccine which, in addition to the delivery means of the active principle for the immune composition, enables the determination of an appropriate immunization patterns suitable for eliciting a strong and long-lasting immune response when adapted to humans, as proved in a murine model commonly used for malaria.

The invention accordingly relates to lentiviral vector particles which are lentiviral vector particles, in particular replication-incompetent lentiviral vector particles, especially replication-incompetent HIV-based vector particles characterized in that (i) they are pseudotyped with a determined heterologous viral envelope protein or viral envelope proteins originating from a RNA virus and (ii) they comprise in their genome at least one recombinant polynucleotide encoding at least one polypeptide(s) carrying epitope(s) of a pre-erythrocytic stage antigen of a *Plasmodium* parasite capable of infecting a mammalian host, wherein said epitope(s) encompass(es) T-epitope(s).

In a particular embodiment of the invention, the encoded polypeptide of a pre-erythrocytic stage antigen of a *Plasmodium* parasite further comprises B-epitope(s).

According to the invention, the lentiviral vector particles are either designed to express proficient (i.e., integrative-competent) or deficient (i.e., integrative-incompetent) particles.

The expressions "malaria parasite" and "*Plasmodium* parasite>> are used interchangeably in the present application. They designate every and all forms of the parasite that are associated with the various stages of the cycle in the mammalian, especially human host, including in particular sporozoites, especially spororoites present in the blood flow after inoculation, or sporozoites developing in the hepatocytes, merozoites, including especially merozoites produced in the hepatocytes (forms of the pre-erythrocytic stage and including forms of the erythrocytic stage of the cycle such as merozoites contained in red-blood cells of the cycle). These forms of the parasite are characterized by various specific antigens that are well known and identified in the art, and can also be designated by reference to the stage of the infection.

The expressions "T-epitope" and "B-epitope" refer to antigenic determinants that are involved respectively in the adaptive immune response driven by T cells and in the immune response driven by B cells. In particular said T-epitopes and respectively B-epitopes elicit T cell, respectively B cell immune response when delivered to the host in suitable conditions.

The lentiviral vector particles (or lentiviral vectors or lentiviral-based vector particles) defined in the present invention are pseudotyped lentiviral vectors consisting of vector particles bearing envelope protein or envelope proteins which originate from a virus different from the particular lentivirus, especially HIV, in particular HIV-1, which provides the vector genome of the lentiviral vector particles. Accordingly, said envelope protein or envelope proteins, are "heterologous" viral envelope protein or viral envelope proteins with respect to the vector genome of the particles. In the following pages, reference will also be made to "envelope protein(s)" to encompass any type of envelope protein or envelope proteins suitable to perform the invention.

When reference is made to "lentiviral" vectors (lentiviral-based vectors) in the application, it encompasses, in a particular embodiment, HIV-based vectors and especially HIV-1-based vectors.

The lentiviral vectors according to the invention are replacement vectors, meaning that the sequences of the original lentivirus encoding the lentiviral proteins are essentially deleted in the genome of the vector or, when present, are modified, and especially mutated, especially truncated, to prevent expression of biologically active lentiviral proteins, in particular, in the case of HIV, to prevent the expression by said transfer vector, of functional ENV, GAG, and POL proteins and optionally of further structural and/or accessory and/or regulatory proteins of the lentivirus, especially of HIV.

The "vector genome" of the vector particles is a recombinant vector which also comprises the polynucleotide or transgene of interest encoding the polypeptide(s) of malaria parasite. The lentiviral-based sequence and polynucleotide/transgene of the vector genome are borne by a plasmid vector thus giving rise to the "transfer vector" also referred to as "sequence vector". Accordingly, these expressions are used interchangeably in the present application.

The vector genome as defined herein accordingly contains, apart from the so-called recombinant polynucleotide placed under control of proper regulatory sequences for its expression, the sequences of the original lentiviral genome which are non-coding regions of said genome, and are necessary to provide recognition signals for DNA or RNA synthesis and processing (mini-viral genome). These sequences are cis-acting sequences necessary for packaging, reverse transcription and transcription and furthermore for the particular purpose of the invention, they contain a functional sequence favouring nuclear import in cells and accordingly transgene transfer efficiency in said cells, which element is described as a DNA Flap element and contains or consists of the so-called central cPPT-CTS nucleotidic domain present in lentiviral genome sequences or in some retroelements such as those of yeasts.

The structure and composition of the vector genome used to prepare the lentiviral vectors of the invention are based on the principles described in the art and on examples of such lentiviral vectors primarily disclosed in (Zennou et al, 2000; Firat H. et al, 2002; VandenDriessche T. et al). Constructs of this type have been deposited at the CNCM (Institut Pasteur, France) as will be referred to herein. In this respect reference is also made to the disclosure, including to the deposited biological material, in patent applications WO 99/55892, WO 01/27300 and WO 01/27304.

According to a particular embodiment of the invention, a vector genome may be a replacement vector in which all the viral protein coding sequences between the 2 long terminal repeats (LTRs) have been replaced by the recombinant polynucleotide encoding the polypeptide of the malaria parasite, and wherein the DNA-Flap element has been re-inserted in association with the required cis-acting sequences described herein. Further features relating to the composition of the vector genome are disclosed in relation to the preparation of the particles.

A lentiviral vector particle of the invention may comprise in its genome more than one recombinant polynucleotide encoding at least one polypeptide carrying epitope(s) of a pre-erythrocytic stage antigen as disclosed herein. In particular, said vector genome comprises two polynucleotides which are consecutive or separated on the genome and which encode different polypeptides of either the same or distinct antigens of the pre-erythrocytic stage of a *Plasmodium* parasite or different polypeptides of distinct antigens of different forms of the malaria parasite, especially antigens of the pre-erythrocytic stage and antigens of the erythrocytic stage of the parasite.

In a particular embodiment, the vector genome contains two recombinant polynucleotides, each of them encoding a distinct polypeptide and each polypeptide originating from a different antigen of the same stage.

By the expression "polypeptide carrying epitope(s) of an antigen", it is intended according to the present invention a polypeptide which may be a native antigen of a *Plasmodium* parasite, a mutated version thereof and in particular a fragment of such a native antigen and especially a truncated version of such a native antigen. A polypeptide has an amino acid sequence which is sufficient to provide one or several epitope(s), and may accordingly have a length of at least about 4 amino acid residues and especially from about 4 to about 8 amino acid residues for conformational B epitopes or at least about 9 amino acid residues and in particular from about 9 to about 19 amino acid residues for sequential T epitopes.

In a particular embodiment of the invention, the recombinant polynucleotide of the lentiviral vector particles encodes a truncated version of an antigen of the malaria parasite, especially a fragment which results from the deletion of a functional domain of the full-length (i.e., native) antigen, when said domain is not useful or is detrimental to the elicitation of an immune response in a host.

In a particular embodiment of the invention, the lentiviral vector particles comprise in their genome, at least one recombinant polynucleotide which encodes a polypeptide(s) of an antigen from the circumsporozoite protein of a *Plasmodium* parasite, esp. of *Plasmodium falciparum* or *Plasmodium malariae, Plasmodium vivax, Plasmodium ovale* or *Plasmodium knowlesi*. It is especially a truncated version of the CSP and in particular a polypeptide devoid of the GPI anchoring motif of the CSP.

In an embodiment of the invention, the lentiviral vector particles comprise in their genome a recombinant polynucleotide which encodes a polypeptide(s) of an antigen selected from the group of the sporozoite surface protein 2 (TRAP/SSP2), liver-stage antigen (LSA in particular LSA3), Pf exported protein 1 (Pf Exp1)/Py hepatocyte erythrocyte protein (PyHEP17), and Pf antigen 2 (where Pf represents *Plasmodium falciparum* and Py represents *Plamsodium yoelii*), sporozoite and liver stage antigen (SALSA), sporozoïte threonine and asparagines-rich (STARP) or other pre-erythrocytic antigen, possibly in addition to the polypeptide of an antigen of the CSP.

In a particular embodiment of the invention, the polypeptide of the antigen of the malaria parasite is a fragment of the CSP protein and it is co-expressed by the vector genome with a polypeptide of another antigen of the malaria parasite, either an antigen from the pre-erythrocytic stage or an antigen of the erythrocytic stage. Antigens of the erythrocytic stage which may be used to design the polynucleotide encoding the polypeptide according to the invention are merozoïte surface protein 1 (MSP2), in particular Merozoïte surface protein 1 (MSP-1), Merozoïte surface protein 2 (MSP-2) merozoïte surface protein 3 (MSP-3), Merozoïte surface protein 4 (MSP-4), Merozoïte surface protein 6 (MSP-6), Ring-infected erythrocyte surface antigen (RESA), Rhoptry associated protein 1 (RAP-1), Apical membrane antigen 1 (AMA-1), Erythrocyte binding antigen (EBA-175), Erythrocyte membrane-associated giant protein or Antigen 332 (Ag332), dnaK-type molecular chaperone, Glutamate-rich protein (GLURP), in particular MSP3-GLURP fusion protein (WO 2004/043488; ref 28), Erythrocyte membrane protein 1 (EMP-1), Serine repeat antigen (SERA), Clustered-asparagine-rich protein (CARP), Cirumsporozoite protein-related antigen precursor (CRA), Cytoadherence-linked asexual protein (CLAG), Acid basic repeat antigen (ABRA) or 101 kDa malaria antigen, Rhoptry antigen protein (RAP-2), Knob-associated histidine-rich protein (KHRP), Rhoptry antigen protein (RAP), Cysteine protease, Hypothetical protein PFE1325w, Protective antigen (MAg-1), Fructose-bisphosphate aldolase, Ribosomal phosphoprotein PO, P-type ATPase, Glucose-regulated protein (GRP78), Asparagine and aspartate-rich protein (AARP1), Interspersed repeat antigen or PFE0070w.}

Antigens of the sexual stage which may be used to design the polynucleotide encoding the polypeptide according to the invention are Sexual stage and sporozoite surface antigen, Antigen Pfg27/25, Antigen QF122, 11-1 polypeptide, Gametocyte-specific surface protein (Pfs230) Ookinete surface protein (P25), Chitinase, Multidrug resistance protein (MRP).

These antigens are disclosed by reference to *P. falciparum* and may have a counterpart in other *Plasmodium* species. They are reported in Vaughan K. et al (18).

Vaughan K et al disclose in particular epitopes of said antigens that may be used by the skilled person as a basis to prepare the recombinant polynucleotide(s) used in the vector of the invention.

The above-cited antigens of *Plasmodium* parasite have been disclosed in the prior art, including through their sequences which are available in data bases.

The circumsporozoite protein (CSP) is one of the preferred antigens for the preparation of the lentiviral vector particles of the invention. It constitutes the sporozoite coat protein, which has been recognized in the past as the target of protective antibodies. Apart from its ability to elicit anti-CS antibodies, this antigen further contains T-epitopes including especially CD8+ T-cells epitopes and CD4+ T-cells epitopes. Particular CSP antigens are disclosed through their amino acid sequences as SEQ ID No 20, 23, 26, 27, 28, 29, 30, 31, or as SEQ ID No 32 for a consensus of these sequences. The sequence of *P. vivax* is given in GenBank as AY674050.1.

In a particular embodiment of the invention, the lentiviral vector particles have in their genome a recombinant polynucleotide which encodes at least a polypeptide of the CSP-antigen of *Plasmodium yoelii* as illustrated in the examples or advantageously of *Plasmodium falciparum*, e.g., a polypeptide corresponding to a fragment of said CSP-antigen devoid of the GPI-anchoring motif in *Plasmodium yoelii* is CSP DGPI having sequence SEQ ID No 21. Said GPI motif corresponds to the last 12 amino acid residues in the C-terminal part in the native amino acid sequence of the CSP antigen of *Plasmodium Yoelii*. The counterpart of said fragment of the CSP protein in *P. Falciparum* is disclosed in the figures and sequences (SEQ ID No 23 for the native protein, SEQ ID No 24 for the sequence devoid of the GPI motif, SEQ ID No 25 for the sequence truncated in the N-terminal end) and used to provide evidence in a suitable murine model, of the capacity of the polypeptide to elicit a protective immune response and even a sterilizing protection against malaria.

In a particular embodiment of the invention, polynucleotide(s) of the lentiviral vector particles has(have) a mammalian codon optimized (CO) nucleotide sequence and optionally the lentiviral sequences of the genome of said particles has a mammalian codon optimized nucleotide sequence.

It has been observed that codon optimized nucleotide sequences, especially when optimized for expression in mammalian and in particular in human cells, enable the production of higher yield of particles in such mammalian or human cells. Production cells are illustrated in the examples. Accordingly, when lentiviral vector particles of the invention are administered to a mammalian, especially to a human host, higher amounts of particles are produced in said host which favour the elicitation of a strong immune response.

In a particular embodiment of the invention, the lentiviral vector particles disclosed herein further contain in their genome, a recombinant polynucleotide which encodes a polypeptide of an antigen of the blood stage of the cycle of the parasite as disclosed above and/or an antigen of the sexual stage.

The polypeptide is either the native antigen or a modified version thereof, especially a fragment which comprises or consists in T-cell epitope(s) or B-cell epitope(s) or both.

Examples of polypeptides expressed as a result of administering the lentiviral vector particles of the invention, are the polypeptides encoded by the vector plasmids (or sequence vectors) disclosed hereafter.

The invention also relates especially to these vector plasmids, deposited at the CNCM (Paris, France) on Apr. 20, 2010 and having the following features and accession number

| | |
|---|---|
| pTRIP-IdeltalU3-CMV-MSP1$_{42}$-CO-WPRE | CNCM I-4303 |
| pTRIP-IdeltalU3-CMV-Hep17-CO-WPRE | CNCM I-4304 |
| pTRIP-IdeltalU3-CMV-Hep17ldeltalSP-CO-WPRE | CNCM I-4305 |
| pTRIP-IdeltalU3-CMV-CSP-CO-WPRE | CNCM I-4306 |
| pTRIP-IdeltalU3-CMV-CSPldeltalSP-CO-WPRE | CNCM I-4307 |
| pTRIP-IdeltalU3-CMV-CSPldeltalGPI-CO-WPRE | CNCM I-4308 |
| pTRIP-IdeltalU3-CMV-CSPldeltalSPldeltalGPI-CO-WPRE | CNCM I-4309 |

These plasmids are described in the figures and sequences of the present application. The sequence of the transgene that they contain is from *P. yoelii*. Said transgene may be advantageously replaced by the appropriate sequence from *P. Falciparum*.

The invention also concerns variants of these plasmids, where the polynucleotide encoding the polynucleotide of a *Plasmodium* antigen is modified to encode a functional immunogenic variant thereof or is substituted by a corresponding polynucleotide codon optimized from another *Plasmodium* strain especially from *Plasmodium falciparum* is modified to substitute the CMV promoter by one of the herein cited promoters.

In the deposited plasmids the polynucleotide encoding the polypeptide of a *Palsmodium yoelii* antigen is codon optimized.

According to the invention, the lentiviral vector particles are pseudotyped with a heterologous viral envelope protein or viral polyprotein of envelope originating from a RNA virus which is not the lentivirus providing the lentiviral sequences of the genome of the lentiviral particles.

As examples of typing envelope proteins for the preparation of the lentiviral vector particles, the invention relates to viral transmembrane glycosylated (so-called G proteins) envelope protein(s) of a Vesicular Stomatitis Virus (VSV), which is(are) for example chosen in the group of VSV-G protein(s) of the Indiana strain, VSV-G protein(s) of the New Jersey strain, VSV-G protein(s) of the Cocal strain, VSV-G protein of the Isfahan strain, VSV-G protein(s) of Chandipura strain, VSV-G protein(s) of Pyri strain or VSV-G protein(s) of the SVCV strain.

The envelope glycoprotein of the vesicular stomatitis virus (VSV-G) is a transmembrane protein that functions as the surface coat of the wild type viral particles. It is also a suitable coat protein for engineered lentiviral vectors. Presently, nine virus species are definitively classified in the VSV gender, and nineteen rhabdoviruses are provisionally classified in this gender, all showing various degrees of cross-neutralisation. When sequenced, the protein G genes indicate sequence similarities. The VSV-G protein presents a N-terminal ectodomain, a transmembrane region and a C-terminal cytoplasmic tail. It is exported to the cell surface via the transGolgi network (endoplasmic reticulum and Golgi apparatus).

Vesicular stomatitis Indiana virus (VSIV) and Vesicular stomatitis New Jersey virus (VSNJV) are preferred strains to pseudotype the lentiviral vectors of the invention, or to design recombinant envelope protein(s) to pseudotype the lentiviral vectors. Their VSV-G proteins are disclosed in GenBank, where several strains are presented. For VSV-G New Jersey strain reference is especially made to the sequence having accession number V01214. For VSV-G of the Indiana strain, reference is made to the sequence having accession number AAA48370.1 in Genbank corresponding to strain JO2428.

Alternatively, among VSV, Chandipura virus (CHPV), Cocal virus (COCV), Perinet virus (PERV), Piry virus (PIRYV), SVCV or Isfahan virus may be good candidates to design pseudotyping envelope proteins, and especially to prepare particles used for a boosting step of the immunization, accordingly providing second envelope protein(s) or third envelope protein(s), or further envelope protein(s) when the vector particles of the invention are used in a prime-boost administration regimen. When used accordingly, Cocal virus envelope protein(s) would be preferred for a late or last administration in a prime-boost regimen. However, Chandipura virus (CHPV) and Piry virus (PIRYV) may provide envelope proteins having low fusogenicity as a result of their lower affinity for their receptor, when comparing the vector titers obtained with particles prepared with different envelopes. Therefore in a first approach these envelopes may be excluded from the choice of envelopes in order to prepare particles with an efficient transduction capacity.

The amino acid sequences and coding sequences of the VSV-G proteins referred to herein are disclosed in patent application WO 2009/019612. Particular examples of these amino acid sequences are also provided in the present application as SEQ ID No 77, 79, 82, 84, 86, 88, 90. Plasmids containing VSV-G encoding sequences are described in said application WO 2009/019612 which is incorporated by reference. The plasmids have been deposited at the CNCM (Paris, France). Nucleotide sequences encoding said envelope proteins are disclosed in the present application as SEQ ID No 76, 78, 81, 83, 85, 87, 89.

In a particular embodiment of the invention, said first and second and if any said third or further, viral envelope protein(s) are capable of uptake by antigen presenting cells and especially by dendritic cells including by liver dendritic cells by mean of fusion and/or of endocytosis. In a particular embodiment, the efficiency of the uptake may be used as a feature to choose the envelope of a VSV for pseudotyping. In this respect the relative titer of transduction (Titer DC/Titer of other transduced cells e.g. 293T cells) may be considered as a test and envelope having a relative good ability to fuse with DC would be preferred. Relative titers of transduction are illustrated in the examples.

Antigen Presenting Cells (APC) and especially Dentritic cells (DC) are proper target cells for pseudotyped lentiviral vectors which are used as immune compositions accordingly.

Polynucleotide encoding VSV envelope protein(s) (VSV-G) also targets splenocytes, in particular Antigen Presenting Cells (APC) or Dendritic Cells (DC), or liver cells including liver dendritic cells, hepatocytes or non parenchymal cells.

The envelope protein(s), also designated sometimes as surface protein in particular viruses, are said to "originate" from a different organism, and especially from different RNA virus strains, meaning that in said protein(s), essential features of the corresponding protein(s) expressed in a determined RNA virus are maintained. Said essential features, relate to the structure or to the function of the protein and are those which enable especially the obtained protein(s) to be expressed at the surface of the vector particles for pseudotyping said vectors. The envelope proteins are then capable of being recognized and internalized in the target cells of the hosts when present on the vector particles.

In a particular embodiment, protein(s) or glycoprotein(s), suitable for use in the design of pseudotyped lentiviral vectors of the kit of compounds are used as multimeric proteins, such as VSV-G protein which is trimeric.

The envelope protein(s) are expressed from a polynucleotide containing the coding sequence for said protein(s), which polynucleotide is inserted in a plasmid (designated envelope expression plasmid or pseudotyping env plasmid) used for the preparation of the lentiviral vector particles of the invention. The polynucleotide encoding the envelope protein(s) is under the control of regulatory sequences for the transcription and/or expression of the coding sequence (including optionally post-transcriptional regulatory elements (PRE) especially a polynucleotide such as the element of the Woodchuck hepatitis virus, i.e. the WPRE sequence obtainable from Invitrogen).

Accordingly, a nucleic acid construct is provided which comprises an internal promoter suitable for the use in mammalian cells, especially in human cells in vivo and the nucleic acid encoding the envelope protein under the control of said promoter. A plasmid containing this construct is used for transfection or for transduction of cells suitable for the preparation of particles. Promoters may in particular be selected for their properties as constitutive promoters, tissue-specific promoters, or inducible promoters. Examples of suitable promoters encompass the promoters of the following genes: EF1α, human PGK, PPI (preproinsulin), thiodextrin, HLA DR invariant chain (P33), HLA DR alpha chain, Ferritin L chain or Ferritin H chain, Chymosin beta 4, Chymosin beta 10, Cystatin Ribosomal Protein L41, CMVie or chimeric promoters such as GAG(CMV early enhancer/chicken β actin) disclosed in Jones S. et al (19).

These promoters may also be used in regulatory expression sequences involved in the expression of gag-pol derived proteins from the encapsidation plasmids.

Alternatively, when the envelope expression plasmid is intended for expression in stable packaging cell lines, especially for stable expression as continuously expressed viral particles, the internal promoter to express the envelope protein(s) is advantageously an inducible promoter such as one disclosed in Cockrell A. S. et al. (20). As examples of such promoters, reference is made to tetracycline and ecdysone inducible promoters. The packaging cell line may be the STAR packaging cell line (ref 20, 21) or a SODk packaging cell line, such as SODk0 derived cell lines, including SODk1 and SODk3 (ref 20, 22, 23, 24).

The nucleotide sequence used for the expression of the envelope protein(s) required for pseudotyping the lentiviral vector particles may alternatively be modified, thus providing a variant with respect to the nucleic acid encoding the native envelope protein(s) used as reference. The modification may be carried out to improve the codons usage (codon optimization) in the cells for the preparation of the vector particles and/or in the transduced cells of the host. It may be modified to express a protein different from the native protein(s), especially one which has an improved pseudotyping capacity, an improved capacity in the level of production, or an improved capacity with respect to prevention of sero-neutralization (also designated as cross-reactive proteins) with other envelope protein(s) used in the kit of compounds.

Such a modification of the polynucleotide encoding the envelope proteins(s) or modification of the envelope protein(s) (to generate variants of native envelopes) may affect and especially improve their level of production in a cell host or their ability to pseudotype the vector particles possibly by improving the density of envelope protein(s) associated with pseudovirions. Said modification may derive from a mutation in the amino acid sequence of said protein(s), for instance by addition, deletion or substitution of one or several nucleotides or nucleotidic fragments or may relate to post translational modifications and in particular to the glycosylation status of said envelope protein(s).

The envelope protein(s) used to pseudotype the lentiviral vectors of the invention are indeed especially glycoproteins.

It has already been shown that pseudotyping viral vectors with Vesicular Stomatitis Virus glycoprotein (VSV-G) enables the transduction of a large range of cell types from different species. This VSV-G glycoprotein, in addition to its broad tropism, has an interesting stability when used for vector pseudotyping. Therefore, VSV-G have been used as a standard for evaluating the efficiency of other pseudotypes (Cronin J. et al, 2005).

According to the invention, the lentiviral vector particles are the product recovered from co-transfection of mammalian cells, with:
- a vector plasmid comprising (i) lentiviral, especially HIV-1, cis-active sequences necessary for packaging, reverse transcription, and transcription and further comprising a functional lentiviral, especially derived from HIV-1, DNA flap element and (ii) a polynucleotide encoding a polypeptide of an antigen of a malaria parasite as disclosed herein under the control of regulatory expression sequences, and optionally comprising sequences for integration;
- an expression plasmid encoding a pseudotyping envelope derived from a RNA virus, said expression plasmid comprising a polynucleotide encoding an envelope protein or proteins for pseudotyping, wherein said envelope pseudotyping protein is advantageously from a VSV and is in particular a VSV-G or a variant thereof and,
- an encapsidation plasmid, which either comprises lentiviral, especially HIV-1, gag-pol packaging sequences suitable for the production of integration-competent vector particles or modified gag-pol packaging sequences suitable for the production of integration-deficient vector particles.

The invention thus also concerns lentiviral vector particles as described above, which are the product recovered from a stable cell line with
- a vector plasmid comprising (i) lentiviral, especially HIV-1, cis-active sequences necessary for packaging, reverse transcription, and transcription and further comprising a functional lentiviral, especially HIV-1, DNA flap element and optionally comprising cis-active sequences necessary for integration, said vector plasmid further comprising (ii) a polynucleotide of a truncated mammalian, especially human, codon-optimized sequence of the cs gene of a *Plasmodium* parasite, under the control of regulatory expression sequences, especially a promoter;
- a VSV-G envelope expression plasmid comprising a polynucleotide encoding a VSV-G envelope protein or envelope proteins, wherein said polynucleotide is under the control of regulating expression sequences, in particular regulatory expression sequences comprising an inducible promoter, and;

an encapsidation plasmid, wherein the encapsidation plasmid either comprises lentiviral, especially HIV-1, gag-pol coding sequences suitable for the production of integration-competent vector particles or modified gag-pol coding sequences suitable for the production of integration-deficient vector particles, wherein said gag-pol sequences are from the same lentivirus sub-family as the DNA flap element, wherein said lentiviral gag-pol or modified gag-pol sequence is under the control of regulating expression sequences.

The stable cell lines expressing the vector particles of the invention are in particular obtained by transduction of the plasmids.

The polynucleotide encodes at least one polypeptide of a malaria antigen according to any embodiment disclosed in the present application. In particular, it encodes a polypeptide which is a truncated mammalian, especially human, codon-optimized sequence of the cs gene of a *Plasmodium* parasite, especially of *Plasmodium falciparum*.

In a particular embodiment, the polynucleotide encodes another polypeptide of a distinct antigen of the malaria parasite, or it encodes two or more polypeptides which originate and/or are derived from distinct antigens of said parasite as disclosed in the various embodiments. Accordingly, the vector plasmid may comprise several expression cassettes for the expression of the various polypeptides or may comprise bicistronic or multicistronic expression cassettes where the polynucleotides encoding the various polypeptides are separated by an IRES sequence of viral origin (Internal Ribosome Entry Site), or it may encode fusion protein(s).

The internal promoter contained the vector genome and controlling the expression of the polynucleotide encoding a polypeptide of an antigen of the malaria parasite (as a transgene or in an expression cassette) may be selected from the promoters of the following genes: EF1α, human PGK, PPI (preproinsulin), thiodextrin, HLA DR invariant chain (P33), HLA DR alpha chain, Ferritin L chain or Ferritin H chain, Chymosin beta 4, Chimosin beta 10, or Cystatin Ribosomal Protein L41 CMVie or chimeric promoters such as GAG(CMV early enhancer/chicken β actin) disclosed in Jones S. et al (19).

A promoter among the above cited internal promoters may also be selected for the expression of the envelope protein(s) and packaging (gag-pol derived) proteins.

Alternatively, vector particles can be produced from co-transfection of the plasmids disclosed herein, in stable packaging cell lines which thus become capable of continuously secreting vector particles. Promoters used in the regulatory expression sequences involved for the expression of the envelope protein(s) are advantageously inducible promoters.

The following particular embodiments may be carried out when preparing the lentiviral vector particles based on human lentivirus, and especially based on HIV virus.

According to the invention, the genome of the lentiviral vector particles is derived from a human lentivirus, especially from the HIV lentivirus. In particular, the pseudotyped lentiviral vector is an HIV-based vector, such as an HIV-1, or HIV-2 based vector, in particular is derived from HIV-1M, for example from the BRU or LAI isolates. Alternatively, the lentiviral vector providing the necessary sequences for the vector genome may be originating from lentiviruses such as EIAV, CAEV, VISNA, FIV, BIV, SIV, HIV-2, HIV-O which are capable of transfecting human cells.

As stated above, when considering it apart from the recombinant polynucleotide that it finally contains, the vector genome is a replacement vector in which the nucleic acid between the 2 long terminal repeats (LTRs) in the original lentivirus genome have been restricted to cis-acting sequences for DNA or RNA synthesis and processing, including for the efficient delivery of the transgene to the nuclear of cells in the host, or at least are deleted or mutated for essential nucleic acid segments that would enable the expression of lentiviral structure proteins including biological functional GAG polyprotein and possibly POL and ENV proteins.

In a particular embodiment, the vector genome is defective for the expression of biologically functional GAG, and advantageously for biologically functional POL and ENV proteins. Accordingly, the vector genome is devoid of the sequence encoding these proteins.

In a particular embodiment, the 5' LTR and 3' LTR sequences of the lentivirus are used in the vector genome, but the 3'-LTR at least is modified with respect to the 3'LTR of the original lentivirus at least in the U3 region which for example can be deleted or partially deleted for the enhancer. The 5'LTR may also be modified, especially in its promoter region where for example a Tat-independent promoter may be substituted for the U3 endogenous promoter.

In a particular embodiment the vector genome comprises one or several of the coding sequences for Vif-, Vpr, Vpu- and Nef-accessory genes (for HIV-1 lentiviral vectors). Alternatively, these sequences can be deleted independently or each other or can be non-functional.

The vector genome of the lentiviral vector particles comprises, as an inserted cis-acting fragment, at least one polynucleotide consisting in the DNA flap element or containing such DNA flap element. In a particular embodiment, the DNA flap is inserted upstream of the polynucleotide encoding the polypeptide of a malaria antigen, and is advantageously—although not necessarily—located in an approximate central position in the vector genome. A DNA flap suitable for the invention may be obtained from a retrovirus, especially from a lentivirus, in particular a human lentivirus especially a HIV-1 retrovirus, or from a retrovirus-like organism such as retrotransposon. It may be alternatively obtained from the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. The DNA flap may be either prepared synthetically (chemical synthesis) or by amplification of the DNA providing the DNA Flap from the appropriate source as defined above such as by Polymerase chain reaction (PCR). In a more preferred embodiment, the DNA flap is obtained from an HIV retrovirus, for example HIV-1 or HIV-2 virus including any isolate of these two types.

The DNA flap (defined in Zennou V. et al. ref 27, 2000, Cell vol 101, 173-185 or in WO 99/55892 and WO 01/27304), is a structure which is central in the genome of some lentiviruses especially in HIV, where it gives rise to a 3-stranded DNA structure normally synthesized during especially HIV reverse transcription and which acts as a cis-determinant of HIV genome nuclear import. The DNA flap enables a central strand displacement event controlled in cis by the central polypurine tract (cPPT) and the central termination sequence (CTS) during reverse transcription.

When inserted in lentiviral-derived vectors, the polynucleotide enabling the DNA flap to be produced during reverse-transcription, stimulates gene transfer efficiency and complements the level of nuclear import to wild-type levels (Zennou et al., Cell, 2000).

Sequences of DNA flaps have been disclosed in the prior art, especially in the above cited patent applications. These sequences are also disclosed as SEQ ID NO 69 to SEQ ID NO 75. They are preferably inserted as a fragment, optionally with additional flanking sequences, in the vector genome, in a position which is preferably near the centre of said vector genome. Alternatively they may be inserted immediately upstream from the promoter controlling the expression of the polynucleotide(s) of the invention. Said fragments comprising the DNA flap, inserted in the vector genome may have a sequence of about 80 to about 200 bp, depending on its origin and preparation.

According to a particular embodiment, a DNA flap has a nucleotide sequence of about 90 to about 140 nucleotides.

In HIV-1, the DNA flap is a stable 99-nucleotide-long plus strand overlap. When used in the genome vector of the lentiviral vector of the invention, it may be inserted as a longer sequence, especially when it is prepared as a PCR fragment. A particular appropriate polynucleotide comprising the structure providing the DNA flap is a 178-base pair polymerase chain reaction (PCR) fragment encompassing the cPPT and CTS regions of the HIV-1 DNA (Zennou et al 2000).

This PCR fragment may especially be derived from infective DNA clone of HIV-1 LAI especially pLAI3 of HIV1, as a fragment corresponding to the sequence from nucleotide 4793 to 4971. If appropriate, restriction sites are added to one or both extremities of the obtained fragment, for cloning. For example, Nar I restriction sites may be added to the 5' extremities of primers used to perform the PCR reaction.

Therefore, the DNA flap used in the present invention, is deleted from the unnecessary 5' and 3' parts of the pol gene of the original lentiviral genome and is recombined with sequences of different origin.

It is specified that the DNA flap used in the genome vector and the polynucleotides of the encapsidation plasmid encoding the GAG and POL polyproteins should originate from the same lentivirus sub-family or from the same retrovirus-like organism.

Preferably, the other cis-activating sequences of the genome vector also originate from the same lentivirus or retrovirus-like organism, as the one providing the DNA flap.

The vector genome may further comprise one or several unique restriction site(s) for cloning the recombinant polynucleotide.

In a preferred embodiment, in said vector genome, the 3' LTR sequence of the lentiviral vector genome is devoid of at least the activator (enhancer) and possibly the promoter of the U3 region. In another particular embodiment, the 3' LTR region is devoid of the U3 region (delta U3). In this respect, reference is made to the description in WO 01/27300 and WO 01/27304.

In a particular embodiment, in the vector genome, the U3 region of the LTR 5' is replaced by a non lentiviral U3 or by a promoter suitable to drive tat-independent primary transcription. In such a case, the vector is independent of tat transactivator.

The vector genome also comprises the psi (ψ) packaging signal. The packaging signal is derived from the N-terminal fragment of the gag ORF. In a particular embodiment, its sequence could be modified by frameshift mutation(s) in order to prevent any interference of a possible transcription/translation of gag peptide, with that of the transgene.

The vector genome may optionally also comprise elements selected among a splice donor site (SD), a splice acceptor site (SA) and/or a Rev-responsive element (RRE).

According to a particular embodiment, the vector plasmid (or added genome vector) comprises the following cis-acting sequences for a transgenic expression cassette:

1. The LTR sequence (Long-Terminal Repeat), required for reverse transcription, the sequences required for transcription and including optionally sequences for viral DNA integration. The 3' LTR is deleted in the U3 region at least for the promoter to provide SIN vectors (Self-inactivating), without perturbing the functions necessary for gene transfer, for two major reasons: first, to avoid trans-activation of a host gene, once the DNA is integrated in the genome and secondly to allow self-inactivation of the viral cis-sequences after retrotranscription. Optionally, the tat-dependent U3 sequence from the 5'-LTR which drives transcription of the genome is replaced by a non endogenous promoter sequence. Thus, in target cells only sequences from the internal promoter will be transcribed (transgene).
2. The ψ region, necessary for viral RNA encapsidation.
3. The RRE sequence (REV Responsive Element) allowing export of viral messenger RNA from the nucleus to the cytosol after binding of the Rev protein.
4. The DNA flap element (cPPT/CTS, normally contained in Pol) to facilitate nuclear import.
5. Optionally post-transcriptional elements such as the WPRE cis-active sequence (Woodchuck hepatitis B virus Post-Responsive Element) also added to optimize stability of mRNA (Zufferey et al., 1999), the matrix or scaffold attachment regions (SAR and MAR sequences) such as those of the immunoglobulin-kappa gene (Park F. et al Mol Ther 2001; 4: 164-173).

The lentiviral vector of the invention is non replicative (replication-incompetent) i.e., the vector and lentiviral vector genome are regarded as suitable to alleviate concerns regarding replication competent lentiviruses and especially are not able to form new particles budding from the infected host cell after administration. This may be achieved in well known ways as the result of the absence in the lentiviral genome of the gag, pol or env genes, or their absence as "functional genes". The gag and pol genes are thus, only provided in trans. This can also be achieved by deleting other viral coding sequence(s) and/or cis-acting genetic elements needed for particles formation.

By "functional" it is meant a gene that is correctly transcribed, and/or correctly expressed. Thus, if present in the lentiviral vector genome of the invention in this embodiment contains sequences of the gag, pol, or env are individually either not transcribed or incompletely transcribed; the expression "incompletely transcribed" refers to the alteration in the transcripts gag, gag-pro or gag-pro-pol, one of these or several of these being not transcribed. Other sequences involved in lentiviral replication may also be mutated in the vector genome, in order to achieve this status. The absence of replication of the lentiviral vector should be distinguished from the replication of the lentiviral genome. Indeed, as described before, the lentiviral genome may contain an origin of replication ensuring the replication of the lentiviral vector genome without ensuring necessarily the replication of the vector particles.

In order to obtain lentiviral vectors according to the invention, the vector genome (as a vector plasmid) must be encapsidated in particles or pseudo-particles. Accordingly, lentiviral proteins, except the envelope proteins, have to be provided in trans to the vector genome in the producing system, especially in producing cells, together with the vector genome, having recourse to at least one encapsidation plasmid carrying the gag gene and either the pol lentiviral gene or an integrative-incompetent pol gene, and preferably lacking some or all of the coding sequences for Vif-, Vpr, Vpu- and Nef-accessory genes (for HIV-1 lentiviral vectors).

A further plasmid is used, which carries a polynucleotide encoding the envelope pseudotyping protein(s) selected for pseudotyping lentiviral vector particles.

In a preferred embodiment, the packaging plasmid encodes only the lentiviral proteins essential for viral particle synthesis. Accessory genes whose presence in the plasmid could raise safety concerns are accordingly removed. Accordingly, viral proteins brought in trans for packaging are respectively as illustrated for those originating from HIV-1:

1. GAG proteins for building of the matrix (MA, with apparent Molecular Weight p17), the capsid (CA, p24) and nucleocapsid (NC, p6).
2. POL encoded enzymes: integrase, protease and reverse transcriptase.
3. TAT and REV regulatory proteins, when TAT is necessary for the initiation of LTR-mediated transcription; TAT expression may be omitted if the U3 region of 5'LTR is substituted for a promoter driving tat-independent transcription. REV may be modified and accordingly used for example in a recombinant protein which would enable recognition of a domain replacing the RRE sequence in the vector genome, or used as a fragment enabling binding to the RRE sequence through its RBD (RNA Binding Domain).

In order to avoid any packaging of the mRNA generated from the genes contained in the packaging plasmid in the viral particles, the ψ region is removed from the packaging plasmid. A heterologous promoter is inserted in the plasmid to avoid recombination issues and a poly-A tail is added 3' from the sequences encoding the proteins. Appropriate promoters have been disclosed above.

The envelope plasmid encodes the envelope protein(s) for pseudotyping which are disclosed herein, under the control of an internal promoter, as disclosed herein.

Any or all the described plasmids for the preparation of the lentiviral vector particles of the invention may be codon optimized (CO) in the segment encoding proteins. Codon optimization according to the invention is preferably performed to improve translation of the coding sequences contained in the plasmids, in mammalian cells, especially human cells. According to the invention, codon optimization is especially suited to directly or indirectly improve the preparation of the vector particles or to improve their uptake by the cells of the host to whom they are administered, or to improve the efficiency of the transfer of the polynucleotide encoding the polypeptide of an antigen of the malaria parasite (transgene) in the genome of the transduced cells of the host. Methods for optimizing codons are well known in the art and codon optimization is especially performed using available programs to that effect. Codon optimization is illustrated for the coding sequences contained in the described pTRIP or pThV plasmids of the invention illustrated in the examples.

In a particular embodiment of the invention, the pseudotyped lentiviral vector is also, or alternatively, integrative-incompetent. In such a case, the vector genome and thus the recombinant polynucleotide which it contains do not integrate into the genome of the transduced cells or in the cells of the host to whom it has been administered.

The present invention relates to the use of a lentiviral vector wherein the expressed integrase protein is defective and which further comprises a polynucleotide especially encoding at least one polypeptide carrying epitope(s) of a pre-erythrocytic stage antigen of a *Plasmodium* parasite, in an immunogenic composition.

By "integration-incompetent", it is meant that the integrase, preferably of lentiviral origin, is devoid of the capacity of integration of the lentiviral genome into the genome of the host cells i.e., an integrase protein mutated to specifically alter its integrase activity.

Integration-incompetent lentiviral vectors are obtained by modifying the pol gene encoding the Integrase, resulting in a mutated pol gene encoding an integrative deficient integrase, said modified pol gene being contained in the encapsidation plasmid. Such integration-incompetent lentiviral vectors have been described in patent application WO 2006/010834. Accordingly the integrase capacity of the protein is altered whereas the correct expression from the encapsidation plasmid of the GAG, PRO and POL proteins and/or the formation of the capsid and hence of the vector particles, as well as other steps of the viral cycle, preceding or subsequent to the integration step, such as the reverse transcription, the nuclear import, stay intact. An integrase is said defective when the integration that it should enable is altered in a way that an integration step takes place less than 1 over 1000, preferably less than 1 over 10000, when compared to a lentiviral vector containing a corresponding wild-type integrase.

In a particular embodiment of the invention, the defective integrase results from a mutation of class 1, preferably amino acid substitutions (one-amino acid substitution) or short deletions fulfilling the requirements of the expression of a defective integrase. The mutation is carried out within the pol gene. These vectors may carry a defective integrase with the mutation D64V in the catalytic domain of the enzyme, which specifically blocks the DNA cleaving and joining reactions of the integration step. The D64V mutation decreases integration of pseudotyped HIV-1 up to $\frac{1}{10,000}$ of wild type, but keep their ability to transduce non dividing cells, allowing efficient transgene expression.

Other mutations in the pol gene which are suitable to affect the integrase capacity of the integrase of HIV-1 are the following: H12N, H12C, H16C, H16V, S81R, D41A, K42A, H51A, Q53C, D55V, D64E, D64V, E69A, K71A, E85A, E87A, D116N, D116I, D116A, N120G, N120I, N120E, E152G, E152A, D-35-E, K156E, K156A, E157A, K159E, K159A, K160A, R166A, D167A, E170A, H171A, K173A, K186Q, K186T, K188T, E198A, R199C, R199T, R199A, D202A, K211A, Q214L, Q216L, Q221 L, W235F, W235E, K236S, K236A, K246A, G247W, D253A, R262A, R263A and K264H.

In a particular embodiment, mutation in the pol gene is performed at either of the following positions D64, D116 or E152, or at several of these positions which are in the catalytic site of the protein. Any substitution at these positions is suitable, including those described above.

Another proposed substitution is the replacement of the amino acids residues RRK (positions 262 to 264) by the amino acids residues AAH.

In a particular embodiment of the invention, when the lentiviral vector is integration-incompetent, the lentiviral genome further comprises an origin of replication (ori), whose sequence is dependent on the nature of cells where the lentiviral genome has to be expressed. Said origin of replication may be from eukaryotic origin, preferably of mammalian origin, most preferably of human origin. It may alternatively be of viral origin, especially coming from DNA circular episomic viruses, such as SV40 or RPS. It is an advantageous embodiment of the invention to have an origin or replication inserted in the lentiviral genome of the lentiviral vector of the invention. Indeed, when the lentiviral genome does not integrate into the cell host genome (because of the defective integrase), the lentiviral genome is lost in cells that undergo frequent cell divisions; this is particularly the case in immune cells, such as B or T cells. The presence of an origin of replication ensures that at least one lentiviral genome is present in each cell, even after cell division, accordingly maximizing the efficiency of the immune response.

The lentiviral vector genome of said lentiviral vectors of the invention may especially be derived from HIV-1 plasmid pTRIPΔU3.CMV-GFP deposited at the CNCM (Paris, France) on Oct. 11, 1999 under number 1-2330 (also described in WO01/27300). The sequence of pTRIPΔU3.CMV-eGFP is provided as SEQ ID No 35 and is described in FIG. 11.

When the vector genome is derived from these particular plasmids, a sequence of a recombinant polynucleotide as disclosed in the present application is inserted therein, in addition or in replacement of the GFP coding fragment. The GFP coding sequence may also be substituted by a different marker. The CMV promoter may also be substituted by another promoter, especially one of the promoters disclosed above, especially in relation to the expression of the transgene.

The WPRE sequence also contained in the particular deposited pTRIP vectors may optionally be deleted.

Vector particles may be produced after transfection of appropriate cells (such as mammalian cells or human cells, such as Human Embryonic Kidney cells illustrated by 293 T cells) by said plasmids, or by other processes. In the cells used for the expression of the lentiviral particles, all or some of the plasmids may be used to stably express their coding polynucleotides, or to transiently or semi-stably express their coding polynucleotides.

The concentration of particles produced can be determined by measuring the P24 (capsid protein for HIV-1) content of cell supernatants.

The lentiviral vector of the invention, once administered into the host, infects cells of the host, possibly specific cells, depending on the envelope proteins it was pseudotyped with. The infection leads to the release of the lentiviral vector genome into the cytoplasm of the host cell where the retrotranscription takes place. Once under a triplex form (via the DNA flap), the lentiviral vector genome is imported into the nucleus, where the polynucleotide(s) encoding polypeptide(s) of antigen(s) of the malaria parasite is (are) expressed via the cellular machinery. When non-dividing cells are transduced (such as DC), the expression may be stable. When dividing cells are transduced, such as B cells, the expression is temporary in absence of origin of replication in the lentiviral genome, because of nucleic acid dilution and cell division. The expression may be longer by providing an origin of replication ensuring a proper diffusion of the lentiviral vector genome into daughter cells after cell division. The stability and/or expression may also be increased by insertion of MAR (Matrix Associated Region) or SAR (Scaffold Associated Region) elements in the vector genome.

Indeed, these SAR or MAR regions are AT-rich sequences and enable to anchor the lentiviral genome to the matrix of the cell chromosome, thus regulating the transcription of the polynucleotide encoding at least one antigenic polypeptide, and particularly stimulating gene expression of the transgene and improving chromatin accessibility.

If the lentiviral genome is non integrative, it does not integrate into the host cell genome. Nevertheless, the at least one polypeptide encoded by the transgene is sufficiently expressed and longer enough to be processed, associated with MHC molecules and finally directed towards the cell surface. Depending on the nature of the polynucleotide(s) encoding polypeptide(s) of antigen(s) of malaria parasite, the at least one polypeptide epitope associated with the MHC molecule triggers a humoral or a cellular immune response.

Unless otherwise stated, or unless technically not relevant, the characteristics disclosed in the present application with respect to any of the various features, embodiments or examples of the structure or use of the lentiviral particles, especially regarding their envelope protein(s), or the recombinant polynucleotide, may be combined according to any possible combinations.

The invention further relates to a combination of compounds for separate administration to a mammalian host, which comprises at least:
(i) lentiviral vector particles of the invention which are pseudotyped with a first determined heterologous viral envelope pseudotyping protein or viral envelope pseudotyping proteins;
(ii) provided separately from lentiviral vector particles in (i), lentiviral vector particles of the invention which are pseudotyped with a second determined heterologous viral envelope pseudotyping protein or viral envelope pseudotyping proteins distinct from said first heterologous viral envelope pseudotyping protein(s);
wherein said first and second viral envelope pseudotyping protein(s) do not sero-neutralize with each other and are suitable for in vivo transduction of mammalian cells, especially of human cells.

The expression "combination of compounds" or alternatively "kit of compounds" means that the lentiviral vector particles constituting active ingredients of the kits or combinations, are provided as separate compounds in said kit or combination, and are intended for separate administration to a host, especially separate administration in time. Accordingly the invention enables to perform a prime-boost administration in a host in need thereof, where the first administration step elicits an immune, especially cellular, immune response and the later administration step(s) boost(s) the immune reaction including the cellular immune response. For each step of administration, it is preferred that the pseudotyping envelope protein(s) of the vector particles is different than the one used in the other step(s). Accordingly, the separate compounds of the kit or combination of the invention have distinct particles at least due to the difference in their pseudotyping envelope proteins.

The compounds of the kit thus are provided separately in time to the host in need thereof, especially to a mammalian host, in particular a human host.

Accordingly, said lentiviral vectors can be provided in separate packages or can be presented in a common package for a separate use thereof.

Therefore, the notice included in the packages and comprising the directions for use, may indicate that said lentiviral vector particles which are pseudotyped with distinct pseudotyping envelope protein or pseudotyping envelope proteins are for separate administration in time, especially for priming and subsequently boosting an immune reaction in a host.

In accordance with the invention, in the combination of compounds it is provided lentiviral vector particles which are pseudotyped with a first determined heterologous viral pseudotyping envelope protein, or viral pseudotyping envelope proteins, and lentiviral viral vector particles which are pseudotyped with a second determined heterologous viral pseudotyping envelope protein or viral pseudotyping envelope proteins. Accordingly, said first and second heterologous viral envelope protein(s) are different and in particular are originating from different virus strains. Thus, the lentiviral vector particles contained in the separate compounds of the of the kit of compounds of the invention are distinct from each other, at least due to the particular pseudotyping envelope protein(s) used for pseudotyping the vector particles.

In a particular embodiment of the invention, the combination of compounds comprises a third or a further type of lentiviral vector particles wherein the pseudotyping envelope protein(s) of the third lentiviral vector is different from said first and second pseudotyping envelope protein(s) and especially originates from a different virus strain.

When particles are successively administered which have different pseudotyping envelopes, the following order of administration with respect to said envelopes could be preferred: Indiana; New Jersey; Isfahan; SVCV/Cocal. Because Cocal pseudotyped lentiviral vectors seroneutralize several other envelopes, it is preferable, in the vaccination chronology, when Cocal envelopes are to be used in the preparation of particles, to administer particles pseudotyped with them as the last one in the administration regimen.

Apart from their pseudotyping envelope protein(s), the lentiviral vectors of the invention may be identical and especially may have identical vector genomes.

Alternatively, their vector genomes may be different, provided they carry the same recombinant determined polynucleotide (also designated as transgene), especially the same recombinant polynucleotide.

In another embodiment of the invention, the vector genomes of the lentiviral vectors are different by having at least one different recombinant polynucleotide, provided at least one of said different polynucleotides encodes polypeptide(s) having common antigenic determinant(s), or common epitope(s). Hence the different polynucleotides may be variants from each other that encode identical or variant polypeptides or may include sequences encoding different polypeptides.

A particular kit of compounds comprises lentiviral vectors wherein in at least one of the separate compounds, the vectors are pseudotyped with recombinant pseudotyping envelope protein(s) comprising combined domains or fragments originating from different envelope protein(s) of different viruses, especially of different genus of different species of VSV.

In a particular embodiment of the invention, at least one the first, second and if any third or further pseudotyping envelope protein(s) is (are) recombinant envelope protein(s) comprising the export determinant of the VSV-G of Indiana strain.

The export determinant of the VSV-G of the Indiana strain is a polypeptide encoded by the cytoplasmic fragment of the open reading frame of the envelope.

The export determinant of the VSV-G of the Indiana strain is a polypeptide comprising or having amino acid sequence YTDIE (amino acids 501 to 505 of SEQ ID NO: 77) in the cytoplasmic tail (Nishimua N. et al. 2002).

Said recombinant envelope protein(s) may comprise the cytoplasmic tail of the VSV-G of an Indiana strain which is the intracellular portion of VSV-G delimited by a hydrophobic transmembrane domain.

A particular kit of compounds comprises lentiviral vectors wherein one or two or more of them is (are) pseudotyped with recombinant envelope protein(s) comprising the cytoplasmic domain of the indiana VSV and the ectodomain of a strain of a different VSV serotype. The transmembrane domain may also be the one of the Indiana VSV-G.

A particular kit of compounds comprises lentiviral vectors wherein one or both of them is (are) pseudotyped with recombinant envelope protein(s) comprising the transmembrane domain and the cytoplasmic domain of the indiana VSV and the ectodomain of the New-Jersey VSV.

Appropriate other modifications encompass mutations, especially point mutations, that improve pseudotyping. Such mutations for the VSV-G proteins may be carried out in the transmembrane domain by substituting or deleting one or several amino acid residues. Other examples of appropriate mutations are disclosed in Fredericksen B. L. et al (1995) or Nishimura N. et al (2003).

It is also especially possible to modify the glycosylation status of the VSV-G, in order to improve transduction efficiency of the lentiviral vector pseudotyped with these VSV-G proteins, when administered to a host.

VSV-G proteins from various strains of VSV are disclosed in the figures and their sequences can also be derived from databases, especially from GenBank. Especially the VSV-G proteins of Indiana and New-Jersey strains may be obtained by reference to the sequences disclosed as GenBank # AF170624 for New-Jersey VSV-G or GenBank # M11048 for Indiana strain.

Considering the glycoproteins of the New-Jersey and Indiana strains of VSV, it has been proposed that glycosylation at two asparagine residues (N180 and N336) favour the efficient pseudotyping of lentiviral vectors. This particular feature may be applied in the preparation of the lentiviral vectors of the invention.

The following constructs encoding VSV-G derived envelope proteins are particular examples of constructs for use in the preparation of the combination of lentiviral vector particles of the invention and are described in WO 2009/019612.

A VSV-G Indiana gene which is codon optimized as shown in SEQ ID No 76. A particular encapsidation plasmid is pThV-VSV.G (IND-CO) deposited at the CNCM (Paris, France) on Oct. 10, 2007, under number I-3842 or in an alternative version of the plasmid construct, on Jul. 31, 2008, under number CNCM I-4056 is suitable for use in preparing pseudotyped particles with an envelope from VSV-G Indiana New-Jersey. Other constructs may be derived from this particular plasmid, especially by substituting the promoter for a promoter among those listed in the present application.

A VSV-G New-Jersey gene codon optimized is disclosed in SEQ ID No 78. A particular encapsidation plasmid is pThV-VSV.G (NJ-CO) deposited at the CNCM (Paris, France) on Oct. 10, 2007, under number I-3843 or in an alternative version of the plasmid construct, on Jul. 31, 2008, under number CNCM 1-4058 is suitable for use in preparing pseudotyped particles with an envelope from VSV-G Indiana New-Jersey. Other constructs may be derived from this particular plasmid, especially by substituting the promoter for a promoter among those listed in the present application.

Other envelope genes suitable to carry out the invention having codon optimized sequences are illustrated in WO 2009/019612 and especially encompass VSV-G Chandipura gene and its expression product, VSV-G Cocal gene and its expression product, VSV-G Piry gene and its expression product, VSV-G Isfahan gene and its expression product, VSV-G Spring viremia carp virus gene and its expression product. A particular encapsidation plasmid, containing an envelope gene for VSV-G Cocal, is pThV-VSV.G (COCAL-CO) deposited at the CNCM (Paris, France) on Jul. 31, 2008, under number CNCM 1-4055. Another particular encapsidation plasmid, containing an envelope gene for VSV-G Isfahan, is pThV-VSV.G (ISFA-CO) deposited at the CNCM (Paris, France) on Jul. 31, 2008, under number CNCM 1-4057. Another particular encapsidation plasmid, containing an envelope gene for VSV-G Spring viremia carp virus, is pThV-VSV.G (SVCV-CO) deposited at the CNCM (Paris, France) on Jul. 31, 2008, under number CNCM 1-4059. These constructs are disclosed in patent application WO2009/019612.

Fusion envelope proteins, especially fusion proteins involving several different fragments of VSV-G proteins of different viruses and to the nucleic acid constructs encoding such proteins are used as alternative embodiments and are also disclosed in WO 2009/019612. A particular fusion envelope is the fusion between the ectodomain of the New-Jersey envelope protein and the transmembrane domain and cytoplasmic domain of the Indiana envelope protein as illustrated in the herein provided sequences.

Another fusion envelope protein suitable to perform the invention comprises the ectodomain of one VSV-G protein selected among VSV-G Chandipura, VSV-G Cocal, VSV-G Pyri, VSV-G Isfahan, or VSV-G SVCV and the transmembrane and cytoplasmic domains of VSV-G Indiana. A nucleic acid molecule encoding said fusion protein is advantageously a codon optimized nucleic acid. Nucleic acid encoding the fusion protein are also described as SEQ ID No 77, 79, 81, 83 85, 87, 89.

In a particular embodiment of the invention, a combination of compounds is provided, wherein the lentiviral particles of the separate compounds encode (i) a polypeptide of the CSP antigen or (ii) a polypeptide of the CSP antigen devoid of the GPI-anchoring motif (CSP deltaGPI) or a CSP protein truncated in the N-terminal end (CSP NTer or also CSP delta SP).

In a particular embodiment, these compounds or some of them further encode at least one additional polypeptide of an antigen of the malaria parasite chosen in the groups disclosed herein, the distinct polypeptides of said antigens being either expressed from the same lentiviral particles or from distinct lentiviral particles.

In another particular embodiment of the invention, these compounds or some of them further encode at least one additional polypeptide of an antigen of the malaria parasite chosen in the groups disclosed herein.

The invention concerns especially lentiviral vector particles or a combination of compounds as herein defined for the prophylactic immunization against malaria parasite infection or against parasite-induced pathology in a mammalian host, especially in a human host.

Accordingly, the lentiviral vector particles, compositions comprising the same or the combination of compounds of the invention, when administered to a host in needs thereof, especially to a mammalian in particular to a human host, elicit an immune response, encompassing activation of naïve lymphocytes and generation of effector T-cell response and generation of immune memory antigen-specific T-cell response against antigen(s) of the malaria parasite. The immune response may either prevent the infection by the malaria parasite when such parasite is inoculated as sporozoite to the host or may prevent the onset or the development of a pathological state resulting from inoculation of malaria parasite in the form of sporozoite or prevent the onset or the development of the consequences of the generation of further forms of said parasite such a merozoite forms.

Accordingly, the lentiviral vector particles or the combination of compounds of the invention are suitable for prevention, control or inhibition of the onset of the pathology caused by inoculation of the parasite or by the induction of the exo-erythrocytic i.e., hepatic, stage of the cycle of the malaria parasite and in an advantageous embodiment are suitable to prevent, alleviate or inhibit the onset or development of the erythrocytic cycle of said parasite. Advantageously, it has been observed that the lentiviral vector particles of the invention used in a prime-boost regimen of administration enable the development of a protective immunity and especially enable a sterilizing protection against the malaria parasite-induced pathology. Such a sterilizing protection may result from controlling the consequences of the infection at the stage of liver infection, if not before, in cycle of the parasite.

In a particular embodiment of the invention, a composition of lentiviral vector particles is prepared wherein said lentiviral vector particles are formulated with a suitable administration vehicle for use for prophylactic immunization against malaria parasite infection or against parasite-induced pathology in a mammalian host, especially in a human host.

Physiologically acceptable vehicles may be chosen with respect to the administration route of the immunization composition. In a preferred embodiment administration may be carried out intramuscularly or, for children intranasally.

Accordingly, a combination of compounds can comprise separately provided compositions of lentiviral vector particles wherein each separate composition of the combination or kit of compounds comprises lentiviral vector particles, pseudotyped with a determined heterologous viral pseudotyping envelope protein or proteins, and wherein said pseudotyping envelope proteins do not cross-react with to sero-neutralize the pseudotyping envelope proteins of the lentiviral vector particles of another composition of the combination or kit of compounds.

Accordingly, such compositions or combination of compounds of said compositions are used for prophylactic immunisation against malaria parasite infection or against parasite-induced pathology in a mammalian host, especially in a human host, said use involving an immunisation pattern comprising administering an effective amount of the lentiviral particles to prime the cellular immune response of the host and later in time administering an effective amount of lentiviral particles to boost the cellular immune response of the host, and optionally repeating (once or several times) said administration step for boosting, wherein the lentiviral particles administered in each of the priming or boosting steps are pseudotyped with distinct pseudotyping envelope protein(s) which do not cross-neutralise with each other, and wherein said priming and boosting steps are separated in time by at least 6 weeks, in particular by at least 8 weeks.

In the examples which follow where mice models have been treated according to the prime-boost regimen with lentiviral vector particles of the invention, it has been shown by the inventors that mice immunized according to such a regimen and challenged 6 months after the last immunization step still exhibit a sterile protection for a significant proportion of the vaccinated mice (more than 40%) which illustrates that the lentiviral vector particles of the invention elicit a long-lasting sterile protection in a host, and would therefore constitute a suitable compound for immunization especially in a human host.

The invention relates, in a particular embodiment, to the lentiviral vector particles or combination of compounds as defined herein, for the prophylactic immunization against malaria parasite infection or against parasite-induced pathology in a mammalian host, especially in a human host, in a dosage regimen comprising separately provided doses of said lentiviral particles wherein the dose intended for priming and boosting the cellular immune response is a moderate dose and the dose intended for boosting the cellular immune response is higher than the dose for priming.

Accordingly, the dose intended for priming and boosting the cellular immune response which is used in the administration pattern, comprises from $10^7$ TU to $10^9$ TU of viral particles when integrative vectors are used, the dose intended for children being in the range of $10^7$ TU and for adults in the range of $10^9$ TU. The dose intended for priming and boosting comprises from $10^8$ to $10^{10}$ of lentiviral particles when integrative-incompetent vectors are used.

The lentiviral vector particles or the combination of compounds of the invention is especially used in a particular embodiment for the prophylactic immunization against malaria parasite infection or against parasite-induced pathology in mammalian, host, especially in a human host, in a dosage and administration regimen which is suitable to obtain at least one of the following effects in the host:

eliciting sterile protection against malaria parasite infection, especially by *Plasmodium falciparum*, *Plasmodium malariae*, *Plasmodium vivax*, *Plasmodium knowlesi* or *Plasmodium ovale* in a human host;

inhibiting extracellular forms of malaria parasite;

preventing hepatocytes infection by malaria parasite or inhibition of liver stage amplification of infection;

eliciting a specific T-cell immune response against malaria parasite antigen(s), especially a CD8+ T-cell response and/or a specific CD4+ T-cell response;

eliciting a B-cell response against parasite antigen(s);

controlling parasitemia so as to reduce or alleviate the effects of infection by the malaria parasite;

eliciting a protective cellular immunity against the infection by the parasite or against the parasite-induced pathology;

eliciting memory T-cell immune response eliciting earlier and higher rebound of the CD4+ and CD8+ T-cell response during infection by the malaria parasite;

eliciting earlier and strong CT (CD8+ T) response by stimulating intra hepatic memory lymphocytes upon *Plasmodium* infection.

preventing malaria parasite escape from immune response thereby allowing long-term control of the infection by the malaria parasite.

Among the above targeted effects, a cellular immune response (T-cell immune response), particularly a CD8-mediated cellular immune response or a CD4-mediated cellular immune response i.e., an immune response which is mediated by activated cells harbouring CD8 or CD4 receptors, preferably Cytotoxic T lymphocytes (CTL) and memory T cell response are advantageously targeted when defining the immunization regimen of the lentiviral particles of the invention.

The immune response can also involve a humoral response i.e., antibodies, elicited by said lentiviral vector particles, produced against said at least one polypeptide of the lentiviral vector. In a particular embodiment, said humoral response is a protective humoral response. The protective humoral response results mainly in maturated antibodies, having a high affinity for their antigen, such as IgG. In a particular aspect, the protective humoral response is T-cell dependent. In a particular embodiment, the protective humoral response induces the production of neutralizing antibodies.

In a particular embodiment of the invention, the lentiviral vector of the invention, even when used in a form which has defective integrase, is able to elicit an early immune response. The expression "early immune response" refers to a protective immune response (protection against the parasite or against the parasite-induced pathology) that is conferred within about one week after the administration of the composition.

In another particularly advantageous embodiment, the immune response conferred by the lentiviral particles of the invention is a long-lasting immune response i.e., said immune response encompasses memory cells response and in particular central memory cells response; in a particular embodiment it can be still detected at least several months, (as illustrated for mice in the examples a protection is still obtained after at least 6 months after the administration of the particles) which allows to consider that the protection may last in a human host over several years following the administration.

When the immune response includes a humoral response, the long-lasting response can be shown by the detection of specific antibodies, by any suitable methods such as ELISA, immunofluorescence (IFA), focus reduction neutralization tests (FRNT), immunoprecipitation, or Western blotting.

In a particular embodiment, said immune response, either humoral or cellular, early immune response and/or long-lasting immune response, is elicited with the non-integrative gene transfer vector, after a single administration of the composition of the invention.

The invention also concerns the use of the lentiviral vector particles or the use of a combination of compounds according to the definition given herein, for the manufacture of an immunogenic composition for prophylactic immunisation against malaria parasite infection or against parasite-induced pathology in a mammalian host, especially in a human host.

The invention also concerns a method of providing immunization in a mammalian host, especially in a human host, comprising the step of administering the lentiviral vectors of the invention to elicit the immune response, and optionally repeating the administration steps one or several times, to boost said response, in accordance with the present disclosure.

In a particular embodiment of the invention, the lentiviral vector particles or the combination of compounds may be used in association with an adjuvant compound suitable for administration to a mammalian, especially a human host, and/or with an immunostimulant compound, together with an appropriate delivery vehicle.

The compositions quoted above can be injected in a host via different routes: subcutaneous (s.c.), intradermal (i.d.), intramuscular (i.m.) or intravenous (i.v.) injection, oral administration and mucosal administration, especially intranasal administration or inhalation. The quantity to be administered (dosage) depends on the subject to be treated, including considering the condition of the patient, the state of the individual's immune system, the route of administration and the size of the host. Suitable dosages range expressed with respect to the content in equivalent p24 antigen of vector particles (for HIV-1 lentiviral vectors) and can be determined.

Other examples and features of the invention will be apparent when reading the examples and the figures which illustrate the preparation and application of the lentiviral vector particles with features that may be individually combined with the definitions given in the present description.

LEGEND OF THE FIGURES

FIG. 1. Nonintegrative lentiviral vector-based vaccination confers total inhibition of liver stage development. A. Study design. Naive mice were primed at week 0 with 100 ng of TRIP.NI CS particles pseudotyped with the VSV-G Indiana (VSV-G Ind) envelope and then boosted at week 8 with 1500 ng of TRIP.NI CS particles pseudotyped with the VSV-G New Jersey (VSV-G NJ) envelope. One group of vaccinated mice were challenged with 80.000 sporozoites (spz) of *Plasmodium yoelii* (17XNL-gfp$^+$ strain) and protective efficacy was measured by quantifying the liver parasite load 40 hours later. A second group of vaccinated mice were challenged with 500 spz of *Plasmodium yoelii* (17XNL-gfp$^+$ strain) and protective efficacy was evaluated by monitoring blood stage parasitemia every other day from day 3 post injection until day 14 by Giemsa-stained blood smears. In the two cases, the challenges were performed one month after the last immunization. B. Results of the parasite loads quantified using real-time RT-PCR for *P. yoelii* 18S rRNA in the livers of challenged mice. Data are presented as the number of copies of *plasmodium* 18S rRNA detected in individual control mice (n=5) and vaccinated mice (n=4). Mean+/−SD of duplicate is shown. C. Results of the monitoring of blood stage parasitemia. 0 indicates absence of parasites, + indicates presence of parasites.

FIG. 2. A. Study design. Mice primed with 100 ng of TRIP.NI CS particles pseudotyped with the VSV-G Indiana (VSV-G Ind) envelope and boosted 8 weeks later with 1500 ng of TRIP.NI CS particles pseudotyped with the VSV-G New Jersey (VSV-G NJ) envelope received a third immunization dose 5 months later with 1500 ng of TRIP.NI CS particles pseudotyped with the VSV-G Cocal. Vaccinated mice were challenged one month later with 500 spz of *Plasmodium yoelii* (17XNL strain) and protective efficacy was evaluated by monitoring blood stage parasitemia every other day from day 3 post injection until day 16 by Giemsa-stained blood smears. B. Percentage of mice completely protected against sporozoite challenge after a nonintegrative lentiviral vector-based regimen. C. Means of parasitemia of naive mice (CO-black curve), vaccinated mice completely protected (VAC-light grey curve) and vaccinated mice partially protected (VAC-grey curve) are depicted. D. Means of parasitemia from naive mice (CO-black), vaccinated mice partially protected (VAC-grey) and vaccinated mice completely protected (VAC-grey), 10 days after the challenge.

Figure 3:
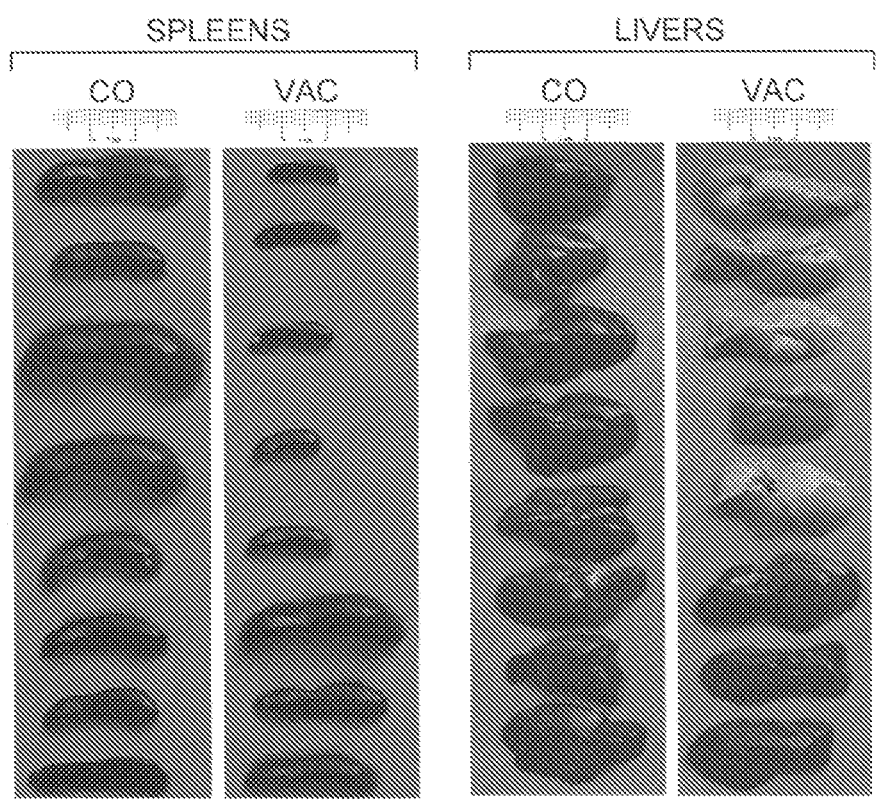

FIG. 3. Gross morphology of spleens and livers from mice vaccinated (VAC) or not (CO) at the final killing (3 weeks post-challenge) with 500 sporozoites of *Plasmodium yoelii*.

Figure 4:
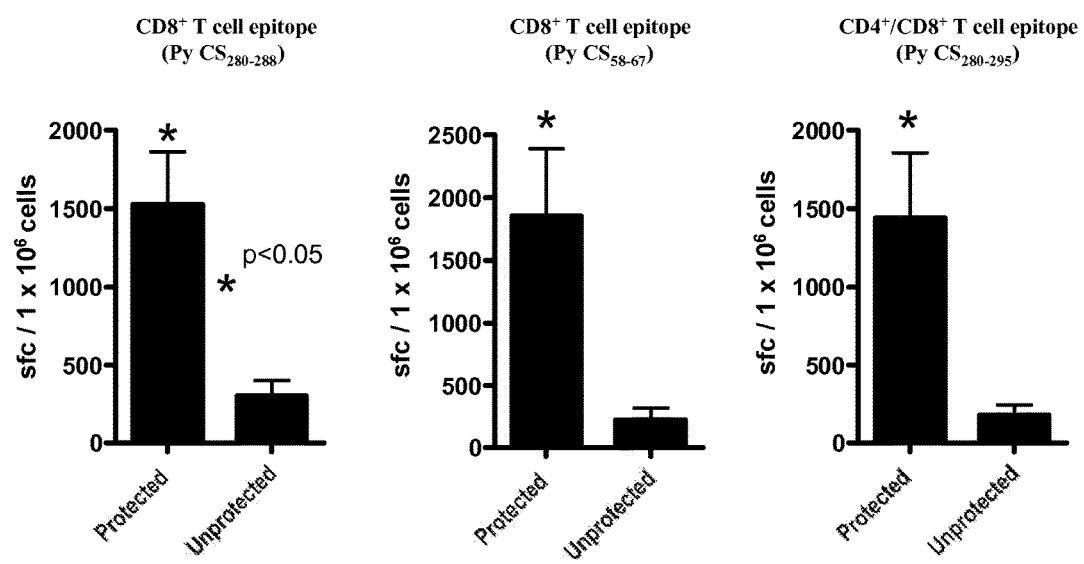

FIG. 4. CS protein-specific T cell responses from splenocytes of vaccinated mice 3 weeks after challenge. Ex vivo IFNg ELISPOT was carried out using splenocytes from vaccinated mice harvested 3 weeks after the challenge with *Plasmodium yoelii*. Splenocytes were stimulated with synthetic peptides representing CD8$^+$ or CD4$^+$ defined epitopes. Data are expressed as mean+/− SD of spot forming cells (sfc) of duplicate wells. n=5 in the protected group and n=3 in the unprotected group. *: different from unprotected group p<0.05.

Figure 5:
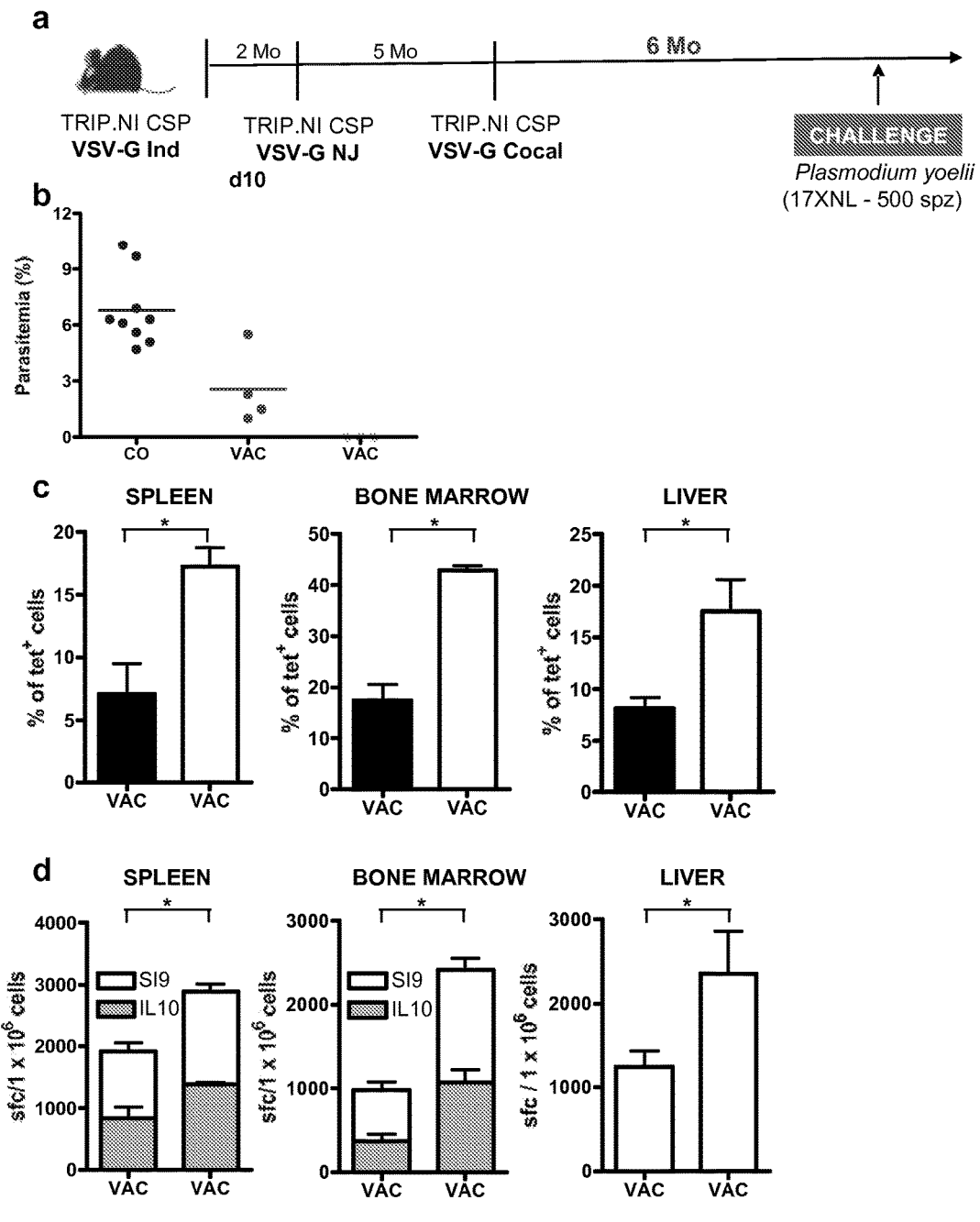

FIG. 5. Optimized non integrative lentiviral vectors confer long term sterile protection against malaria (a) Vaccine schedule. Mice were primed with 100 ng of TRIP.NI CSP particles pseudotyped with the VSV-G Indiana envelope and boosted 8 weeks later with 1500 ng of TRIP.NI CSP particles pseudotyped with the VSV-G New Jersey envelope. Five months later, they received a third injection of TRIP.NI CS particles (1500 ng) pseudotyped with the VSV-G Cocal envelope. Animals were challenged six months later with 500 sporozoites of *Plasmodium yoelii* (17XNL strain) and protective efficacy was evaluated by monitoring blood stage parasitemia every other day from day 3 post injection until day 16. (b) Means of parasitemia from naive mice (CO-black), vaccinated mice partially protected (VAC-light grey (middle)) and vaccinated mice completely protected (VAC-grey (right)), 10 days after the challenge. (c) Tetramer analysis of the % of CSP-specific CD8$^+$ T cells from the spleen, the bone marrow and the liver of mice at the final killing (3 weeks post-challenge). Black bars indicate vaccinated mice partially protected and white bars indicate vaccinated mice completely protected. (d) INF-g ELISPOT quantification of CSP-specific CD8+ T cells in the spleen, the bone marrow and the liver of mice. *P<0.05 (Student's t-test)

FIG. 6. Hep17-specific T cell responses induced by nonintegrative lentiviral vectors. Naive mice (n=5/group) were immunized or not (−) i.p. with a single injection of various doses (100 or 600 ng) of nonintegrative lentiviral vectors coding for Hep17. At 11 days post-immunization, Hep17-specific cellular immune responses against the CD8$^+$ T cell epitopes (A) and the CD4$^+$ T cell epitopes (B) were assessed by IFN-γ ELISPOT. SFC, spot-forming cells.

FIG. 7. Hep17-specific T cell responses induced by integrative lentiviral vectors. Naive mice (n=5/group) were immunized (or not: −) i.m. with a single injection of integrative lentiviral vectors (1×10$^7$ TU) coding for Hep17. At 11 days post-immunization, Hep17-specific cellular immune responses against the CD8$^+$ T cell epitopes (A) and the CD4$^+$ T cell epitopes (B) were assessed by IFN-γ ELISPOT. SFC, spot-forming cells.

Figure 8:
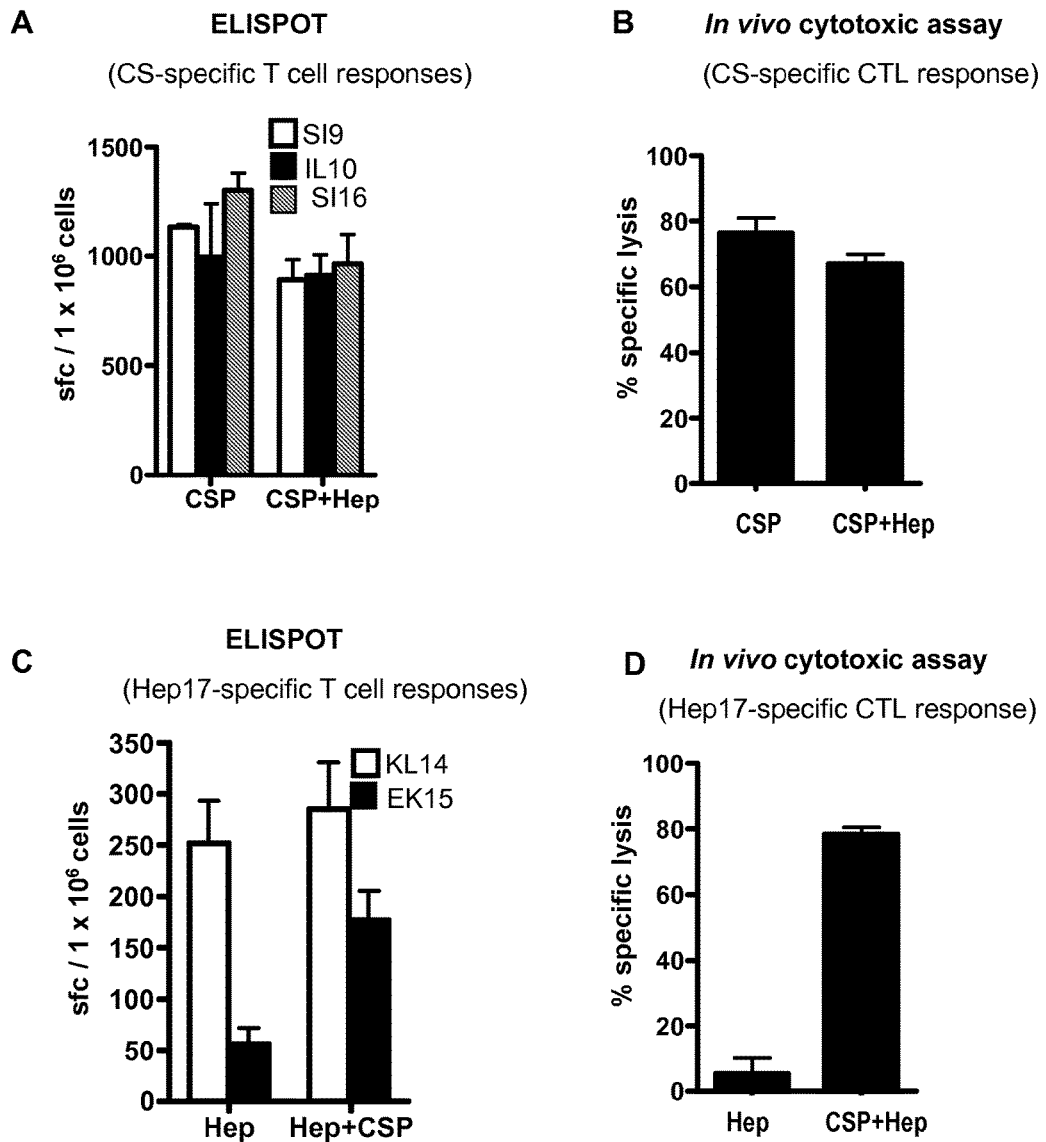

FIG. 8. CS- and Hep17 specific T cell responses elicited after coimmunizations with lentiviral particles. Naive mice (n=5/group) were immunized i.m. with a single injection of integrative lentiviral vectors (1×10$^7$ TU) coding for CS (named CSP in figure A and B) or Hep17 (named Hep17 in figure C and D). For coimmunization experiments, naive mice were injected into one quadriceps with TRIP.I CS and into the opposite quadriceps with TRIP.I Hep17 particles (named CSP+Hep in figure A,B,C,D). At 11 days post-immunization, CS-specific cellular immune responses (A) and Hep17-specific cellular immune responses (C) were assessed by IFN-γ ELISPOT. SFC, spot-forming cells. For in vivo cytotoxic assays, immunized mice were injected at day 11 with target cells pulsed with CS peptides (C) or Hep17 peptides (D). Percentages of specific killing were determined 18 hours later, as described in Material and Methods section.

Figure 9:
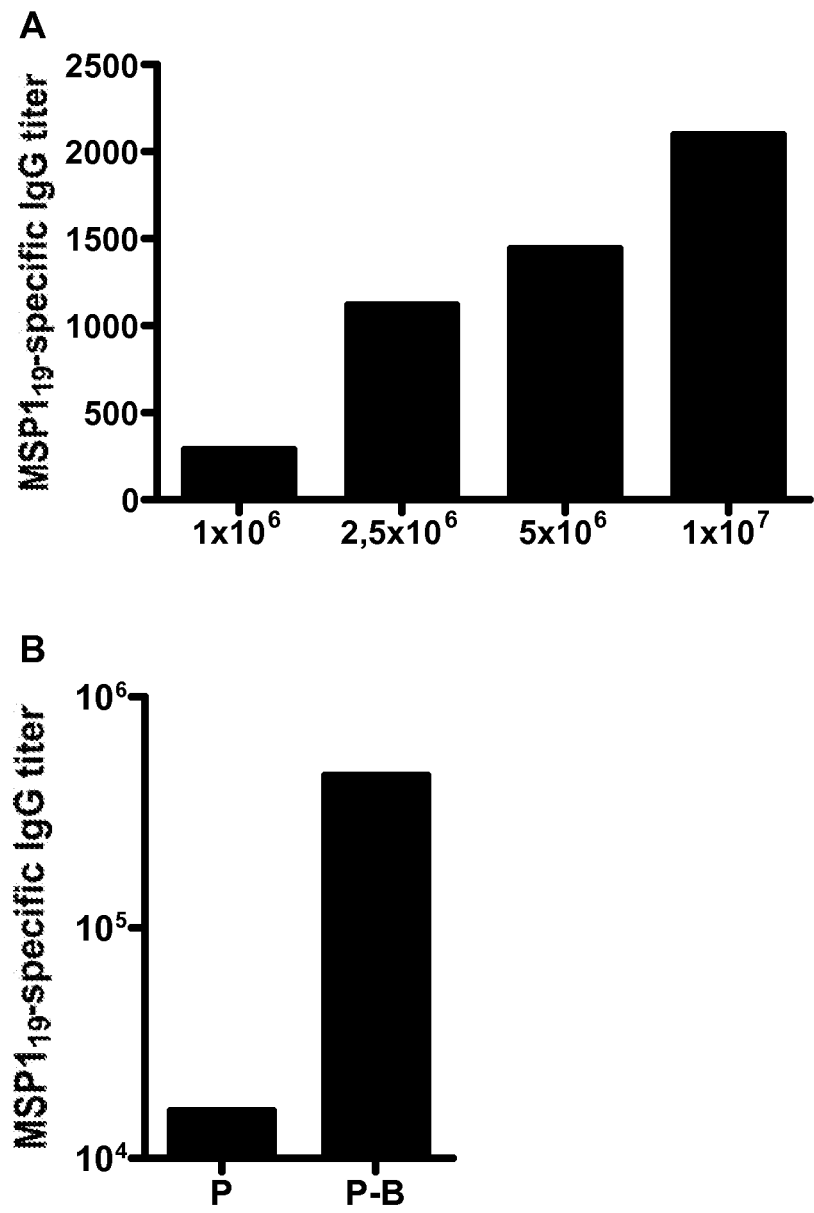

FIG. 9. A single dose of nonintegrative lentiviral vector coding for MSP1$_{42}$ elicits a strong and specific antibody response. A. Groups of adult mice (n=5) were immunized intraperitoneally with graded doses of TRIP.I MSP1$_{42}$. After 21 days, pooled sera (5 mice per group) were assessed for the presence of MSP-1$_{19}$-specific antibodies. B. Mice were primed with 100 ng of TRIP.I MSP1$_{42}$ particles pseudotyped with the VSV-G Indiana envelope. 3 months later, mice were boosted with 1000 ng of TRIP.NI MSP1$_{42}$ particles pseudotyped with the VSV-G cocal envelope. Results are the mean titers of MSP-1$_{19}$-specific antibodies detected in the sera of mice 3 weeks after the last immunization.

FIGS. 10(A) and 10(B). Alignments of *Plasmodium* CSP proteins and sequence of a consensus. The aligned *Plasmodium* CSP proteins are CSP *Plasmodium falciparum* (SEQ ID NO: 23), CSP *Plasmodium yoleii* (SEQ ID NO: 20), CSP *Plasmodium berghei* (SEQ ID NO: 26), CSP *Plasmodium malariae* (SEQ ID NO: 27), CSP *Plasmodium coatneyi* (SEQ ID NO: 28), CSP *Plasmodium knowlesi* (SEQ ID NO: 29), CSP *Plasmodium reichenowi* (SEQ ID NO: 30), and CSP *Plasmodium gallinaceum* (SEQ ID NO: 31). The consensus sequence is (SEQ ID NO: 32).

Figure 11:
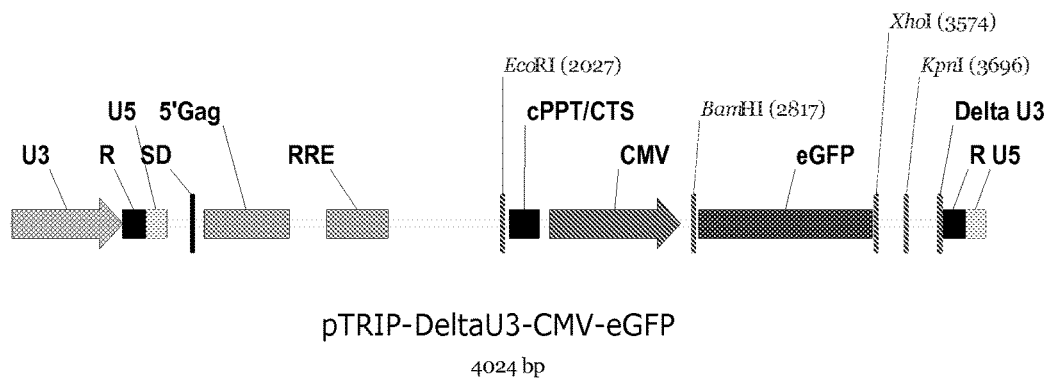

FIG. 11. Restriction map of plasmid pTRIP-DeltaU3-CMV-eGFP. SEQ ID No 33

Figure 12:
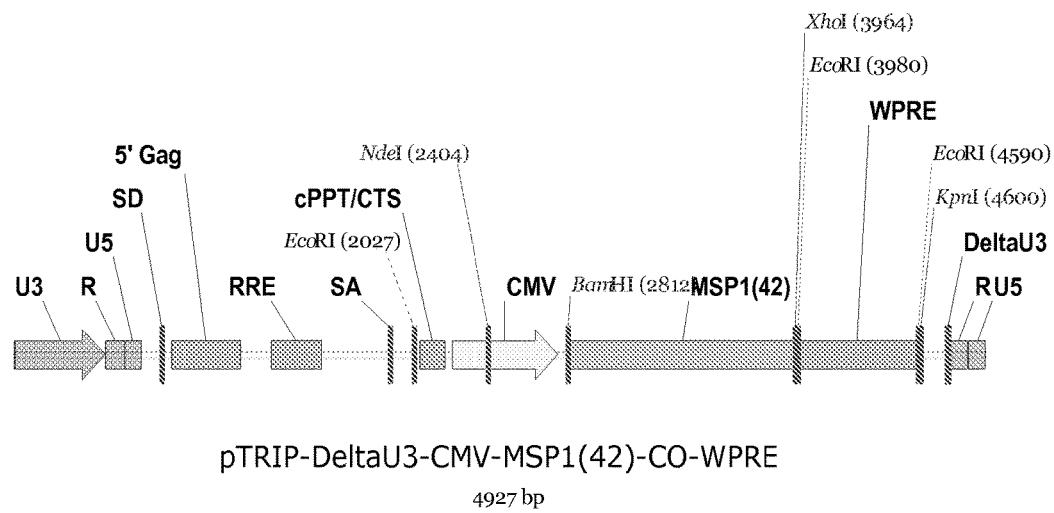

FIG. 12. Restriction map of plasmid pTRIP-ΔU3-CMV-MSP1$_{42}$ CO-WPRE (CNCM I-4303 or SEQ ID No 34).

Figure 13:
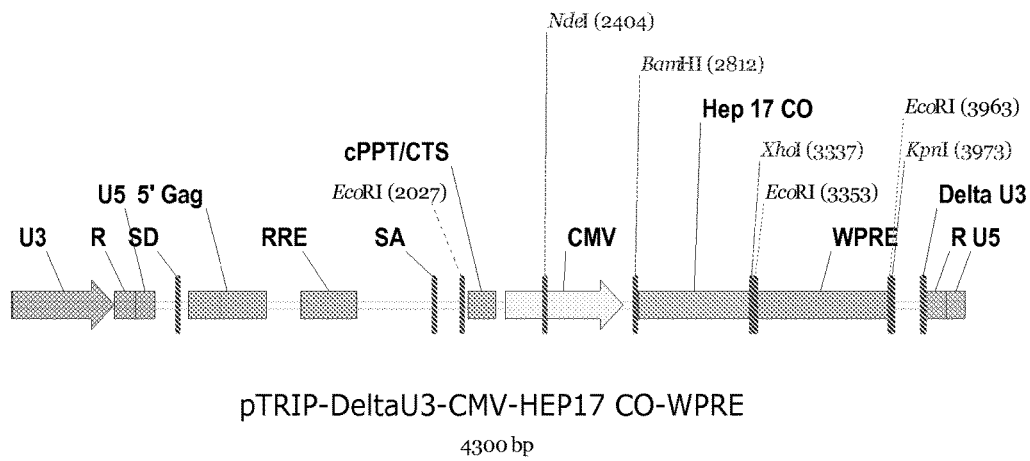

FIG. 13. Restriction map of plasmid pTRIP-ΔU3-CMV-Hep17 CO-WPRE (CNCM I-4304 or SEQ ID No 37).

Figure 14:
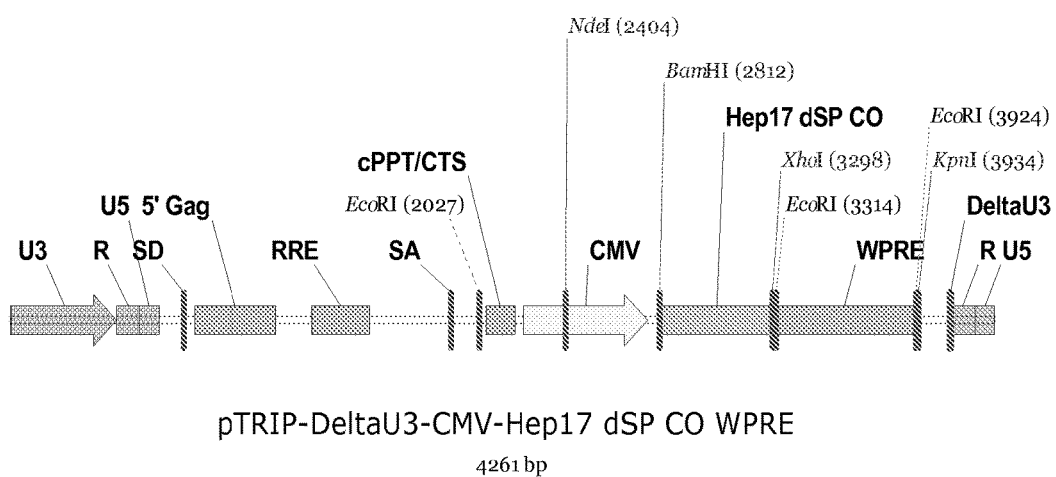

FIG. 14. Restriction map of plasmid pTRIP-ΔU3-CMV-Hep17 ΔSP CO-WPRE (CNCM I-4305 or SEQ ID No 40).

Figure 15:
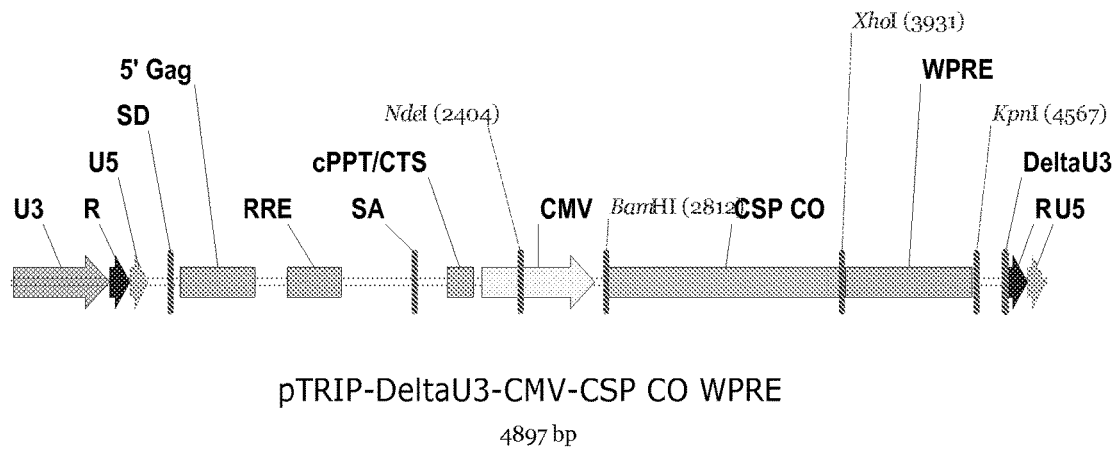

FIG. 15. Restriction map of plasmid pTRIP-ΔU3-CMV-CSP CO-WPRE (CNCM I-4306 or SEQ ID No 43).

Figure 16:
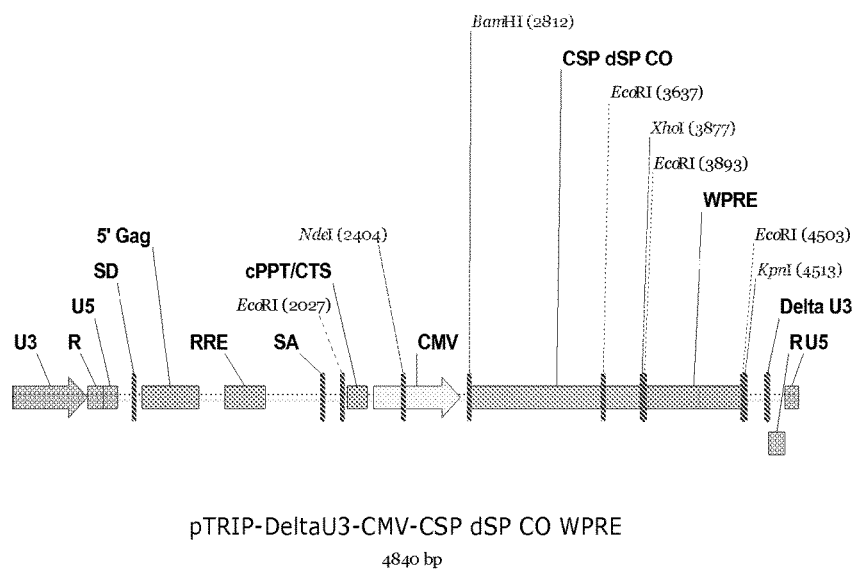

FIG. 16. Restriction map of plasmid pTRIP-ΔU3-CMV-CSP ΔSP CO-WPRE (CNCM I-4307 or SEQ ID No 45).

Figure 17:
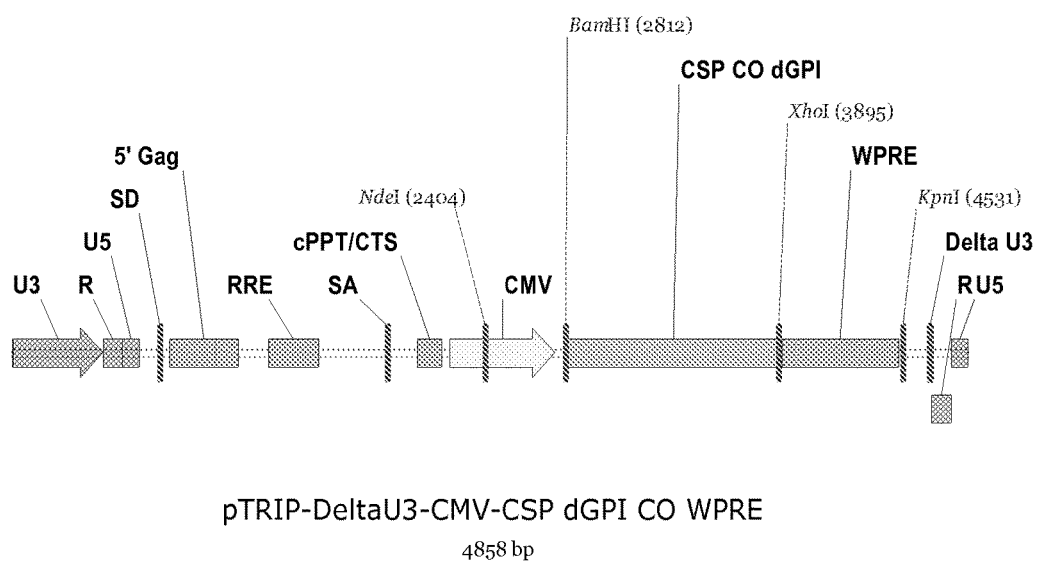

FIG. 17. Restriction map of plasmid pTRIP-ΔU3-CMV-CSP ΔGPI CO-WPRE (CNCM I-4308 or SEQ ID No 47).

EXAMPLES

With a view to assess whether lentiviral vectors may represent an alternative strategy, a nonintegrative lentiviral vector coding for a truncated form of the circumsporozoite (CS) protein of *Plasmodium yoelii* (TRIP.NI CS) was designed and assayed in an animal mice model relevant for malaria. The CS protein is distributed uniformly over the surface of sporozoites and is also detected in infected liver cells[4, 5]. Thus, the induction of humoral immune responses against the CS protein reduces the hepatocyte infectivity, whereas the cellular immune responses against this antigen kill parasite-infected hepatocytes. This concept was recently supported by an elegant study that demonstrated that the CS protein was the main target of protective immunity in the irradiated sporozoite immunization model[6]. Moreover, among all the vaccine candidates tested so far in clinical trials, only the CS protein-based vaccine RTS,S has been shown to reduce significantly malaria incidence and cases of severe malaria in endemic countries[7, 8].

In order to elicit optimal immune responses against the CS protein, we combined three strategies: 1) to increase the level of antigen expression in transduced cells, we inserted in the vector backone a mammalian codon-optimized sequence of the CS protein under the control of the strong cytomegalovirus promoter and we added downstream the transgene the woodchuck post-transcriptional regulatory element sequence to increase mRNA stabilization and export to the cytoplasm; 2) we deleted the GPI anchoring sequence located at the 3' end of the cs gene since deletion of GPI-anchoring motif has been shown to improve the immunogenicity of the CS protein[9] 3) to increase the specific immune response, and in particular, to protect mice from infection by sporozoite challenge, mice received LV-based boosters. To circumvent the presence of neutralizing anti-envelope antibodies induced after the first immunization, lentiviral particles used for boost immunizations were pseudotyped with VSV-G envelopes from non-cross-reactive serotypes (VSV-G Indiana for the prime, VSV-G New Jersey and Cocal for the first and the second boost, respectively).

In a first series of experiment, mice were primed with a moderate dose of TRIP.NI CS and boosted 8 weeks later with a high dose of TRIP.NI CS (FIG. 1a). To evaluate protection induced by this prime-boost regimen, BALB/c mice were challenged with 80·10$^3$ sporozoites of *Plasmodium yoelii* (17XNL gfp+ strain), the invasive form of the parasite present in the mosquito. The challenge was performed 4 weeks after the completion of immunization regimen. Forty hours after the challenge, the level of inhibition of liver stage development was determined by quantifying plasmodial 18S rRNA in the livers of mice. For this purpose, liver-extracted RNA was used for real-time PCR amplification of the plasmodial 18S rRNA sequences, using the EXPRESS One-Step SYBR® GreenER™ kit (invitrogen) and specific primers for the amplification of the 18S rRNA of *Plasmodium yoelii*. As shown in FIG. 1b, the inhibition of liver stage development of the parasite was complete for all immunized mice, i.e., no parasite 18S rRNA could be detected by quantitative RT-PCR. In parallel experiments, protection was also assessed by examining blood smears of immunized mice, which were challenged with 500 *Plasmodium yoelii* sporozoites, for the occurrence of erythrocytic stages. Peripheral blood smears were obtained daily from day 3 to 14 post-challenge, stained with Giemsa and examined by microscopy, to determine whether immunized mice became parasitemic, i.e., failed to develop protection. As shown in FIG. 1c, complete protection occurred in 60% of immunized mice.

In a second series of experiments, we added a third injection of TRIP.NI CS pseudotyped with a VSV-G Cocal envelope which does not cross-react with antibodies directed against the Indiana and New Jersey serotypes. One month after the last boost, immunized mice were challenged intravenously with 500 sporozoites, (FIG. 2a). Protective efficacy was evaluated by monitoring blood stage parasitemia every other day from day 3 post injection until day 21 by Giemsa-stained blood smears. After 5 days, all naive mice exhibited patent blood stage parasitemia. By contrast, 62.5% of immunized mice showed sterile immunity (as defined by the absence of parasitemia over the following 21 days) (FIG. 2b). Moreover, as compared with naive mice, immunized mice that developed parasitemia displayed a significant delay in the course of erythrocyte invasion (FIG. 2c). At day 10 post-challenge, immunized mice partially protected showed a twofold reduction in the level of parasitemia compared to naive mice, demonstrating that in this case, the vaccine afforded also an immune control, albeit partial, of the parasite (FIG. 2d).

Hepatosplenomegaly is a prominent feature of malaria. We then performed a qualitative analysis of the organs from mice scarified 3 weeks post-challenge. Naive mice infected with the parasite displayed dramatic splenomegaly (FIG. 3). Moreover, spleens and livers showed dark pigmentation resulting from the accumulation of hemozoin produced by the parasite during digestion of red blood cell hemoglobin. By contrast, the capacity of 5 out of 8 vaccinated mice to mount a sterile immune response coincided with preservation of livers and spleens that displayed normal size and pigmentation.

In an attempt to understand why ⅓ of immunized mice did not shown sterile protection, we evaluated the CS protein-specific immune responses in vaccinated animals scarified at 3 weeks post-challenge. Challenged naive mice displayed no detectable CS protein-specific IFN-p producing T cells (data not shown). By contrast, in the vaccinated group, mice fully protected exhibited five to eight fold greater CSP-specific T cell responses as compared with mice vaccinated but partially protected, emphasizing the critical importance of the strength of T cell responses for immune control (FIG. 4).

Importantly, we also performed challenge experiments at 6 months after the last immunization. In this case, more than 40% of the vaccinated mice still failed to develop detectable parasitemia following challenge, illustrating the long-lasting sterile protection conferred by our vaccine strategy (FIG. 5).

Taken together, these data demonstrated that a prime-boost regimen based on non integrative lentiviral vectors can confer a high degree of protection against challenging infectious agents such as *plasmodium*.

Based on these results, we are currently developing a multi-stage vaccine approach. The rationale of this strategy is to improve the protective efficiency conferred by our vaccine approach by inducing a multi-immune response directed against antigens expressed in the liver stage and targeted by T-cell responses, as well as antigens expressed in the blood-stage and targeted by antibody responses. To this end, we have selected two pre-erythrocytic stage antigens (CS protein and Hepatocyte Erythrocyte Protein 17 kDa—HEP17) and one erythrocytic stage antigen (The 42-kDa fragment of the Merozoite Surface Protein 1—MSP-$1_{42}$). These antigens were selected because it has been shown that cytotoxic T cell responses specific of Hep17 are partially protective against sporozoite challenge and antibody responses specific of MSP-$1_{42}$ can also protect mice against a lethal challenge with blood-stage parasites[10, 11]. Lentiviral vectors coding for Hep17 or MSP-$1_{42}$, were constructed as detailed in the Material and Methods part. To evaluate the immunogenicity of a single injection of lentiviral particles expressing Hep17, groups of mice (n=5/group) were immunized with 100 ng ($3.2 \times 10^7$ TU) or 600 ng ($1.9 \times 10^8$ TU) of TRIP.NI Hep17 and specific immune responses were assayed by Elispot. As shown in FIG. 6, relatively weak CD8 and CD4 responses could be detected in the spleens of immunized mice after stimulation with the 9-mer and 15-mer previously described[12].

We also tested the immunogenicity of TRIP.I Hep17 lentiviral particles. Groups of mice (n=5) were immunized im with $1 \times 10^7$ TRIP.I Hep17 particles. Hep-17-specific IFNg Elispot responses were evaluated 11 days later on splenocytes from immunized mice. As shown in FIG. 7, the most robust responses were detected against the CD4+ T cell epitopes (KL14 and EK15) and against one CD8+ T cell epitope (LA9). We also evaluated the T-cell responses obtained after co-immunization of TRIP.I Hep17 particles with TRIP.I CS particles. Mice received two injections: one injection of $1 \times 10^7$ TRIP.I Hep17 particles in the left quadriceps and one injection of $1 \times 10^7$ TRIP.I CS particles in the right quadriceps. In parallel, groups of mice were immunized with TRIP.I CS particles alone ($1 \times 10^7$ TU im) or TRIP.I Hep17 particles alone ($1 \times 10^7$ TU im). At day 11, one part of immunized mice were scarified for Elispot experiments. There was no huge difference between the frequency of CS-specific IFNg T cells in mice immunized with TRIP.CS particles alone or with TRIP.I CS and TRIP.I Hep17 particles (FIG. 8A). To evaluate cytotoxic T cell response in immunized mice, we performed an in vivo cytotoxic assay (as described in Material and Methods). At day 11, groups of mice immunized with TRIP.I CS particles alone or coimmunized with TRIP.I CS and Hep17 particles were challenged by iv injection with target cells pulsed with CS peptides. As expected, mice immunized with TRIP.I CS particles lyzed efficiently target cells and we did not detect significant difference between group of mice immunized with TRIP.I CS particles alone and group of mice that received both TRIP.I CS and TRIP.I Hep17 particles (FIG. 8B). Taken together, these results demonstrated that TRIP.I Hep17 particles co-administered with TRIP.I CS particles did not significantly interfere with the CS-specific T cell response elicited by TRIP.I CS particles. We also evaluated the frequency of Hep17-specific IFNg T cells in mice immunized with TRIP.I Hep17 alone or co-administrated with TRIP.I CS particles. Frequencies of specific T cells responding to stimulation to the five 9-mer peptides (CD8+ T cell epitopes) were the same in the two groups, as well as those measured after stimulation with the KL14 epitope (CD4+ T cell epitope). Strikingly, the responses detected against the CD4+ T cell epitope EK15 were twice higher in mice co-immunized than in mice immunized with TRIP.I Hep17 alone (FIG. 8C). As shown in FIG. 8D, the cytotoxic capacity of T cells against Hep17 peptides-pulsed targets were also greatly increased in mice co-immunized with TRIP.I Hep17 and TRIP.I CS particles. Collectively, these data demonstrate that CS-specific immune response enhances cytotoxic T cell responses specific for Hep17.

We next evaluated the ability of lentiviral vectors to initiate a B cell response against the blood stage malaria antigen merozoite surface protein-1 (MSP1). Mice (n=5) were immunized with various doses of integrative lentiviral vectors coding for the 42-kDa region of MSP1 from *Plasmodium yoelii* (TRIP.I MSP$1_{42}$) fused to at the N terminus to the secretory signal of the calreticuline. Three weeks after immunization, pooled sera collected from each group of immunized mice were tested for the presence of total anti-MSP1 antibodies directed against the protective C-terminal 19-kDa region (MSP-$1_{19}$)[13, 14] of the antigen. As shown in FIG. 9A, mice immunized with a dose as low as $1 \times 10^6$ TU displayed detectable levels of anti-MSP-$1_{19}$ antibodies and immunizations with $1 \times 10^7$ TU of this vector induced a strong secretion of anti-MSP-$1_{19}$ Ig with a mean titer reaching $2 \times 10^3$. To know whether anti-MSP1 response conferred by lentiviral vector immunization could be enhanced by a second immunization, mice immunized with 100 ng of TRIP.I MSP$1_{42}$ particles pseudotyped with VSV-G Indiana envelope were boosted 3 months later with 1000 ng of TRIP.NI MSP$1_{42}$ particles pseudotyped with the VSV-G Cocal envelope (FIG. 9B). 3 weeks after the last immunization, the levels of anti-MSP-$1_{19}$ antibodies in prime-boosted mice reached a mean value of $4 \times 10^5$ whereas the titer in the plasma of mice solely primed was $2 \times 10^4$. In conclusion, immunization with integrative lentiviral vectors can induce potent anti-MSP-$1_{19}$ Ig that have been shown to be protective against infection of red blood cells by parasites.

Material and Methods

Animals and Parasites.

Balb/c Ola Hsd (six-week-old female) were purchased from Harlan Laboratories (Gannat, France). All animal experiments were conducted in accordance with the guidelines of Animal Care at the Pasteur Institute. Infection experiments were performed with the *Plasmodium yoelii* (17XNL strain) wild-type or genetically modified to express the green fluorescent protein, allowing the detection of oocysts and sporozoites in living mosquitoes. *Plasmodium*

*yoelii* was maintained by alternate cyclic passages in *Anopheles stephensi* and Balb/c mice. Mosquitoes were reared at the Center for Production and Infection of *Anopheles* (CE-PIA) of the Pasteur Institute using standard procedures.

Plasmid Vectors Construction.

The mammalian codon optimized form of the gene coding for the full-length of the Py CS protein (amino acids 1-367; GenBank Accession No. M58295) was synthesized by Geneart. Since deletion of the GPI-anchoring motif has been shown to improve the immunogenicity of the CS protein, we constructed a codon optimized form of the cs gene deleted of the sequence encoding the last 11 amino acids. This sequence was obtained by PCR amplification of a fragment of the codon optimized cs gene using the following oligonucleotides (Sigma-Proligo): (forward) 5'GGTACC GGATCCGCCACCATGAAGAAA TGCACC-3' (SEQ ID NO: 1) (underlined is the BamHI site); (reverse) 5'-AG CTCGAGTCATCACAGGCTGTTGGACACGATGTTG AAGATGC-3' (SEQ ID NO: 2) (underlined is the XhoI site). The resulting amplicon was cloned in a pCR 2.1-TOPO plasmid (Invitrogen) and sequenced (plasmid referred as pCR 2.1-TOPO CS). The pTRIP CS vector plasmid was generated by replacing the GFP sequence from pTRIP CMV-GFP-WPRE digested BamHI/XhoI by the truncated codon-optimized CS sequence obtained after a BamHI/xhoI digestion of the pCR 2.1-TOPO CS. For pTRIP Hep17, a mammalian codon-optimized sequence (Geneart) of the Py Hep17 gene (GenBank Accession No. U43539) including a kozak sequence and flanked of a BamH1 site in 5' and a XhoI site in 3' was cloned in pTRIP CMV-WPRE digested BamH1/XhoI. For MSP1 construct, a composite mammalian codon optimized sequence (Geneart) was designed to include: a sequence coding for the secretion signal of the calreticuline (MLLSVPLLLGLLGLAVA) (SEQ ID NO: 3) fused to the codon optimized sequence of the Py MSP1$_{42}$ (GenBank Accession No. JO04668). The entire sequence digested BamH1/XhoI was cloned in pTRIP CMV-WPRE digested BamH1/XhoI.

Sequences of the pTRIP vectors are respectively designated as: SEQ ID NO 34, 37, 40, 43, 45 and 47.

Lentiviral Vector Production.

Vector particles were produced by transient calcium phosphate co-transfection of 293T cells with the vector plasmid pTRIP CS, a VSV-G envelope expression plasmid (pHCMV-G) and the pD64V encapsidation GAG POL plasmid for the production of integration-deficient vectors (the D64V substitution in the catalytic domain of the integrase blocks the DNA cleaving and joining reactions of the integration step) as previously described[15]. Quantification of the p24 antigen content of concentrated vector particles was performed with a commercial HIV-1 p24 enzyme-linked immunoabsorbent assay (ELISA) kit (Perkin Elmer Life Sciences). Vector titers of TRIP.I and TRIP.NI particles were determined by transducing HeLa cells treated with aphidicolin (SIGMA) and performing a quantitative PCR as previously described[15]. The titers of integrative and nonintegrative lentiviral vectors were similar according to p24 content and quantitative PCR measured in growth-arrested cells.

Mice Immunization and Challenge.

Six-week-old BALB/c mice were intraperitoneally (i.p.) immunized with 100 ng of TRIP.NI CS vector particles pseudotyped with the VSV-G Indiana envelope, diluted in 0.1 ml Dulbecco's phosphate-buffered saline. Eight weeks later, mice were boosted i.p. with 1500 ng of TRIP.NI CS vector particles pseudotyped with the VSV-G New Jersey envelope. Challenge of the immunized and the control mice consisted of the injection of 80,000 sporozoites intravenously 4 or more weeks after the last immunization. The outcome of the challenge was determined by measuring the parasite burden in the liver of mice by using a quantitative real-time RT-PCR method, as detailed later. We also determined, in control and immunized groups of mice, whether or not mice developed parasitemia after i.v. inoculation of 500 sporozoites, by microscopic examination of Giemsa-stained thin blood smears obtained daily, from the third day after challenge up to day 14. Briefly, a small drop of blood from challenged mice was placed on a microscope slide. The drop was smeared by using a second slide, air-dried, and fixed in 100% methanol for 30 seconds. Fixed slides were stained for 30 minutes in a fresh solution of 10% Giemsa (Reactfs RAL) diluted in water (Volvic), rinsed with water and dried in air. The slides were observed with ×100 oil immersion objective.

Quantification of *P. yoelii* by Real-Time RT-PCR.

Quantification of the parasite loads in the liver of the challenged mice was performed as previously described[16] with some modifications. 40 hours after challenge, livers were harvested and RNA was extracted with the RNeasy mini kit (Qiagen). 2 µg of RNA was used for the quantification of parasite specific 18S rRNA. The reaction of real-time RT-PCR was carried out with the EXPRESS One-Step SYBR® GreenER™ kit (invitrogen) and specific primers for the amplification of the 18S rRNA of *P. yoelii*. The sequences of the primers (Sigma-Proligo) are: 5'-GGGGATTGGTTTTGACGTTTTTGCG-3' (SEQ ID NO: 4) (forward primer) and 5'-AAGCATTAAATAAAGC-GAATACATCCTTAT-3' (SEQ ID NO: 5) (reverse primer). Experiments were performed with a LightCycler™ apparatus (Roche diagnostics). The quantity of parasite RNA copies was assessed by extrapolation of threshold fluorescence values onto an internal standard curve prepared from serial dilutions of a plasmid construct (pCR 2.1-TOPO plasmid-Invitrogen) containing the 18S cDNA PCR-amplified fragment of the parasite.

Elispot Assay.

Nitrocellulose microplates (MAHA S4510, Millipore) were coated with capture antibody (Mouse IFNg Elispot pair, BD Pharmingen) and blocked with complete medium composed of RPMI 1640 Glutamax supplemented with 10% FCS, antibiotic, Hepes, non-essential amino-acids, b-mercaptoethanol and sodium pyruvate. Splenocytes from vector-immunized mice were added to the plates in triplicates at $0.125 \times 10^6$ cells/well. For quantification of CS-specific CD8$^+$ T cell responses, splenocytes were incubated with 2 µg/ml of the peptides (PolyPeptide Laboratories France) SYVPSAEQI (SEQ ID NO: 6) (Py CS$_{280-288}$) or IYNRNIVNRL (SEQ ID NO: 7) (Py CS$_{58-67}$). To evaluate the CS-specific CD4$^+$ T cell responses, splenocytes were incubated with 2 µg/ml of the peptides SYVPSAEQILEFVKQI (SEQ ID NO: 8) (Py CS$_{280-295}$). Twenty hours later, spots were revealed with the biotin-conjugated antibody (Mouse IFNg Elispot pair, BD Pharmingen) followed by streptavidin-AP (Roche) and BCIP/NB substrate solution (Promega). Spots were counted using a Bioreader 2000 (Biosys, Karben, Germany) and results were expressed as IFNγ spot-forming cells (sfc) per million splenocytes. The same protocol was applied for quantification of Hep17-specific T cell responses. Peptides used for stimulation in Elispot and in vivo cytotoxic assay are summarized in Table 1. The sequences presented in Table 1 are identified by the following sequence identification numbers: SYVPSAEQI (SEQ ID NO: 6), IYNRNIVNRL (SEQ ID NO: 7), SYVPSAEQ-ILEFVKQI (SEQ ID NO: 8), KIYNRNIVNRLLGD (SEQ ID NO: 9), YNRNIVNRLLGDALNGKPEEK (SEQ ID NO: 10), LRKINVALA (SEQ ID NO: 11), EEIVKLTKN (SEQ ID NO: 12), KKSLRKINV (SEQ ID NO: 13), INVALATAL (SEQ ID NO: 14), LSVVSAILL (SEQ ID NO: 15), EEIVKLTKNKKSLRK (SEQ ID NO: 16), and KSLRKIN-VALATAL (SEQ ID NO: 17).

In Vivo Cytotoxic Assay.

For target cell preparation, splenocytes from naive mice were labelled with various concentrations (high, 5 µM; Low, 1 µM) of CFSE (carboxyfluorescein-diacetate succinimydyl ester, Vybrant CFDA-SE cell-tracer kit, Molecular Probes). Splenocytes labelled with high concentrations of CFSE were pulsed with combination of peptides at 5 µg/ml. The control population stained with low doses of CFSE was incubated in medium without peptides. Each mouse received $10^7$ CFSE-labelled cells of a mix containing an equal number of cells from each fraction, through the retroorbital vein. After 15-18 h, single-cell suspensions from spleen were analyzed by flow cytometry (Becton Dickinson, CellQuest software). The disappearance of peptide-pulsed cells was determined by comparing the ratio of pulsed (High CFSE fluorescence intensity) to unpulsed (Low CFSE fluorescence intensity) populations in immunized versus naive mice. The percentage of specific killing was established according to the following calculation: $(1-((CFSE_{low}\ naive/CFSE_{high}\ naive)/(CFSE_{low}\ immunized/CFSE_{high}\ immunized)))*100$.

tein expression vector pGEX-2T (Amersham Biosciences, Bucks, UK). *Escherichia coli* BL21 star (Invitrogen) were transformed with pGEX-2T MSP1$_{19}$ and growth and induction were performed according to the manufacturer's instructions (pGEX vectors, GST gene fusion system, Amersham). After induction of the expression of the protein in BL21, cells were harvested and lysed using BugBuster reagent (Novagen). Recombinant protein was purified by GST bind resin chromatography using GST bind purification kit (Novagen) as per manufacturer's instructions.

Measurement of Serum Antibody Responses.

Sera were collected 3 weeks after the last immunization for the assessment of MSP1$_{19}$-specific antibodies by enzyme-linked immunosorbent assay (ELISA). Recombinant GST-MSP1$_{19}$ fusion protein or GST control were adsorbed overnight at 4° C. to 96 well Nunc-Immuno Maxisorp plates (Fischer Scientific, Wohlen, Germany) at 2 µg/ml in PBS. After three washes with 0.05% Tween 20 in PBS, wells were blocked by the addition of 100 µl of PBS containing 10% of foetal bovine serum (FBS) at room temperature for 1 hour. Plates were washed three times with 0.05% Tween 20 in PBS and 100 µl of tenfold serial dilutions of serum were added to the wells. After incubation for 2 hours at room temperature, the wells were washed and 100 µl of peroxydase goat anti-mouse immunoglobulin (H+L) (Jackson Immuno Research) diluted 1/4000 in PBS

TABLE 1

Sequences of CS and Hep17 synthetic peptides.

CSP
CD8+ T cell epitopes

| | | | |
|---|---|---|---|
| SI9 | Rs 280-88 | SYVPSAEQI | Dominant |
| IL10 | Rs 58-67 | IYNRNIVNRL | Subdominant |

CD4+ T helper cell epitopes with overlapping CD8+ T cell epitopes

| | | | |
|---|---|---|---|
| SI16 | Rs 280-95 | SYVPSAEQILEFVKQI | Dominant |
| KD14 | Rs 57-70 | KIYNRNIVNRLLGD | Dominant (nested dom. CD8+T cell epitope) |
| YK21 | Rs 59-79 | YNRNIVNRLLGDALNGKPEEK | Subdominant (nested subdom. CD8+ T cell epitope) |

PyHEP17
CD8+ T cell epitopes (9-mer)

| | | | |
|---|---|---|---|
| L9A | Rs 73-81 | LRKINVALA | Subdominant |
| EN9 | Rs 61-69 | EEIVKLTKN | Subdominant |
| KV9 | Rs 70-78 | KKSLRKINV | Subdominant |
| IL9 | Rs 76-84 | INVALATAL | Subdominant |
| LL9 | Rs 84-92 | LSVVSAILL | Subdominant |

CD4+ T cell epitope with nested CD8+ T cell epitopes (15-mer)

| | | | |
|---|---|---|---|
| EK15 | Rs 61-75 | EEIVKLTKNKKSLRK | Dominant |
| KL14 | Rs 71-84 | KSLRKINVALATAL | Dominant |

Ref
CSP:
G. Del Giudice et al., Immunol Lett 25 (1990), pp. 59-63
E. D. Franke, Infect Immun 68 (2000), pp. 3403-3411
L. Renia,, Proc Natl Acad Sci USA 88 (1991), pp. 7963-7967.
W. R. Weiss,, J Exp Med 171 (1990), pp. 763-773.
Py HEP17
Y. Charoenvit,, Infect Immun 67 (1999), pp. 5604-5614.
C. Dobaño, Mol Immunol 44 (11) (2007), pp. 3037-3048.

Recombinant MSP1$_{19}$ Protein.

*P. yoelii* YM MSP1$_{19}$ (aa 1649-1757) was amplified by PCR using the forward primer 5'-CGTGGATCCATG-GACGGCATGGATCTGCTG-3' (SEQ ID NO: 18) and the reverse primer 5'-GATGAATTCGGAGCTGCTGCTGCA-GAACACG-3' (SEQ ID NO: 19) from pTRIP MSP1$_{42}$ and cloned into the glutathione S-transferase (GST)-fusion pro- 10% FBS was added to each well. After incubation for 1 hour at room temperature, wells were washed and 100 µl of tetramethylbenzidine substrate reagent (BD Pharmingen) was added to each well. The plates were incubated at room temperature for 30 min, and 100 µl of 1N H$_2$SO$_4$ was added to stop the reaction. The plates were read for optical density at 450 nm. The endpoint titer was calculated as the recip-

REFERENCES

1. Nussenzweig, R. S., et al Protective immunity produced by the injection of x-irradiated sporozoites of *plasmodium berghei*. *Nature* 216, 160-162 (1967).
2. Gwadz, R. W., et al Preliminary studies on vaccination of rhesus monkeys with irradiated sporozoites of *Plasmodium knowlesi* and characterization of surface antigens of these parasites. *Bull World Health Organ* 57 Suppl 1, 165-173 (1979).
3. Clyde, D. F., et al Immunization of man against sporozite-induced *falciparum* malaria. *Am J Med Sci* 266, 169-177 (1973).
4. Kappe, S. H., Buscaglia, C. A. & Nussenzweig, V. *Plasmodium* sporozoite molecular cell biology. *Annu Rev Cell Dev Biol* 20, 29-59 (2004).
5. Singh, A. P. et al. *Plasmodium* circumsporozoite protein promotes the development of the liver stages of the parasite. *Cell* 131, 492-504 (2007).
6. Kumar, K. A. et al. The circumsporozoite protein is an immunodominant protective antigen in irradiated sporozoites. *Nature* 444, 937-940 (2006).
7. Abdulla, S. et al. Safety and immunogenicity of RTS,S/AS02D malaria vaccine in infants. *N Engl J Med* 359, 2533-2544 (2008).
8. Bejon, P. et al. Efficacy of RTS,S/AS01E vaccine against malaria in children 5 to 17 months of age. *N Engl J Med* 359, 2521-2532 (2008).
9. Bruna-Romero, O., Rocha, C. D., Tsuji, M. & Gazzinelli, R. T. Enhanced protective immunity against malaria by vaccination with a recombinant adenovirus encoding the circumsporozoite protein of *Plasmodium* lacking the GPI-anchoring motif. *Vaccine* 22, 3575-3584 (2004).
10. Doolan, D. L. et al. Identification and characterization of the protective hepatocyte erythrocyte protein 17 kDa gene of *Plasmodium yoelii*, homolog of *Plasmodium falciparum* exported protein 1. *J Biol Chem* 271, 17861-17868 (1996).
11. Draper, S. J. et al. Effective induction of high-titer antibodies by viral vector vaccines. *Nat Med* 14, 819-821 (2008).
12. Dobano, C. & Doolan, D. L. Identification of minimal CD8+ and CD4+ T cell epitopes in the *Plasmodium yoelii* hepatocyte erythrocyte protein 17 kDa. *Mol Immunol* 44, 3037-3048 (2007).
13. Hirunpetcharat, C. et al. Complete protective immunity induced in mice by immunization with the 19-kilodalton carboxyl-terminal fragment of the merozoite surface protein-1 (MSP1[19]) of *Plasmodium yoelii* expressed in *Saccharomyces cerevisiae*: correlation of protection with antigen-specific antibody titer, but not with effector CD4+ T cells. *J Immunol* 159, 3400-3411 (1997).
14. Ahlborg, N., et al Protective immune responses to the 42-kilodalton (kDa) region of *Plasmodium yoelii* merozoite surface protein 1 are induced by the C-terminal 19-kDa region but not by the adjacent 33-kDa region. *Infect Immun* 70, 820-825 (2002).
15. Coutant, F., Frenkiel, M. P., Despres, P. & Charneau, P. Protective antiviral immunity conferred by a nonintegrative lentiviral vector-based vaccine. *PLoS ONE* 3, e3973 (2008).
16. Bruna-Romero, O. et al. Detection of malaria liver-stages in mice infected through the bite of a single *Anopheles* mosquito using a highly sensitive real-time PCR. *Int J Parasitol* 31, 1499-1502 (2001).
17. Daneshvar, C. et al. Laboratory Features of Human *Plasmodium knowlesi* Infection—Clinical Infectious Diseases (2009); 49: 852-860.
18. Vaughan K et al., Meta-analysis of immune epitope data for all Plasmodia: overview and applications for malarial immunobiology and vaccine-related issues, Parasite Immunology, 2009, 31, 78-97
19. Jones Stephanie et al, Lentiviral vector design for optimal T cell receptor gene expression in the transduction of peripheral blood lymphocytes and tumor-infiltrating lymphocyte, Human Gene Therapy, 20: 630-640 (June 2009).
20. Cockrell A. S. et al., Gene delivery by lentivirus vectors. Mol. Biotechnol. (2007) 36: 184-204.
21. Ikedia Y. et al. (2003). Continuous high titer HIV-1 vector production. Nature Biotechnology, 21: 569-572.
22. Cockrell A. S. et al. (2006). A trans-lentiviral packaging cell line for high-titer conditional self-inactivating HIV-1 vectors. Molecular Therapy, 14: 276-284.
23. Xu K. et al. (2001). Generation of a stable cell line producing high-titer self-inactivating lentiviral vectors.
24. Kafri. T. et al. (1999). A packaging cell line for lentivirus vectors. Journal of virolog 73: 576-584.
25. Zenou V. et al (2000) HIV genome nuclear import is mediated by a central DNA flap Cell. 101: 173-185.
26. Firat H. et al. The Journal of Gene Medicine (2002); 4: 38-45.
27. VandenDriesshe T. et al (2002), Lentiviral vectors containing the Human Immunodeficiency Virus type-1 central polypurine tract can efficiently transduce nondividing hepatocytes and antigen-presenting cells in vivo. Blood. 2002 Aug. 1; 100(3): 813-22.
28. Meral E. et al (2009) VACCINE, vol. 27, Issue 49, 16 Nov. 2009, pages 6862-6868.
29. Cronin J et al (2005)—Altering the Tropism of Lentiviral vectors through Pseudotyping-Curr Gene Ther. 2005, August; 5(4): 387-398.
30. Fredericksen B. L. et al. J. Virol. 1995-69: 1435-1443.
31. Nishimura N et al. PNAS 2002-99; 6755-6760.

The invention claimed is:

1. A lentiviral vector particle (i) which is pseudotyped with at least one determined heterologous viral envelope protein originating from a RNA virus and (ii) which comprises in its genome at least one recombinant polynucleotide encoding at least one polypeptide comprising at least one epitope of a pre-erythrocytic stage antigen of a *Plasmodium* parasite capable of infecting a mammalian host.

2. The lentiviral vector according to claim 1 which is a replication-incompetent HIV-based vector particle.

3. The lentiviral vector particle according to claim 1 wherein the at least one recombinant polynucleotide comprises a nucleic acid sequence encoding a polypeptide(s) of an antigen from the circumsporozoite protein (CSP).

4. The lentiviral vector particle according to claim 1, wherein the at least one recombinant polynucleotide has a mammalian codon optimized nucleotide sequence.

5. The lentiviral vector particle according to claim 1, wherein the at least one recombinant polynucleotide encodes at least a polypeptide of the CSP antigen, said polypeptide being devoid of the glycosylphosphatidylinositol (GPI)-anchoring motif of said CSP.

6. The lentiviral vector particle according to claim 1, which is an integration-deficient vector particle.

7. The lentiviral vector particle according to claim 1, which is an integration-competent vector particle.

8. The lentiviral vector particle according to claim 1, which is pseudotyped with at least one viral transmembrane glycosylated (G) envelope protein(s) of a Vesicular Stomatitis Virus (VSV) chosen from the group consisting of VSV-G protein(s) of the Indiana strain, VSV-G protein(s) of the New Jersey strain, VSV-G protein(s) of the Cocal strain, VSV-G protein of the Isfahan strain, VSV-G protein(s) of Chandipura strain, VSV-G protein(s) of Pyri strain and VSV-G protein(s) of the SVCV strain.

9. The lentiviral vector particle according to claim 1, recovered from mammalian cells co-transfected with:
  a) a vector plasmid comprising lentiviral cis-active sequences necessary for packaging, reverse transcription, and transcription; a functional lentiviral DNA flap element; and a polynucleotide of a truncated mammalian codon-optimized sequence of the circumsporozoite (cs) gene of a *Plasmodium* parasite, under the control of regulatory expression sequences;
  b) a VSV-G envelope expression plasmid comprising a polynucleotide encoding a VSV-G envelope protein or envelope proteins under the control of regulatory expression sequences; and
  c) an encapsidation plasmid comprising lentiviral gag-pol coding sequences suitable for the production of integration-competent vector particles or modified gag-pol coding sequences suitable for the production of integration-deficient vector particles, wherein said gag-pol sequences are from the same lentivirus sub-family as the DNA flap element, wherein said gag-pol or modified gag-pol sequences are under the control of regulatory expression sequences.

10. The lentiviral vector particles according to claim 1 recovered from a stable cell line transfected with
  a) a vector plasmid comprising lentiviral cis-active sequences necessary for packaging, reverse transcription, and transcription; a functional lentiviral DNA flap element; and a polynucleotide of a truncated mammalian codon-optimized sequence of the cs gene of a *Plasmodium* parasite, under the control of regulatory expression sequences;
  b) a VSV-G envelope expression plasmid comprising a polynucleotide encoding a VSV-G envelope protein or envelope proteins under the control of regulatory expression sequences; and
  c) an encapsidation plasmid comprising lentiviral gag-pol coding sequences suitable for the production of integration-competent vector particles or modified gag-pol coding sequences suitable for the production of integration-deficient vector particles, wherein said gag-pol sequences are from the same lentivirus sub-family as the DNA flap element, wherein said gag-pol or modified gag-pol sequences are under the control of regulatory expression sequences.

11. The lentiviral particles according to claim 1, which comprises in its genome lentiviral-based sequences devoid of functional lentiviral genes, wherein said lentiviral-based sequence comprise:
  cis-active sequences necessary for packaging, reverse transcription, and transcription and a functional lentiviral DNA flap element, wherein said cis-acting sequences comprise at least one modification selected from:
  a) the 3' long terminal repeat (LTR) sequence from the lentiviral genome is truncated and devoid of the enhancer of the U3 region;
  b) the 3' LTR sequence from the lentiviral genome is truncated and devoid of the U3 region or partly deleted in the U3 region; and
  c) the U3 region of the LTR5' is replaced by a non lentiviral U3 region or by a promoter suitable to drive tat-independent primary transcription.

12. A combination of lentiviral vector particles for separate administration to a mammalian host, which comprises:
  (i) a lentiviral vector particle according to claim 1, pseudotyped with at least one first determined heterologous viral envelope protein; and
  (ii) provided separately from lentiviral vector particles in (i), a lentiviral vector particle according to claim 1, pseudotyped with at least one second determined heterologous viral envelope protein;
  wherein said first and second at least one viral envelope protein do not sero-neutralize with each other and are suitable for in vivo transduction of mammalian cells.

13. A combination of lentiviral vector particles according to the claim 12, wherein said first and second at least one viral envelope proteins are selected from:
  VSV-G of Indiana strain and VSV-G of New Jersey strain;
  wherein one or both of said first and second envelope proteins are modified versions of native VSV-G of Indiana strain or/and VSV-G of New Jersey strain;
  a chimeric VSV-G protein wherein at least one of the following domains is from an Indiana strain: the export determinant YTDIE (amino acids 501 to 505 of SEQ ID NO: 77), the cytoplasmic tail, the transmembrane domain and the cytoplasmic domain; and
  the first at least one viral envelope protein is either VSV-G of Indiana strain or VSV-G of New Jersey strain and the second at least one viral envelope protein is selected from the group consisting of VSV-G protein(s) of the Cocal strain, VSV-G protein of the Isfahan strain, VSV-G protein(s) of Chandipura strain, VSV-G protein(s) of Pyri strain and VSV-G protein(s) of the SVCV strain.

14. A composition comprising a lentiviral vector particle according to claim 1 and a physiologically acceptable vehicle.

15. The composition of claim 14, further comprising an adjuvant and/or an immunostimulant.

16. The lentiviral vector particle of claim 10, wherein the functional lentiviral DNA flap element and the lentiviral gag-pol sequences are from HIV-1.

17. The lentiviral vector particle of claim 11, wherein the lentiviral-based sequences are from HIV-1.

* * * * *